United States Patent
Roobrouck et al.

(10) Patent No.: US 12,371,496 B2
(45) Date of Patent: Jul. 29, 2025

(54) T CELL RECRUITING POLYPEPTIDES BASED ON CD3 REACTIVITY

(71) Applicant: Ablynx N.V., Ghent-Zwijnaarde (BE)

(72) Inventors: Annelies Roobrouck, Oudenaarde (BE); Diane Van Hoorick, Laarne (BE); João Vieira, Didcot (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 1085 days.

(21) Appl. No.: 17/246,771

(22) Filed: May 3, 2021

(65) Prior Publication Data

US 2021/0363251 A1 Nov. 25, 2021

Related U.S. Application Data

(63) Continuation of application No. 15/573,298, filed as application No. PCT/EP2016/060919 on May 13, 2016, now Pat. No. 11,046,767.

(60) Provisional application No. 62/160,794, filed on May 13, 2015.

(51) Int. Cl.
| | |
|---|---|
| *C07K 16/00* | (2006.01) |
| *A61P 35/00* | (2006.01) |
| *C07K 16/18* | (2006.01) |
| *C07K 16/28* | (2006.01) |
| *C07K 16/30* | (2006.01) |
| *C07K 16/32* | (2006.01) |
| *A61K 39/00* | (2006.01) |

(52) U.S. Cl.
CPC .......... *C07K 16/2809* (2013.01); *A61P 35/00* (2018.01); *C07K 16/18* (2013.01); *C07K 16/2863* (2013.01); *C07K 16/2887* (2013.01); *C07K 16/30* (2013.01); *C07K 16/32* (2013.01); *A61K 2039/505* (2013.01); *C07K 2317/14* (2013.01); *C07K 2317/31* (2013.01); *C07K 2317/565* (2013.01); *C07K 2317/567* (2013.01); *C07K 2317/569* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS 11,046,767 B2 6/2021 Roobrouck et al.

FOREIGN PATENT DOCUMENTS

| JP | 2008-523783 A | 7/2008 |
|---|---|---|
| JP | 2014-500879 A | 1/2014 |
| JP | 2015-509951 A | 4/2015 |
| WO | WO 1999/042077 A2 | 8/1999 |
| WO | WO 2011/119484 A1 | 9/2011 |
| WO | WO 2012/066058 A1 | 5/2012 |
| WO | WO 2015/044386 A1 | 4/2015 |

OTHER PUBLICATIONS

Almagro et al., Humanization of antibodies. Front Biosci. Jan. 1, 2008;13:1619-33. doi: 10.2741/2786.
Amann et al., Therapeutic window of MuS110, a single-chain antibody construct bispecific for murine EpCAM and murine CD3. Cancer Res. Jan. 1, 2008;68(1):143-51. doi: 10.1158/0008-5472.CAN-07-2182.
Bates et al., Genetic immunization for antibody generation in research animals by intravenous delivery of plasmid DNA. Biotechniques. Feb. 2006;40(2):199-208.
Bhagwat et al., Anti-CD3 antibody decreases inflammation and improves outcome in a murine model of Pneumocystis pneumonia. J Immunol. Jan. 1, 2010;184(1):497-502. doi: 10.4049/jimmunol.0901864. Epub Nov. 30, 2009.
De Genst et al., Antibody repertoire development in camelids. Dev Comp Immunol. 2006;30(1-2):187-98. doi: 10.1016/j.dci.2005.06.010.
Decanniere et al., A single-domain antibody fragment in complex with RNase A: non-canonical loop structures and nanomolar affinity using two CDR loops. Structure. Apr. 15, 1999;7(4):361-70.
Hazen et al., an improved and robust DNA immunization method to develop antibodies against extracellular loops of multi-transmembrane proteins. MAbs. Jan.-Feb. 2014;6(1):95-107.
Krause et al., An insertion mutation that distorts antibody binding site architecture enhances function of a human antibody. mBio. Feb. 8, 2011;2(1):e00345-10. doi: 10.1128/mBio.00345-10. Print 2011.
Loffler et al., A recombinant bispecific single-chain antibody, CD19 × CD3, induces rapid and high lymphoma-directed cytotoxicity by unstimulated T lymphocytes. Blood. Mar. 15, 2000;95(6):2098-103.
Lutje Hulsik et al., A gp41 MPER-specific llama VHH requires a hydrophobic CDR3 for neutralization but not for antigen recognition. PLoS Pathog. Mar. 2013;9(3):e1003202. doi: 10.1371/journal.ppat.1003202. Epub Mar. 7, 2013.
Moonsom et al., Production of polyclonal and monoclonal antibodies against CD54 molecules by intrasplenic immunization of plasmid DNA encoding CD54 protein. Immunol Lett. Feb. 1, 2001;76(1):25-30.
Richards et al., Phase I evaluation of humanized OKT3: toxicity and immunomodulatory effects of hOKT3gamma4. Cancer Res. May 1, 1999;59(9):2096-101.

(Continued)

*Primary Examiner* — Meera Natarajan

(74) *Attorney, Agent, or Firm* — Wolf, Greenfield & Sacks, P.C.

(57) ABSTRACT

T cell recruiting polypeptides are provided that bind CD3 on a T cell. The polypeptides can be used in methods for treatment of cancers.

19 Claims, 22 Drawing Sheets

Figure 1:
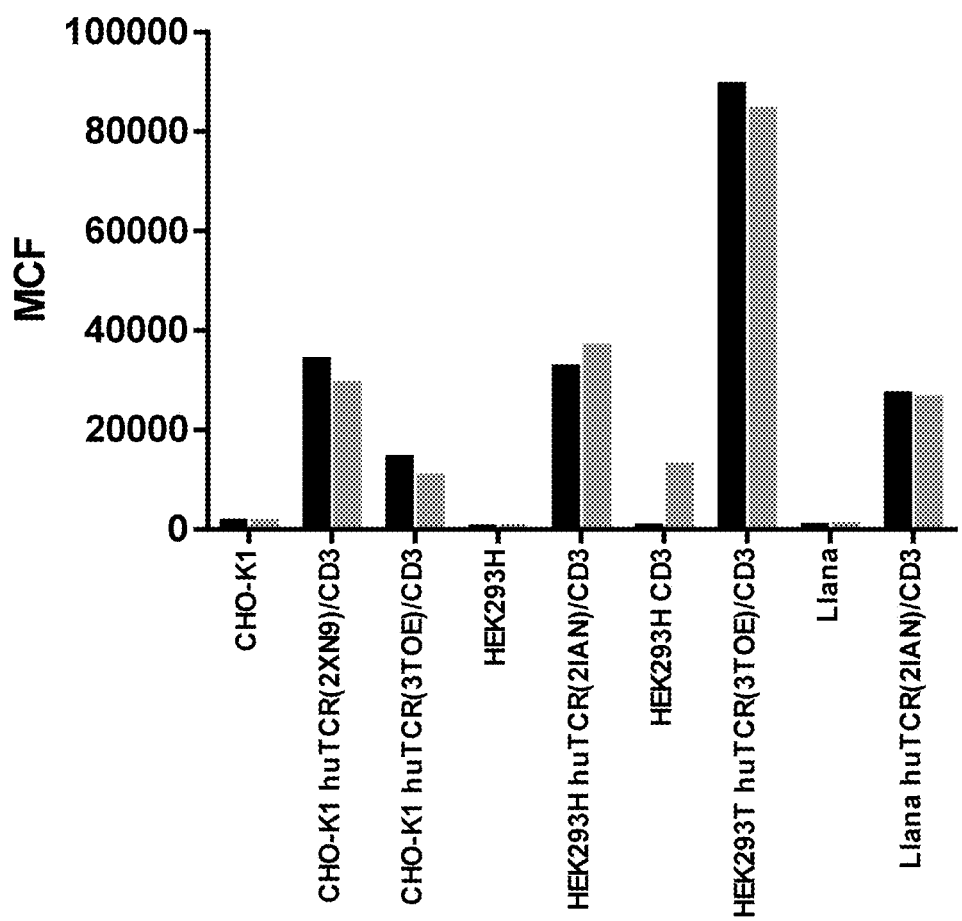

Specification includes a Sequence Listing.

(56) References Cited

OTHER PUBLICATIONS

Skinner et al., Potential use of additivity of mutational effects in simplifying protein engineering. Proc Natl Acad Sci U S A. Oct. 1, 1996; 93(20): 10753-10757. doi: 10.1073/pnas.93.20.10753.

Smolarek et al., Variable fragments of heavy chain antibodies (VHHs): a new magic bullet molecule of medicine? Postepy Hig Med Dosw (Online). Jun. 14, 2012;66:348-58.

Strokappe et al., Llama antibody fragments recognizing various epitopes of the CD4bs neutralize a broad range of HIV-1 subtypes A, B and C. PLoS One. 2012;7(3):e33298. doi: 10.1371/journal.pone.0033298. Epub Mar. 15, 2012.

Yoshinaga et al., Ig L-chain shuffling for affinity maturation of phage library-derived human anti-human MCP-1 antibody blocking its chemotactic activity. J Biochem. May 2008;143(5):593-601. doi: 10.1093/jb/mvn009. Epub Jan. 23, 2008.

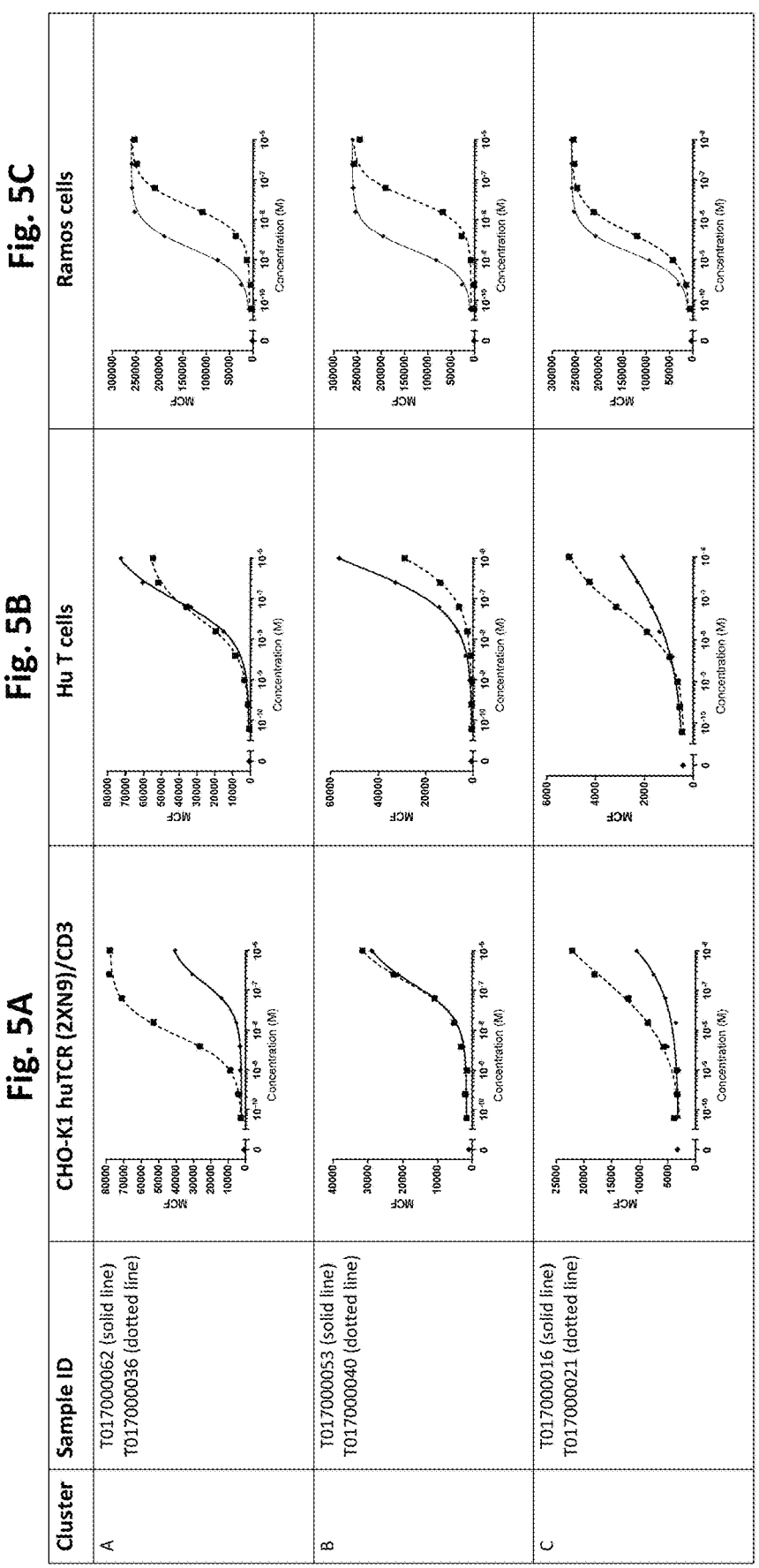

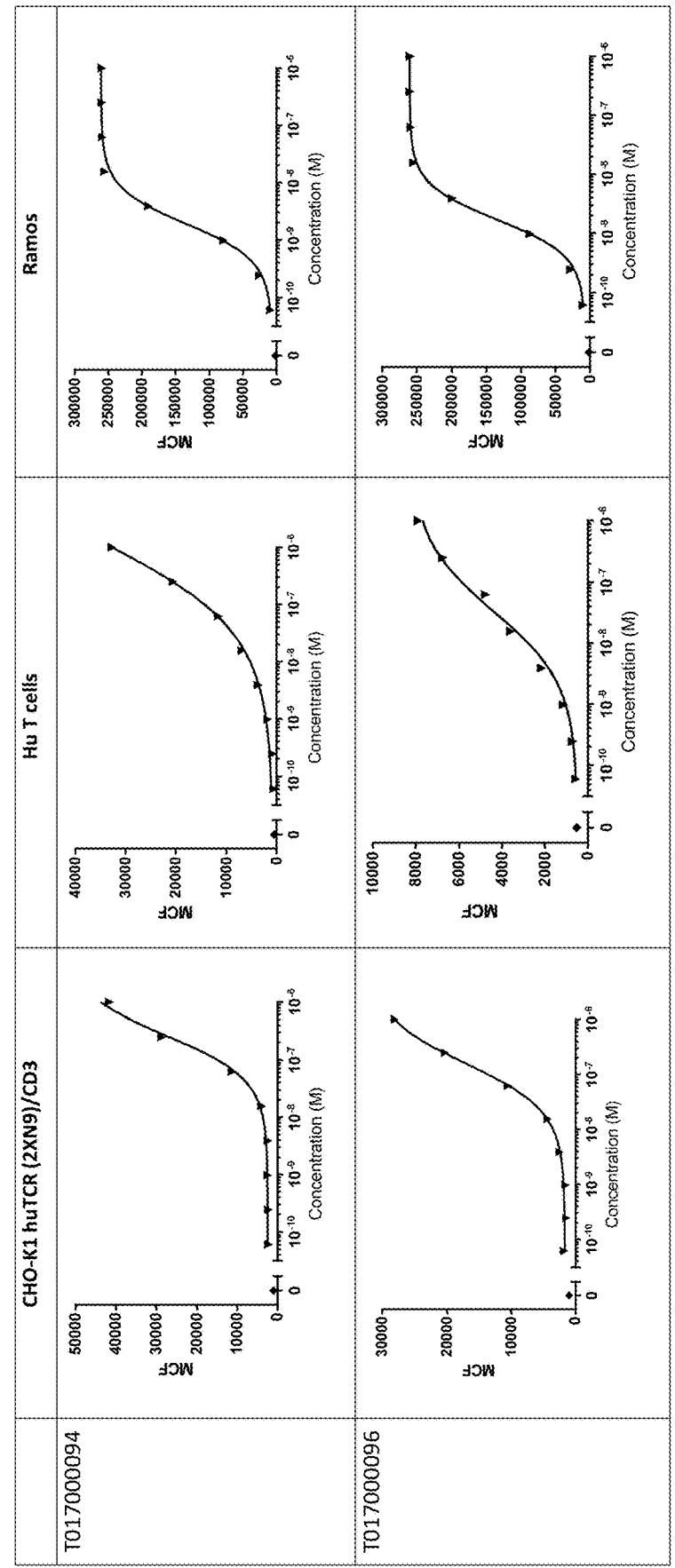

Fig. 21
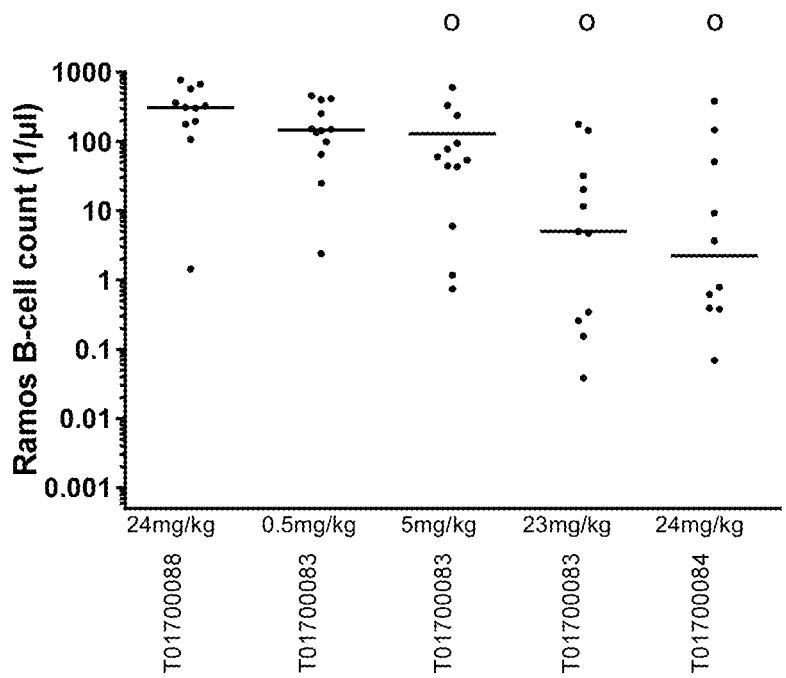
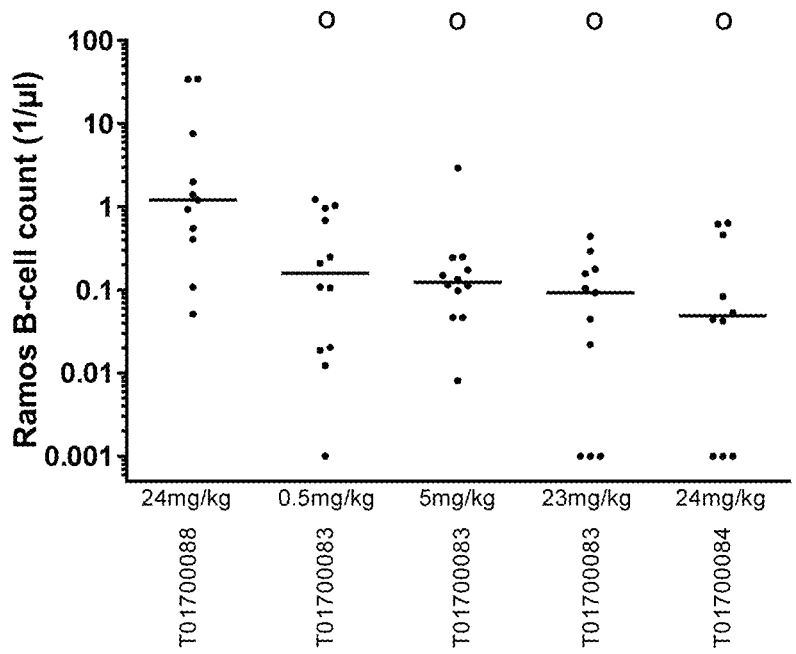

Fig. 22
Bone marrow
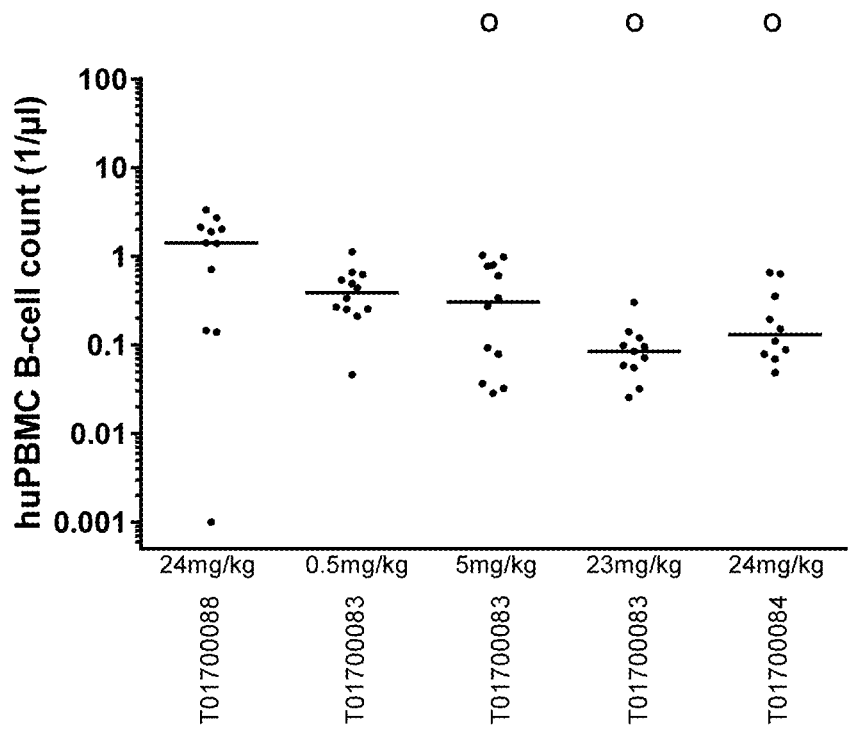
SPLEEN
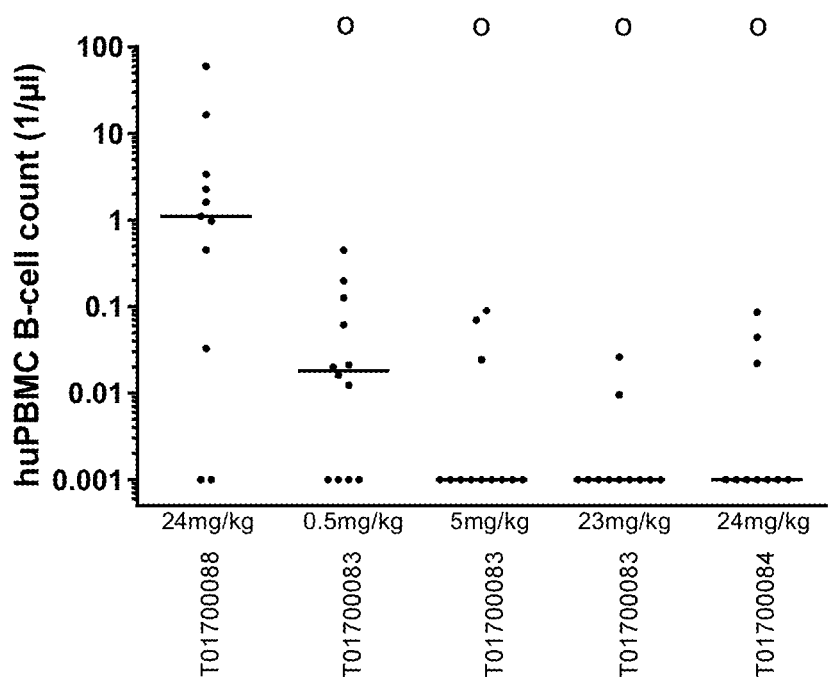

SEQUENCE LISTING

<160> NUMBER OF SEQ ID NOS: 388

<210> SEQ ID NO 1
<211> LENGTH: 124
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Gly Trp Phe Arg Gln Ala Pro Gly Lys Glu Arg Glu Phe Val
        35                  40                  45

Ala Ala Ile Val Trp Ser Gly Gly Asn Thr Tyr Tyr Glu Asp Ser Val
    50                  55                  60

Lys Gly Arg Phe Thr Ile Ser Arg Asp Asn Ala Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
                100                 105                 110

Tyr Trp Gly Gln Gly Thr Gln Val Thr Val Ser Ser
            115                 120

<210> SEQ ID NO 2
<211> LENGTH: 124
<212> TYPE: PRT

<213> ORGANISM: Artificial Sequence
<220> FEATURE:
<223> OTHER INFORMATION: Nanobody sequence

<400> SEQUENCE: 2

```
Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Ala Trp Phe Arg Gln Ser Pro Gly Lys Glu Arg Glu Phe Val
        35                  40                  45

Ala Ala Ile Val Trp Ser Asp Gly Asn Thr Tyr Tyr Glu Asp Phe Val
    50                  55                  60

Lys Gly Arg Phe Thr Ile Ser Arg Asp Ser Ala Lys Asn Thr Leu Tyr
65                  70                  75                  80

Leu Gln Met Thr Asn Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120
```

<210> SEQ ID NO 3
<211> LENGTH: 124
<212> TYPE: PRT
<213> ORGANISM: Artificial Sequence
<220> FEATURE:
<223> OTHER INFORMATION: Nanobody sequence

<400> SEQUENCE: 3

```
Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Ala Trp Phe Arg Gln Ser Pro Gly Lys Glu Arg Glu Phe Val
        35                  40                  45

Ala Ala Ile Val Trp Ser Asp Gly Asn Thr Tyr Tyr Glu Asp Phe Val
    50                  55                  60

Lys Gly Arg Phe Thr Ile Ser Arg Asp Ser Val Lys Asn Thr Leu Tyr
65                  70                  75                  80

Leu Gln Met Thr Asn Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120
```

<210> SEQ ID NO 4
<211> LENGTH: 124
<212> TYPE: PRT
<213> ORGANISM: Artificial Sequence
<220> FEATURE:
<223> OTHER INFORMATION: Nanobody sequence

<400> SEQUENCE: 4

```
Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30
```

```
Ser Met Ala Trp Phe Arg Gln Ala Pro Gly Lys Glu Arg Glu Phe Val
        35                  40                  45

Ala Ala Ile Val Trp Ser Asp Gly Asn Thr Tyr Tyr Glu Asp Phe Val
    50                  55                  60

Lys Gly Arg Phe Thr Ile Ser Arg Asp Ser Ala Lys Asn Thr Leu Tyr
65                  70                  75                  80

Leu Gln Met Thr Asn Leu Glu Pro Glu Asp Thr Ala Leu Tyr Tyr Cys
            85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120
```

<210> SEQ ID NO 5
<211> LENGTH: 124
<212> TYPE: PRT
<213> ORGANISM: Artificial Sequence
<220> FEATURE:
<223> OTHER INFORMATION: Nanobody sequence

<400> SEQUENCE: 5

```
Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Ala Trp Phe Arg Gln Ala Pro Gly Lys Glu Arg Glu Phe Val
        35                  40                  45

Ala Ala Ile Val Trp Ser Asp Gly Asn Thr Tyr Tyr Glu Asp Phe Val
    50                  55                  60

Lys Gly Arg Phe Thr Ile Ser Arg Asp Ser Ala Lys Asn Thr Leu Tyr
65                  70                  75                  80

Leu Gln Met Thr Asn Leu Glu Pro Gly Asp Thr Ala Leu Tyr Tyr Cys
            85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120
```

<210> SEQ ID NO 6
<211> LENGTH: 124
<212> TYPE: PRT
<213> ORGANISM: Artificial Sequence
<220> FEATURE:
<223> OTHER INFORMATION: Nanobody sequence

<400> SEQUENCE: 6

```
Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Ala Trp Phe Arg Gln Ala Pro Gly Lys Glu Arg Glu Phe Val
        35                  40                  45

Ala Ala Ile Val Trp Ser Asp Gly Asn Thr Tyr Tyr Glu Asp Phe Val
    50                  55                  60

Lys Gly Arg Phe Thr Ile Ser Arg Asp Ser Ala Lys Asn Thr Leu Ser
65                  70                  75                  80

Leu His Met Thr Asn Leu Lys Pro Glu Asp Thr Ala Val Tyr Tyr Cys
```

```
                    85                  90                  95

Ala Ala Lys Ile Arg Pro Tyr Ile Phe Lys Ile Ala Gly Gln Tyr Asp
                100                 105                 110

Tyr Trp Gly Gln Gly Thr Gln Val Thr Val Ser Ser
            115                 120

<210> SEQ ID NO 7
<211> LENGTH: 124
<212> TYPE: PRT
<213> ORGANISM: Artificial Sequence
<220> FEATURE:
<223> OTHER INFORMATION: Nanobody sequence

<400> SEQUENCE: 7

Glu Val Gln Pro Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
                20                  25                  30

Ser Met Ala Trp Phe Arg Gln Ala Pro Gly Lys Glu Arg Glu Phe Val
            35                  40                  45

Ala Ala Ile Val Trp Ser Asp Gly Asn Thr Tyr Tyr Glu Asp Phe Val
        50                  55                  60

Lys Gly Arg Phe Thr Ile Ser Arg Asp Ser Ala Lys Asn Thr Leu Ser
65                  70                  75                  80

Leu His Met Thr Asn Leu Lys Pro Glu Asp Thr Ala Val Tyr Tyr Cys
                85                  90                  95

Ala Ala Lys Ile Arg Pro Tyr Ile Phe Lys Ile Ala Gly Gln Tyr Asp
                100                 105                 110

Tyr Trp Gly Gln Gly Thr Gln Val Thr Val Ser Ser
            115                 120

<210> SEQ ID NO 8
<211> LENGTH: 124
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
                20                  25                  30

Ser Met Ala Trp Phe Arg Gln Ala Pro Gly Lys Glu Arg Glu Phe Val
            35                  40                  45

Ala Ala Ile Val Trp Ser Asp Gly Asn Thr Tyr Tyr Glu Asp Phe Val
        50                  55                  60

Lys Gly Arg Phe Thr Ile Ser Arg Asp Ser Ala Lys Asn Thr Leu Ser
65                  70                  75                  80

Leu His Met Ala Asn Leu Lys Pro Glu Asp Thr Ala Val Tyr Tyr Cys
                85                  90                  95

Ala Ala Lys Ile Arg Pro Tyr Ile Phe Lys Ile Ala Gly Gln Tyr Asp
                100                 105                 110

Tyr Trp Gly Gln Gly Thr Leu Val Thr Val Ser Ser
            115                 120

<210> SEQ ID NO 9
<211> LENGTH: 124
```

```
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Pro Val Gln Ser Gly Gly
1               5                   10                  15

Ser Leu Arg Leu Ser Cys Ala Asn Ser Gly Arg Thr Tyr Arg Gly Tyr
            20                  25                  30

Ser Met Gly Trp Phe Arg Gln Ala Pro Gly Lys Glu Arg Glu Phe Val
        35                  40                  45

Ala Ala Ile Val Trp Ser Asp Gly Asn Ser Tyr Tyr Glu Asp Phe Val
    50                  55                  60

Lys Gly Arg Phe Thr Ile Ser Arg Asp Ser Ala Lys Asn Ile Met Tyr
65                  70                  75                  80

Leu Gln Met Thr Asn Leu Lys Pro Glu Asp Thr Ala Val Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Pro Val Gln Ala Gly Gly
1               5                   10                  15

Ser Leu Arg Leu Ser Cys Ala Asn Ser Gly Arg Thr Tyr Arg Gly Tyr
            20                  25                  30

Ser Met Ala Trp Phe Arg Gln Ser Pro Gly Lys Glu Arg Gly Phe Val
        35                  40                  45

Ala Ala Ile Thr Trp Ser Glu Gly Asn Ala Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Thr Asn Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120

<210> SEQ ID NO 11
<211> LENGTH: 124
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Pro Val Gln Ala Gly Gly
1               5                   10                  15

Ser Leu Arg Leu Ser Cys Ala Asn Ser Gly Arg Thr Tyr Arg Gly Tyr
```

-continued

```
                20                  25                  30
Ser Met Ala Trp Phe Arg Gln Ser Pro Gly Lys Glu Arg Glu Phe Val
            35                  40                  45
Ala Ala Ile Thr Trp Ser Gly Asn Ala Tyr Tyr Glu Asp Phe Val
        50                  55                  60
Lys Gly Arg Phe Thr Ile Ser Arg Asp Asn Ala Lys Asn Thr Leu Tyr
65                  70                  75                  80
Leu Gln Met Thr Asn Leu Lys Pro Glu Asp Thr Ala Leu Tyr Tyr Cys
                85                  90                  95
Ala Ala Lys Ile Arg Pro Tyr Ile Phe Lys Ile Ala Gly Gln Tyr Asp
            100                 105                 110
Tyr Trp Gly Gln Gly Thr Leu Val Thr Val Ser Ser
            115                 120
```

<210> SEQ ID NO 12
<211> LENGTH: 124
<212> TYPE: PRT
<213> ORGANISM: Artificial Sequence
<220> FEATURE:
<223> OTHER INFORMATION: Nanobody sequence

<400> SEQUENCE: 12

```
Glu Val Gln Leu Val Glu Ser Gly Gly Gly Pro Val Gln Ala Gly Gly
1               5                   10                  15
Ser Leu Arg Leu Ser Cys Ala Asn Ser Gly Arg Thr Tyr Arg Gly Tyr
                20                  25                  30
Ser Met Ala Trp Phe Arg Gln Ser Pro Gly Lys Glu Arg Glu Phe Val
            35                  40                  45
Ala Ala Ile Thr Trp Ser Gly Asn Ala Tyr Tyr Glu Asp Phe Val
        50                  55                  60
Arg Gly Arg Phe Thr Ile Ser Arg Asp Asn Ala Lys Asn Thr Leu Tyr
65                  70                  75                  80
Leu Gln Met Thr Asn Leu Lys Pro Glu Asp Thr Ala Leu Tyr Tyr Cys
                85                  90                  95
Ala Ala Lys Ile Arg Pro Tyr Ile Phe Lys Ile Ala Gly Gln Tyr Asp
            100                 105                 110
Tyr Trp Gly Gln Gly Thr Leu Val Thr Val Ser Ser
            115                 120
```

<210> SEQ ID NO 13
<211> LENGTH: 124
<212> TYPE: PRT
<213> ORGANISM: Artificial Sequence
<220> FEATURE:
<223> OTHER INFORMATION: Nanobody sequence

<400> SEQUENCE: 13

```
Glu Val Gln Leu Val Glu Ser Gly Gly Gly Pro Val Gln Ala Gly Gly
1               5                   10                  15
Ser Leu Arg Leu Ser Cys Ala Asn Ser Arg Arg Thr Tyr Arg Gly Tyr
                20                  25                  30
Ser Met Ala Trp Phe Arg Gln Ser Pro Gly Lys Glu Arg Glu Phe Val
            35                  40                  45
Ala Ala Ile Thr Trp Ser Gly Asn Ala Tyr Tyr Glu Asp Phe Val
        50                  55                  60
Lys Gly Arg Phe Thr Ile Ser Arg Asp Asn Ala Lys Asn Thr Leu Tyr
65                  70                  75                  80
```

```
Leu Gln Met Thr Asn Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120

<210> SEQ ID NO 14
<211> LENGTH: 124
<212> TYPE: PRT
<213> ORGANISM: Artificial Sequence
<220> FEATURE:
<223> OTHER INFORMATION: Nanobody sequence

<400> SEQUENCE: 14

Glu Val Gln Leu Val Glu Ser Gly Gly Gly Pro Val Gln Ala Gly Gly
1               5                   10                  15

Ser Leu Arg Leu Ser Cys Ala Ser Ser Gly Arg Thr Tyr Arg Gly Tyr
            20                  25                  30

Ser Met Ala Trp Phe Arg Gln Ser Pro Gly Lys Glu Arg Glu Phe Val
        35                  40                  45

Ala Ala Ile Thr Trp Ser Glu Gly Asn Ala Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Thr Asn Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120

<210> SEQ ID NO 15
<211> LENGTH: 124
<212> TYPE: PRT
<213> ORGANISM: Artificial Sequence
<220> FEATURE:
<223> OTHER INFORMATION: Nanobody sequence

<400> SEQUENCE: 15

Glu Val Gln Leu Val Glu Ser Gly Gly Gly Pro Val Gln Ala Gly Gly
1               5                   10                  15

Ser Leu Arg Leu Ser Cys Ala Asn Ser Gly Arg Thr Tyr Arg Gly Tyr
            20                  25                  30

Ser Met Ala Trp Phe Arg Gln Ser Pro Gly Lys Glu Arg Glu Phe Val
        35                  40                  45

Ala Ala Ile Thr Trp Ser Glu Gly Asn Ala Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Thr Asn Leu Lys Pro Glu Asp Thr Ala Leu Tyr Tyr Cys
                85                  90                  95

Ala Ala Lys Thr Arg Pro Tyr Ile Phe Lys Ile Ala Gly Gln Tyr Asp
            100                 105                 110

Tyr Trp Gly Gln Gly Thr Gln Val Thr Val Ser Ser
        115                 120

<210> SEQ ID NO 16
```

<211> LENGTH: 124
<212> TYPE: PRT
<213> ORGANISM: Artificial Sequence
<220> FEATURE:
<223> OTHER INFORMATION: Nanobody sequence

<400> SEQUENCE: 16

Glu Val Gln Leu Val Glu Ser Gly Gly Gly Pro Val Gln Ala Gly Gly
1               5                   10                  15

Ser Leu Arg Leu Ser Cys Ala Asp Ser Gly Arg Thr Tyr Arg Gly Tyr
            20                  25                  30

Ser Met Ala Trp Phe Arg Gln Ser Pro Gly Lys Glu Arg Glu Phe Val
        35                  40                  45

Ala Ala Ile Thr Trp Ser Gly Asn Ala Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Thr Asn Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120

<210> SEQ ID NO 17
<211> LENGTH: 124
<212> TYPE: PRT
<213> ORGANISM: Artificial Sequence
<220> FEATURE:
<223> OTHER INFORMATION: Nanobody sequence

<400> SEQUENCE: 17

Glu Val Gln Leu Val Glu Ser Gly Gly Gly Pro Val Gln Ala Gly Gly
1               5                   10                  15

Ser Leu Arg Leu Ser Cys Ala Asn Ser Gly Arg Thr Tyr Arg Gly Tyr
            20                  25                  30

Gly Met Ala Trp Phe Arg Gln Ser Pro Gly Lys Glu Arg Glu Phe Val
        35                  40                  45

Ala Ala Ile Thr Trp Ser Gly Asn Ala Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Thr Asn Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120

<210> SEQ ID NO 18
<211> LENGTH: 124
<212> TYPE: PRT
<213> ORGANISM: Artificial Sequence
<220> FEATURE:
<223> OTHER INFORMATION: Nanobody sequence

<400> SEQUENCE: 18

Glu Val Gln Leu Val Glu Ser Gly Gly Gly Pro Val Gln Ala Gly Gly
1               5                   10                  15

```
Ser Leu Arg Leu Ser Cys Ala Asn Ser Gly Arg Thr Tyr Arg Gly Tyr
            20                  25                  30

Ser Met Ala Trp Phe Arg Gln Ser Pro Gly Lys Glu Arg Glu Phe Val
            35                  40                  45

Ala Ala Ile Thr Trp Ser Glu Gly Asn Ala Tyr Tyr Glu Asp Phe Val
        50                  55                  60

Lys Gly Arg Phe Thr Ile Ser Arg Asp Asn Ala Lys Asn Thr Leu Tyr
65                  70                  75                  80

Leu Gln Met Thr Asn Leu Arg Pro Glu Asp Thr Ala Leu Tyr Tyr Cys
            85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120

<210> SEQ ID NO 19
<211> LENGTH: 124
<212> TYPE: PRT
<213> ORGANISM: Artificial Sequence
<220> FEATURE:
<223> OTHER INFORMATION: Nanobody sequence

<400> SEQUENCE: 19

Glu Val Gln Leu Val Glu Ser Gly Gly Leu Val Gln Ala Gly Gly
1               5                   10                  15

Ser Leu Thr Leu Ser Cys Ala Asn Ser Gly Arg Thr Tyr Arg Gly Tyr
            20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Pro Tyr Tyr Glu Asp Phe Val
        50                  55                  60

Lys Gly Arg Phe Thr Ile Ser Arg Asp Asn Ala Lys Asn Thr Leu Tyr
65                  70                  75                  80

Leu Arg Met Thr Arg Leu Glu Pro Glu Asp Thr Ala Leu Tyr Tyr Cys
            85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120

<210> SEQ ID NO 20
<211> LENGTH: 124
<212> TYPE: PRT
<213> ORGANISM: Artificial Sequence
<220> FEATURE:
<223> OTHER INFORMATION: Nanobody sequence

<400> SEQUENCE: 20

Glu Val Gln Leu Val Glu Ser Gly Gly Gly Pro Val Gln Ala Gly Gly
1               5                   10                  15

Ser Leu Thr Leu Ser Cys Ala Asn Ser Gly Arg Thr Tyr Arg Gly Tyr
            20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Pro Tyr Tyr Glu Asp Phe Val
        50                  55                  60

Lys Gly Arg Phe Thr Ile Ser Arg Asp Asn Ala Lys Asn Thr Leu Tyr
65                  70                  75                  80
```

Leu Arg Met Thr Arg Leu Glu Pro Glu Asp Thr Ala Leu Tyr Tyr Cys
            85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120

<210> SEQ ID NO 21
<211> LENGTH: 124
<212> TYPE: PRT
<213> ORGANISM: Artificial Sequence
<220> FEATURE:
<223> OTHER INFORMATION: Nanobody sequence

<400> SEQUENCE: 21

Glu Val Gln Leu Val Glu Ser Gly Gly Gly Pro Val Gln Ala Gly Gly
1               5                   10                  15

Ser Leu Thr Leu Ser Cys Ala Asn Ser Gly Arg Thr Tyr Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Glu Gly Asn Pro Tyr Tyr Glu Asp Phe Ala
    50                  55                  60

Lys Gly Arg Phe Thr Ile Ser Arg Asp Asn Ala Lys Asn Thr Leu Tyr
65                  70                  75                  80

Leu Arg Met Thr Arg Leu Glu Pro Glu Asp Thr Ala Leu Tyr Tyr Cys
            85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120

<210> SEQ ID NO 22
<211> LENGTH: 124
<212> TYPE: PRT
<213> ORGANISM: Artificial Sequence
<220> FEATURE:
<223> OTHER INFORMATION: Nanobody sequence

<400> SEQUENCE: 22

Glu Val Gln Leu Val Glu Ser Gly Gly Gly Pro Val Gln Ala Gly Gly
1               5                   10                  15

Ser Leu Thr Leu Ser Cys Ala Asn Ser Gly Arg Ala Tyr Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Glu Gly Asn Pro Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Arg Met Thr Arg Leu Glu Pro Glu Asp Thr Ala Leu Tyr Tyr Cys
            85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120

```
<210> SEQ ID NO 23
<211> LENGTH: 124
<212> TYPE: PRT
<213> ORGANISM: Artificial Sequence
<220> FEATURE:
<223> OTHER INFORMATION: Nanobody sequence

<400> SEQUENCE: 23
```

Glu Val Gln Leu Val Glu Ser Gly Gly Gly Pro Val Gln Ala Gly Gly
1               5                   10                  15

Ser Leu Thr Leu Ser Cys Ala Asn Ser Gly Arg Thr Tyr Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Gly Gly Asn Pro Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Arg Met Thr Arg Leu Glu Pro Glu Asp Thr Ala Leu Tyr Tyr Cys
                85                  90                  95

Ala Ala Lys Ile Arg Pro Tyr Ile Phe Lys Val Ala Gly Gln Tyr Asp
            100                 105                 110

Tyr Trp Gly Gln Gly Thr Gln Val Thr Val Ser Ser
        115                 120

```
<210> SEQ ID NO 24
<211> LENGTH: 124
<212> TYPE: PRT
<213> ORGANISM: Artificial Sequence
<220> FEATURE:
<223> OTHER INFORMATION: Nanobody sequence

<400> SEQUENCE: 24
```

Glu Val Gln Leu Val Glu Ser Gly Gly Gly Pro Val Gln Ala Gly Gly
1               5                   10                  15

Ser Leu Thr Leu Ser Cys Ala Asn Ser Arg Arg Thr Tyr Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Gly Gly Asn Pro Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Arg Met Thr Arg Leu Glu Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120

```
<210> SEQ ID NO 25
<211> LENGTH: 124
<212> TYPE: PRT
<213> ORGANISM: Artificial Sequence
<220> FEATURE:
<223> OTHER INFORMATION: Nanobody sequence

<400> SEQUENCE: 25
```

Glu Val Gln Leu Val Glu Ser Gly Gly Gly Pro Val Gln Thr Gly Gly
1               5                   10                  15

Ser Leu Arg Leu Ser Cys Val Ala Ser Gly Arg Thr Tyr Arg Gly Tyr
        20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Thr Tyr Tyr Glu Asp Phe Val
50                  55                  60

Lys Gly Arg Phe Thr Ile Ser Arg Asp Asn Ala Lys Asn Thr Leu Tyr
65                  70                  75                  80

Leu Gln Met Thr Gly Leu Lys Pro Glu Asp Thr Ala Leu Tyr Tyr Cys
                85                  90                  95

Ala Ala Lys Ile Arg Pro Tyr Ile Phe Lys Ile Pro Gly Gln Tyr Asp
            100                 105                 110

Tyr Trp Gly Gln Gly Thr Leu Val Thr Val Ser Ser
        115                 120

<210> SEQ ID NO 26
<211> LENGTH: 124
<212> TYPE: PRT
<213> ORGANISM: Artificial Sequence
<220> FEATURE:
<223> OTHER INFORMATION: Nanobody sequence

<400> SEQUENCE: 26

Glu Val Gln Leu Val Glu Ser Gly Gly Gly Pro Val Gln Thr Gly Gly
1               5                   10                  15

Ser Leu Arg Leu Ser Cys Val Ala Ser Gly Arg Thr Tyr Arg Gly Tyr
        20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Thr Tyr Tyr Glu Asp Phe Val
50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Pro Glu Asp Thr Ala Leu Tyr Tyr Cys
                85                  90                  95

Ala Ala Lys Ile Arg Pro Tyr Ile Phe Lys Ile Pro Gly Gln Tyr Asp
            100                 105                 110

Tyr Trp Gly Gln Gly Thr Leu Val Thr Val Ser Ser
        115                 120

<210> SEQ ID NO 27
<211> LENGTH: 124
<212> TYPE: PRT
<213> ORGANISM: Artificial Sequence
<220> FEATURE:
<223> OTHER INFORMATION: Nanobody sequence

<400> SEQUENCE: 27

Glu Val Gln Pro Val Glu Ser Gly Gly Gly Pro Val Gln Thr Gly Gly
1               5                   10                  15

Ser Leu Arg Leu Ser Cys Val Ala Ser Gly Arg Thr Tyr Arg Gly Tyr
        20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Thr Tyr Tyr Glu Asp Phe Val
50                  55                  60

Lys Gly Arg Phe Thr Ile Ser Arg Asp Asn Ala Lys Asn Thr Leu Tyr

```
                65                  70                  75                  80
Leu Gln Met Thr Ser Leu Lys Pro Glu Asp Thr Ala Leu Tyr Tyr Cys
                    85                  90                  95

Ala Ala Lys Ile Arg Pro Tyr Ile Phe Lys Ile Pro Gly Gln Tyr Asp
                100                 105                 110

Tyr Trp Gly Gln Gly Thr Leu Val Thr Val Ser Ser
            115                 120
```

<210> SEQ ID NO 28
<211> LENGTH: 124
<212> TYPE: PRT
<213> ORGANISM: Artificial Sequence
<220> FEATURE:
<223> OTHER INFORMATION: Nanobody sequence

<400> SEQUENCE: 28

```
Glu Val Gln Leu Val Glu Ser Gly Gly Gly Pro Val Gln Thr Gly Gly
1               5                   10                  15

Ser Leu Arg Leu Ser Cys Val Ala Ser Gly Arg Thr Tyr Arg Gly Tyr
            20                  25                  30

Ser Met Ala Trp Phe Arg Gln Pro Pro Gly Lys Glu Arg Gly Phe Val
            35                  40                  45

Ala Ala Ile Thr Trp Ser Gly Gly Asn Thr Tyr Tyr Glu Asp Phe Val
            50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Pro Glu Asp Thr Ala Leu Tyr Tyr Cys
                    85                  90                  95

Ala Ala Lys Ile Arg Pro Tyr Ile Phe Lys Ile Pro Gly Gln Tyr Asp
                100                 105                 110

Tyr Trp Gly Gln Gly Thr Leu Val Thr Val Ser Ser
            115                 120
```

<210> SEQ ID NO 29
<211> LENGTH: 124
<212> TYPE: PRT
<213> ORGANISM: Artificial Sequence
<220> FEATURE:
<223> OTHER INFORMATION: Nanobody sequence

<400> SEQUENCE: 29

```
Glu Val Gln Leu Val Glu Ser Gly Gly Gly Pro Val Gln Thr Gly Gly
1               5                   10                  15

Ser Leu Arg Leu Ser Cys Val Ala Pro Gly Arg Thr Tyr Arg Gly Tyr
            20                  25                  30

Ser Met Ala Trp Phe Arg Gln Pro Pro Gly Lys Glu Arg Glu Phe Val
            35                  40                  45

Ala Ala Ile Thr Trp Ser Gly Gly Asn Thr Tyr Tyr Glu Asp Phe Val
            50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Pro Glu Asp Thr Ala Leu Tyr Tyr Cys
                    85                  90                  95

Ala Ala Lys Ile Arg Pro Tyr Ile Phe Lys Ile Pro Gly Gln Tyr Asp
                100                 105                 110

Tyr Trp Gly Gln Gly Thr Leu Val Thr Val Ser Ser
            115                 120
```

```
<210> SEQ ID NO 30
<211> LENGTH: 124
<212> TYPE: PRT
<213> ORGANISM: Artificial Sequence
<220> FEATURE:
<223> OTHER INFORMATION: Nanobody sequence

<400> SEQUENCE: 30

Glu Val Gln Leu Val Glu Ser Gly Gly Gly Pro Val Gln Thr Gly Gly
1               5                   10                  15

Ser Leu Arg Leu Ser Cys Val Ala Ser Gly Arg Thr Tyr Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Glu Gly Asn Thr Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Ala Ser Leu Lys Pro Glu Asp Thr Ala Leu Tyr Tyr Cys
                85                  90                  95

Ala Ala Lys Ile Arg Pro Tyr Ile Phe Lys Ile Pro Gly Gln Tyr Asp
            100                 105                 110

Tyr Trp Gly Gln Gly Thr Leu Val Thr Val Ser Ser
        115                 120

<210> SEQ ID NO 31
<211> LENGTH: 124
<212> TYPE: PRT
<213> ORGANISM: Artificial Sequence
<220> FEATURE:
<223> OTHER INFORMATION: Nanobody sequence

<400> SEQUENCE: 31

Glu Val Gln Leu Val Glu Ser Gly Gly Gly Leu Val Gln Thr Gly Gly
1               5                   10                  15

Ser Leu Arg Leu Ser Cys Val Ala Ser Gly Arg Thr Tyr Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Glu Gly Asn Thr Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Pro Glu Asp Thr Ala Leu Tyr Tyr Cys
                85                  90                  95

Ala Ala Lys Ile Arg Pro Tyr Ile Phe Lys Ile Pro Gly Gln Tyr Asp
            100                 105                 110

Tyr Trp Gly Gln Gly Thr Gln Val Thr Val Ser Ser
        115                 120

<210> SEQ ID NO 32
<211> LENGTH: 124
<212> TYPE: PRT
<213> ORGANISM: Artificial Sequence
<220> FEATURE:
<223> OTHER INFORMATION: Nanobody sequence

<400> SEQUENCE: 32

Glu Val Gln Leu Val Glu Ser Gly Gly Gly Pro Val Gln Thr Gly Gly
```

```
1               5                   10                  15
Ser Leu Arg Leu Ser Cys Val Ala Ser Gly Arg Thr Tyr Arg Gly Tyr
                20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Thr Tyr Tyr Glu Asp Phe Val
        50                  55                  60

Lys Gly Arg Phe Thr Ile Ser Arg Asp Asn Ala Lys Ser Thr Leu Tyr
65                      70                  75                  80

Leu Gln Met Thr Ser Leu Lys Pro Glu Asp Thr Ala Leu Tyr Tyr Cys
                85                  90                  95

Ala Ala Lys Ile Arg Pro Tyr Ile Phe Lys Ile Pro Gly Gln Tyr Asp
            100                 105                 110

Tyr Trp Gly Gln Gly Thr Gln Val Thr Val Ser Ser
            115                 120
```

<210> SEQ ID NO 33
<211> LENGTH: 124
<212> TYPE: PRT
<213> ORGANISM: Artificial Sequence
<220> FEATURE:
<223> OTHER INFORMATION: Nanobody sequence

<400> SEQUENCE: 33

```
Glu Val Gln Leu Val Glu Ser Gly Gly Gly Pro Val Gln Thr Gly Gly
1               5                   10                  15

Ser Leu Arg Leu Ser Cys Val Ala Ser Gly Arg Thr Tyr Arg Gly Tyr
                20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Thr Tyr Tyr Glu Asp Leu Val
        50                  55                  60

Lys Gly Arg Phe Thr Ile Ser Arg Asp Asn Ala Lys Asn Thr Leu Tyr
65                      70                  75                  80

Leu Gln Met Thr Ser Leu Lys Pro Glu Asp Thr Ala Leu Tyr Tyr Cys
                85                  90                  95

Ala Ala Lys Ile Arg Pro Tyr Ile Phe Lys Ile Pro Gly Gln Tyr Asp
            100                 105                 110

Tyr Trp Gly Gln Gly Thr Gln Val Thr Val Ser Ser
            115                 120
```

<210> SEQ ID NO 34
<211> LENGTH: 124
<212> TYPE: PRT
<213> ORGANISM: Artificial Sequence
<220> FEATURE:
<223> OTHER INFORMATION: Nanobody sequence

<400> SEQUENCE: 34

```
Glu Val Gln Leu Val Glu Ser Gly Gly Gly Pro Val Gln Thr Gly Gly
1               5                   10                  15

Ser Leu Arg Leu Ser Cys Val Ala Ser Gly Arg Thr Tyr Arg Gly Tyr
                20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Thr Tyr Tyr Glu Asp Phe Val
        50                  55                  60
```

```
Lys Gly Arg Phe Thr Ile Ser Arg Asp Asn Ala Lys Asn Thr Leu Tyr
65                  70                  75                  80

Leu Gln Met Thr Ser Leu Lys Pro Glu Asp Thr Ala Leu Tyr Tyr Cys
                85                  90                  95

Ala Ala Lys Ile Arg Pro Tyr Ile Phe Lys Val Pro Gly Gln Tyr Asp
            100                 105                 110

Tyr Trp Gly Gln Gly Thr Gln Val Thr Val Ser Ser
            115                 120
```

<210> SEQ ID NO 35
<211> LENGTH: 124
<212> TYPE: PRT
<213> ORGANISM: Artificial Sequence
<220> FEATURE:
<223> OTHER INFORMATION: Nanobody sequence

<400> SEQUENCE: 35

```
Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Phe Arg Gly Tyr
            20                  25                  30

Ser Met Ala Trp Phe Arg Gln Pro Pro Gly Lys Glu Arg Glu Phe Val
            35                  40                  45

Ala Ala Ile Thr Trp Ser Glu Gly Asn Thr Tyr Tyr Glu Asp Phe Val
            50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
            115                 120
```

<210> SEQ ID NO 36
<211> LENGTH: 124
<212> TYPE: PRT
<213> ORGANISM: Artificial Sequence
<220> FEATURE:
<223> OTHER INFORMATION: Nanobody sequence

<400> SEQUENCE: 36

```
Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Gly Trp Phe Arg Gln Ala Pro Gly Arg Glu Arg Glu Phe Val
            35                  40                  45

Ala Ala Ile Val Trp Ser Asp Gly Asn Thr Tyr Tyr Glu Asp Ser Val
            50                  55                  60

Lys Gly Arg Phe Thr Ile Ser Arg Asp Asn Ala Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
            115                 120
```

<210> SEQ ID NO 37
<211> LENGTH: 124
<212> TYPE: PRT
<213> ORGANISM: Artificial Sequence
<220> FEATURE:
<223> OTHER INFORMATION: Nanobody sequence

<400> SEQUENCE: 37

```
Glu Val Gln Leu Val Glu Ser Gly Gly Pro Ala Gln Ala Gly Gly
1               5                   10                  15

Ser Leu Arg Leu Ser Cys Ala Ala Ser Gly Arg Thr Tyr Arg Gly Tyr
            20                  25                  30

Ser Met Gly Trp Phe Arg Gln Ala Pro Gly Arg Glu Arg Glu Phe Val
            35                  40                  45

Ala Ala Ile Val Trp Ser Asp Gly Asn Thr Tyr Tyr Glu Asp Ser Val
            50                  55                  60

Lys Gly Arg Phe Thr Ile Ser Arg Asp Asn Ala Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
            115                 120
```

<210> SEQ ID NO 38
<211> LENGTH: 124
<212> TYPE: PRT
<213> ORGANISM: Artificial Sequence
<220> FEATURE:
<223> OTHER INFORMATION: Nanobody sequence

<400> SEQUENCE: 38

```
Glu Val Gln Leu Val Glu Ser Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Gly Trp Phe Arg Arg Ala Pro Gly Arg Glu Arg Glu Phe Val
            35                  40                  45

Ala Ala Ile Val Trp Ser Asp Gly Asn Thr Tyr Tyr Glu Asp Pro Val
            50                  55                  60

Lys Gly Arg Phe Thr Ile Ser Arg Asp Asn Ala Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
            115                 120
```

<210> SEQ ID NO 39
<211> LENGTH: 124
<212> TYPE: PRT
<213> ORGANISM: Artificial Sequence
<220> FEATURE:
<223> OTHER INFORMATION: Nanobody sequence

<400> SEQUENCE: 39

-continued

```
Glu Val Gln Leu Val Glu Ser Gly Gly Gly Pro Val Gln Ala Gly Asp
1               5                   10                  15

Ser Leu Arg Leu Ser Cys Ala Ala Ser Gly Arg Ala Tyr Arg Gly Tyr
            20                  25                  30

Ser Met Gly Trp Phe Arg Gln Val Pro Gly Lys Glu Arg Glu Phe Val
        35                  40                  45

Ala Ala Ile Val Trp Thr Asp Gly Asn Thr Tyr Tyr Glu Asp Ser Val
    50                  55                  60

Lys Gly Arg Phe Thr Ile Ser Arg Asp Ile Thr Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
            115                 120
```

<210> SEQ ID NO 40
<211> LENGTH: 124
<212> TYPE: PRT
<213> ORGANISM: Artificial Sequence
<220> FEATURE:
<223> OTHER INFORMATION: Nanobody sequence

<400> SEQUENCE: 40

```
Glu Val Gln Leu Val Glu Phe Gly Gly Gly Pro Val Gln Ala Gly Asp
1               5                   10                  15

Ser Leu Arg Leu Ser Cys Ala Ala Ser Gly Arg Ala Tyr Arg Gly Tyr
            20                  25                  30

Ser Met Gly Trp Phe Arg Gln Val Pro Gly Lys Glu Arg Glu Phe Val
        35                  40                  45

Ala Ala Ile Val Trp Thr Asp Gly Asn Thr Tyr Tyr Glu Asp Ser Val
    50                  55                  60

Lys Gly Arg Phe Thr Ile Ser Arg Asp Ile Thr Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
            115                 120
```

<210> SEQ ID NO 41
<211> LENGTH: 124
<212> TYPE: PRT
<213> ORGANISM: Artificial Sequence
<220> FEATURE:
<223> OTHER INFORMATION: Nanobody sequence

<400> SEQUENCE: 41

```
Glu Val Gln Leu Val Glu Ser Gly Gly Gly Pro Val Gln Ala Gly Asp
1               5                   10                  15

Ser Leu Arg Leu Ser Cys Ala Ala Ser Gly Arg Ala Tyr Arg Gly Tyr
            20                  25                  30

Ser Met Gly Trp Phe Arg Gln Val Pro Gly Lys Glu Arg Glu Phe Val
        35                  40                  45

Ala Ala Ile Ala Trp Thr Asp Gly Asn Thr Tyr Tyr Glu Asp Ser Val
    50                  55                  60
```

```
Lys Gly Arg Phe Thr Ile Ser Arg Asp Ile Thr Lys Asn Thr Met Tyr
 65                  70                  75                  80

Leu Gln Met Thr Ser Leu Lys Pro Glu Asp Ser Ala Thr Tyr Tyr Cys
                 85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120
```

<210> SEQ ID NO 42
<211> LENGTH: 124
<212> TYPE: PRT
<213> ORGANISM: Artificial Sequence
<220> FEATURE:
<223> OTHER INFORMATION: Nanobody sequence

<400> SEQUENCE: 42

```
Glu Val Gln Leu Val Glu Ser Gly Gly Pro Val Gln Ala Gly Asp
1               5                   10                  15

Ser Leu Arg Leu Ser Cys Ala Ala Ser Gly Arg Ala Tyr Arg Gly Tyr
                20                  25                  30

Ser Met Gly Trp Phe Arg Gln Val Pro Gly Lys Glu Arg Glu Phe Val
            35                  40                  45

Ala Ala Ile Val Trp Thr Asp Gly Asn Thr Tyr Tyr Glu Asp Ser Val
        50                  55                  60

Lys Gly Arg Phe Thr Ile Ser Arg Asp Val Thr Lys Asn Thr Met Tyr
 65                  70                  75                  80

Leu Gln Met Thr Ser Leu Lys Pro Glu Asp Ser Ala Thr Tyr Tyr Cys
                 85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120
```

<210> SEQ ID NO 43
<211> LENGTH: 124
<212> TYPE: PRT
<213> ORGANISM: Artificial Sequence
<220> FEATURE:
<223> OTHER INFORMATION: Nanobody sequence

<400> SEQUENCE: 43

```
Glu Val Gln Leu Val Glu Ser Arg Gly Gly Pro Val Gln Ala Gly Asp
1               5                   10                  15

Ser Leu Arg Leu Ser Cys Ala Ala Ser Gly Arg Ala Tyr Arg Gly Tyr
                20                  25                  30

Ser Met Gly Trp Phe Arg Gln Val Pro Gly Lys Glu Arg Glu Phe Val
            35                  40                  45

Ala Ala Ile Val Trp Thr Asp Gly Asn Thr Tyr Tyr Glu Asp Ser Val
        50                  55                  60

Lys Gly Arg Phe Thr Ile Ser Arg Asp Ile Thr Lys Asn Thr Met Tyr
 65                  70                  75                  80

Leu Gln Met Thr Ser Leu Lys Pro Glu Asp Ser Ala Thr Tyr Tyr Cys
                 85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
```

<210> SEQ ID NO 44
<211> LENGTH: 124
<212> TYPE: PRT
<213> ORGANISM: Artificial Sequence
<220> FEATURE:
<223> OTHER INFORMATION: Nanobody sequence

<400> SEQUENCE: 44

```
Glu Val Gln Leu Val Glu Ser Gly Gly Gly Pro Val Gln Ala Gly Asp
1               5                   10                  15

Ser Leu Arg Leu Ser Cys Ala Ala Ser Gly Arg Ala Tyr Arg Gly Tyr
            20                  25                  30

Ser Met Gly Trp Phe Arg Gln Val Pro Gly Lys Glu Arg Glu Phe Val
        35                  40                  45

Ala Ala Ile Val Trp Thr Asp Gly Asn Ala Tyr Tyr Glu Asp Ser Val
    50                  55                  60

Lys Gly Arg Phe Thr Ile Ser Arg Asp Ile Thr Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120
```

<210> SEQ ID NO 45
<211> LENGTH: 124
<212> TYPE: PRT
<213> ORGANISM: Artificial Sequence
<220> FEATURE:
<223> OTHER INFORMATION: Nanobody sequence

<400> SEQUENCE: 45

```
Glu Val Gln Leu Val Glu Ser Gly Gly Gly Pro Val Gln Ala Gly Asp
1               5                   10                  15

Ser Leu Arg Leu Ser Cys Ala Ala Ser Gly Arg Ala Tyr Arg Gly Tyr
            20                  25                  30

Ser Met Gly Trp Phe Arg Arg Val Pro Gly Lys Glu Arg Glu Phe Val
        35                  40                  45

Ala Ala Ile Val Trp Thr Asp Gly Asn Thr Tyr Tyr Glu Asp Ser Val
    50                  55                  60

Lys Gly Arg Phe Thr Ile Ser Arg Asp Ile Thr Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
        115                 120
```

<210> SEQ ID NO 46
<211> LENGTH: 123
<212> TYPE: PRT
<213> ORGANISM: Artificial Sequence
<220> FEATURE:
<223> OTHER INFORMATION: Nanobody sequence

<400> SEQUENCE: 46

```
Glu Val Gln Leu Val Ser Gly Gly Pro Val Gln Ala Gly Asp Ser
1               5                   10                  15

Leu Arg Leu Ser Cys Ala Ala Ser Gly Arg Ala Tyr Arg Gly Tyr Ser
            20                  25                  30

Met Gly Trp Phe Arg Gln Val Pro Gly Lys Glu Arg Glu Phe Val Ala
        35                  40                  45

Ala Ile Val Trp Thr Asp Gly Asn Thr Tyr Tyr Glu Asp Ser Val Lys
    50                  55                  60

Gly Arg Phe Thr Ile Ser Arg Asp Ile Thr Lys Asn Thr Met Tyr Leu
65                  70                  75                  80

Gln Met Thr Ser Leu Lys Pro Glu Asp Ser Ala Thr Tyr Tyr Cys Ala
                85                  90                  95

Ala Lys Ile Arg Pro Tyr Ile Phe Lys Ile Ala Gly Tyr Asp Tyr
            100                 105                 110

Trp Gly Gln Gly Thr Gln Val Thr Val Ser Ser
        115                 120
```

<210> SEQ ID NO 47
<211> LENGTH: 124
<212> TYPE: PRT
<213> ORGANISM: Artificial Sequence
<220> FEATURE:
<223> OTHER INFORMATION: Nanobody sequence

<400> SEQUENCE: 47

```
Glu Val Gln Leu Val Glu Ser Gly Gly Gly Pro Val Gln Ala Gly Asp
1               5                   10                  15

Ser Leu Arg Leu Ser Cys Ala Ala Ser Gly Arg Thr Tyr Arg Gly Tyr
            20                  25                  30

Ser Met Gly Trp Phe Arg Gln Val Pro Gly Lys Glu Arg Glu Phe Val
        35                  40                  45

Ala Ala Ile Val Trp Thr Asp Gly Asn Thr Tyr Tyr Glu Asp Ser Val
    50                  55                  60

Lys Gly Arg Phe Thr Ile Ser Arg Asp Asn Thr Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
        115                 120
```

<210> SEQ ID NO 48
<211> LENGTH: 124
<212> TYPE: PRT
<213> ORGANISM: Artificial Sequence
<220> FEATURE:
<223> OTHER INFORMATION: Nanobody sequence

<400> SEQUENCE: 48

```
Lys Val Gln Leu Val Glu Ser Gly Gly Gly Pro Val Gln Ala Gly Asp
1               5                   10                  15

Ser Leu Arg Leu Ser Cys Ala Ala Ser Gly Arg Thr Tyr Arg Gly Tyr
            20                  25                  30

Ser Met Gly Trp Phe Arg Gln Val Pro Gly Lys Glu Arg Glu Phe Val
        35                  40                  45

Ala Ala Ile Val Trp Thr Asp Gly Asn Thr Tyr Tyr Glu Asp Ser Val
```

```
                    50                  55                  60
Lys Gly Arg Phe Thr Ile Ser Arg Asp Asn Thr Lys Asn Thr Met Tyr
 65                  70                  75                  80

Leu Gln Met Thr Ser Leu Lys Pro Glu Asp Ser Ala Thr Tyr Tyr Cys
                     85                  90                  95

Ala Ala Lys Ile Arg Pro Tyr Ile Phe Lys Ile Ala Gly Gln Tyr Asp
                    100                 105                 110

Tyr Trp Gly Gln Gly Thr Leu Val Thr Val Ser Ser
                    115                 120

<210> SEQ ID NO 49
<211> LENGTH: 124
<212> TYPE: PRT
<213> ORGANISM: Artificial Sequence
<220> FEATURE:
<223> OTHER INFORMATION: Nanobody sequence

<400> SEQUENCE: 49

Glu Val Gln Leu Val Glu Ser Gly Gly Gly Pro Val Gln Ala Gly Asp
 1               5                  10                  15

Ser Leu Arg Leu Ser Cys Ala Ala Ser Gly Arg Thr Tyr Arg Gly Tyr
                20                  25                  30

Ser Met Gly Trp Phe Arg Gln Val Pro Gly Lys Glu Arg Glu Phe Val
                35                  40                  45

Ala Ala Ile Val Trp Thr Asp Gly Asn Thr Tyr Tyr Glu Asp Ser Val
                50                  55                  60

Lys Gly Arg Phe Thr Ile Ser Arg Asp Ile Thr Lys Asn Thr Met Tyr
 65                  70                  75                  80

Leu His Met Thr Ser Leu Lys Pro Glu Asp Ser Ala Thr Tyr Tyr Cys
                     85                  90                  95

Ala Ala Lys Ile Arg Pro Tyr Ile Phe Lys Ile Ala Gly Gln Tyr Asp
                    100                 105                 110

Tyr Trp Gly Gln Gly Thr Gln Val Thr Val Ser Ser
                    115                 120

<210> SEQ ID NO 50
<211> LENGTH: 124
<212> TYPE: PRT
<213> ORGANISM: Artificial Sequence
<220> FEATURE:
<223> OTHER INFORMATION: Nanobody sequence

<400> SEQUENCE: 50

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Ala Tyr Arg Gly Tyr
                20                  25                  30

Ser Met Gly Trp Phe Arg Gln Val Pro Gly Lys Glu Arg Glu Phe Val
                35                  40                  45

Ala Ala Ile Val Trp Thr Asp Gly Asn Thr Tyr Tyr Glu Asp Ser Val
                50                  55                  60

Lys Gly Arg Phe Thr Ile Ser Arg Asp Ile Thr Lys Asn Thr Met Tyr
 65                  70                  75                  80

Leu Gln Met Thr Ser Leu Lys Pro Glu Asp Ser Ala Thr Tyr Tyr Cys
                     85                  90                  95

Ala Ala Lys Ile Arg Pro Tyr Ile Phe Lys Ile Ala Gly Gln Tyr Asp
                    100                 105                 110
```

Tyr Trp Gly Gln Gly Thr Gln Val Thr Val Ser Ser
            115                 120

<210> SEQ ID NO 51
<211> LENGTH: 120
<212> TYPE: PRT
<213> ORGANISM: Artificial Sequence
<220> FEATURE:
<223> OTHER INFORMATION: Nanobody sequence

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Ile Tyr Lys Ser Phe
            20                  25                  30

Asp Met Gly Trp Tyr Arg Gln Ala Pro Gly Lys Gln Arg Asp Leu Val
        35                  40                  45

Ala Val Ile Gly Ser Arg Gly Asn Asn Arg Gly Arg Thr Asn Tyr Ala
    50                  55                  60

Asp Ser Val Lys Gly Arg Phe Thr Ile Ser Arg Asp Gly Thr Gly Asn
65                  70                  75                  80

Thr Val Tyr Leu Leu Met Asn Lys Leu Arg Pro Glu Asp Thr Ala Ile
                85                  90                  95

Tyr Tyr Cys Asn Thr Ala Pro Leu Val Ala Gly Arg Pro Trp Gly Arg
            100                 105                 110

Gly Thr Leu Val Thr Val Ser Ser
            115                 120

<210> SEQ ID NO 52
<211> LENGTH: 129
<212> TYPE: PRT
<213> ORGANISM: Artificial Sequence
<220> FEATURE:
<223> OTHER INFORMATION: Nanobody sequence

<400> SEQUENCE: 52

Glu Val Gln Leu Val Glu Ser Gly Gly Gly Leu Val Gln Gly Gly Gly
1               5                   10                  15

Ser Leu Ser Leu Ser Cys Ala Ala Ser Gly Arg Thr Phe Ser Ser Tyr
            20                  25                  30

Ala Met Ala Trp Phe Arg Gln Pro Pro Gly Lys Glu Arg Glu Phe Val
        35                  40                  45

Ala Ser Ile Ser Trp Ser Gly Glu Asn Thr Asn Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Lys Ile Ala Lys Thr Tyr Pro Asp Asn Trp Tyr Trp Thr Lys
            100                 105                 110

Ser Asn Asn Tyr Asn Tyr Trp Gly Gln Gly Thr Gln Val Thr Val Ser
            115                 120                 125

Ser

<210> SEQ ID NO 53
<211> LENGTH: 124
<212> TYPE: PRT
<213> ORGANISM: Artificial Sequence
<220> FEATURE:

<223> OTHER INFORMATION: Nanobody sequence

<400> SEQUENCE: 53

```
Glu Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Phe Ser Thr Asn
            20                  25                  30

Pro Met Gly Trp Phe Arg Gln Val Pro Gly Lys Glu Arg Glu Leu Ile
        35                  40                  45

Ala Ala Val Arg Trp Ala Asp Gly Asn Thr Phe Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Ser Leu Lys Ser Glu Asp Thr Ala Thr Tyr Tyr Cys
                85                  90                  95

Ala Ala Gly Arg Pro Trp Ser Ala Tyr His Ser Pro Ala Glu Tyr Val
            100                 105                 110

His Trp Gly Gln Gly Thr Gln Val Thr Val Ser Ser
        115                 120
```

<210> SEQ ID NO 54
<211> LENGTH: 124
<212> TYPE: PRT
<213> ORGANISM: Artificial Sequence
<220> FEATURE:
<223> OTHER INFORMATION: Nanobody sequence

<400> SEQUENCE: 54

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Thr Asn
            20                  25                  30

Pro Met Gly Trp Phe Arg Gln Ser Pro Gly Lys Glu Arg Ser Leu Ile
        35                  40                  45

Ala Ala Val Arg Trp Ala Asp Gly Asn Thr Phe Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Ser Leu Lys Ser Glu Asp Thr Ala Thr Tyr Tyr Cys
                85                  90                  95

Ala Ala Gly Arg Pro Trp Ser Ala Tyr His Ser Pro Ala Glu Tyr Val
            100                 105                 110

His Trp Gly Gln Gly Thr Gln Val Thr Val Ser Ser
        115                 120
```

<210> SEQ ID NO 55
<211> LENGTH: 124
<212> TYPE: PRT
<213> ORGANISM: Artificial Sequence
<220> FEATURE:
<223> OTHER INFORMATION: Nanobody sequence

<400> SEQUENCE: 55

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Thr Asn
            20                  25                  30

Pro Met Gly Trp Phe Arg Gln Ser Pro Gly Lys Glu Arg Ser Leu Ile
```

```
                35                  40                  45
Ala Ala Ala Arg Trp Ala Asp Gly Asn Thr Phe Tyr Ala Asp Ser Val
             50                  55                  60
Lys Gly Arg Phe Thr Ile Ser Arg Asp Asn Ala Lys Lys Thr Val Tyr
65                  70                  75                  80
Leu Gln Met Asn Ser Leu Lys Ser Glu Asp Thr Ala Thr Tyr Tyr Cys
                 85                  90                  95
Ala Ala Gly Arg Pro Trp Ser Ala Tyr His Ser Pro Ala Glu Tyr Val
             100                 105                 110
His Trp Gly Gln Gly Thr Gln Val Thr Val Ser Ser
         115                 120
```

<210> SEQ ID NO 56
<211> LENGTH: 124
<212> TYPE: PRT
<213> ORGANISM: Artificial Sequence
<220> FEATURE:
<223> OTHER INFORMATION: Nanobody sequence

<400> SEQUENCE: 56

```
Glu Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Phe Ser Thr Asn
             20                  25                  30
Pro Met Gly Trp Phe Arg Gln Ser Pro Gly Lys Glu Arg Ser Leu Ile
             35                  40                  45
Ala Ala Val Arg Trp Ala Asp Gly Asn Thr Phe Tyr Ala Asp Ser Val
             50                  55                  60
Lys Gly Arg Phe Thr Ile Ser Arg Asp Asn Ala Lys Lys Thr Val Tyr
65                  70                  75                  80
Leu Gln Met Asn Ser Leu Arg Ser Glu Asp Thr Ala Thr Tyr Tyr Cys
                 85                  90                  95
Ala Ala Gly Arg Pro Trp Ser Ala Tyr His Ser Pro Ala Glu Tyr Val
             100                 105                 110
His Trp Gly Gln Gly Thr Leu Val Thr Val Ser Ser
         115                 120
```

<210> SEQ ID NO 57
<211> LENGTH: 114
<212> TYPE: PRT
<213> ORGANISM: Artificial Sequence
<220> FEATURE:
<223> OTHER INFORMATION: Nanobody sequence

<400> SEQUENCE: 57

```
Glu Val Gln Leu Val Glu Ser Gly Gly Gly Ala Val Gln Pro Gly Gly
1               5                   10                  15
Ser Leu Arg Leu Ser Cys Ala Ala Ser Gly Ile Arg Ile Ser Arg Asn
             20                  25                  30
Met Met Gly Trp Phe Arg Gln Ala Pro Gly Lys Gln Arg Asp Leu Val
             35                  40                  45
Ala Arg Ile Thr Pro Gly Gly Asp Thr Tyr Tyr Val Asp Ser Val Lys
             50                  55                  60
Gly Arg Phe Ser Ile Ser Lys Asp Asn Ala Lys Asn Thr Val Tyr Leu
65                  70                  75                  80
Gln Met Asn Ser Leu Lys Pro Glu Asp Thr Ala Val Tyr Tyr Cys Asn
                 85                  90                  95
```

Ser Tyr Ser Thr Leu Gly Ser Trp Gly Gln Gly Thr Gln Val Thr Val
                100                 105                 110

Ser Ser

<210> SEQ ID NO 58
<211> LENGTH: 114
<212> TYPE: PRT
<213> ORGANISM: Artificial Sequence
<220> FEATURE:
<223> OTHER INFORMATION: Nanobody sequence

<400> SEQUENCE: 58

Glu Val Gln Leu Val Glu Ser Gly Gly Ala Val Gln Pro Gly Gly
1               5                   10                  15

Ser Leu Arg Leu Ser Cys Val Ala Ser Gly Ile Arg Ile Ser Arg Asn
                20                  25                  30

Met Met Gly Trp Phe Arg Arg Thr Pro Gly Arg Glu Arg Asn Met Val
                35                  40                  45

Ala Arg Ile Ser Pro Gly Gly Ala Thr Tyr Tyr Val Asp Ser Val Lys
            50                  55                  60

Gly Arg Phe Ser Ile Ser Lys Asp Asp Ser Lys Asn Thr Val Tyr Leu
65                  70                  75                  80

Gln Met Asp Ser Leu Lys Pro Glu Asp Thr Ala Val Tyr Tyr Cys Asn
                85                  90                  95

Ser Tyr Ser Thr Leu Gly Ser Trp Gly Gln Gly Thr Gln Val Thr Val
                100                 105                 110

Ser Ser

<210> SEQ ID NO 59
<211> LENGTH: 114
<212> TYPE: PRT
<213> ORGANISM: Artificial Sequence
<220> FEATURE:
<223> OTHER INFORMATION: Nanobody sequence

<400> SEQUENCE: 59

Glu Val Gln Leu Val Glu Ser Gly Gly Ala Val Gln Pro Gly Gly
1               5                   10                  15

Ser Leu Arg Leu Ser Cys Val Ala Ser Gly Ile Arg Ile Ser Arg Asn
                20                  25                  30

Met Met Gly Trp Phe Arg Arg Thr Pro Gly Arg Glu Arg Asn Met Val
                35                  40                  45

Ala Arg Ile Ser Pro Gly Gly Ala Thr Tyr Tyr Val Asp Ser Val Lys
            50                  55                  60

Gly Arg Phe Ser Ile Ser Lys Asp Asp Ser Lys Asn Thr Val Tyr Leu
65                  70                  75                  80

Gln Met Asp Ser Leu Lys Pro Glu Asp Thr Ala Val Tyr Tyr Cys Asn
                85                  90                  95

Ser Tyr Ser Thr Leu Gly Ser Trp Gly Gln Gly Thr Leu Val Thr Val
                100                 105                 110

Ser Ser

<210> SEQ ID NO 60
<211> LENGTH: 114
<212> TYPE: PRT
<213> ORGANISM: Artificial Sequence
<220> FEATURE:
<223> OTHER INFORMATION: Nanobody sequence

<400> SEQUENCE: 60

Glu Val Gln Leu Val Glu Ser Gly Gly Ala Val Gln Pro Gly Gly
1               5                   10                  15

Ser Leu Arg Leu Ser Cys Val Ala Ser Gly Ile Arg Ile Ser Arg Asn
            20                  25                  30

Met Met Gly Trp Phe Arg Arg Thr Pro Gly Arg Gly Arg Asn Met Val
        35                  40                  45

Ala Arg Ile Ser Pro Gly Gly Ala Thr Tyr Tyr Val Asp Ser Val Lys
    50                  55                  60

Gly Arg Phe Ser Ile Ser Lys Asp Asp Ser Lys Asn Thr Val Tyr Leu
65                  70                  75                  80

Gln Met Asp Ser Leu Lys Pro Glu Asp Thr Ala Val Tyr Tyr Cys Asn
                85                  90                  95

Ser Tyr Ser Thr Leu Gly Ser Trp Gly Gln Gly Thr Gln Val Thr Val
            100                 105                 110

Ser Ser

<210> SEQ ID NO 61
<211> LENGTH: 114
<212> TYPE: PRT
<213> ORGANISM: Artificial Sequence
<220> FEATURE:
<223> OTHER INFORMATION: Nanobody sequence

<400> SEQUENCE: 61

Glu Val Gln Leu Val Glu Ser Gly Gly Gly Ala Val Gln Pro Gly Gly
1               5                   10                  15

Ser Leu Arg Leu Ser Cys Ala Ala Ser Gly Ile Arg Ile Ser Arg Asn
            20                  25                  30

Met Met Gly Trp Phe Arg Gln Ala Pro Gly Lys Ser Arg Asp Met Val
        35                  40                  45

Ala Arg Ile Ser Pro Gly Gly Asp Thr Tyr Tyr Val Asp Ser Val Lys
    50                  55                  60

Gly Arg Phe Ser Ile Ser Lys Asp Asn Ala Lys Asn Thr Val Tyr Leu
65                  70                  75                  80

Gln Met Asn Ser Leu Arg Pro Glu Asp Thr Ala Ile Tyr Tyr Cys Asn
                85                  90                  95

Ser Tyr Ser Thr Leu Gly Ser Trp Gly Gln Gly Thr Leu Val Thr Val
            100                 105                 110

Ser Ser

<210> SEQ ID NO 62
<211> LENGTH: 114
<212> TYPE: PRT
<213> ORGANISM: Artificial Sequence
<220> FEATURE:
<223> OTHER INFORMATION: Nanobody sequence

<400> SEQUENCE: 62

Glu Val Gln Leu Val Glu Ser Gly Gly Gly Ala Val Gln Pro Gly Gly
1               5                   10                  15

Ser Leu Arg Leu Ser Cys Val Ala Ser Gly Ile Arg Ile Ser Asn His
            20                  25                  30

Met Met Gly Trp Phe Arg Gln Ala Pro Gly Glu Gln Arg Asp Met Val
        35                  40                  45

Ala Arg Ile Ser Pro Gly Gly Asp Thr Tyr Tyr Val Val Asp Ser Val Lys
    50                  55                  60

```
Gly Arg Phe Ser Ile Ser Lys Asp Asn Ala Lys Asn Thr Val Tyr Leu
65                  70                  75                  80

Gln Met Asn Asn Leu Lys Leu Glu Asp Thr Ala Val Tyr Tyr Cys Asn
                85                  90                  95

Ser Tyr Arg Thr Leu Gly Ser Trp Gly Gln Gly Thr Gln Val Thr Val
            100                 105                 110

Ser Ser

<210> SEQ ID NO 63
<211> LENGTH: 114
<212> TYPE: PRT
<213> ORGANISM: Artificial Sequence
<220> FEATURE:
<223> OTHER INFORMATION: Nanobody sequence

<400> SEQUENCE: 63

Glu Val Gln Leu Val Glu Ser Gly Gly Gly Val Val Gln Pro Gly Gly
1               5                   10                  15

Ser Leu Arg Leu Ser Cys Ala Ala Ser Gly Ile Arg Ile Ser Thr His
                20                  25                  30

Thr Met Gly Trp Phe Arg Gln Ala Pro Glu Lys Gln Arg Glu Met Val
            35                  40                  45

Ala Gln Ile Ser Pro Gly Gly Lys Thr Tyr Tyr Ile Asp Ser Val Lys
        50                  55                  60

Gly Arg Phe Thr Ile Ser Lys Asp Asn Ala Lys Asn Thr Val Phe Leu
65                  70                  75                  80

Arg Met Asn Asp Leu Lys Pro Asp Thr Ala Val Tyr Tyr Cys Asn
                85                  90                  95

Ser Tyr Ser Thr Leu Gly Val Trp Gly Gln Gly Thr Leu Val Thr Val
            100                 105                 110

Ser Ser

<210> SEQ ID NO 64
<211> LENGTH: 114
<212> TYPE: PRT
<213> ORGANISM: Artificial Sequence
<220> FEATURE:
<223> OTHER INFORMATION: Nanobody sequence

<400> SEQUENCE: 64

Glu Val Gln Leu Val Glu Ser Gly Gly Gly Val Val Gln Pro Gly Gly
1               5                   10                  15

Ser Leu Arg Leu Ser Cys Ala Ala Ser Gly Ile Arg Ile Ser Thr His
                20                  25                  30

Thr Met Gly Trp Phe Arg Gln Ala Pro Glu Lys Gln Arg Glu Met Val
            35                  40                  45

Ala Gln Ile Ser Pro Gly Gly Lys Thr Tyr Tyr Ile Asp Ser Val Lys
        50                  55                  60

Gly Arg Phe Thr Ile Ser Lys Asp Asn Ala Lys Asn Thr Val Phe Leu
65                  70                  75                  80

Arg Met Asn Asp Leu Lys Pro Asp Asp Thr Ala Val Tyr Tyr Cys Asn
                85                  90                  95

Ser Tyr Ser Thr Leu Gly Val Trp Gly Gln Gly Thr Gln Val Thr Val
            100                 105                 110

Ser Ser
```

```
<210> SEQ ID NO 65
<211> LENGTH: 114
<212> TYPE: PRT
<213> ORGANISM: Artificial Sequence
<220> FEATURE:
<223> OTHER INFORMATION: Nanobody sequence

<400> SEQUENCE: 65
```

Glu Val Gln Leu Val Glu Ser Gly Gly Gly Val Val Gln Pro Gly Gly
1               5                   10                  15

Ser Leu Arg Leu Ser Cys Ala Ala Ser Gly Ile Arg Ile Ser Thr His
            20                  25                  30

Thr Met Gly Trp Phe Arg Gln Ala Pro Glu Lys Gln Arg Glu Met Val
        35                  40                  45

Ala Gln Ile Ser Pro Gly Gly Lys Thr Tyr Tyr Ile Asp Ser Val Lys
    50                  55                  60

Gly Arg Phe Thr Ile Ser Lys Asp Asn Ala Lys Asn Thr Val Phe Leu
65                  70                  75                  80

Arg Met Asn Asp Leu Lys Pro Asp Gly Thr Ala Val Tyr Tyr Cys Asn
                85                  90                  95

Ser Tyr Ser Thr Leu Gly Val Trp Gly Gln Gly Thr Gln Val Thr Val
            100                 105                 110

Ser Ser

```
<210> SEQ ID NO 66
<211> LENGTH: 124
<212> TYPE: PRT
<213> ORGANISM: Artificial Sequence
<220> FEATURE:
<223> OTHER INFORMATION: Nanobody sequence

<400> SEQUENCE: 66
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Asn Met Asn
            20                  25                  30

Pro Leu Gly Trp Phe Arg Gln Ser Pro Gly Lys Glu Arg Glu Phe Val
        35                  40                  45

Ala Ala His Arg Trp Ser Asp Gly Asn Thr Tyr Tyr Val Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Ala Phe Arg Ser Pro Gly Glu Tyr Val
            100                 105                 110

Tyr Trp Gly Gln Gly Thr Gln Val Thr Val Ser Ser
        115                 120

```
<210> SEQ ID NO 67
<211> LENGTH: 124
<212> TYPE: PRT
<213> ORGANISM: Artificial Sequence
<220> FEATURE:
<223> OTHER INFORMATION: Nanobody sequence

<400> SEQUENCE: 67
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Thr Asn
        20                  25                  30

Pro Met Gly Trp Phe Arg Gln Ser Pro Gly Asn Glu Arg Glu Phe Val
        35                  40                  45

Ala Ala His Arg Trp Ser Asp Gly Asn Thr Tyr Tyr Ala Asp Ser Val
50                      55                  60

Lys Gly Arg Phe Ala Ile Ser Arg Asp Asn Ala Lys Lys Thr Val Tyr
65                      70                  75                  80

Leu Gln Met Asn Ser Leu Lys Ser Glu Asp Thr Ala Val Tyr Tyr Cys
                85                  90                  95

Ala Ala Gly Arg Pro Trp Ser Ser Tyr Arg Ser Pro Asp Glu Tyr Val
            100                 105                 110

Tyr Trp Gly Gln Gly Thr Gln Val Thr Val Ser Ser
        115                 120

<210> SEQ ID NO 68
<211> LENGTH: 124
<212> TYPE: PRT
<213> ORGANISM: Artificial Sequence
<220> FEATURE:
<223> OTHER INFORMATION: Nanobody sequence

<400> SEQUENCE: 68

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Asn Thr Asn
        20                  25                  30

Pro Met Gly Trp Phe Arg Gln Phe Ala Gly Lys Glu Arg Glu Phe Val
        35                  40                  45

Ala Ala His Arg Trp Ser Asp Gly Asn Thr Tyr Tyr Val Asp Ser Val
50                      55                  60

Lys Gly Arg Phe Thr Ile Ser Arg Asp Asn Ala Lys Asn Thr Val Tyr
65                      70                  75                  80

Leu Gln Met Asn Ser Leu Lys Ser Glu Asp Thr Ala Val Tyr Tyr Cys
                85                  90                  95

Ala Ala Gly Arg Pro Trp Ser Ser Tyr Arg Ser Pro Asp Glu Tyr Val
            100                 105                 110

Tyr Trp Gly Gln Gly Thr Gln Val Thr Val Ser Ser
        115                 120

<210> SEQ ID NO 69
<211> LENGTH: 124
<212> TYPE: PRT
<213> ORGANISM: Artificial Sequence
<220> FEATURE:
<223> OTHER INFORMATION: Nanobody sequence

<400> SEQUENCE: 69

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Met Asn
        20                  25                  30

Pro Met Gly Trp Phe Arg Gln Ser Pro Gly Arg Glu Arg Glu Phe Val
        35                  40                  45

Ala Ala His Arg Trp Ser Asp Gly Asn Thr Tyr Tyr Val Asp Ser Val
50                      55                  60

Lys Gly Arg Phe Thr Ile Ser Arg Asp Asn Ala Lys Asn Thr Val Tyr
65                      70                  75                  80

```
Leu Gln Met Ser Ser Leu Lys Ser Glu Asp Thr Ala Val Tyr Tyr Cys
                85                  90                  95

Ala Ala Gly Arg Pro Trp Ser Ser Tyr Arg Ser Pro Thr Glu Tyr Val
            100                 105                 110

Tyr Trp Gly Gln Gly Thr Leu Val Thr Val Ser Ser
            115                 120
```

<210> SEQ ID NO 70
<211> LENGTH: 124
<212> TYPE: PRT
<213> ORGANISM: Artificial Sequence
<220> FEATURE:
<223> OTHER INFORMATION: Nanobody sequence

<400> SEQUENCE: 70

```
Glu Val Gln Leu Val Glu Ser Gly Gly Ala Val Gln Ala Gly Gly
1               5                   10                  15

Ser Leu Arg Leu Ser Cys Ala Ala Ser Gly Arg Ser Phe Ser Thr Asn
            20                  25                  30

Pro Met Gly Trp Phe Arg Gln Phe Pro Arg Lys Glu Arg Glu Phe Val
            35                  40                  45

Ala Ala His Arg Trp Ser Asp Gly Asn Thr Tyr Tyr Ala Asp Ser Val
        50                  55                  60

Lys Gly Arg Phe Thr Ile Ser Arg Asp Asn Ala Lys His Thr Val Tyr
65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Ala Ala His Ser Pro Asn Glu Tyr Val
            100                 105                 110

Tyr Trp Gly Gln Gly Thr Gln Val Thr Val Ser Ser
            115                 120
```

<210> SEQ ID NO 71
<211> LENGTH: 124
<212> TYPE: PRT
<213> ORGANISM: Artificial Sequence
<220> FEATURE:
<223> OTHER INFORMATION: Nanobody sequence

<400> SEQUENCE: 71

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Ala Asn
            20                  25                  30

Pro Met Gly Trp Phe Arg Gln Phe Pro Gly Lys Glu Arg Glu Ser Val
            35                  40                  45

Ala Ala His Arg Trp Ser Asp Gly Asn Thr Tyr Tyr Ala Asp Ser Val
        50                  55                  60

Lys Gly Arg Phe Thr Ile Ser Arg Asp Asn Ala Lys His Thr Val Tyr
65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Ala Ala His Ser Pro Asn Glu Tyr Val
            100                 105                 110

Tyr Trp Gly Gln Gly Thr Gln Val Thr Val Ser Ser
            115                 120
```

<210> SEQ ID NO 72
<211> LENGTH: 124
<212> TYPE: PRT
<213> ORGANISM: Artificial Sequence
<220> FEATURE:
<223> OTHER INFORMATION: Nanobody sequence

<400> SEQUENCE: 72

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Gly Phe Ser Thr Asn
            20                  25                  30

Pro Met Gly Trp Phe Arg Gln Ser Pro Gly Lys Glu Arg Glu Phe Val
        35                  40                  45

Ala Ala His Arg Trp Ser Asp Gly Asn Thr Tyr Tyr Val Asp Ser Val
    50                  55                  60

Lys Gly Arg Phe Ala Ile Ser Arg Asp Asn Ala Lys Asn Thr Val His
65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Asp Tyr Arg Ala Pro Ser Glu Tyr Ile
            100                 105                 110

Tyr Trp Gly Gln Gly Thr Gln Val Thr Val Ser Ser
        115                 120

<210> SEQ ID NO 73
<211> LENGTH: 124
<212> TYPE: PRT
<213> ORGANISM: Artificial Sequence
<220> FEATURE:
<223> OTHER INFORMATION: Nanobody sequence

<400> SEQUENCE: 73

Glu Val Gln Leu Val Glu Ser Gly Gly Gly Leu Val Arg Ala Gly Gly
1               5                   10                  15

Ser Leu Arg Leu Ser Cys Ala Ala Ser Gly Arg Gly Phe Ser Thr Asn
            20                  25                  30

Pro Met Gly Trp Phe Arg Gln Ser Pro Gly Lys Glu Arg Glu Phe Val
        35                  40                  45

Ala Ala His Arg Trp Ser Asp Gly Asn Thr Tyr Tyr Val Asp Ser Val
    50                  55                  60

Lys Gly Arg Phe Ala Ile Ser Arg Asp Asn Ala Lys Asn Thr Val His
65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Asp Phe Arg Ala Pro Ser Glu Tyr Ile
            100                 105                 110

Tyr Ser Gly Pro Gly Thr Gln Val Thr Val Ser Ser
        115                 120

<210> SEQ ID NO 74
<211> LENGTH: 124
<212> TYPE: PRT
<213> ORGANISM: Artificial Sequence
<220> FEATURE:
<223> OTHER INFORMATION: Nanobody sequence

<400> SEQUENCE: 74

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Asn Thr Asn
            20                  25                  30

Pro Met Gly Trp Phe Arg Gln Ser Pro Gly Lys Glu Arg Glu Phe Leu
            35                  40                  45

Ala Ala Val Arg Trp His Asp Gly Ser Thr Tyr Tyr Thr Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Ala Tyr His Ser Pro Asn Glu Tyr Val
            100                 105                 110

Tyr Trp Gly Gln Gly Thr Leu Val Thr Val Ser Ser
            115                 120

<210> SEQ ID NO 75
<211> LENGTH: 124
<212> TYPE: PRT
<213> ORGANISM: Artificial Sequence
<220> FEATURE:
<223> OTHER INFORMATION: Nanobody sequence

<400> SEQUENCE: 75

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Ala Phe Asn Thr Asn
            20                  25                  30

Pro Met Gly Trp Phe Arg Gln Ser Pro Gly Lys Glu Arg Glu Phe Leu
            35                  40                  45

Ala Ala Val Arg Trp His Asp Gly Ser Thr Tyr Tyr Thr Asp Ser Val
 50                  55                  60

Lys Gly Arg Phe Thr Ile Ser Arg Asp Asn Ala Lys Asn Thr Val Cys
 65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Ala Tyr His Ser Pro Asn Glu Tyr Val
            100                 105                 110

Tyr Trp Gly Gln Gly Thr Gln Val Thr Val Ser Ser
            115                 120

<210> SEQ ID NO 76
<211> LENGTH: 124
<212> TYPE: PRT
<213> ORGANISM: Artificial Sequence
<220> FEATURE:
<223> OTHER INFORMATION: Nanobody sequence

<400> SEQUENCE: 76

Glu Val Gln Leu Val Glu Phe Gly Gly Gly Leu Val Gln Ala Gly Gly
 1               5                  10                  15

Ser Leu Arg Leu Ser Cys Ala Ala Ser Gly Arg Ala Phe Ser Thr Asn
            20                  25                  30

Pro Met Gly Trp Phe Arg Gln Ser Pro Gly Lys Glu Arg Glu Phe Val
            35                  40                  45

Gly Ala Val Arg Trp Ser Asp Gly Ser Thr Tyr Ser Ala Asp Ser Val
 50                  55                  60

Lys Gly Arg Phe Thr Val Phe Arg Asp Asn Ala Lys Asn Thr Val Tyr

```
                65                  70                  75                  80
Leu Gln Met Asn Ser Leu Lys Ser Glu Asp Thr Ala Val Tyr Tyr Cys
                    85                  90                  95

Ala Ala Gly Arg Pro Trp Ser Ala Tyr His Ser Pro Lys Glu Tyr Val
                100                 105                 110

Tyr Trp Gly Gln Gly Thr Leu Val Thr Val Ser Ser
            115                 120
```

<210> SEQ ID NO 77
<211> LENGTH: 124
<212> TYPE: PRT
<213> ORGANISM: Artificial Sequence
<220> FEATURE:
<223> OTHER INFORMATION: Nanobody sequence

<400> SEQUENCE: 77

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Phe Ser Thr Asn
                20                  25                  30

Pro Met Gly Trp Phe Arg Gln Ser Pro Gly Lys Glu Arg Glu Phe Val
            35                  40                  45

Ala Ala His Arg Trp Ser Asp Gly Ser Thr Phe Val Ala Asp Ser Val
    50                  55                  60

Lys Gly Arg Phe Thr Ile Ser Arg Asp Asn Ala Lys Asn Thr Val Ser
65                  70                  75                  80

Leu Gln Met Asn Ser Leu Lys Ser Ala Asp Thr Ala Val Tyr Tyr Cys
                    85                  90                  95

Ala Ala Gly Arg Pro Trp Ser Ala Tyr His Ser Pro Arg Glu Tyr Ile
                100                 105                 110

Tyr Trp Gly Arg Gly Thr Gln Val Thr Val Ser Ser
            115                 120
```

<210> SEQ ID NO 78
<211> LENGTH: 124
<212> TYPE: PRT
<213> ORGANISM: Artificial Sequence
<220> FEATURE:
<223> OTHER INFORMATION: Nanobody sequence

<400> SEQUENCE: 78

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Phe Ser Thr Asn
                20                  25                  30

Pro Met Gly Trp Phe Arg Gln Ser Pro Gly Lys Glu Arg Glu Phe Val
            35                  40                  45

Ala Ala His Arg Trp Ser Asp Gly Ser Thr Phe Val Ala Asp Ser Val
    50                  55                  60

Lys Gly Arg Phe Thr Ile Ser Arg Asp Asn Ala Lys Asn Thr Val Ser
65                  70                  75                  80

Leu Gln Met Asn Ser Leu Lys Ser Ala Asp Thr Ala Val Tyr Tyr Cys
                    85                  90                  95

Ala Ala Gly Arg Pro Trp Ser Ala Tyr His Ser Pro Arg Glu Tyr Ile
                100                 105                 110

Tyr Trp Gly Arg Gly Thr Leu Val Thr Val Ser Ser
            115                 120
```

<210> SEQ ID NO 79
<211> LENGTH: 124
<212> TYPE: PRT
<213> ORGANISM: Artificial Sequence
<220> FEATURE:
<223> OTHER INFORMATION: Nanobody sequence

<400> SEQUENCE: 79

Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Ala Phe Ser Thr Asn
            20                  25                  30

Pro Met Gly Trp Phe Arg Gln Ser Pro Gly Gln Glu Arg Glu Phe Leu
        35                  40                  45

Ala Ala Val Arg Trp Ala Asp Gly Asn Thr Tyr Tyr Thr Asp Ser Val
    50                  55                  60

Lys Gly Arg Ala Thr Ile Ser Arg Asp Asn Ala Lys Lys Thr Val Tyr
65                  70                  75                  80

Leu Gln Leu Asn Asn Leu Lys Ser Glu Asp Ala Ala Val Tyr Tyr Cys
                85                  90                  95

Ala Ala Gly Arg Pro Trp Ser Ala Tyr His Ala Pro Lys Glu Tyr Ile
            100                 105                 110

Tyr Trp Gly Gln Gly Thr Leu Val Thr Val Ser Ser
        115                 120

<210> SEQ ID NO 80
<211> LENGTH: 124
<212> TYPE: PRT
<213> ORGANISM: Artificial Sequence
<220> FEATURE:
<223> OTHER INFORMATION: Nanobody sequence

<400> SEQUENCE: 80

Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Ala Phe Ser Thr Asn
            20                  25                  30

Pro Met Gly Trp Phe Arg Gln Ser Pro Gly Gln Glu Arg Glu Phe Leu
        35                  40                  45

Ala Ala Val Arg Trp Ala Asp Gly Asn Thr Tyr Tyr Thr Asp Ser Val
    50                  55                  60

Lys Gly Arg Ala Thr Ile Ser Arg Asp Asn Ala Lys Lys Thr Val Tyr
65                  70                  75                  80

Leu Gln Leu Asn Asn Leu Lys Ser Glu Asp Ala Ala Val Tyr Tyr Cys
                85                  90                  95

Ala Ala Gly Arg Pro Trp Ser Ala Tyr His Ala Pro Lys Glu Tyr Ile
            100                 105                 110

Tyr Trp Gly Gln Gly Thr Gln Val Thr Val Ser Ser
        115                 120

<210> SEQ ID NO 81
<211> LENGTH: 10
<212> TYPE: PRT
<213> ORGANISM: Artificial Sequence
<220> FEATURE:
<223> OTHER INFORMATION: CDR1

<400> SEQUENCE: 81

Gly Arg Thr Tyr Arg Gly Tyr Ser Met Gly

```
<210> SEQ ID NO 82
<211> LENGTH: 10
<212> TYPE: PRT
<213> ORGANISM: Artificial Sequence
<220> FEATURE:
<223> OTHER INFORMATION: CDR1

<400> SEQUENCE: 82

Gly Arg Thr Tyr Arg Gly Tyr Ser Met Ala
1               5                   10

<210> SEQ ID NO 83
<211> LENGTH: 10
<212> TYPE: PRT
<213> ORGANISM: Artificial Sequence
<220> FEATURE:
<223> OTHER INFORMATION: CDR1

<400> SEQUENCE: 83

Arg Arg Thr Tyr Arg Gly Tyr Ser Met Ala
1               5                   10

<210> SEQ ID NO 84
<211> LENGTH: 10
<212> TYPE: PRT
<213> ORGANISM: Artificial Sequence
<220> FEATURE:
<223> OTHER INFORMATION: CDR1

<400> SEQUENCE: 84

Gly Arg Thr Tyr Arg Gly Tyr Gly Met Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: CDR1

<400> SEQUENCE: 85

Gly Arg Ala Tyr Arg Gly Tyr Ser Met Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: CDR1

<400> SEQUENCE: 86

Gly Arg Thr Phe Arg Gly Tyr Ser Met Ala
1               5                   10

<210> SEQ ID NO 87
<211> LENGTH: 10
<212> TYPE: PRT
<213> ORGANISM: Artificial Sequence
<220> FEATURE:
<223> OTHER INFORMATION: CDR1

<400> SEQUENCE: 87

Gly Arg Ala Tyr Arg Gly Tyr Ser Met Gly
1               5                   10
```

<210> SEQ ID NO 88
<211> LENGTH: 10
<212> TYPE: PRT
<213> ORGANISM: Artificial Sequence
<220> FEATURE:
<223> OTHER INFORMATION: CDR1

<400> SEQUENCE: 88

Gly Asp Ile Tyr Lys Ser Phe Asp Met Gly
1               5                   10

<210> SEQ ID NO 89
<211> LENGTH: 10
<212> TYPE: PRT
<213> ORGANISM: Artificial Sequence
<220> FEATURE:
<223> OTHER INFORMATION: CDR1

<400> SEQUENCE: 89

Gly Arg Thr Phe Ser Ser Tyr Ala Met Ala
1               5                   10

<210> SEQ ID NO 90
<211> LENGTH: 10
<212> TYPE: PRT
<213> ORGANISM: Artificial Sequence
<220> FEATURE:
<223> OTHER INFORMATION: CDR1

<400> SEQUENCE: 90

Gly Arg Thr Phe Ser Thr Asn Pro Met Gly
1               5                   10

<210> SEQ ID NO 91
<211> LENGTH: 10
<212> TYPE: PRT
<213> ORGANISM: Artificial Sequence
<220> FEATURE:
<223> OTHER INFORMATION: CDR1

<400> SEQUENCE: 91

Gly Ile Arg Ile Ser Arg Asn Met Met Gly
1               5                   10

<210> SEQ ID NO 92
<211> LENGTH: 10
<212> TYPE: PRT
<213> ORGANISM: Artificial Sequence
<220> FEATURE:
<223> OTHER INFORMATION: CDR1

<400> SEQUENCE: 92

Gly Ile Arg Ile Ser Asn His Met Met Gly
1               5                   10

<210> SEQ ID NO 93
<211> LENGTH: 10
<212> TYPE: PRT
<213> ORGANISM: Artificial Sequence
<220> FEATURE:
<223> OTHER INFORMATION: CDR1

<400> SEQUENCE: 93

Gly Ile Arg Ile Ser Thr His Thr Met Gly
1               5                   10

<210> SEQ ID NO 94
<211> LENGTH: 10
<212> TYPE: PRT
<213> ORGANISM: Artificial Sequence
<220> FEATURE:
<223> OTHER INFORMATION: CDR1

<400> SEQUENCE: 94

Gly Arg Ser Phe Asn Met Asn Pro Leu Gly
1               5                   10

<210> SEQ ID NO 95
<211> LENGTH: 10
<212> TYPE: PRT
<213> ORGANISM: Artificial Sequence
<220> FEATURE:
<223> OTHER INFORMATION: CDR1

<400> SEQUENCE: 95

Gly Arg Ala Phe Asn Thr Asn Pro Met Gly
1               5                   10

<210> SEQ ID NO 96
<211> LENGTH: 10
<212> TYPE: PRT
<213> ORGANISM: Artificial Sequence
<220> FEATURE:
<223> OTHER INFORMATION: CDR1

<400> SEQUENCE: 96

Gly Arg Ala Phe Ser Met Asn Pro Met Gly
1               5                   10

<210> SEQ ID NO 97
<211> LENGTH: 10
<212> TYPE: PRT
<213> ORGANISM: Artificial Sequence
<220> FEATURE:
<223> OTHER INFORMATION: CDR1

<400> SEQUENCE: 97

Gly Arg Ser Phe Ser Thr Asn Pro Met Gly
1               5                   10

<210> SEQ ID NO 98
<211> LENGTH: 10
<212> TYPE: PRT
<213> ORGANISM: Artificial Sequence
<220> FEATURE:
<223> OTHER INFORMATION: CDR1

<400> SEQUENCE: 98

Gly Arg Ser Phe Ser Ala Asn Pro Met Gly
1               5                   10

<210> SEQ ID NO 99
<211> LENGTH: 10
<212> TYPE: PRT
<213> ORGANISM: Artificial Sequence
<220> FEATURE:
<223> OTHER INFORMATION: CDR1

<400> SEQUENCE: 99

Gly Arg Gly Phe Ser Thr Asn Pro Met Gly
1               5                   10

```
<210> SEQ ID NO 100
<211> LENGTH: 10
<212> TYPE: PRT
<213> ORGANISM: Artificial Sequence
<220> FEATURE:
<223> OTHER INFORMATION: CDR1

<400> SEQUENCE: 100

Gly Arg Ala Phe Ser Thr Asn Pro Met Gly
1               5                   10

<210> SEQ ID NO 101
<211> LENGTH: 10
<212> TYPE: PRT
<213> ORGANISM: Artificial Sequence
<220> FEATURE:
<223> OTHER INFORMATION: CDR2

<400> SEQUENCE: 101

Ala Ile Val Trp Ser Gly Gly Asn Thr Tyr
1               5                   10

<210> SEQ ID NO 102
<211> LENGTH: 10
<212> TYPE: PRT
<213> ORGANISM: Artificial Sequence
<220> FEATURE:
<223> OTHER INFORMATION: CDR2

<400> SEQUENCE: 102

Ala Ile Val Trp Ser Asp Gly Asn Thr Tyr
1               5                   10

<210> SEQ ID NO 103
<211> LENGTH: 10
<212> TYPE: PRT
<213> ORGANISM: Artificial Sequence
<220> FEATURE:
<223> OTHER INFORMATION: CDR2

<400> SEQUENCE: 103

Ala Ile Val Trp Ser Asp Gly Asn Ser Tyr
1               5                   10

<210> SEQ ID NO 104
<211> LENGTH: 10
<212> TYPE: PRT
<213> ORGANISM: Artificial Sequence
<220> FEATURE:
<223> OTHER INFORMATION: CDR2

<400> SEQUENCE: 104

Ala Ile Thr Trp Ser Glu Gly Asn Ala Tyr
1               5                   10

<210> SEQ ID NO 105
<211> LENGTH: 10
<212> TYPE: PRT
<213> ORGANISM: Artificial Sequence
<220> FEATURE:
<223> OTHER INFORMATION: CDR2

<400> SEQUENCE: 105

Ala Ile Thr Trp Ser Glu Gly Asn Pro Tyr
1               5                   10

<210> SEQ ID NO 106
```

```
<211> LENGTH: 10
<212> TYPE: PRT
<213> ORGANISM: Artificial Sequence
<220> FEATURE:
<223> OTHER INFORMATION: CDR2

<400> SEQUENCE: 106

Ala Ile Thr Trp Ser Glu Gly Asn Thr Tyr
1               5                   10

<210> SEQ ID NO 107
<211> LENGTH: 10
<212> TYPE: PRT
<213> ORGANISM: Artificial Sequence
<220> FEATURE:
<223> OTHER INFORMATION: CDR2

<400> SEQUENCE: 107

Ala Ile Val Trp Thr Asp Gly Asn Thr Tyr
1               5                   10

<210> SEQ ID NO 108
<211> LENGTH: 10
<212> TYPE: PRT
<213> ORGANISM: Artificial Sequence
<220> FEATURE:
<223> OTHER INFORMATION: CDR2

<400> SEQUENCE: 108

Ala Ile Ala Trp Thr Asp Gly Asn Thr Tyr
1               5                   10

<210> SEQ ID NO 109
<211> LENGTH: 10
<212> TYPE: PRT
<213> ORGANISM: Artificial Sequence
<220> FEATURE:
<223> OTHER INFORMATION: CDR2

<400> SEQUENCE: 109

Ala Ile Val Trp Thr Asp Gly Asn Ala Tyr
1               5                   10

<210> SEQ ID NO 110
<211> LENGTH: 13
<212> TYPE: PRT
<213> ORGANISM: Artificial Sequence
<220> FEATURE:
<223> OTHER INFORMATION: CDR2

<400> SEQUENCE: 110

Val Ile Gly Ser Arg Gly Asn Asn Arg Gly Arg Thr Asn
1               5                   10

<210> SEQ ID NO 111
<211> LENGTH: 10
<212> TYPE: PRT
<213> ORGANISM: Artificial Sequence
<220> FEATURE:
<223> OTHER INFORMATION: CDR2

<400> SEQUENCE: 111

Ser Ile Ser Trp Ser Gly Glu Asn Thr Asn
1               5                   10

<210> SEQ ID NO 112
<211> LENGTH: 10
```

```
<212> TYPE: PRT
<213> ORGANISM: Artificial Sequence
<220> FEATURE:
<223> OTHER INFORMATION: CDR2

<400> SEQUENCE: 112

Ala Val Arg Trp Ala Asp Gly Asn Thr Phe
1               5                   10

<210> SEQ ID NO 113
<211> LENGTH: 10
<212> TYPE: PRT
<213> ORGANISM: Artificial Sequence
<220> FEATURE:
<223> OTHER INFORMATION: CDR2

<400> SEQUENCE: 113

Ala Ala Arg Trp Ala Asp Gly Asn Thr Phe
1               5                   10

<210> SEQ ID NO 114
<211> LENGTH: 9
<212> TYPE: PRT
<213> ORGANISM: Artificial Sequence
<220> FEATURE:
<223> OTHER INFORMATION: CDR2

<400> SEQUENCE: 114

Arg Ile Thr Pro Gly Gly Asp Thr Tyr
1               5

<210> SEQ ID NO 115
<211> LENGTH: 9
<212> TYPE: PRT
<213> ORGANISM: Artificial Sequence
<220> FEATURE:
<223> OTHER INFORMATION: CDR2

<400> SEQUENCE: 115

Arg Ile Ser Pro Gly Gly Ala Thr Tyr
1               5

<210> SEQ ID NO 116
<211> LENGTH: 9
<212> TYPE: PRT
<213> ORGANISM: Artificial Sequence
<220> FEATURE:
<223> OTHER INFORMATION: CDR2

<400> SEQUENCE: 116

Arg Ile Ser Pro Gly Gly Asp Thr Tyr
1               5

<210> SEQ ID NO 117
<211> LENGTH: 9
<212> TYPE: PRT
<213> ORGANISM: Artificial Sequence
<220> FEATURE:
<223> OTHER INFORMATION: CDR2

<400> SEQUENCE: 117

Gln Ile Ser Pro Gly Gly Lys Thr Tyr
1               5

<210> SEQ ID NO 118
<211> LENGTH: 10
<212> TYPE: PRT
```

```
<213> ORGANISM: Artificial Sequence
<220> FEATURE:
<223> OTHER INFORMATION: CDR2

<400> SEQUENCE: 118

Ala His Arg Trp Ser Asp Gly Asn Thr Tyr
1               5                   10

<210> SEQ ID NO 119
<211> LENGTH: 10
<212> TYPE: PRT
<213> ORGANISM: Artificial Sequence
<220> FEATURE:
<223> OTHER INFORMATION: CDR2

<400> SEQUENCE: 119

Ala Val Arg Trp His Asp Gly Ser Thr Tyr
1               5                   10

<210> SEQ ID NO 120
<211> LENGTH: 10
<212> TYPE: PRT
<213> ORGANISM: Artificial Sequence
<220> FEATURE:
<223> OTHER INFORMATION: CDR2

<400> SEQUENCE: 120

Ala Val Arg Trp Ser Asp Gly Ser Thr Tyr
1               5                   10

<210> SEQ ID NO 121
<211> LENGTH: 10
<212> TYPE: PRT
<213> ORGANISM: Artificial Sequence
<220> FEATURE:
<223> OTHER INFORMATION: CDR2

<400> SEQUENCE: 121

Ala His Arg Trp Ser Asp Gly Ser Thr Phe
1               5                   10

<210> SEQ ID NO 122
<211> LENGTH: 10
<212> TYPE: PRT
<213> ORGANISM: Artificial Sequence
<220> FEATURE:
<223> OTHER INFORMATION: CDR2

<400> SEQUENCE: 122

Ala Val Arg Trp Ala Asp Gly Asn Thr Tyr
1               5                   10

<210> SEQ ID NO 123
<211> LENGTH: 15
<212> TYPE: PRT
<213> ORGANISM: Artificial Sequence
<220> FEATURE:
<223> OTHER INFORMATION: CDR3

<400> SEQUENCE: 123

Lys Ile Arg Pro Tyr Ile Phe Lys Ile Ala Gly Gln Tyr Asp Tyr
1               5                   10                  15

<210> SEQ ID NO 124
<211> LENGTH: 15
<212> TYPE: PRT
<213> ORGANISM: Artificial Sequence
```

```
<220> FEATURE:
<223> OTHER INFORMATION: CDR3

<400> SEQUENCE: 124

Lys Thr Arg Pro Tyr Ile Phe Lys Ile Ala Gly Gln Tyr Asp Tyr
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: CDR3

<400> SEQUENCE: 125

Lys Ile Arg Pro Tyr Ile Phe Lys Val Ala Gly Gln Tyr Asp Tyr
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: CDR3

<400> SEQUENCE: 126

Lys Ile Arg Pro Tyr Ile Phe Lys Ile Pro Gly Gln Tyr Asp Tyr
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: CDR3

<400> SEQUENCE: 127

Lys Ile Arg Pro Tyr Ile Phe Lys Val Pro Gly Gln Tyr Asp Tyr
1               5                   10                  15

<210> SEQ ID NO 128
<211> LENGTH: 8
<212> TYPE: PRT
<213> ORGANISM: Artificial Sequence
<220> FEATURE:
<223> OTHER INFORMATION: CDR3

<400> SEQUENCE: 128

Ala Pro Leu Val Ala Gly Arg Pro
1               5

<210> SEQ ID NO 129
<211> LENGTH: 20
<212> TYPE: PRT
<213> ORGANISM: Artificial Sequence
<220> FEATURE:
<223> OTHER INFORMATION: CDR3

<400> SEQUENCE: 129

Lys Ile Ala Lys Thr Tyr Pro Asp Asn Trp Tyr Trp Thr Lys Ser Asn
1               5                   10                  15

Asn Tyr Asn Tyr
            20

<210> SEQ ID NO 130
<211> LENGTH: 15
```

```
<212> TYPE: PRT
<213> ORGANISM: Artificial Sequence
<220> FEATURE:
<223> OTHER INFORMATION: CDR3

<400> SEQUENCE: 130

Gly Arg Pro Trp Ser Ala Tyr His Ser Pro Ala Glu Tyr Val His
1               5                   10                  15

<210> SEQ ID NO 131
<211> LENGTH: 6
<212> TYPE: PRT
<213> ORGANISM: Artificial Sequence
<220> FEATURE:
<223> OTHER INFORMATION: CDR3

<400> SEQUENCE: 131

Tyr Ser Thr Leu Gly Ser
1               5

<210> SEQ ID NO 132
<211> LENGTH: 6
<212> TYPE: PRT
<213> ORGANISM: Artificial Sequence
<220> FEATURE:
<223> OTHER INFORMATION: CDR3

<400> SEQUENCE: 132

Tyr Arg Thr Leu Gly Ser
1               5

<210> SEQ ID NO 133
<211> LENGTH: 6
<212> TYPE: PRT
<213> ORGANISM: Artificial Sequence
<220> FEATURE:
<223> OTHER INFORMATION: CDR3

<400> SEQUENCE: 133

Tyr Ser Thr Leu Gly Val
1               5

<210> SEQ ID NO 134
<211> LENGTH: 15
<212> TYPE: PRT
<213> ORGANISM: Artificial Sequence
<220> FEATURE:
<223> OTHER INFORMATION: CDR3

<400> SEQUENCE: 134

Gly Arg Pro Trp Ser Ala Phe Arg Ser Pro Gly Glu Tyr Val Tyr
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: CDR3

<400> SEQUENCE: 135

Gly Arg Pro Trp Ser Ser Tyr Arg Ser Pro Asp Glu Tyr Val Tyr
1               5                   10                  15

<210> SEQ ID NO 136
<211> LENGTH: 15
<212> TYPE: PRT
```

```
<213> ORGANISM: Artificial Sequence
<220> FEATURE:
<223> OTHER INFORMATION: CDR3

<400> SEQUENCE: 136

Gly Arg Pro Trp Ser Ser Tyr Arg Ser Pro Thr Glu Tyr Val Tyr
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: CDR3

<400> SEQUENCE: 137

Gly Arg Pro Trp Ser Ala Ala His Ser Pro Asn Glu Tyr Val Tyr
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: CDR3

<400> SEQUENCE: 138

Gly Arg Pro Trp Ser Asp Tyr Arg Ala Pro Ser Glu Tyr Ile Tyr
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: CDR3

<400> SEQUENCE: 139

Gly Arg Pro Trp Ser Asp Phe Arg Ala Pro Ser Glu Tyr Ile Tyr
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: CDR3

<400> SEQUENCE: 140

Gly Arg Pro Trp Ser Ala Tyr His Ser Pro Asn Glu Tyr Val Tyr
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: CDR3

<400> SEQUENCE: 141

Gly Arg Pro Trp Ser Ala Tyr His Ser Pro Lys Glu Tyr Val Tyr
1               5                   10                  15

<210> SEQ ID NO 142
<211> LENGTH: 15
<212> TYPE: PRT
<213> ORGANISM: Artificial Sequence
```

```
<220> FEATURE:
<223> OTHER INFORMATION: CDR3

<400> SEQUENCE: 142

Gly Arg Pro Trp Ser Ala Tyr His Ser Pro Arg Glu Tyr Ile Tyr
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: CDR3

<400> SEQUENCE: 143

Gly Arg Pro Trp Ser Ala Tyr His Ala Pro Lys Glu Tyr Ile Tyr
1               5                   10                  15

<210> SEQ ID NO 144
<211> LENGTH: 25
<212> TYPE: PRT
<213> ORGANISM: Artificial Sequence
<220> FEATURE:
<223> OTHER INFORMATION: FR1

<400> SEQUENCE: 144

Glu Val Gln Leu Val Glu Ser Gly Gly Gly Pro Val Gln Ala Gly Gly
1               5                   10                  15

Ser Leu Arg Leu Ser Cys Ala Ala Ser
            20                  25

<210> SEQ ID NO 145
<211> LENGTH: 25
<212> TYPE: PRT
<213> ORGANISM: Artificial Sequence
<220> FEATURE:
<223> OTHER INFORMATION: FR1

<400> SEQUENCE: 145

Glu Val Gln Pro Val Glu Ser Gly Gly Gly Pro Val Gln Ala Gly Gly
1               5                   10                  15

Ser Leu Arg Leu Ser Cys Ala Ala Ser
            20                  25

<210> SEQ ID NO 146
<211> LENGTH: 25
<212> TYPE: PRT
<213> ORGANISM: Artificial Sequence
<220> FEATURE:
<223> OTHER INFORMATION: FR1

<400> SEQUENCE: 146

Glu Val Gln Leu Val Glu Ser Gly Gly Gly Pro Val Gln Ser Gly Gly
1               5                   10                  15

Ser Leu Arg Leu Ser Cys Ala Asn Ser
            20                  25

<210> SEQ ID NO 147
<211> LENGTH: 25
<212> TYPE: PRT
<213> ORGANISM: Artificial Sequence
<220> FEATURE:
<223> OTHER INFORMATION: FR1

<400> SEQUENCE: 147
```

Glu Val Gln Leu Val Glu Ser Gly Gly Gly Pro Val Gln Ala Gly Gly
1               5                   10                  15

Ser Leu Arg Leu Ser Cys Ala Asn Ser
            20                  25

<210> SEQ ID NO 148
<211> LENGTH: 25
<212> TYPE: PRT
<213> ORGANISM: Artificial Sequence
<220> FEATURE:
<223> OTHER INFORMATION: FR1

<400> SEQUENCE: 148

Glu Val Gln Leu Val Glu Ser Gly Gly Gly Pro Val Gln Ala Gly Gly
1               5                   10                  15

Ser Leu Arg Leu Ser Cys Ala Ser Ser
            20                  25

<210> SEQ ID NO 149
<211> LENGTH: 25
<212> TYPE: PRT
<213> ORGANISM: Artificial Sequence
<220> FEATURE:
<223> OTHER INFORMATION: FR1

<400> SEQUENCE: 149

Glu Val Gln Leu Val Glu Ser Gly Gly Gly Pro Val Gln Ala Gly Gly
1               5                   10                  15

Ser Leu Arg Leu Ser Cys Ala Asp Ser
            20                  25

<210> SEQ ID NO 150
<211> LENGTH: 25
<212> TYPE: PRT
<213> ORGANISM: Artificial Sequence
<220> FEATURE:
<223> OTHER INFORMATION: FR1

<400> SEQUENCE: 150

Glu Val Gln Leu Val Glu Ser Gly Gly Gly Leu Val Gln Ala Gly Gly
1               5                   10                  15

Ser Leu Thr Leu Ser Cys Ala Asn Ser
            20                  25

<210> SEQ ID NO 151
<211> LENGTH: 25
<212> TYPE: PRT
<213> ORGANISM: Artificial Sequence
<220> FEATURE:
<223> OTHER INFORMATION: FR1

<400> SEQUENCE: 151

Glu Val Gln Leu Val Glu Ser Gly Gly Gly Pro Val Gln Ala Gly Gly
1               5                   10                  15

Ser Leu Thr Leu Ser Cys Ala Asn Ser
            20                  25

<210> SEQ ID NO 152
<211> LENGTH: 25
<212> TYPE: PRT
<213> ORGANISM: Artificial Sequence
<220> FEATURE:
<223> OTHER INFORMATION: FR1

<400> SEQUENCE: 152

Glu Val Gln Leu Val Glu Ser Gly Gly Gly Pro Val Gln Thr Gly Gly
1               5                   10                  15

Ser Leu Arg Leu Ser Cys Val Ala Ser
            20                  25

<210> SEQ ID NO 153
<211> LENGTH: 25
<212> TYPE: PRT
<213> ORGANISM: Artificial Sequence
<220> FEATURE:
<223> OTHER INFORMATION: FR1

<400> SEQUENCE: 153

Glu Val Gln Pro Val Glu Ser Gly Gly Gly Pro Val Gln Thr Gly Gly
1               5                   10                  15

Ser Leu Arg Leu Ser Cys Val Ala Ser
            20                  25

<210> SEQ ID NO 154
<211> LENGTH: 25
<212> TYPE: PRT
<213> ORGANISM: Artificial Sequence
<220> FEATURE:
<223> OTHER INFORMATION: FR1

<400> SEQUENCE: 154

Glu Val Gln Leu Val Glu Ser Gly Gly Gly Pro Val Gln Thr Gly Gly
1               5                   10                  15

Ser Leu Arg Leu Ser Cys Val Ala Pro
            20                  25

<210> SEQ ID NO 155
<211> LENGTH: 25
<212> TYPE: PRT
<213> ORGANISM: Artificial Sequence
<220> FEATURE:
<223> OTHER INFORMATION: FR1

<400> SEQUENCE: 155

Glu Val Gln Leu Val Glu Ser Gly Gly Gly Leu Val Gln Thr Gly Gly
1               5                   10                  15

Ser Leu Arg Leu Ser Cys Val Ala Ser
            20                  25

<210> SEQ ID NO 156
<211> LENGTH: 25
<212> TYPE: PRT
<213> ORGANISM: Artificial Sequence
<220> FEATURE:
<223> OTHER INFORMATION: FR1

<400> SEQUENCE: 156

Glu Val Gln Leu Val Glu Ser Gly Gly Gly Pro Ala Gln Ala Gly Gly
1               5                   10                  15

Ser Leu Arg Leu Ser Cys Ala Ala Ser
            20                  25

<210> SEQ ID NO 157
<211> LENGTH: 25
<212> TYPE: PRT
<213> ORGANISM: Artificial Sequence
<220> FEATURE:
<223> OTHER INFORMATION: FR1

```
<400> SEQUENCE: 157

Glu Val Gln Leu Val Glu Ser Gly Gly Gly Pro Val Gln Ala Gly Asp
1               5                   10                  15

Ser Leu Arg Leu Ser Cys Ala Ala Ser
            20                  25

<210> SEQ ID NO 158
<211> LENGTH: 25
<212> TYPE: PRT
<213> ORGANISM: Artificial Sequence
<220> FEATURE:
<223> OTHER INFORMATION: FR1

<400> SEQUENCE: 158

Glu Val Gln Leu Val Glu Phe Gly Gly Gly Pro Val Gln Ala Gly Asp
1               5                   10                  15

Ser Leu Arg Leu Ser Cys Ala Ala Ser
            20                  25

<210> SEQ ID NO 159
<211> LENGTH: 25
<212> TYPE: PRT
<213> ORGANISM: Artificial Sequence
<220> FEATURE:
<223> OTHER INFORMATION: FR1

<400> SEQUENCE: 159

Glu Val Gln Leu Val Glu Ser Arg Gly Gly Pro Val Gln Ala Gly Asp
1               5                   10                  15

Ser Leu Arg Leu Ser Cys Ala Ala Ser
            20                  25

<210> SEQ ID NO 160
<211> LENGTH: 24
<212> TYPE: PRT
<213> ORGANISM: Artificial Sequence
<220> FEATURE:
<223> OTHER INFORMATION: FR1

<400> SEQUENCE: 160

Glu Val Gln Leu Val Ser Gly Gly Gly Pro Val Gln Ala Gly Asp Ser
1               5                   10                  15

Leu Arg Leu Ser Cys Ala Ala Ser
            20

<210> SEQ ID NO 161
<211> LENGTH: 25
<212> TYPE: PRT
<213> ORGANISM: Artificial Sequence
<220> FEATURE:
<223> OTHER INFORMATION: FR1

<400> SEQUENCE: 161

Lys Val Gln Leu Val Glu Ser Gly Gly Gly Pro Val Gln Ala Gly Asp
1               5                   10                  15

Ser Leu Arg Leu Ser Cys Ala Ala Ser
            20                  25

<210> SEQ ID NO 162
<211> LENGTH: 25
<212> TYPE: PRT
<213> ORGANISM: Artificial Sequence
<220> FEATURE:
<223> OTHER INFORMATION: FR1
```

<400> SEQUENCE: 162

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 163
<211> LENGTH: 25
<212> TYPE: PRT
<213> ORGANISM: Artificial Sequence
<220> FEATURE:
<223> OTHER INFORMATION: FR1

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 164
<211> LENGTH: 25
<212> TYPE: PRT
<213> ORGANISM: Artificial Sequence
<220> FEATURE:
<223> OTHER INFORMATION: FR1

<400> SEQUENCE: 164

Glu Val Gln Leu Val Glu Ser Gly Gly Gly Leu Val Gln Gly Gly Gly
1               5                   10                  15

Ser Leu Ser Leu Ser Cys Ala Ala Ser
            20                  25

<210> SEQ ID NO 165
<211> LENGTH: 25
<212> TYPE: PRT
<213> ORGANISM: Artificial Sequence
<220> FEATURE:
<223> OTHER INFORMATION: FR1

<400> SEQUENCE: 165

Glu Val Gln Leu Val Glu Ser Gly Gly Gly Ser Val Gln Ala Gly Gly
1               5                   10                  15

Ser Leu Arg Leu Ser Cys Ala Ala Ser
            20                  25

<210> SEQ ID NO 166
<211> LENGTH: 25
<212> TYPE: PRT
<213> ORGANISM: Artificial Sequence
<220> FEATURE:
<223> OTHER INFORMATION: FR1

<400> SEQUENCE: 166

Glu Val Gln Leu Val Glu Ser Gly Gly Gly Ala Val Gln Pro Gly Gly
1               5                   10                  15

Ser Leu Arg Leu Ser Cys Ala Ala Ser
            20                  25

<210> SEQ ID NO 167
<211> LENGTH: 25
<212> TYPE: PRT
<213> ORGANISM: Artificial Sequence
<220> FEATURE:

```
<223> OTHER INFORMATION: FR1

<400> SEQUENCE: 167

Glu Val Gln Leu Val Glu Ser Gly Gly Gly Ala Val Gln Pro Gly Gly
1               5                   10                  15

Ser Leu Arg Leu Ser Cys Val Ala Ser
            20                  25

<210> SEQ ID NO 168
<211> LENGTH: 25
<212> TYPE: PRT
<213> ORGANISM: Artificial Sequence
<220> FEATURE:
<223> OTHER INFORMATION: FR1

<400> SEQUENCE: 168

Glu Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 169
<211> LENGTH: 25
<212> TYPE: PRT
<213> ORGANISM: Artificial Sequence
<220> FEATURE:
<223> OTHER INFORMATION: FR1

<400> SEQUENCE: 169

Glu Val Gln Leu Val Glu Ser Gly Gly Gly Ala Val Gln Ala Gly Gly
1               5                   10                  15

Ser Leu Arg Leu Ser Cys Ala Ala Ser
            20                  25

<210> SEQ ID NO 170
<211> LENGTH: 25
<212> TYPE: PRT
<213> ORGANISM: Artificial Sequence
<220> FEATURE:
<223> OTHER INFORMATION: FR1

<400> SEQUENCE: 170

Glu Val Gln Leu Val Glu Ser Gly Gly Gly Leu Val Arg Ala Gly Gly
1               5                   10                  15

Ser Leu Arg Leu Ser Cys Ala Ala Ser
            20                  25

<210> SEQ ID NO 171
<211> LENGTH: 25
<212> TYPE: PRT
<213> ORGANISM: Artificial Sequence
<220> FEATURE:
<223> OTHER INFORMATION: FR1

<400> SEQUENCE: 171

Glu Val Gln Leu Val Glu Phe Gly Gly Gly Leu Val Gln Ala Gly Gly
1               5                   10                  15

Ser Leu Arg Leu Ser Cys Ala Ala Ser
            20                  25

<210> SEQ ID NO 172
<211> LENGTH: 25
<212> TYPE: PRT
<213> ORGANISM: Artificial Sequence
```

```
<220> FEATURE:
<223> OTHER INFORMATION: FR1

<400> SEQUENCE: 172

Glu Val Gln Leu Val Glu Ser Gly Gly Gly Leu Val Gln Ala Gly Asp
1               5                   10                  15
Ser Leu Arg Leu Ser Cys Ala Ala Ser
            20                  25

<210> SEQ ID NO 173
<211> LENGTH: 25
<212> TYPE: PRT
<213> ORGANISM: Artificial Sequence
<220> FEATURE:
<223> OTHER INFORMATION: FR1

<400> SEQUENCE: 173

Glu Val Gln Leu Val Glu Ser Gly Gly Gly Leu Val Gln Ala Gly Ala
1               5                   10                  15
Ser Leu Arg Leu Ser Cys Ala Ala Ser
            20                  25

<210> SEQ ID NO 174
<211> LENGTH: 14
<212> TYPE: PRT
<213> ORGANISM: Artificial Sequence
<220> FEATURE:
<223> OTHER INFORMATION: FR2

<400> SEQUENCE: 174

Trp Phe Arg Gln Ala Pro Gly Lys Glu Arg Glu Phe Val Ala
1               5                   10

<210> SEQ ID NO 175
<211> LENGTH: 14
<212> TYPE: PRT
<213> ORGANISM: Artificial Sequence
<220> FEATURE:
<223> OTHER INFORMATION: FR2

<400> SEQUENCE: 175

Trp Phe Arg Gln Ser Pro Gly Lys Glu Arg Glu Phe Val Ala
1               5                   10

<210> SEQ ID NO 176
<211> LENGTH: 14
<212> TYPE: PRT
<213> ORGANISM: Artificial Sequence
<220> FEATURE:
<223> OTHER INFORMATION: FR2

<400> SEQUENCE: 176

Trp Phe Arg Gln Ser Pro Gly Lys Glu Arg Gly Phe Val Ala
1               5                   10

<210> SEQ ID NO 177
<211> LENGTH: 14
<212> TYPE: PRT
<213> ORGANISM: Artificial Sequence
<220> FEATURE:
<223> OTHER INFORMATION: FR2

<400> SEQUENCE: 177

Trp Phe Arg Gln Pro Pro Gly Lys Glu Arg Glu Phe Val Ala
1               5                   10
```

```
<210> SEQ ID NO 178
<211> LENGTH: 14
<212> TYPE: PRT
<213> ORGANISM: Artificial Sequence
<220> FEATURE:
<223> OTHER INFORMATION: FR2

<400> SEQUENCE: 178

Trp Phe Arg Gln Pro Pro Gly Lys Glu Arg Gly Phe Val Ala
1               5                   10

<210> SEQ ID NO 179
<211> LENGTH: 14
<212> TYPE: PRT
<213> ORGANISM: Artificial Sequence
<220> FEATURE:
<223> OTHER INFORMATION: FR2

<400> SEQUENCE: 179

Trp Phe Arg Gln Ala Pro Gly Arg Glu Arg Glu Phe Val Ala
1               5                   10

<210> SEQ ID NO 180
<211> LENGTH: 14
<212> TYPE: PRT
<213> ORGANISM: Artificial Sequence
<220> FEATURE:
<223> OTHER INFORMATION: FR2

<400> SEQUENCE: 180

Trp Phe Arg Arg Ala Pro Gly Arg Glu Arg Glu Phe Val Ala
1               5                   10

<210> SEQ ID NO 181
<211> LENGTH: 14
<212> TYPE: PRT
<213> ORGANISM: Artificial Sequence
<220> FEATURE:
<223> OTHER INFORMATION: FR2

<400> SEQUENCE: 181

Trp Phe Arg Gln Val Pro Gly Lys Glu Arg Glu Phe Val Ala
1               5                   10

<210> SEQ ID NO 182
<211> LENGTH: 14
<212> TYPE: PRT
<213> ORGANISM: Artificial Sequence
<220> FEATURE:
<223> OTHER INFORMATION: FR2

<400> SEQUENCE: 182

Trp Phe Arg Arg Val Pro Gly Lys Glu Arg Glu Phe Val Ala
1               5                   10

<210> SEQ ID NO 183
<211> LENGTH: 14
<212> TYPE: PRT
<213> ORGANISM: Artificial Sequence
<220> FEATURE:
<223> OTHER INFORMATION: FR2

<400> SEQUENCE: 183

Trp Tyr Arg Gln Ala Pro Gly Lys Gln Arg Asp Leu Val Ala
1               5                   10
```

```
<210> SEQ ID NO 184
<211> LENGTH: 14
<212> TYPE: PRT
<213> ORGANISM: Artificial Sequence
<220> FEATURE:
<223> OTHER INFORMATION: FR2

<400> SEQUENCE: 184

Trp Phe Arg Gln Val Pro Gly Lys Glu Arg Glu Leu Ile Ala
1               5                   10

<210> SEQ ID NO 185
<211> LENGTH: 14
<212> TYPE: PRT
<213> ORGANISM: Artificial Sequence
<220> FEATURE:
<223> OTHER INFORMATION: FR2

<400> SEQUENCE: 185

Trp Phe Arg Gln Ser Pro Gly Lys Glu Arg Ser Leu Ile Ala
1               5                   10

<210> SEQ ID NO 186
<211> LENGTH: 14
<212> TYPE: PRT
<213> ORGANISM: Artificial Sequence
<220> FEATURE:
<223> OTHER INFORMATION: FR2

<400> SEQUENCE: 186

Trp Phe Arg Gln Ala Pro Gly Lys Gln Arg Asp Leu Val Ala
1               5                   10

<210> SEQ ID NO 187
<211> LENGTH: 14
<212> TYPE: PRT
<213> ORGANISM: Artificial Sequence
<220> FEATURE:
<223> OTHER INFORMATION: FR2

<400> SEQUENCE: 187

Trp Phe Arg Arg Thr Pro Gly Arg Glu Arg Asn Met Val Ala
1               5                   10

<210> SEQ ID NO 188
<211> LENGTH: 14
<212> TYPE: PRT
<213> ORGANISM: Artificial Sequence
<220> FEATURE:
<223> OTHER INFORMATION: FR2

<400> SEQUENCE: 188

Trp Phe Arg Arg Thr Pro Gly Arg Gly Arg Asn Met Val Ala
1               5                   10

<210> SEQ ID NO 189
<211> LENGTH: 14
<212> TYPE: PRT
<213> ORGANISM: Artificial Sequence
<220> FEATURE:
<223> OTHER INFORMATION: FR2

<400> SEQUENCE: 189

Trp Phe Arg Gln Ala Pro Gly Lys Ser Arg Asp Met Val Ala
1               5                   10

<210> SEQ ID NO 190
```

```
<211> LENGTH: 14
<212> TYPE: PRT
<213> ORGANISM: Artificial Sequence
<220> FEATURE:
<223> OTHER INFORMATION: FR2

<400> SEQUENCE: 190

Trp Phe Arg Gln Ala Pro Gly Glu Gln Arg Asp Met Val Ala
1               5                   10

<210> SEQ ID NO 191
<211> LENGTH: 14
<212> TYPE: PRT
<213> ORGANISM: Artificial Sequence
<220> FEATURE:
<223> OTHER INFORMATION: FR2

<400> SEQUENCE: 191

Trp Phe Arg Gln Ala Pro Glu Lys Gln Arg Glu Met Val Ala
1               5                   10

<210> SEQ ID NO 192
<211> LENGTH: 14
<212> TYPE: PRT
<213> ORGANISM: Artificial Sequence
<220> FEATURE:
<223> OTHER INFORMATION: FR2

<400> SEQUENCE: 192

Trp Phe Arg Gln Ser Pro Gly Asn Glu Arg Glu Phe Val Ala
1               5                   10

<210> SEQ ID NO 193
<211> LENGTH: 14
<212> TYPE: PRT
<213> ORGANISM: Artificial Sequence
<220> FEATURE:
<223> OTHER INFORMATION: FR2

<400> SEQUENCE: 193

Trp Phe Arg Gln Phe Ala Gly Lys Glu Arg Glu Phe Val Ala
1               5                   10

<210> SEQ ID NO 194
<211> LENGTH: 14
<212> TYPE: PRT
<213> ORGANISM: Artificial Sequence
<220> FEATURE:
<223> OTHER INFORMATION: FR2

<400> SEQUENCE: 194

Trp Phe Arg Gln Ser Pro Gly Arg Glu Arg Glu Phe Val Ala
1               5                   10

<210> SEQ ID NO 195
<211> LENGTH: 14
<212> TYPE: PRT
<213> ORGANISM: Artificial Sequence
<220> FEATURE:
<223> OTHER INFORMATION: FR2

<400> SEQUENCE: 195

Trp Phe Arg Gln Phe Pro Arg Lys Glu Arg Glu Phe Val Ala
1               5                   10

<210> SEQ ID NO 196
<211> LENGTH: 14
```

```
<212> TYPE: PRT
<213> ORGANISM: Artificial Sequence
<220> FEATURE:
<223> OTHER INFORMATION: FR2

<400> SEQUENCE: 196

Trp Phe Arg Gln Phe Pro Gly Lys Glu Arg Glu Ser Val Ala
1               5                   10

<210> SEQ ID NO 197
<211> LENGTH: 14
<212> TYPE: PRT
<213> ORGANISM: Artificial Sequence
<220> FEATURE:
<223> OTHER INFORMATION: FR2

<400> SEQUENCE: 197

Trp Phe Arg Gln Ser Pro Gly Lys Glu Arg Glu Phe Leu Ala
1               5                   10

<210> SEQ ID NO 198
<211> LENGTH: 14
<212> TYPE: PRT
<213> ORGANISM: Artificial Sequence
<220> FEATURE:
<223> OTHER INFORMATION: FR2

<400> SEQUENCE: 198

Trp Phe Arg Gln Ser Pro Gly Lys Glu Arg Glu Phe Val Gly
1               5                   10

<210> SEQ ID NO 199
<211> LENGTH: 14
<212> TYPE: PRT
<213> ORGANISM: Artificial Sequence
<220> FEATURE:
<223> OTHER INFORMATION: FR2

<400> SEQUENCE: 199

Trp Phe Arg Gln Ser Pro Gly Gln Glu Arg Glu Phe Leu Ala
1               5                   10

<210> SEQ ID NO 200
<211> LENGTH: 39
<212> TYPE: PRT
<213> ORGANISM: Artificial Sequence
<220> FEATURE:
<223> OTHER INFORMATION: FR3

<400> SEQUENCE: 200

Tyr Glu Asp Ser Val Lys Gly Arg Phe Thr Ile Ser Arg Asp Asn Ala
1               5                   10                  15

Lys Asn Thr Met Tyr Leu Gln Met Thr Ser Leu Lys Pro Glu Asp Ser
            20                  25                  30

Ala Thr Tyr Tyr Cys Ala Ala
        35

<210> SEQ ID NO 201
<211> LENGTH: 39
<212> TYPE: PRT
<213> ORGANISM: Artificial Sequence
<220> FEATURE:
<223> OTHER INFORMATION: FR3

<400> SEQUENCE: 201

Tyr Glu Asp Phe Val Lys Gly Arg Phe Thr Ile Ser Arg Asp Ser Ala
```

```
1               5                   10                  15
Lys Asn Thr Leu Tyr Leu Gln Met Thr Asn Leu Lys Pro Glu Asp Thr
            20                  25                  30

Ala Leu Tyr Tyr Cys Ala Ala
        35

<210> SEQ ID NO 202
<211> LENGTH: 39
<212> TYPE: PRT
<213> ORGANISM: Artificial Sequence
<220> FEATURE:
<223> OTHER INFORMATION: FR3

<400> SEQUENCE: 202

Tyr Glu Asp Phe Val Lys Gly Arg Phe Thr Ile Ser Arg Asp Ser Val
1               5                   10                  15

Lys Asn Thr Leu Tyr Leu Gln Met Thr Asn Leu Lys Pro Glu Asp Thr
            20                  25                  30

Ala Leu Tyr Tyr Cys Ala Ala
        35

<210> SEQ ID NO 203
<211> LENGTH: 39
<212> TYPE: PRT
<213> ORGANISM: Artificial Sequence
<220> FEATURE:
<223> OTHER INFORMATION: FR3

<400> SEQUENCE: 203

Tyr Glu Asp Phe Val Lys Gly Arg Phe Thr Ile Ser Arg Asp Ser Ala
1               5                   10                  15

Lys Asn Thr Leu Tyr Leu Gln Met Thr Asn Leu Glu Pro Glu Asp Thr
            20                  25                  30

Ala Leu Tyr Tyr Cys Ala Ala
        35

<210> SEQ ID NO 204
<211> LENGTH: 39
<212> TYPE: PRT
<213> ORGANISM: Artificial Sequence
<220> FEATURE:
<223> OTHER INFORMATION: FR3

<400> SEQUENCE: 204

Tyr Glu Asp Phe Val Lys Gly Arg Phe Thr Ile Ser Arg Asp Ser Ala
1               5                   10                  15

Lys Asn Thr Leu Tyr Leu Gln Met Thr Asn Leu Glu Pro Gly Asp Thr
            20                  25                  30

Ala Leu Tyr Tyr Cys Ala Ala
        35

<210> SEQ ID NO 205
<211> LENGTH: 39
<212> TYPE: PRT
<213> ORGANISM: Artificial Sequence
<220> FEATURE:
<223> OTHER INFORMATION: FR3

<400> SEQUENCE: 205

Tyr Glu Asp Phe Val Lys Gly Arg Phe Thr Ile Ser Arg Asp Ser Ala
1               5                   10                  15

Lys Asn Thr Leu Ser Leu His Met Thr Asn Leu Lys Pro Glu Asp Thr
```

```
                20                  25                  30

Ala Val Tyr Tyr Cys Ala Ala
        35

<210> SEQ ID NO 206
<211> LENGTH: 39
<212> TYPE: PRT
<213> ORGANISM: Artificial Sequence
<220> FEATURE:
<223> OTHER INFORMATION: FR3

<400> SEQUENCE: 206

Tyr Glu Asp Phe Val Lys Gly Arg Phe Thr Ile Ser Arg Asp Ser Ala
1               5                   10                  15

Lys Asn Thr Leu Ser Leu His Met Ala Asn Leu Lys Pro Glu Asp Thr
            20                  25                  30

Ala Val Tyr Tyr Cys Ala Ala
        35

<210> SEQ ID NO 207
<211> LENGTH: 39
<212> TYPE: PRT
<213> ORGANISM: Artificial Sequence
<220> FEATURE:
<223> OTHER INFORMATION: FR3

<400> SEQUENCE: 207

Tyr Glu Asp Phe Val Lys Gly Arg Phe Thr Ile Ser Arg Asp Ser Ala
1               5                   10                  15

Lys Asn Ile Met Tyr Leu Gln Met Thr Asn Leu Lys Pro Glu Asp Thr
            20                  25                  30

Ala Val Tyr Tyr Cys Ala Ala
        35

<210> SEQ ID NO 208
<211> LENGTH: 39
<212> TYPE: PRT
<213> ORGANISM: Artificial Sequence
<220> FEATURE:
<223> OTHER INFORMATION: FR3

<400> SEQUENCE: 208

Tyr Glu Asp Phe Val Lys Gly Arg Phe Thr Ile Ser Arg Asp Asn Ala
1               5                   10                  15

Lys Asn Thr Leu Tyr Leu Gln Met Thr Asn Leu Lys Pro Glu Asp Thr
            20                  25                  30

Ala Leu Tyr Tyr Cys Ala Ala
        35

<210> SEQ ID NO 209
<211> LENGTH: 39
<212> TYPE: PRT
<213> ORGANISM: Artificial Sequence
<220> FEATURE:
<223> OTHER INFORMATION: FR3

<400> SEQUENCE: 209

Tyr Glu Asp Phe Val Arg Gly Arg Phe Thr Ile Ser Arg Asp Asn Ala
1               5                   10                  15

Lys Asn Thr Leu Tyr Leu Gln Met Thr Asn Leu Lys Pro Glu Asp Thr
            20                  25                  30

Ala Leu Tyr Tyr Cys Ala Ala
```

<210> SEQ ID NO 210
<211> LENGTH: 39
<212> TYPE: PRT
<213> ORGANISM: Artificial Sequence
<220> FEATURE:
<223> OTHER INFORMATION: FR3

<400> SEQUENCE: 210

Tyr Glu Asp Phe Val Lys Gly Arg Phe Thr Ile Ser Arg Asp Asn Ala
1               5                   10                  15

Lys Asn Thr Leu Tyr Leu Gln Met Thr Asn Leu Arg Pro Glu Asp Thr
            20                  25                  30

Ala Leu Tyr Tyr Cys Ala Ala
        35

<210> SEQ ID NO 211
<211> LENGTH: 39
<212> TYPE: PRT
<213> ORGANISM: Artificial Sequence
<220> FEATURE:
<223> OTHER INFORMATION: FR3

<400> SEQUENCE: 211

Tyr Glu Asp Phe Val Lys Gly Arg Phe Thr Ile Ser Arg Asp Asn Ala
1               5                   10                  15

Lys Asn Thr Leu Tyr Leu Arg Met Thr Arg Leu Glu Pro Glu Asp Thr
            20                  25                  30

Ala Leu Tyr Tyr Cys Ala Ala
        35

<210> SEQ ID NO 212
<211> LENGTH: 39
<212> TYPE: PRT
<213> ORGANISM: Artificial Sequence
<220> FEATURE:
<223> OTHER INFORMATION: FR3

<400> SEQUENCE: 212

Tyr Glu Asp Phe Ala Lys Gly Arg Phe Thr Ile Ser Arg Asp Asn Ala
1               5                   10                  15

Lys Asn Thr Leu Tyr Leu Arg Met Thr Arg Leu Glu Pro Glu Asp Thr
            20                  25                  30

Ala Leu Tyr Tyr Cys Ala Ala
        35

<210> SEQ ID NO 213
<211> LENGTH: 39
<212> TYPE: PRT
<213> ORGANISM: Artificial Sequence
<220> FEATURE:
<223> OTHER INFORMATION: FR3

<400> SEQUENCE: 213

Tyr Glu Asp Phe Val Lys Gly Arg Phe Thr Ile Ser Arg Asp Asn Ala
1               5                   10                  15

Lys Asn Thr Leu Tyr Leu Gln Met Thr Gly Leu Lys Pro Glu Asp Thr
            20                  25                  30

Ala Leu Tyr Tyr Cys Ala Ala
        35

```
<210> SEQ ID NO 214
<211> LENGTH: 39
<212> TYPE: PRT
<213> ORGANISM: Artificial Sequence
<220> FEATURE:
<223> OTHER INFORMATION: FR3

<400> SEQUENCE: 214

Tyr Glu Asp Phe Val Lys Gly Arg Phe Thr Ile Ser Arg Asp Asn Ala
1               5                   10                  15

Lys Asn Thr Leu Tyr Leu Gln Met Thr Ser Leu Lys Pro Glu Asp Thr
            20                  25                  30

Ala Leu Tyr Tyr Cys Ala Ala
        35

<210> SEQ ID NO 215
<211> LENGTH: 39
<212> TYPE: PRT
<213> ORGANISM: Artificial Sequence
<220> FEATURE:
<223> OTHER INFORMATION: FR3

<400> SEQUENCE: 215

Tyr Glu Asp Phe Val Lys Gly Arg Phe Thr Ile Ser Arg Asp Asn Ala
1               5                   10                  15

Lys Asn Thr Leu Tyr Leu Gln Met Ala Ser Leu Lys Pro Glu Asp Thr
            20                  25                  30

Ala Leu Tyr Tyr Cys Ala Ala
        35

<210> SEQ ID NO 216
<211> LENGTH: 39
<212> TYPE: PRT
<213> ORGANISM: Artificial Sequence
<220> FEATURE:
<223> OTHER INFORMATION: FR3

<400> SEQUENCE: 216

Tyr Glu Asp Phe Val Lys Gly Arg Phe Thr Ile Ser Arg Asp Asn Ala
1               5                   10                  15

Lys Ser Thr Leu Tyr Leu Gln Met Thr Ser Leu Lys Pro Glu Asp Thr
            20                  25                  30

Ala Leu Tyr Tyr Cys Ala Ala
        35

<210> SEQ ID NO 217
<211> LENGTH: 39
<212> TYPE: PRT
<213> ORGANISM: Artificial Sequence
<220> FEATURE:
<223> OTHER INFORMATION: FR3

<400> SEQUENCE: 217

Tyr Glu Asp Leu Val Lys Gly Arg Phe Thr Ile Ser Arg Asp Asn Ala
1               5                   10                  15

Lys Asn Thr Leu Tyr Leu Gln Met Thr Ser Leu Lys Pro Glu Asp Thr
            20                  25                  30

Ala Leu Tyr Tyr Cys Ala Ala
        35

<210> SEQ ID NO 218
<211> LENGTH: 39
<212> TYPE: PRT
```

```
<213> ORGANISM: Artificial Sequence
<220> FEATURE:
<223> OTHER INFORMATION: FR3

<400> SEQUENCE: 218

Tyr Glu Asp Pro Val Lys Gly Arg Phe Thr Ile Ser Arg Asp Asn Ala
1               5                   10                  15

Lys Asn Thr Met Tyr Leu Gln Met Thr Ser Leu Lys Pro Glu Asp Ser
            20                  25                  30

Ala Thr Tyr Tyr Cys Ala Ala
        35

<210> SEQ ID NO 219
<211> LENGTH: 39
<212> TYPE: PRT
<213> ORGANISM: Artificial Sequence
<220> FEATURE:
<223> OTHER INFORMATION: FR3

<400> SEQUENCE: 219

Tyr Glu Asp Ser Val Lys Gly Arg Phe Thr Ile Ser Arg Asp Ile Thr
1               5                   10                  15

Lys Asn Thr Met Tyr Leu Gln Met Thr Ser Leu Lys Pro Glu Asp Ser
            20                  25                  30

Ala Thr Tyr Tyr Cys Ala Ala
        35

<210> SEQ ID NO 220
<211> LENGTH: 39
<212> TYPE: PRT
<213> ORGANISM: Artificial Sequence
<220> FEATURE:
<223> OTHER INFORMATION: FR3

<400> SEQUENCE: 220

Tyr Glu Asp Ser Val Lys Gly Arg Phe Thr Ile Ser Arg Asp Val Thr
1               5                   10                  15

Lys Asn Thr Met Tyr Leu Gln Met Thr Ser Leu Lys Pro Glu Asp Ser
            20                  25                  30

Ala Thr Tyr Tyr Cys Ala Ala
        35

<210> SEQ ID NO 221
<211> LENGTH: 39
<212> TYPE: PRT
<213> ORGANISM: Artificial Sequence
<220> FEATURE:
<223> OTHER INFORMATION: FR3

<400> SEQUENCE: 221

Tyr Glu Asp Ser Val Lys Gly Arg Phe Thr Ile Ser Arg Asp Asn Thr
1               5                   10                  15

Lys Asn Thr Met Tyr Leu Gln Met Thr Ser Leu Lys Pro Glu Asp Ser
            20                  25                  30

Ala Thr Tyr Tyr Cys Ala Ala
        35

<210> SEQ ID NO 222
<211> LENGTH: 39
<212> TYPE: PRT
<213> ORGANISM: Artificial Sequence
<220> FEATURE:
<223> OTHER INFORMATION: FR3
```

<400> SEQUENCE: 222

Tyr Glu Asp Ser Val Lys Gly Arg Phe Thr Ile Ser Arg Asp Ile Thr
1               5                   10                  15

Lys Asn Thr Met Tyr Leu His Met Thr Ser Leu Lys Pro Glu Asp Ser
            20                  25                  30

Ala Thr Tyr Tyr Cys Ala Ala
        35

<210> SEQ ID NO 223
<211> LENGTH: 39
<212> TYPE: PRT
<213> ORGANISM: Artificial Sequence
<220> FEATURE:
<223> OTHER INFORMATION: FR3

<400> SEQUENCE: 223

Tyr Ala Asp Ser Val Lys Gly Arg Phe Thr Ile Ser Arg Asp Gly Thr
1               5                   10                  15

Gly Asn Thr Val Tyr Leu Leu Met Asn Lys Leu Arg Pro Glu Asp Thr
            20                  25                  30

Ala Ile Tyr Tyr Cys Asn Thr
        35

<210> SEQ ID NO 224
<211> LENGTH: 39
<212> TYPE: PRT
<213> ORGANISM: Artificial Sequence
<220> FEATURE:
<223> OTHER INFORMATION: FR3

<400> SEQUENCE: 224

Tyr Arg Asn Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 225
<211> LENGTH: 39
<212> TYPE: PRT
<213> ORGANISM: Artificial Sequence
<220> FEATURE:
<223> OTHER INFORMATION: FR3

<400> SEQUENCE: 225

Tyr Ala Asp Ser Val Lys Gly Arg Phe Thr Ile Ser Arg Asp Asn Ala
1               5                   10                  15

Lys Lys Thr Val Tyr Leu Gln Met Asn Ser Leu Lys Ser Glu Asp Thr
            20                  25                  30

Ala Thr Tyr Tyr Cys Ala Ala
        35

<210> SEQ ID NO 226
<211> LENGTH: 39
<212> TYPE: PRT
<213> ORGANISM: Artificial Sequence
<220> FEATURE:
<223> OTHER INFORMATION: FR3

<400> SEQUENCE: 226

-continued

Tyr Ala Asp Ser Val Lys Gly Arg Phe Thr Ile Ser Arg Asp Asn Ala
1               5                   10                  15

Lys Lys Thr Val Tyr Leu Gln Met Asn Ser Leu Arg Ser Glu Asp Thr
            20                  25                  30

Ala Thr Tyr Tyr Cys Ala Ala
        35

<210> SEQ ID NO 227
<211> LENGTH: 39
<212> TYPE: PRT
<213> ORGANISM: Artificial Sequence
<220> FEATURE:
<223> OTHER INFORMATION: FR3

<400> SEQUENCE: 227

Tyr Val Asp Ser Val Lys Gly Arg Phe Ser Ile Ser Lys Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Asn Ser
        35

<210> SEQ ID NO 228
<211> LENGTH: 39
<212> TYPE: PRT
<213> ORGANISM: Artificial Sequence
<220> FEATURE:
<223> OTHER INFORMATION: FR3

<400> SEQUENCE: 228

Tyr Val Asp Ser Val Lys Gly Arg Phe Ser Ile Ser Lys Asp Ser
1               5                   10                  15

Lys Asn Thr Val Tyr Leu Gln Met Asp Ser Leu Lys Pro Glu Asp Thr
            20                  25                  30

Ala Val Tyr Tyr Cys Asn Ser
        35

<210> SEQ ID NO 229
<211> LENGTH: 39
<212> TYPE: PRT
<213> ORGANISM: Artificial Sequence
<220> FEATURE:
<223> OTHER INFORMATION: FR3

<400> SEQUENCE: 229

Tyr Val Asp Ser Val Lys Gly Arg Phe Ser Ile Ser Lys Asp Asn Ala
1               5                   10                  15

Lys Asn Thr Val Tyr Leu Gln Met Asn Ser Leu Arg Pro Glu Asp Thr
            20                  25                  30

Ala Ile Tyr Tyr Cys Asn Ser
        35

<210> SEQ ID NO 230
<211> LENGTH: 39
<212> TYPE: PRT
<213> ORGANISM: Artificial Sequence
<220> FEATURE:
<223> OTHER INFORMATION: FR3

<400> SEQUENCE: 230

Val Val Asp Ser Val Lys Gly Arg Phe Ser Ile Ser Lys Asp Asn Ala
1               5                   10                  15

-continued

Lys Asn Thr Val Tyr Leu Gln Met Asn Asn Leu Lys Leu Glu Asp Thr
            20                  25                  30

Ala Val Tyr Tyr Cys Asn Ser
        35

<210> SEQ ID NO 231
<211> LENGTH: 39
<212> TYPE: PRT
<213> ORGANISM: Artificial Sequence
<220> FEATURE:
<223> OTHER INFORMATION: FR3

<400> SEQUENCE: 231

Tyr Ile Asp Ser Val Lys Gly Arg Phe Thr Ile Ser Lys Asp Asn Ala
1               5                   10                  15

Lys Asn Thr Val Phe Leu Arg Met Asn Asp Leu Lys Pro Asp Asp Thr
            20                  25                  30

Ala Val Tyr Tyr Cys Asn Ser
        35

<210> SEQ ID NO 232
<211> LENGTH: 39
<212> TYPE: PRT
<213> ORGANISM: Artificial Sequence
<220> FEATURE:
<223> OTHER INFORMATION: FR3

<400> SEQUENCE: 232

Tyr Ile Asp Ser Val Lys Gly Arg Phe Thr Ile Ser Lys Asp Asn Ala
1               5                   10                  15

Lys Asn Thr Val Phe Leu Arg Met Asn Asp Leu Lys Pro Asp Gly Thr
            20                  25                  30

Ala Val Tyr Tyr Cys Asn Ser
        35

<210> SEQ ID NO 233
<211> LENGTH: 39
<212> TYPE: PRT
<213> ORGANISM: Artificial Sequence
<220> FEATURE:
<223> OTHER INFORMATION: FR3

<400> SEQUENCE: 233

Tyr Val Asp Ser Val Lys Gly Arg Phe Thr Ile Ser Arg Asp Asn Ala
1               5                   10                  15

Lys Asn Thr Val Tyr Leu Gln Met Asn Ser Leu Lys Ser Glu Asp Thr
            20                  25                  30

Ala Val Tyr Tyr Cys Ala Ala
        35

<210> SEQ ID NO 234
<211> LENGTH: 39
<212> TYPE: PRT
<213> ORGANISM: Artificial Sequence
<220> FEATURE:
<223> OTHER INFORMATION: FR3

<400> SEQUENCE: 234

Tyr Ala Asp Ser Val Lys Gly Arg Phe Ala Ile Ser Arg Asp Asn Ala
1               5                   10                  15

Lys Lys Thr Val Tyr Leu Gln Met Asn Ser Leu Lys Ser Glu Asp Thr
            20                  25                  30

Ala Val Tyr Tyr Cys Ala Ala
        35

<210> SEQ ID NO 235
<211> LENGTH: 39
<212> TYPE: PRT
<213> ORGANISM: Artificial Sequence
<220> FEATURE:
<223> OTHER INFORMATION: FR3

<400> SEQUENCE: 235

Tyr Val Asp Ser Val Lys Gly Arg Phe Thr Ile Ser Arg Asp Asn Ala
1               5                   10                  15

Lys Asn Thr Val Tyr Leu Gln Met Ser Ser Leu Lys Ser Glu Asp Thr
            20                  25                  30

Ala Val Tyr Tyr Cys Ala Ala
        35

<210> SEQ ID NO 236
<211> LENGTH: 39
<212> TYPE: PRT
<213> ORGANISM: Artificial Sequence
<220> FEATURE:
<223> OTHER INFORMATION: FR3

<400> SEQUENCE: 236

Tyr Ala Asp Ser Val Lys Gly Arg Phe Thr Ile Ser Arg Asp Asn Ala
1               5                   10                  15

Lys His Thr Val Tyr Leu Gln Met Asn Ser Leu Lys Ser Glu Asp Thr
            20                  25                  30

Ala Val Tyr Tyr Cys Ala Ala
        35

<210> SEQ ID NO 237
<211> LENGTH: 39
<212> TYPE: PRT
<213> ORGANISM: Artificial Sequence
<220> FEATURE:
<223> OTHER INFORMATION: FR3

<400> SEQUENCE: 237

Tyr Val Asp Ser Val Lys Gly Arg Phe Ala Ile Ser Arg Asp Asn Ala
1               5                   10                  15

Lys Asn Thr Val His Leu Gln Met Asn Ser Leu Lys Ser Glu Asp Thr
            20                  25                  30

Ala Val Tyr Tyr Cys Ala Ala
        35

<210> SEQ ID NO 238
<211> LENGTH: 39
<212> TYPE: PRT
<213> ORGANISM: Artificial Sequence
<220> FEATURE:
<223> OTHER INFORMATION: FR3

<400> SEQUENCE: 238

Tyr Thr Asp Ser Val Lys Gly Arg Phe Thr Ile Ser Arg Asp Asn Ala
1               5                   10                  15

Lys Asn Thr Val Tyr Leu Gln Met Asn Ser Leu Lys Ser Glu Asp Thr
            20                  25                  30

Ala Val Tyr Tyr Cys Ala Ala
        35

<210> SEQ ID NO 239
<211> LENGTH: 39
<212> TYPE: PRT
<213> ORGANISM: Artificial Sequence
<220> FEATURE:
<223> OTHER INFORMATION: FR3

<400> SEQUENCE: 239

Tyr Thr Asp Ser Val Lys Gly Arg Phe Thr Ile Ser Arg Asp Asn Ala
1               5                   10                  15

Lys Asn Thr Val Cys Leu Gln Met Asn Ser Leu Lys Ser Glu Asp Thr
            20                  25                  30

Ala Val Tyr Tyr Cys Ala Ala
        35

<210> SEQ ID NO 240
<211> LENGTH: 39
<212> TYPE: PRT
<213> ORGANISM: Artificial Sequence
<220> FEATURE:
<223> OTHER INFORMATION: FR3

<400> SEQUENCE: 240

Ser Ala Asp Ser Val Lys Gly Arg Phe Thr Val Phe Arg Asp Asn Ala
1               5                   10                  15

Lys Asn Thr Val Tyr Leu Gln Met Asn Ser Leu Lys Ser Glu Asp Thr
            20                  25                  30

Ala Val Tyr Tyr Cys Ala Ala
        35

<210> SEQ ID NO 241
<211> LENGTH: 39
<212> TYPE: PRT
<213> ORGANISM: Artificial Sequence
<220> FEATURE:
<223> OTHER INFORMATION: FR3

<400> SEQUENCE: 241

Val Ala Asp Ser Val Lys Gly Arg Phe Thr Ile Ser Arg Asp Asn Ala
1               5                   10                  15

Lys Asn Thr Val Ser Leu Gln Met Asn Ser Leu Lys Ser Ala Asp Thr
            20                  25                  30

Ala Val Tyr Tyr Cys Ala Ala
        35

<210> SEQ ID NO 242
<211> LENGTH: 39
<212> TYPE: PRT
<213> ORGANISM: Artificial Sequence
<220> FEATURE:
<223> OTHER INFORMATION: FR3

<400> SEQUENCE: 242

Tyr Thr Asp Ser Val Lys Gly Arg Ala Thr Ile Ser Arg Asp Asn Ala
1               5                   10                  15

Lys Lys Thr Val Tyr Leu Gln Leu Asn Asn Leu Lys Ser Glu Asp Ala
            20                  25                  30

Ala Val Tyr Tyr Cys Ala Ala
        35

<210> SEQ ID NO 243
<211> LENGTH: 11

```
<212> TYPE: PRT
<213> ORGANISM: Artificial Sequence
<220> FEATURE:
<223> OTHER INFORMATION: FR4

<400> SEQUENCE: 243

Trp Gly Gln Gly Thr Gln Val Thr Val Ser Ser
1               5                   10

<210> SEQ ID NO 244
<211> LENGTH: 11
<212> TYPE: PRT
<213> ORGANISM: Artificial Sequence
<220> FEATURE:
<223> OTHER INFORMATION: FR4

<400> SEQUENCE: 244

Trp Gly Gln Gly Thr Leu Val Thr Val Ser Ser
1               5                   10

<210> SEQ ID NO 245
<211> LENGTH: 11
<212> TYPE: PRT
<213> ORGANISM: Artificial Sequence
<220> FEATURE:
<223> OTHER INFORMATION: FR4

<400> SEQUENCE: 245

Trp Gly Arg Gly Thr Leu Val Thr Val Ser Ser
1               5                   10

<210> SEQ ID NO 246
<211> LENGTH: 11
<212> TYPE: PRT
<213> ORGANISM: Artificial Sequence
<220> FEATURE:
<223> OTHER INFORMATION: FR4

<400> SEQUENCE: 246

Ser Gly Pro Gly Thr Gln Val Thr Val Ser Ser
1               5                   10

<210> SEQ ID NO 247
<211> LENGTH: 11
<212> TYPE: PRT
<213> ORGANISM: Artificial Sequence
<220> FEATURE:
<223> OTHER INFORMATION: FR4

<400> SEQUENCE: 247

Trp Gly Arg Gly Thr Gln Val Thr Val Ser Ser
1               5                   10

<210> SEQ ID NO 248
<211> LENGTH: 327
<212> TYPE: PRT
<213> ORGANISM: Artificial Sequence
<220> FEATURE:
<223> OTHER INFORMATION: Nanobody sequence

<400> SEQUENCE: 248

Glu Val Gln Leu Val Glu Ser Gly Gly Gly Leu Val Gln Gly Gly Gly
1               5                   10                  15

Ser Leu Ser Leu Ser Cys Ala Ala Ser Gly Arg Thr Phe Ser Ser Tyr
            20                  25                  30

Ala Met Ala Trp Phe Arg Gln Pro Pro Gly Lys Glu Arg Glu Phe Val
```

-continued

```
                35                  40                  45
Ala Ser Ile Ser Trp Ser Gly Glu Asn Thr Asn Tyr Arg Asn Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Lys Ile Ala Lys Thr Tyr Pro Asp Asn Trp Tyr Trp Thr Lys
                100                 105                 110

Ser Asn Asn Tyr Asn Tyr Trp Gly Gln Gly Thr Leu Val Thr Val Ser
                115                 120                 125

Ser Gly Gly Gly Ser Gly Gly Gly Ser Gly Gly Gly Gly Ser
    130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Leu Val
                165                 170                 175

Gln Gly Gly Gly Ser Leu Ser Leu Ser Cys Ala Ala Ser Gly Arg Thr
                180                 185                 190

Phe Ser Ser Tyr Ala Met Ala Trp Phe Arg Gln Pro Gly Lys Glu
                195                 200                 205

Arg Glu Phe Val Ala Ser Ile Ser Trp Ser Gly Glu Asn Thr Asn Tyr
210                 215                 220

Arg Asn Ser Val Lys Gly Arg Phe Thr Ile Ser Arg Asp Asn Ala Lys
225                 230                 235                 240

Asn Thr Val Tyr Leu Gln Met Asn Ser Leu Lys Pro Glu Asp Thr Ala
                245                 250                 255

Val Tyr Tyr Cys Ala Ala Lys Ile Ala Lys Thr Tyr Pro Asp Asn Trp
                260                 265                 270

Tyr Trp Thr Lys Ser Asn Asn Tyr Asn Tyr Trp Gly Gln Gly Thr Leu
                275                 280                 285

Val Thr Val Ser Ser Gly Ala Ala Asp Tyr Lys Asp His Asp Gly Asp
290                 295                 300

Tyr Lys Asp His Asp Ile Asp Tyr Lys Asp Asp Asp Lys Gly Ala
305                 310                 315                 320

Ala His His His His His His
                325
```

<210> SEQ ID NO 249
<211> LENGTH: 283
<212> TYPE: PRT
<213> ORGANISM: Artificial Sequence
<220> FEATURE:
<223> OTHER INFORMATION: Nanobody sequence

<400> SEQUENCE: 249

```
Glu Val Gln Leu Val Glu Ser Gly Gly Gly Leu Val Gln Pro Gly Gly
  1               5                  10                  15

Ser Leu Arg Leu Ser Cys Thr Phe Ser Gly Gly Thr Phe Ser Ser Tyr
                 20                  25                  30

Thr Met Gly Trp Phe Arg Gln Ala Pro Gly Lys Glu Arg Glu Phe Val
                 35                  40                  45

Ala Glu Val Arg Trp Gly Gly Val Thr Thr Tyr Ser Asn Ser Leu Lys
 50                  55                  60

Asp Arg Phe Ser Ile Ser Glu Asp Ser Val Lys Asn Ala Val Tyr Leu
```

```
                65                  70                  75                  80
        Gln Met Asn Ser Leu Lys Pro Glu Asp Thr Ala Val Tyr Tyr Cys Ala
                            85                  90                  95

Ala Val Arg Gln Met Tyr Met Thr Val Val Pro Asp Tyr Trp Gly Gln
                            100                 105                 110

Gly Thr Leu Val Thr Val Ser Gly Gly Gly Ser Glu Val Gln
                            115                 120             125

Leu Val Glu Ser Gly Gly Ser Val Gln Ala Gly Gly Ser Leu Arg
        130                     135                 140

Leu Ser Cys Ala Ala Ser Gly Arg Thr Phe Ser Thr Asn Pro Met Gly
        145                 150                  155                 160

Trp Phe Arg Gln Val Pro Gly Lys Glu Arg Glu Leu Ile Ala Ala Val
                            165                 170                 175

Arg Trp Ala Asp Gly Asn Thr Phe Tyr Ala Asp Ser Val Lys Gly Arg
                            180                 185                 190

Phe Thr Ile Ser Arg Asp Asn Ala Lys Lys Thr Val Tyr Leu Gln Met
                            195                 200                 205

Asn Ser Leu Lys Ser Glu Asp Thr Ala Thr Tyr Tyr Cys Ala Ala Gly
                210                     215                 220

Arg Pro Trp Ser Ala Tyr His Ser Pro Ala Glu Tyr Val His Trp Gly
        225                 230                  235                 240

Gln Gly Thr Leu Val Thr Val Ser Ser Gly Ala Ala Asp Tyr Lys Asp
                            245                 250                 255

His Asp Gly Asp Tyr Lys Asp His Asp Ile Asp Tyr Lys Asp Asp Asp
                            260                 265                 270

Asp Lys Gly Ala Ala His His His His His His
                    275                 280

<210> SEQ ID NO 250
<211> LENGTH: 288
<212> TYPE: PRT
<213> ORGANISM: Artificial Sequence
<220> FEATURE:
<223> OTHER INFORMATION: Nanobody sequence

<400> SEQUENCE: 250

Glu Val Gln Leu Val Glu Ser Gly Gly Gly Leu Val Gln Pro Gly Gly
        1               5                   10                  15

Ser Leu Arg Leu Ser Cys Thr Phe Ser Gly Gly Thr Phe Ser Ser Tyr
                        20                  25                  30

Thr Met Gly Trp Phe Arg Gln Ala Pro Gly Lys Glu Arg Glu Phe Val
                    35                  40                  45

Ala Glu Val Arg Trp Gly Gly Val Thr Thr Tyr Ser Asn Ser Leu Lys
        50                  55                  60

Asp Arg Phe Ser Ile Ser Glu Asp Ser Val Lys Asn Ala Val Tyr Leu
        65                  70                  75                  80

Gln Met Asn Ser Leu Lys Pro Glu Asp Thr Ala Val Tyr Tyr Cys Ala
                            85                  90                  95

Ala Val Arg Gln Met Tyr Met Thr Val Val Pro Asp Tyr Trp Gly Gln
                            100                 105                 110

Gly Thr Leu Val Thr Val Ser Ser Gly Gly Gly Ser Glu Val Gln
                            115                 120             125

Leu Val Glu Ser Gly Gly Gly Leu Val Gln Gly Gly Ser Leu Ser
        130                     135                 140

Leu Ser Cys Ala Ala Ser Gly Arg Thr Phe Ser Ser Tyr Ala Met Ala
```

```
                145                 150                 155                 160
Trp Phe Arg Gln Pro Pro Gly Lys Glu Arg Glu Phe Val Ala Ser Ile
                165                 170                 175

Ser Trp Ser Gly Glu Asn Thr Asn Tyr Arg Asn Ser Val Lys Gly Arg
                180                 185                 190

Phe Thr Ile Ser Arg Asp Asn Ala Lys Asn Thr Val Tyr Leu Gln Met
                195                 200                 205

Asn Ser Leu Lys Pro Glu Asp Thr Ala Val Tyr Tyr Cys Ala Ala Lys
        210                 215                 220

Ile Ala Lys Thr Tyr Pro Asp Asn Trp Tyr Trp Thr Lys Ser Asn Asn
225                 230                 235                 240

Tyr Asn Tyr Trp Gly Gln Gly Thr Leu Val Thr Val Ser Ser Gly Ala
                245                 250                 255

Ala Asp Tyr Lys Asp His Asp Gly Asp Tyr Lys Asp His Asp Ile Asp
                260                 265                 270

Tyr Lys Asp Asp Asp Lys Gly Ala Ala His His His His His His
        275                 280                 285
```

<210> SEQ ID NO 251
<211> LENGTH: 292
<212> TYPE: PRT
<213> ORGANISM: Artificial Sequence
<220> FEATURE:
<223> OTHER INFORMATION: Nanobody sequence

<400> SEQUENCE: 251

```
Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
                20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
        50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
                100                 105                 110

Gly Thr Leu Val Thr Val Ser Ser Gly Gly Gly Ser Asp Val Gln
            115                 120                 125

Leu Gln Ala Ser Gly Gly Gly Ser Val Gln Ala Gly Gly Ser Leu Arg
        130                 135                 140

Leu Ser Cys Ala Ala Ser Gly Tyr Thr Ile Gly Pro Tyr Cys Met Gly
145                 150                 155                 160

Trp Phe Arg Gln Ala Pro Gly Lys Glu Arg Glu Gly Val Ala Ala Ile
                165                 170                 175

Asn Met Gly Gly Gly Ile Thr Tyr Tyr Ala Asp Ser Val Lys Gly Arg
                180                 185                 190

Phe Thr Ile Ser Gln Asp Asn Ala Lys Asn Thr Val Tyr Leu Leu Met
                195                 200                 205

Asn Ser Leu Glu Pro Glu Asp Thr Ala Ile Tyr Tyr Cys Ala Ala Asp
        210                 215                 220

Ser Thr Ile Tyr Ala Ser Tyr Tyr Glu Cys Gly His Gly Leu Ser Thr
```

```
                        225                 230                 235                 240
Gly Gly Tyr Gly Tyr Asp Ser Trp Gly Gln Gly Thr Gln Val Thr Val
                245                 250                 255

Ser Ser Gly Ala Ala Asp Tyr Lys Asp His Asp Gly Asp Tyr Lys Asp
                260                 265                 270

His Asp Ile Asp Tyr Lys Asp Asp Asp Lys Gly Ala Ala His His
                275                 280                 285

His His His His
        290

<210> SEQ ID NO 252
<211> LENGTH: 287
<212> TYPE: PRT
<213> ORGANISM: Artificial Sequence
<220> FEATURE:
<223> OTHER INFORMATION: Nanobody sequence

<400> SEQUENCE: 252

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Ser Glu Val Gln Leu Val Glu Ser Gly Gly Ser Val Gln Ala Gly
    130                 135                 140

Gly Ser Leu Arg Leu Ser Cys Ala Ala Ser Gly Arg Thr Phe Ser Thr
145                 150                 155                 160

Asn Pro Met Gly Trp Phe Arg Gln Val Pro Gly Lys Glu Arg Glu Leu
                165                 170                 175

Ile Ala Ala Val Arg Trp Ala Asp Gly Asn Thr Phe Tyr Ala Asp Ser
            180                 185                 190

Val Lys Gly Arg Phe Thr Ile Ser Arg Asp Asn Ala Lys Lys Thr Val
        195                 200                 205

Tyr Leu Gln Met Asn Ser Leu Lys Ser Glu Asp Thr Ala Thr Tyr Tyr
    210                 215                 220

Cys Ala Ala Gly Arg Pro Trp Ser Ala Tyr His Ser Pro Ala Glu Tyr
225                 230                 235                 240

Val His Trp Gly Gln Gly Thr Leu Val Thr Val Ser Ser Gly Ala Ala
                245                 250                 255

Asp Tyr Lys Asp His Asp Gly Asp Tyr Lys Asp His Asp Ile Asp Tyr
            260                 265                 270

Lys Asp Asp Asp Lys Gly Ala Ala His His His His His His
        275                 280                 285
```

```
<210> SEQ ID NO 253
<211> LENGTH: 292
<212> TYPE: PRT
<213> ORGANISM: Artificial Sequence
<220> FEATURE:
<223> OTHER INFORMATION: Nanobody sequence

<400> SEQUENCE: 253

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Ser Glu Val Gln Leu Val Glu Ser Gly Gly Gly Leu Val Gln Gly Gly
        130                 135                 140

Gly Ser Leu Ser Leu Ser Cys Ala Ala Ser Gly Arg Thr Phe Ser Ser
145                 150                 155                 160

Tyr Ala Met Ala Trp Phe Arg Gln Pro Pro Gly Lys Glu Arg Glu Phe
                165                 170                 175

Val Ala Ser Ile Ser Trp Ser Gly Glu Asn Thr Asn Tyr Arg Asn Ser
            180                 185                 190

Val Lys Gly Arg Phe Thr Ile Ser Arg Asp Asn Ala Lys Asn Thr Val
        195                 200                 205

Tyr Leu Gln Met Asn Ser Leu Lys Pro Glu Asp Thr Ala Val Tyr Tyr
    210                 215                 220

Cys Ala Ala Lys Ile Ala Lys Thr Tyr Pro Asp Asn Trp Tyr Trp Thr
225                 230                 235                 240

Lys Ser Asn Asn Tyr Asn Tyr Trp Gly Gln Gly Thr Leu Val Thr Val
                245                 250                 255

Ser Ser Gly Ala Ala Asp Tyr Lys Asp His Asp Gly Asp Tyr Lys Asp
            260                 265                 270

His Asp Ile Asp Tyr Lys Asp Asp Asp Lys Gly Ala Ala His His
        275                 280                 285

His His His His
    290

<210> SEQ ID NO 254
<211> LENGTH: 296
<212> TYPE: PRT
<213> ORGANISM: Artificial Sequence
<220> FEATURE:
<223> OTHER INFORMATION: Nanobody sequence

<400> SEQUENCE: 254

Glu Val Gln Leu Val Glu Ser Gly Gly Gly Leu Val Gln Pro Gly Gly
1               5                   10                  15
```

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
        50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
            115                 120                 125

Ser Asp Val Gln Leu Gln Ala Ser Gly Gly Gly Ser Val Gln Ala Gly
            130                 135                 140

Gly Ser Leu Arg Leu Ser Cys Ala Ala Ser Gly Tyr Thr Ile Gly Pro
145                 150                 155                 160

Tyr Cys Met Gly Trp Phe Arg Gln Ala Pro Gly Lys Glu Arg Glu Gly
                165                 170                 175

Val Ala Ala Ile Asn Met Gly Gly Ile Thr Tyr Tyr Ala Asp Ser
            180                 185                 190

Val Lys Gly Arg Phe Thr Ile Ser Gln Asp Asn Ala Lys Asn Thr Val
            195                 200                 205

Tyr Leu Leu Met Asn Ser Leu Glu Pro Glu Asp Thr Ala Ile Tyr Tyr
        210                 215                 220

Cys Ala Ala Asp Ser Thr Ile Tyr Ala Ser Tyr Glu Cys Gly His
225                 230                 235                 240

Gly Leu Ser Thr Gly Gly Tyr Gly Tyr Asp Ser Trp Gly Gln Gly Thr
                245                 250                 255

Gln Val Thr Val Ser Ser Gly Ala Ala Asp Tyr Lys Asp His Asp Gly
            260                 265                 270

Asp Tyr Lys Asp His Asp Ile Asp Tyr Lys Asp Asp Asp Asp Lys Gly
            275                 280                 285

Ala Ala His His His His His His
    290                 295

<210> SEQ ID NO 255
<211> LENGTH: 313
<212> TYPE: PRT
<213> ORGANISM: Artificial Sequence
<220> FEATURE:
<223> OTHER INFORMATION: Nanobody sequence

<400> SEQUENCE: 255

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
        50                  55                  60

Asp Arg Phe Ser Ile Ser Glu Asp Ser Val Lys Asn Ala Val Tyr Leu
65                  70                  75                  80

```
Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Ser Val Gln Ala Gly Gly Ser Leu Arg Leu Ser
                165                 170                 175

Cys Ala Ala Ser Gly Arg Thr Phe Ser Thr Asn Pro Met Gly Trp Phe
            180                 185                 190

Arg Gln Val Pro Gly Lys Glu Arg Glu Leu Ile Ala Ala Val Arg Trp
            195                 200                 205

Ala Asp Gly Asn Thr Phe Tyr Ala Asp Ser Val Lys Gly Arg Phe Thr
            210                 215                 220

Ile Ser Arg Asp Asn Ala Lys Lys Thr Val Tyr Leu Gln Met Asn Ser
225                 230                 235                 240

Leu Lys Ser Glu Asp Thr Ala Thr Tyr Tyr Cys Ala Ala Gly Arg Pro
                245                 250                 255

Trp Ser Ala Tyr His Ser Pro Ala Glu Tyr Val His Trp Gly Gln Gly
            260                 265                 270

Thr Leu Val Thr Val Ser Ser Gly Ala Ala Asp Tyr Lys Asp His Asp
            275                 280                 285

Gly Asp Tyr Lys Asp His Asp Ile Asp Tyr Lys Asp Asp Asp Asp Lys
            290                 295                 300

Gly Ala Ala His His His His His His
305                 310

<210> SEQ ID NO 256
<211> LENGTH: 318
<212> TYPE: PRT
<213> ORGANISM: Artificial Sequence
<220> FEATURE:
<223> OTHER INFORMATION: Nanobody sequence

<400> SEQUENCE: 256

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125
```

```
Gly Ser Gly Gly Gly Gly Ser Gly Gly Gly Ser Gly Gly Gly Gly
        130                 135                 140

Ser Gly Gly Gly Ser Gly Gly Gly Ser Glu Val Gln Leu Val
145                 150                 155                 160

Glu Ser Gly Gly Gly Leu Val Gln Gly Gly Ser Leu Ser Leu Ser
                    165                 170                 175

Cys Ala Ala Ser Gly Arg Thr Phe Ser Ser Tyr Ala Met Ala Trp Phe
                180                 185                 190

Arg Gln Pro Pro Gly Lys Glu Arg Glu Phe Val Ala Ser Ile Ser Trp
            195                 200                 205

Ser Gly Glu Asn Thr Asn Tyr Arg Asn Ser Val Lys Gly Arg Phe Thr
        210                 215                 220

Ile Ser Arg Asp Asn Ala Lys Asn Thr Val Tyr Leu Gln Met Asn Ser
225                 230                 235                 240

Leu Lys Pro Glu Asp Thr Ala Val Tyr Tyr Cys Ala Ala Lys Ile Ala
                245                 250                 255

Lys Thr Tyr Pro Asp Asn Trp Tyr Trp Thr Lys Ser Asn Asn Tyr Asn
                260                 265                 270

Tyr Trp Gly Gln Gly Thr Leu Val Thr Val Ser Ser Gly Ala Ala Asp
            275                 280                 285

Tyr Lys Asp His Asp Gly Asp Tyr Lys Asp His Asp Ile Asp Tyr Lys
        290                 295                 300

Asp Asp Asp Asp Lys Gly Ala Ala His His His His His His
305                 310                 315
```

<210> SEQ ID NO 257
<211> LENGTH: 322
<212> TYPE: PRT
<213> ORGANISM: Artificial Sequence
<220> FEATURE:
<223> OTHER INFORMATION: Nanobody sequence

<400> SEQUENCE: 257

```
Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Gly Gly Gly Gly Ser Gly Gly Gly Ser Asp Val Gln Leu Gln
145                 150                 155                 160

Ala Ser Gly Gly Gly Ser Val Gln Ala Gly Gly Ser Leu Arg Leu Ser
                165                 170                 175
```

```
Cys Ala Ala Ser Gly Tyr Thr Ile Gly Pro Tyr Cys Met Gly Trp Phe
                180                 185                 190

Arg Gln Ala Pro Gly Lys Glu Arg Glu Gly Val Ala Ala Ile Asn Met
            195                 200                 205

Gly Gly Gly Ile Thr Tyr Tyr Ala Asp Ser Val Lys Gly Arg Phe Thr
        210                 215                 220

Ile Ser Gln Asp Asn Ala Lys Asn Thr Val Tyr Leu Leu Met Asn Ser
225                 230                 235                 240

Leu Glu Pro Glu Asp Thr Ala Ile Tyr Tyr Cys Ala Ala Asp Ser Thr
                245                 250                 255

Ile Tyr Ala Ser Tyr Tyr Glu Cys Gly His Gly Leu Ser Thr Gly Gly
            260                 265                 270

Tyr Gly Tyr Asp Ser Trp Gly Gln Gly Thr Gln Val Thr Val Ser Ser
        275                 280                 285

Gly Ala Ala Asp Tyr Lys Asp His Asp Gly Asp Tyr Lys Asp His Asp
    290                 295                 300

Ile Asp Tyr Lys Asp Asp Asp Lys Gly Ala Ala His His His His
305                 310                 315                 320

His His

<210> SEQ ID NO 258
<211> LENGTH: 287
<212> TYPE: PRT
<213> ORGANISM: Artificial Sequence
<220> FEATURE:
<223> OTHER INFORMATION: Nanobody sequence

<400> SEQUENCE: 258

Glu Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Phe Ser Thr Asn
                20                  25                  30

Pro Met Gly Trp Phe Arg Gln Val Pro Gly Lys Glu Arg Glu Leu Ile
            35                  40                  45

Ala Ala Val Arg Trp Ala Asp Gly Asn Thr Phe Tyr Ala Asp Ser Val
        50                  55                  60

Lys Gly Arg Phe Thr Ile Ser Arg Asp Asn Ala Lys Lys Thr Val Tyr
65                  70                  75                  80

Leu Gln Met Asn Ser Leu Lys Ser Glu Asp Thr Ala Thr Tyr Tyr Cys
                85                  90                  95

Ala Ala Gly Arg Pro Trp Ser Ala Tyr His Ser Pro Ala Glu Tyr Val
            100                 105                 110

His Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Gly Ser Leu Arg Leu Ser Cys Thr Phe Ser Gly Gly
145                 150                 155                 160

Thr Phe Ser Ser Tyr Thr Met Gly Trp Phe Arg Gln Ala Pro Gly Lys
                165                 170                 175

Glu Arg Glu Phe Val Ala Glu Val Arg Trp Gly Gly Val Thr Thr Tyr
            180                 185                 190

Ser Asn Ser Leu Lys Asp Arg Phe Ser Ile Ser Glu Asp Ser Val Lys
        195                 200                 205

Asn Ala Val Tyr Leu Gln Met Asn Ser Leu Lys Pro Glu Asp Thr Ala
```

```
                210                 215                 220
Val Tyr Tyr Cys Ala Ala Val Arg Gln Met Tyr Met Thr Val Val Pro
225                 230                 235                 240

Asp Tyr Trp Gly Gln Gly Thr Leu Val Thr Val Ser Ser Gly Ala Ala
                245                 250                 255

Asp Tyr Lys Asp His Asp Gly Asp Tyr Lys Asp His Asp Ile Asp Tyr
                260                 265                 270

Lys Asp Asp Asp Asp Lys Gly Ala Ala His His His His His His
                275                 280                 285

<210> SEQ ID NO 259
<211> LENGTH: 313
<212> TYPE: PRT
<213> ORGANISM: Artificial Sequence
<220> FEATURE:
<223> OTHER INFORMATION: Nanobody sequence

<400> SEQUENCE: 259

Glu Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Phe Ser Thr Asn
                20                  25                  30

Pro Met Gly Trp Phe Arg Gln Val Pro Gly Lys Glu Arg Glu Leu Ile
                35                  40                  45

Ala Ala Val Arg Trp Ala Asp Gly Asn Thr Phe Tyr Ala Asp Ser Val
            50                  55                  60

Lys Gly Arg Phe Thr Ile Ser Arg Asp Asn Ala Lys Lys Thr Val Tyr
65                  70                  75                  80

Leu Gln Met Asn Ser Leu Lys Ser Glu Asp Thr Ala Thr Tyr Tyr Cys
                85                  90                  95

Ala Ala Gly Arg Pro Trp Ser Ala Tyr His Ser Pro Ala Glu Tyr Val
                100                 105                 110

His Trp Gly Gln Gly Thr Leu Val Thr Val Ser Ser Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Thr Phe Ser Gly Gly Thr Phe Ser Ser Tyr Thr
                180                 185                 190

Met Gly Trp Phe Arg Gln Ala Pro Gly Lys Glu Arg Glu Phe Val Ala
            195                 200                 205

Glu Val Arg Trp Gly Gly Val Thr Thr Tyr Ser Asn Ser Leu Lys Asp
        210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Val Pro Asp Tyr Trp Gly Gln Gly
                260                 265                 270

Thr Leu Val Thr Val Ser Ser Gly Ala Ala Asp Tyr Lys Asp His Asp
                275                 280                 285

Gly Asp Tyr Lys Asp His Asp Ile Asp Tyr Lys Asp Asp Asp Asp Lys
```

Gly Ala Ala His His His His His
305            310

<210> SEQ ID NO 260
<211> LENGTH: 318
<212> TYPE: PRT
<213> ORGANISM: Artificial Sequence
<220> FEATURE:
<223> OTHER INFORMATION: Nanobody sequence

<400> SEQUENCE: 260

Glu Val Gln Leu Val Glu Ser Gly Gly Gly Leu Val Gln Gly Gly Gly
1               5                   10                  15

Ser Leu Ser Leu Ser Cys Ala Ala Ser Gly Arg Thr Phe Ser Ser Tyr
            20                  25                  30

Ala Met Ala Trp Phe Arg Gln Pro Pro Gly Lys Glu Arg Glu Phe Val
        35                  40                  45

Ala Ser Ile Ser Trp Ser Gly Glu Asn Thr Asn Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Lys Ile Ala Lys Thr Tyr Pro Asp Asn Trp Tyr Trp Thr Lys
            100                 105                 110

Ser Asn Asn Tyr Asn Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Gly Leu Val
                165                 170                 175

Gln Pro Gly Gly Ser Leu Arg Leu Ser Cys Thr Phe Ser Gly Gly Thr
            180                 185                 190

Phe Ser Ser Tyr Thr Met Gly Trp Phe Arg Gln Ala Pro Gly Lys Glu
        195                 200                 205

Arg Glu Phe Val Ala Glu Val Arg Trp Gly Gly Val Thr Thr Tyr Ser
    210                 215                 220

Asn Ser Leu Lys Asp Arg Phe Ser Ile Ser Glu Asp Ser Val Lys Asn
225                 230                 235                 240

Ala Val Tyr Leu Gln Met Asn Ser Leu Lys Pro Glu Asp Thr Ala Val
                245                 250                 255

Tyr Tyr Cys Ala Ala Val Arg Gln Met Tyr Met Thr Val Val Pro Asp
            260                 265                 270

Tyr Trp Gly Gln Gly Thr Leu Val Thr Val Ser Ser Gly Ala Ala Asp
        275                 280                 285

Tyr Lys Asp His Asp Gly Asp Tyr Lys Asp His Asp Ile Asp Tyr Lys
    290                 295                 300

Asp Asp Asp Asp Lys Gly Ala Ala His His His His His His
305                 310                 315

<210> SEQ ID NO 261
<211> LENGTH: 322
<212> TYPE: PRT

<213> ORGANISM: Artificial Sequence
<220> FEATURE:
<223> OTHER INFORMATION: Nanobody sequence

<400> SEQUENCE: 261

Glu Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65              70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
        115                 120                 125

Val Thr Val Ser Ser Gly Gly Gly Ser Gly Gly Gly Ser Gly
130                 135                 140

Gly Gly Gly Ser Gly Gly Gly Gly Ser Gly Gly Gly Gly Ser Gly Gly
145                 150                 155                 160

Gly Gly Ser Gly Gly Gly Ser Glu Val Gln Leu Val Glu Ser Gly
                165                 170                 175

Gly Gly Leu Val Gln Pro Gly Gly Ser Leu Arg Leu Ser Cys Thr Phe
            180                 185                 190

Ser Gly Gly Thr Phe Ser Ser Tyr Thr Met Gly Trp Phe Arg Gln Ala
        195                 200                 205

Pro Gly Lys Glu Arg Glu Phe Val Ala Glu Val Arg Trp Gly Gly Val
        210                 215                 220

Thr Thr Tyr Ser Asn Ser Leu Lys Asp Arg Phe Ser Ile Ser Glu Asp
225                 230                 235                 240

Ser Val Lys Asn Ala Val Tyr Leu Gln Met Asn Ser Leu Lys Pro Glu
                245                 250                 255

Asp Thr Ala Val Tyr Tyr Cys Ala Ala Val Arg Gln Met Tyr Met Thr
            260                 265                 270

Val Val Pro Asp Tyr Trp Gly Gln Gly Thr Leu Val Thr Val Ser Ser
        275                 280                 285

Gly Ala Ala Asp Tyr Lys Asp His Asp Gly Asp Tyr Lys Asp His Asp
    290                 295                 300

Ile Asp Tyr Lys Asp Asp Asp Lys Gly Ala Ala His His His His
305                 310                 315                 320

His His

<210> SEQ ID NO 262
<211> LENGTH: 326
<212> TYPE: PRT
<213> ORGANISM: Artificial Sequence
<220> FEATURE:
<223> OTHER INFORMATION: Nanobody sequence

<400> SEQUENCE: 262

Glu Val Gln Leu Val Glu Ser Gly Gly Gly Ser Val Gln Ala Gly Gly

```
              1               5                  10                 15
            Ser Leu Arg Leu Ser Cys Ala Ala Ser Gly Arg Thr Phe Ser Thr Asn
                           20                 25                 30
            Pro Met Gly Trp Phe Arg Gln Val Pro Gly Lys Glu Arg Glu Leu Ile
                           35                 40                 45
            Ala Ala Val Arg Trp Ala Asp Gly Asn Thr Phe Tyr Ala Asp Ser Val
                           50                 55                 60
            Lys Gly Arg Phe Thr Ile Ser Arg Asp Asn Ala Lys Lys Thr Val Tyr
             65                 70                 75                 80
            Leu Gln Met Asn Ser Leu Lys Ser Glu Asp Thr Ala Thr Tyr Tyr Cys
                           85                 90                 95
            Ala Ala Gly Arg Pro Trp Ser Ala Tyr His Ser Pro Ala Glu Tyr Val
                           100                105                110
            His Trp Gly Gln Gly Thr Leu Val Thr Val Ser Ser Gly Gly Gly Gly
                           115                120                125
            Ser Gly Gly Gly Gly Ser Gly Gly Gly Ser Gly Gly Gly Gly Ser
                           130                135                140
            Gly Gly Gly Gly Ser Gly Gly Gly Ser Gly Gly Gly Gly Ser Asp
             145                150                155                160
            Val Gln Leu Gln Ala Ser Gly Gly Ser Val Gln Ala Gly Ser
                           165                170                175
            Leu Arg Leu Ser Cys Ala Ala Ser Gly Tyr Thr Ile Gly Pro Tyr Cys
                           180                185                190
            Met Gly Trp Phe Arg Gln Ala Pro Gly Lys Glu Arg Glu Gly Val Ala
                           195                200                205
            Ala Ile Asn Met Gly Gly Gly Ile Thr Tyr Tyr Ala Asp Ser Val Lys
                           210                215                220
            Gly Arg Phe Thr Ile Ser Gln Asp Asn Ala Lys Asn Thr Val Tyr Leu
             225                230                235                240
            Leu Met Asn Ser Leu Glu Pro Glu Asp Thr Ala Ile Tyr Tyr Cys Ala
                           245                250                255
            Ala Asp Ser Thr Ile Tyr Ala Ser Tyr Tyr Glu Cys Gly His Gly Leu
                           260                265                270
            Ser Thr Gly Gly Tyr Gly Tyr Asp Ser Trp Gly Gln Gly Thr Gln Val
                           275                280                285
            Thr Val Ser Ser Gly Ala Ala Asp Tyr Lys Asp His Asp Gly Asp Tyr
                           290                295                300
            Lys Asp His Asp Ile Asp Tyr Lys Asp Asp Asp Lys Gly Ala Ala
             305                310                315                320
            His His His His His His
                           325

<210> SEQ ID NO 263
<211> LENGTH: 292
<212> TYPE: PRT
<213> ORGANISM: Artificial Sequence
<220> FEATURE:
<223> OTHER INFORMATION: Nanobody sequence

<400> SEQUENCE: 263

Glu Val Gln Leu Val Glu Ser Gly Gly Gly Leu Val Gln Gly Gly Gly
             1                  5                 10                 15
            Ser Leu Ser Leu Ser Cys Ala Ala Ser Gly Arg Thr Phe Ser Ser Tyr
                           20                 25                 30
            Ala Met Ala Trp Phe Arg Gln Pro Pro Gly Lys Glu Arg Glu Phe Val
```

```
              35                  40                  45
Ala Ser Ile Ser Trp Ser Gly Glu Asn Thr Asn Tyr Arg Asn Ser Val
 50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Glu Asp Thr Ala Val Tyr Tyr Cys
                 85                  90                  95
Ala Ala Lys Ile Ala Lys Thr Tyr Pro Asp Asn Trp Tyr Trp Thr Lys
                100                 105                 110
Ser Asn Asn Tyr Asn Tyr Trp Gly Gln Gly Thr Leu Val Thr Val Ser
                115                 120                 125
Ser Gly Gly Gly Gly Ser Gly Gly Gly Ser Glu Val Gln Leu Val Glu
130                 135                 140
Ser Gly Gly Gly Leu Val Gln Pro Gly Gly Ser Leu Arg Leu Ser Cys
145                 150                 155                 160
Thr Phe Ser Gly Gly Thr Phe Ser Ser Tyr Thr Met Gly Trp Phe Arg
                165                 170                 175
Gln Ala Pro Gly Lys Glu Arg Glu Phe Val Ala Glu Val Arg Trp Gly
                180                 185                 190
Gly Val Thr Thr Tyr Ser Asn Ser Leu Lys Asp Arg Phe Ser Ile Ser
                195                 200                 205
Glu Asp Ser Val Lys Asn Ala Val Tyr Leu Gln Met Asn Ser Leu Lys
210                 215                 220
Pro Glu Asp Thr Ala Val Tyr Tyr Cys Ala Ala Val Arg Gln Met Tyr
225                 230                 235                 240
Met Thr Val Val Pro Asp Tyr Trp Gly Gln Gly Thr Leu Val Thr Val
                245                 250                 255
Ser Ser Gly Ala Ala Asp Tyr Lys Asp His Asp Gly Asp Tyr Lys Asp
                260                 265                 270
His Asp Ile Asp Tyr Lys Asp Asp Asp Lys Gly Ala Ala His His
                275                 280                 285
His His His His
    290

<210> SEQ ID NO 264
<211> LENGTH: 331
<212> TYPE: PRT
<213> ORGANISM: Artificial Sequence
<220> FEATURE:
<223> OTHER INFORMATION: Nanobody sequence

<400> SEQUENCE: 264

Glu Val Gln Leu Val Glu Ser Gly Gly Gly Leu Val Gln Gly Gly Gly
 1                   5                  10                  15
Ser Leu Ser Leu Ser Cys Ala Ala Ser Gly Arg Thr Phe Ser Ser Tyr
                 20                  25                  30
Ala Met Ala Trp Phe Arg Gln Pro Pro Gly Lys Glu Arg Glu Phe Val
                 35                  40                  45
Ala Ser Ile Ser Trp Ser Gly Glu Asn Thr Asn Tyr Arg Asn Ser Val
 50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Glu Asp Thr Ala Val Tyr Tyr Cys
                 85                  90                  95
Ala Ala Lys Ile Ala Lys Thr Tyr Pro Asp Asn Trp Tyr Trp Thr Lys
```

```
                100               105              110
Ser Asn Asn Tyr Asn Tyr Trp Gly Gln Gly Thr Leu Val Thr Val Ser
            115                 120             125
Ser Gly Gly Gly Gly Ser Gly Gly Gly Ser Gly Gly Gly Gly Ser
        130             135             140
Gly Gly Gly Ser Gly Gly Gly Ser Gly Gly Gly Ser Gly
145             150             155             160
Gly Gly Gly Ser Asp Val Gln Leu Gln Ala Ser Gly Gly Ser Val
                165             170             175
Gln Ala Gly Gly Ser Leu Arg Leu Ser Cys Ala Ala Ser Gly Tyr Thr
            180             185             190
Ile Gly Pro Tyr Cys Met Gly Trp Phe Arg Gln Ala Pro Gly Lys Glu
        195             200             205
Arg Glu Gly Val Ala Ala Ile Asn Met Gly Gly Ile Thr Tyr Tyr
    210             215             220
Ala Asp Ser Val Lys Gly Arg Phe Thr Ile Ser Gln Asp Asn Ala Lys
225             230             235             240
Asn Thr Val Tyr Leu Leu Met Asn Ser Leu Glu Pro Glu Asp Thr Ala
            245             250             255
Ile Tyr Tyr Cys Ala Ala Asp Ser Thr Ile Tyr Ala Ser Tyr Tyr Glu
        260             265             270
Cys Gly His Gly Leu Ser Thr Gly Gly Tyr Gly Tyr Asp Ser Trp Gly
            275             280             285
Gln Gly Thr Gln Val Thr Val Ser Ser Gly Ala Ala Asp Tyr Lys Asp
            290             295             300
His Asp Gly Asp Tyr Lys Asp His Asp Ile Asp Tyr Lys Asp Asp Asp
305             310             315             320
Asp Lys Gly Ala Ala His His His His His His
            325             330
```

<210> SEQ ID NO 265
<211> LENGTH: 313
<212> TYPE: PRT
<213> ORGANISM: Artificial Sequence
<220> FEATURE:
<223> OTHER INFORMATION: Nanobody sequence

<400> SEQUENCE: 265

```
Glu Val Gln Leu Val Glu Ser Gly Gly Gly Pro Val Gln Ala Gly Gly
1               5                   10                  15
Ser Leu Arg Leu Ser Cys Ala Ala Ser Gly Arg Thr Phe Arg Gly Tyr
            20                  25                  30
Ser Met Ala Trp Phe Arg Gln Pro Pro Gly Lys Glu Arg Glu Phe Val
        35                  40                  45
Ala Ala Ile Thr Trp Ser Gly Asn Thr Tyr Tyr Glu Asp Phe Val
    50                  55                  60
Lys Gly Arg Phe Thr Ile Ser Arg Asp Asn Ala Lys Asn Thr Leu Tyr
65                  70                  75                  80
Leu Gln Met Thr Ser Leu Lys Pro Glu Asp Thr Ala Leu Tyr Tyr Cys
            85                  90                  95
Ala Ala Lys Ile Arg Pro Tyr Ile Phe Lys Ile Ala Gly Gln Tyr Asp
            100                 105                 110
Tyr Trp Gly Gln Gly Thr Leu Val Thr Val Ser Ser Gly Gly Gly Gly
            115                 120                 125
Ser Gly Gly Gly Gly Ser Gly Gly Gly Gly Ser Gly Gly Gly Gly Ser
```

```
                130             135             140
Gly Gly Gly Gly Ser Gly Gly Gly Ser Gly Gly Gly Ser Glu
145             150             155             160

Val Gln Leu Val Glu Ser Gly Gly Leu Val Gln Pro Gly Ser
                165             170             175

Leu Arg Leu Ser Cys Thr Phe Ser Gly Thr Phe Ser Ser Tyr Thr
                180             185             190

Met Gly Trp Phe Arg Gln Ala Pro Gly Lys Glu Arg Glu Phe Val Ala
            195             200             205

Glu Val Arg Trp Gly Gly Val Thr Thr Tyr Ser Asn Ser Leu Lys Asp
        210             215             220

Arg Phe Ser Ile Ser Glu Asp Ser Val Lys Asn Ala Val Tyr Leu Gln
225             230             235             240

Met Asn Ser Leu Lys Pro Glu Asp Thr Ala Val Tyr Tyr Cys Ala Ala
                245             250             255

Val Arg Gln Met Tyr Met Thr Val Val Pro Asp Tyr Trp Gly Gln Gly
                260             265             270

Thr Leu Val Thr Val Ser Ser Gly Ala Ala Asp Tyr Lys Asp His Asp
                275             280             285

Gly Asp Tyr Lys Asp His Asp Ile Asp Tyr Lys Asp Asp Asp Lys
                290             295             300

Gly Ala Ala His His His His His His
305             310

<210> SEQ ID NO 266
<211> LENGTH: 313
<212> TYPE: PRT
<213> ORGANISM: Artificial Sequence
<220> FEATURE:
<223> OTHER INFORMATION: Nanobody sequence

<400> SEQUENCE: 266

Glu Val Gln Leu Val Glu Ser Gly Gly Pro Val Gln Ala Gly Gly
1               5               10              15

Ser Leu Arg Leu Ser Cys Ala Ala Ser Gly Arg Thr Tyr Arg Gly Tyr
                20              25              30

Ser Met Gly Trp Phe Arg Gln Ala Pro Gly Lys Glu Arg Glu Phe Val
            35              40              45

Ala Ala Ile Val Trp Ser Gly Gly Asn Thr Tyr Tyr Glu Asp Ser Val
50              55              60

Lys Gly Arg Phe Thr Ile Ser Arg Asp Asn Ala Lys Asn Thr Met Tyr
65              70              75              80

Leu Gln Met Thr Ser Leu Lys Pro Glu Asp Ser Ala Thr Tyr Tyr Cys
                85              90              95

Ala Ala Lys Ile Arg Pro Tyr Ile Phe Lys Ile Ala Gly Gln Tyr Asp
                100             105             110

Tyr Trp Gly Gln Gly Thr Leu Val Thr Val Ser Ser Gly Gly Gly Gly
            115             120             125

Ser Gly Gly Gly Gly Ser Gly Gly Gly Gly Ser Gly Gly Gly Ser
        130             135             140

Gly Gly Gly Gly Ser Gly Gly Gly Ser Gly Gly Gly Ser Glu
145             150             155             160

Val Gln Leu Val Glu Ser Gly Gly Leu Val Gln Pro Gly Ser
                165             170             175

Leu Arg Leu Ser Cys Thr Phe Ser Gly Gly Thr Phe Ser Ser Tyr Thr
```

```
                    180                 185                 190
Met Gly Trp Phe Arg Gln Ala Pro Gly Lys Glu Arg Glu Phe Val Ala
                195                 200                 205
Glu Val Arg Trp Gly Gly Val Thr Thr Tyr Ser Asn Ser Leu Lys Asp
            210                 215                 220
Arg Phe Ser Ile Ser Glu Asp Ser Val Lys Asn Ala Val Tyr Leu Gln
225                 230                 235                 240
Met Asn Ser Leu Lys Pro Glu Asp Thr Ala Val Tyr Tyr Cys Ala Ala
                245                 250                 255
Val Arg Gln Met Tyr Met Thr Val Pro Asp Tyr Trp Gly Gln Gly
            260                 265                 270
Thr Leu Val Thr Val Ser Ser Gly Ala Ala Asp Tyr Lys Asp His Asp
            275                 280                 285
Gly Asp Tyr Lys Asp His Asp Ile Asp Tyr Lys Asp Asp Asp Lys
            290                 295                 300
Gly Ala Ala His His His His His His
305                 310
```

<210> SEQ ID NO 267
<211> LENGTH: 313
<212> TYPE: PRT
<213> ORGANISM: Artificial Sequence
<220> FEATURE:
<223> OTHER INFORMATION: Nanobody sequence

<400> SEQUENCE: 267

```
Glu Val Gln Leu Val Glu Ser Gly Gly Pro Val Gln Ala Gly Gly
1               5                   10                  15
Ser Leu Arg Leu Ser Cys Ala Ala Ser Gly Arg Thr Tyr Arg Gly Tyr
            20                  25                  30
Ser Met Ala Trp Phe Arg Gln Ser Pro Gly Lys Glu Arg Glu Phe Val
            35                  40                  45
Ala Ala Ile Val Trp Ser Asp Gly Asn Thr Tyr Tyr Glu Asp Phe Val
        50                  55                  60
Lys Gly Arg Phe Thr Ile Ser Arg Asp Ser Ala Lys Asn Thr Leu Tyr
65                  70                  75                  80
Leu Gln Met Thr Asn Leu Lys Pro Glu Asp Thr Ala Leu Tyr Tyr Cys
                85                  90                  95
Ala Ala Lys Ile Arg Pro Tyr Ile Phe Lys Ile Ala Gly Gln Tyr Asp
                100                 105                 110
Tyr Trp Gly Gln Gly Thr Leu Val Thr Val Ser Ser Gly Gly Gly Gly
            115                 120                 125
Ser Gly Gly Gly Gly Ser Gly Gly Gly Ser Gly Gly Gly Gly Ser
            130                 135                 140
Gly Gly Gly Gly Ser Gly Gly Gly Ser Gly Gly Gly Gly Ser Glu
145                 150                 155                 160
Val Gln Leu Val Glu Ser Gly Gly Gly Leu Val Gln Pro Gly Gly Ser
                165                 170                 175
Leu Arg Leu Ser Cys Thr Phe Ser Gly Gly Thr Phe Ser Ser Tyr Thr
            180                 185                 190
Met Gly Trp Phe Arg Gln Ala Pro Gly Lys Glu Arg Glu Phe Val Ala
                195                 200                 205
Glu Val Arg Trp Gly Gly Val Thr Thr Tyr Ser Asn Ser Leu Lys Asp
            210                 215                 220
Arg Phe Ser Ile Ser Glu Asp Ser Val Lys Asn Ala Val Tyr Leu Gln
```

```
                225                 230                 235                 240
Met Asn Ser Leu Lys Pro Glu Asp Thr Ala Val Tyr Tyr Cys Ala Ala
                    245                 250                 255

Val Arg Gln Met Tyr Met Thr Val Val Pro Asp Tyr Trp Gly Gln Gly
                260                 265                 270

Thr Leu Val Thr Val Ser Ser Gly Ala Ala Asp Tyr Lys Asp His Asp
                275                 280                 285

Gly Asp Tyr Lys Asp His Asp Ile Asp Tyr Lys Asp Asp Asp Asp Lys
                290                 295                 300

Gly Ala Ala His His His His His His
305                 310

<210> SEQ ID NO 268
<211> LENGTH: 309
<212> TYPE: PRT
<213> ORGANISM: Artificial Sequence
<220> FEATURE:
<223> OTHER INFORMATION: Nanobody sequence

<400> SEQUENCE: 268

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Ile Tyr Lys Ser Phe
                20                  25                  30

Asp Met Gly Trp Tyr Arg Gln Ala Pro Gly Lys Gln Arg Asp Leu Val
                35                  40                  45

Ala Val Ile Gly Ser Arg Gly Asn Asn Arg Gly Arg Thr Asn Tyr Ala
                50                  55                  60

Asp Ser Val Lys Gly Arg Phe Thr Ile Ser Arg Asp Gly Thr Gly Asn
65                  70                  75                  80

Thr Val Tyr Leu Leu Met Asn Lys Leu Arg Pro Glu Asp Thr Ala Ile
                85                  90                  95

Tyr Tyr Cys Asn Thr Ala Pro Leu Val Ala Gly Arg Pro Trp Gly Arg
                100                 105                 110

Gly Thr Leu Val Thr Val Ser Ser Gly Gly Gly Gly Ser Gly Gly Gly
                115                 120                 125

Gly Ser Gly Gly Gly Gly Ser Gly Gly Gly Ser Gly Gly Gly Gly
                130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Thr Phe Ser Gly Gly Thr Phe Ser Ser Tyr Thr Met Gly Trp Phe
                180                 185                 190

Arg Gln Ala Pro Gly Lys Glu Arg Glu Phe Val Ala Glu Val Arg Trp
                195                 200                 205

Gly Gly Val Thr Thr Tyr Ser Asn Ser Leu Lys Asp Arg Phe Ser Ile
                210                 215                 220

Ser Glu Asp Ser Val Lys Asn Ala Val Tyr Leu Gln Met Asn Ser Leu
225                 230                 235                 240

Lys Pro Glu Asp Thr Ala Val Tyr Tyr Cys Ala Ala Val Arg Gln Met
                245                 250                 255

Tyr Met Thr Val Val Pro Asp Tyr Trp Gly Gln Gly Thr Leu Val Thr
                260                 265                 270

Val Ser Ser Gly Ala Ala Asp Tyr Lys Asp His Asp Gly Asp Tyr Lys
```

```
            275                 280                 285
Asp His Asp Ile Asp Tyr Lys Asp Asp Asp Lys Gly Ala Ala His
    290                 295                 300

His His His His His
305

<210> SEQ ID NO 269
<211> LENGTH: 313
<212> TYPE: PRT
<213> ORGANISM: Artificial Sequence
<220> FEATURE:
<223> OTHER INFORMATION: Nanobody sequence

<400> SEQUENCE: 269

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Asn Met Asn
            20                  25                  30

Pro Leu Gly Trp Phe Arg Gln Ser Pro Gly Lys Glu Arg Glu Phe Val
        35                  40                  45

Ala Ala His Arg Trp Ser Asp Gly Asn Thr Tyr Tyr Val Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Ala Phe Arg Ser Pro Gly Glu Tyr Val
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Thr Phe Ser Gly Thr Phe Ser Ser Tyr Thr
            180                 185                 190

Met Gly Trp Phe Arg Gln Ala Pro Gly Lys Glu Arg Glu Phe Val Ala
        195                 200                 205

Glu Val Arg Trp Gly Gly Val Thr Thr Tyr Ser Asn Ser Leu Lys Asp
    210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Val Pro Asp Tyr Trp Gly Gln Gly
            260                 265                 270

Thr Leu Val Thr Val Ser Ser Gly Ala Ala Asp Tyr Lys Asp His Asp
        275                 280                 285

Gly Asp Tyr Lys Asp His Asp Ile Asp Tyr Lys Asp Asp Asp Asp Lys
    290                 295                 300

Gly Ala Ala His His His His His His
305                 310
```

-continued

<210> SEQ ID NO 270
<211> LENGTH: 313
<212> TYPE: PRT
<213> ORGANISM: Artificial Sequence
<220> FEATURE:
<223> OTHER INFORMATION: Nanobody sequence

<400> SEQUENCE: 270

Glu Val Gln Leu Val Glu Ser Gly Gly Gly Val Gln Ala Gly Gly
1               5                  10                  15

Ser Leu Arg Leu Ser Cys Ala Ala Ser Gly Arg Thr Phe Ser Thr Asn
            20                  25                  30

Pro Met Gly Trp Phe Arg Gln Val Pro Gly Lys Glu Arg Glu Leu Ile
        35                  40                  45

Ala Ala Val Arg Trp Ala Asp Gly Asn Thr Phe Tyr Ala Asp Ser Val
50                  55                  60

Lys Gly Arg Phe Thr Ile Ser Arg Asp Asn Ala Lys Lys Thr Val Tyr
65                  70                  75                  80

Leu Gln Met Asn Ser Leu Lys Ser Glu Asp Thr Ala Thr Tyr Tyr Cys
                85                  90                  95

Ala Ala Gly Arg Pro Trp Ser Ala Tyr His Ser Pro Ala Glu Tyr Val
            100                 105                 110

His Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Leu Val Gln Pro Gly Gly Ser
                165                 170                 175

Leu Arg Leu Ser Cys Thr Phe Ser Gly Gly Thr Phe Ser Ser Tyr Thr
            180                 185                 190

Met Gly Trp Phe Arg Gln Ala Pro Gly Lys Glu Arg Glu Phe Val Ala
        195                 200                 205

Glu Val Arg Trp Gly Gly Val Thr Thr Tyr Ser Asn Ser Leu Lys Asp
    210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Pro Asp Tyr Trp Gly Gln Gly
            260                 265                 270

Thr Leu Val Thr Val Ser Ser Gly Ala Ala Asp Tyr Lys Asp His Asp
        275                 280                 285

Gly Asp Tyr Lys Asp His Asp Ile Asp Tyr Lys Asp Asp Asp Lys
    290                 295                 300

Gly Ala Ala His His His His His His
305                 310

<210> SEQ ID NO 271
<211> LENGTH: 318
<212> TYPE: PRT
<213> ORGANISM: Artificial Sequence
<220> FEATURE:
<223> OTHER INFORMATION: Nanobody sequence

<400> SEQUENCE: 271

```
Glu Val Gln Leu Val Glu Ser Gly Gly Gly Leu Val Gln Gly Gly Gly
1               5                   10                  15

Ser Leu Ser Leu Ser Cys Ala Ala Ser Gly Arg Thr Phe Ser Ser Tyr
            20                  25                  30

Ala Met Ala Trp Phe Arg Gln Pro Pro Gly Lys Glu Arg Glu Phe Val
        35                  40                  45

Ala Ser Ile Ser Trp Ser Gly Glu Asn Thr Asn Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Lys Ile Ala Lys Thr Tyr Pro Asp Asn Trp Tyr Trp Thr Lys
            100                 105                 110

Ser Asn Asn Tyr Asn Tyr Trp Gly Gln Gly Thr Leu Val Thr Val Ser
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Gly Leu Val
            165                 170                 175

Gln Pro Gly Gly Ser Leu Arg Leu Ser Cys Thr Phe Ser Gly Gly Thr
            180                 185                 190

Phe Ser Ser Tyr Thr Met Gly Trp Phe Arg Gln Ala Pro Gly Lys Glu
            195                 200                 205

Arg Glu Phe Val Ala Glu Val Arg Trp Gly Val Thr Thr Tyr Ser
210                 215                 220

Asn Ser Leu Lys Asp Arg Phe Ser Ile Ser Glu Asp Ser Val Lys Asn
225                 230                 235                 240

Ala Val Tyr Leu Gln Met Asn Ser Leu Lys Pro Glu Asp Thr Ala Val
            245                 250                 255

Tyr Tyr Cys Ala Ala Val Arg Gln Met Tyr Met Thr Val Val Pro Asp
            260                 265                 270

Tyr Trp Gly Gln Gly Thr Leu Val Thr Val Ser Ser Gly Ala Ala Asp
    275                 280                 285

Tyr Lys Asp His Asp Gly Asp Tyr Lys Asp His Asp Ile Asp Tyr Lys
            290                 295                 300

Asp Asp Asp Asp Lys Gly Ala Ala His His His His His His
305                 310                 315

<210> SEQ ID NO 272
<211> LENGTH: 303
<212> TYPE: PRT
<213> ORGANISM: Artificial Sequence
<220> FEATURE:
<223> OTHER INFORMATION: Nanobody sequence

<400> SEQUENCE: 272

Glu Val Gln Leu Val Glu Ser Gly Gly Gly Ala Val Gln Pro Gly Gly
1               5                   10                  15

Ser Leu Arg Leu Ser Cys Ala Ala Ser Gly Ile Arg Ile Ser Arg Asn
            20                  25                  30

Met Met Gly Trp Phe Arg Gln Ala Pro Gly Lys Gln Arg Asp Leu Val
        35                  40                  45
```

```
Ala Arg Ile Thr Pro Gly Gly Asp Thr Tyr Tyr Val Asp Ser Val Lys
 50                  55                  60

Gly Arg Phe Ser Ile Ser Lys Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ser Tyr Ser Thr Leu Gly Ser Trp Gly Gln Gly Thr Leu Val Thr Val
                100                 105                 110

Ser Ser Gly Gly Gly Gly Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Ser Glu Val Gln Leu Val Glu Ser Gly Gly Gly Leu
145                 150                 155                 160

Val Gln Pro Gly Gly Ser Leu Arg Leu Ser Cys Thr Phe Ser Gly Gly
                165                 170                 175

Thr Phe Ser Ser Tyr Thr Met Gly Trp Phe Arg Gln Ala Pro Gly Lys
                180                 185                 190

Glu Arg Glu Phe Val Ala Glu Val Arg Trp Gly Gly Val Thr Thr Tyr
                195                 200                 205

Ser Asn Ser Leu Lys Asp Arg Phe Ser Ile Ser Glu Asp Ser Val Lys
 210                 215                 220

Asn Ala Val Tyr Leu Gln Met Asn Ser Leu Lys Pro Glu Asp Thr Ala
225                 230                 235                 240

Val Tyr Tyr Cys Ala Ala Val Arg Gln Met Tyr Met Thr Val Val Pro
                245                 250                 255

Asp Tyr Trp Gly Gln Gly Thr Leu Val Thr Val Ser Ser Gly Ala Ala
                260                 265                 270

Asp Tyr Lys Asp His Asp Gly Asp Tyr Lys Asp His Asp Ile Asp Tyr
                275                 280                 285

Lys Asp Asp Asp Asp Lys Gly Ala Ala His His His His His His
290                 295                 300
```

<210> SEQ ID NO 273
<211> LENGTH: 313
<212> TYPE: PRT
<213> ORGANISM: Artificial Sequence
<220> FEATURE:
<223> OTHER INFORMATION: Nanobody sequence

<400> SEQUENCE: 273

```
Glu Val Gln Leu Val Glu Ser Gly Gly Gly Leu Val Gln Pro Gly Gly
 1               5                  10                  15

Ser Leu Arg Leu Ser Cys Thr Phe Ser Gly Gly Thr Phe Ser Ser Tyr
                 20                  25                  30

Thr Met Gly Trp Phe Arg Gln Ala Pro Gly Lys Glu Arg Glu Phe Val
             35                  40                  45

Ala Glu Val Arg Trp Gly Gly Val Thr Thr Tyr Ser Asn Ser Leu Lys
     50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                 85                  90                  95

Ala Val Arg Gln Met Tyr Met Thr Val Val Pro Asp Tyr Trp Gly Gln
             100                 105                 110
```

Gly Thr Leu Val Thr Val Ser Ser Gly Gly Gly Ser Gly Gly
            115                 120                 125

Gly Ser Gly Gly Gly Ser Gly Gly Gly Ser Gly Gly Gly
        130                 135                 140

Ser Gly Gly Gly Ser Gly Gly Gly Ser Glu Val Gln Leu Val
145                 150                 155                 160

Glu Ser Gly Gly Gly Pro Val Gln Ala Gly Ser Leu Arg Leu Ser
                165                 170                 175

Cys Ala Ala Ser Gly Arg Thr Tyr Arg Gly Tyr Ser Met Ala Trp Phe
            180                 185                 190

Arg Gln Ser Pro Gly Lys Glu Arg Glu Phe Val Ala Ala Ile Val Trp
        195                 200                 205

Ser Asp Gly Asn Thr Tyr Tyr Glu Asp Phe Val Lys Gly Arg Phe Thr
    210                 215                 220

Ile Ser Arg Asp Ser Ala Lys Asn Thr Leu Tyr Leu Gln Met Thr Asn
225                 230                 235                 240

Leu Lys Pro Glu Asp Thr Ala Leu Tyr Tyr Cys Ala Ala Lys Ile Arg
                245                 250                 255

Pro Tyr Ile Phe Lys Ile Ala Gly Gln Tyr Asp Tyr Trp Gly Gln Gly
            260                 265                 270

Thr Leu Val Thr Val Ser Ser Gly Ala Ala Asp Tyr Lys Asp His Asp
        275                 280                 285

Gly Asp Tyr Lys Asp His Asp Ile Asp Tyr Lys Asp Asp Asp Lys
    290                 295                 300

Gly Ala Ala His His His His His His
305                 310

<210> SEQ ID NO 274
<211> LENGTH: 309
<212> TYPE: PRT
<213> ORGANISM: Artificial Sequence
<220> FEATURE:
<223> OTHER INFORMATION: Nanobody sequence

<400> SEQUENCE: 274

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

```
Glu Ser Gly Gly Gly Leu Val Gln Pro Gly Gly Ser Leu Arg Leu Ser
                165                 170                 175

Cys Ala Ala Ser Gly Asp Ile Tyr Lys Ser Phe Asp Met Gly Trp Tyr
            180                 185                 190

Arg Gln Ala Pro Gly Lys Gln Arg Asp Leu Val Ala Val Ile Gly Ser
        195                 200                 205

Arg Gly Asn Asn Arg Gly Arg Thr Asn Tyr Ala Asp Ser Val Lys Gly
    210                 215                 220

Arg Phe Thr Ile Ser Arg Asp Gly Thr Gly Asn Thr Val Tyr Leu Leu
225                 230                 235                 240

Met Asn Lys Leu Arg Pro Glu Asp Thr Ala Ile Tyr Tyr Cys Asn Thr
            245                 250                 255

Ala Pro Leu Val Ala Gly Arg Pro Trp Gly Arg Gly Thr Leu Val Thr
        260                 265                 270

Val Ser Ser Gly Ala Ala Asp Tyr Lys Asp His Asp Gly Asp Tyr Lys
    275                 280                 285

Asp His Asp Ile Asp Tyr Lys Asp Asp Asp Lys Gly Ala Ala His
290                 295                 300

His His His His His
305

<210> SEQ ID NO 275
<211> LENGTH: 303
<212> TYPE: PRT
<213> ORGANISM: Artificial Sequence
<220> FEATURE:
<223> OTHER INFORMATION: Nanobody sequence

<400> SEQUENCE: 275

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
        100                 105                 110

Gly Thr Leu Val Thr Val Ser Ser Gly Gly Gly Gly Ser Gly Gly Gly
    115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Ala Val Gln Pro Gly Gly Ser Leu Arg Leu Ser
                165                 170                 175

Cys Ala Ala Ser Gly Ile Arg Ile Ser Arg Asn Met Met Gly Trp Phe
            180                 185                 190

Arg Gln Ala Pro Gly Lys Gln Arg Asp Leu Val Ala Arg Ile Thr Pro
        195                 200                 205
```

Gly Gly Asp Thr Tyr Tyr Val Asp Ser Val Lys Gly Arg Phe Ser Ile
    210             215                 220

Ser Lys Asp Asn Ala Lys Asn Thr Val Tyr Leu Gln Met Asn Ser Leu
225             230                 235                 240

Lys Pro Glu Asp Thr Ala Val Tyr Tyr Cys Asn Ser Tyr Ser Thr Leu
            245                 250                 255

Gly Ser Trp Gly Gln Gly Thr Leu Val Thr Val Ser Ser Gly Ala Ala
            260                 265                 270

Asp Tyr Lys Asp His Asp Gly Asp Tyr Lys Asp His Asp Ile Asp Tyr
        275                 280                 285

Lys Asp Asp Asp Lys Gly Ala Ala His His His His His His
290                 295                 300

<210> SEQ ID NO 276
<211> LENGTH: 313
<212> TYPE: PRT
<213> ORGANISM: Artificial Sequence
<220> FEATURE:
<223> OTHER INFORMATION: Nanobody sequence

<400> SEQUENCE: 276

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Gly Gly Gly Ser Gly Gly Gly
        130                 135                 140

Ser Gly Gly Gly Ser Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

Cys Ala Ala Ser Gly Arg Ser Phe Asn Met Asn Pro Leu Gly Trp Phe
            180                 185                 190

Arg Gln Ser Pro Gly Lys Glu Arg Glu Phe Val Ala Ala His Arg Trp
        195                 200                 205

Ser Asp Gly Asn Thr Tyr Tyr Val Asp Ser Val Lys Gly Arg Phe Thr
    210                 215                 220

Ile Ser Arg Asp Asn Ala Lys Asn Thr Val Tyr Leu Gln Met Asn Ser
225                 230                 235                 240

Leu Lys Ser Glu Asp Thr Ala Val Tyr Tyr Cys Ala Ala Gly Arg Pro
                245                 250                 255

Trp Ser Ala Phe Arg Ser Pro Gly Glu Tyr Val Tyr Trp Gly Gln Gly
            260                 265                 270

```
Thr Leu Val Thr Val Ser Ser Gly Ala Ala Asp Tyr Lys Asp His Asp
            275                 280                 285

Gly Asp Tyr Lys Asp His Asp Ile Asp Tyr Lys Asp Asp Asp Asp Lys
            290                 295                 300

Gly Ala Ala His His His His His His
305                 310

<210> SEQ ID NO 277
<211> LENGTH: 313
<212> TYPE: PRT
<213> ORGANISM: Artificial Sequence
<220> FEATURE:
<223> OTHER INFORMATION: Nanobody sequence

<400> SEQUENCE: 277

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Gly Gly Gly Gly
            130                 135                 140

Ser Gly Gly Gly Gly Ser Gly Gly Gly Gly Ser Glu Val Gln Leu Val
145                 150                 155                 160

Glu Ser Gly Gly Gly Ser Val Gln Ala Gly Gly Ser Leu Arg Leu Ser
            165                 170                 175

Cys Ala Ala Ser Gly Arg Thr Phe Ser Thr Asn Pro Met Gly Trp Phe
            180                 185                 190

Arg Gln Val Pro Gly Lys Glu Arg Glu Leu Ile Ala Ala Val Arg Trp
            195                 200                 205

Ala Asp Gly Asn Thr Phe Tyr Ala Asp Ser Val Lys Gly Arg Phe Thr
            210                 215                 220

Ile Ser Arg Asp Asn Ala Lys Lys Thr Val Tyr Leu Gln Met Asn Ser
225                 230                 235                 240

Leu Lys Ser Glu Asp Thr Ala Thr Tyr Tyr Cys Ala Ala Gly Arg Pro
            245                 250                 255

Trp Ser Ala Tyr His Ser Pro Ala Glu Tyr Val His Trp Gly Gln Gly
            260                 265                 270

Thr Leu Val Thr Val Ser Ser Gly Ala Ala Asp Tyr Lys Asp His Asp
            275                 280                 285

Gly Asp Tyr Lys Asp His Asp Ile Asp Tyr Lys Asp Asp Asp Asp Lys
            290                 295                 300

Gly Ala Ala His His His His His His
305                 310
```

<210> SEQ ID NO 278
<211> LENGTH: 318
<212> TYPE: PRT
<213> ORGANISM: Artificial Sequence
<220> FEATURE:
<223> OTHER INFORMATION: Nanobody sequence

<400> SEQUENCE: 278

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Leu Val Gln Gly Gly Ser Leu Ser Leu Ser
                165                 170                 175

Cys Ala Ala Ser Gly Arg Thr Phe Ser Ser Tyr Ala Met Ala Trp Phe
            180                 185                 190

Arg Gln Pro Pro Gly Lys Glu Arg Glu Phe Val Ala Ser Ile Ser Trp
        195                 200                 205

Ser Gly Glu Asn Thr Asn Tyr Arg Asn Ser Val Lys Gly Arg Phe Thr
    210                 215                 220

Ile Ser Arg Asp Asn Ala Lys Asn Thr Val Tyr Leu Gln Met Asn Ser
225                 230                 235                 240

Leu Lys Pro Glu Asp Thr Ala Val Tyr Tyr Cys Ala Ala Lys Ile Ala
                245                 250                 255

Lys Thr Tyr Pro Asp Asn Trp Tyr Trp Thr Lys Ser Asn Asn Tyr Asn
            260                 265                 270

Tyr Trp Gly Gln Gly Thr Leu Val Thr Val Ser Ser Gly Ala Ala Asp
        275                 280                 285

Tyr Lys Asp His Asp Gly Asp Tyr Lys Asp His Asp Ile Asp Tyr Lys
    290                 295                 300

Asp Asp Asp Asp Lys Gly Ala Ala His His His His His
305                 310                 315

<210> SEQ ID NO 279
<211> LENGTH: 313
<212> TYPE: PRT
<213> ORGANISM: Artificial Sequence
<220> FEATURE:
<223> OTHER INFORMATION: Nanobody sequence

<400> SEQUENCE: 279

```
Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

Glu Ser Gly Gly Gly Pro Val Gln Ala Gly Gly Ser Leu Arg Leu Ser
                165                 170                 175

Cys Ala Ala Ser Gly Arg Thr Tyr Arg Gly Tyr Ser Met Gly Trp Phe
            180                 185                 190

Arg Gln Ala Pro Gly Lys Glu Arg Glu Phe Val Ala Ala Ile Val Trp
            195                 200                 205

Ser Gly Gly Asn Thr Tyr Tyr Glu Asp Ser Val Lys Gly Arg Phe Thr
        210                 215                 220

Ile Ser Arg Asp Asn Ala Lys Asn Thr Met Tyr Leu Gln Met Thr Ser
225                 230                 235                 240

Leu Lys Pro Glu Asp Ser Ala Thr Tyr Tyr Cys Ala Ala Lys Ile Arg
                245                 250                 255

Pro Tyr Ile Phe Lys Ile Ala Gly Gln Tyr Asp Tyr Trp Gly Gln Gly
            260                 265                 270

Thr Leu Val Thr Val Ser Ser Gly Ala Ala Asp Tyr Lys Asp His Asp
        275                 280                 285

Gly Asp Tyr Lys Asp His Asp Ile Asp Tyr Lys Asp Asp Asp Lys
    290                 295                 300

Gly Ala Ala His His His His His His
305                 310

<210> SEQ ID NO 280
<211> LENGTH: 313
<212> TYPE: PRT
<213> ORGANISM: Artificial Sequence
<220> FEATURE:
<223> OTHER INFORMATION: Nanobody sequence

<400> SEQUENCE: 280

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45
```

Ala Glu Val Arg Trp Gly Gly Val Thr Thr Tyr Ser Asn Ser Leu Lys
            50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Gly Gly Gly Ser Gly Gly Gly
            130                 135                 140

Ser Gly Gly Gly Ser Gly Gly Gly Ser Glu Val Gln Leu Val
145                 150                 155                 160

Glu Ser Gly Gly Gly Leu Val Gln Thr Gly Gly Ser Leu Arg Leu Ser
                165                 170                 175

Cys Val Ala Ser Gly Arg Thr Tyr Arg Gly Tyr Ser Met Ala Trp Phe
            180                 185                 190

Arg Gln Pro Pro Gly Lys Glu Arg Glu Phe Val Ala Ala Ile Thr Trp
            195                 200                 205

Ser Glu Gly Asn Thr Tyr Tyr Glu Asp Phe Val Lys Gly Arg Phe Thr
210                 215                 220

Ile Ser Arg Asp Asn Ala Lys Asn Thr Leu Tyr Leu Gln Met Thr Ser
225                 230                 235                 240

Leu Lys Pro Glu Asp Thr Ala Leu Tyr Tyr Cys Ala Ala Lys Ile Arg
                245                 250                 255

Pro Tyr Ile Phe Lys Ile Pro Gly Gln Tyr Asp Tyr Trp Gly Gln Gly
            260                 265                 270

Thr Leu Val Thr Val Ser Ser Gly Ala Ala Asp Tyr Lys Asp His Asp
            275                 280                 285

Gly Asp Tyr Lys Asp His Asp Ile Asp Tyr Lys Asp Asp Asp Asp Lys
            290                 295                 300

Gly Ala Ala His His His His His His
305                 310

<210> SEQ ID NO 281
<211> LENGTH: 313
<212> TYPE: PRT
<213> ORGANISM: Artificial Sequence
<220> FEATURE:
<223> OTHER INFORMATION: Nanobody sequence

<400> SEQUENCE: 281

Glu Val Gln Leu Val Glu Ser Gly Gly Gly Leu Val Gln Pro Gly Gly
 1               5                  10                  15

Ser Leu Arg Leu Ser Cys Thr Phe Ser Gly Gly Thr Phe Ser Ser Tyr
                20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
            50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                85                  90                  95

```
Ala Val Arg Gln Met Tyr Met Thr Val Val Pro Asp Tyr Trp Gly Gln
            100                 105                 110

Gly Thr Leu Val Thr Val Ser Gly Gly Gly Ser Gly Gly Gly
            115                 120                 125

Gly Ser Gly Gly Gly Ser Gly Gly Gly Ser Gly Gly Gly Gly
    130                 135                 140

Ser Gly Gly Gly Ser Gly Gly Gly Ser Glu Val Gln Leu Val
145                 150                 155                 160

Glu Ser Gly Gly Gly Pro Val Gln Ala Gly Gly Ser Leu Arg Leu Ser
                165                 170                 175

Cys Ala Ala Ser Gly Arg Thr Phe Arg Gly Tyr Ser Met Ala Trp Phe
                180                 185                 190

Arg Gln Pro Pro Gly Lys Glu Arg Glu Phe Val Ala Ala Ile Thr Trp
            195                 200                 205

Ser Glu Gly Asn Thr Tyr Tyr Glu Asp Phe Val Lys Gly Arg Phe Thr
    210                 215                 220

Ile Ser Arg Asp Asn Ala Lys Asn Thr Leu Tyr Leu Gln Met Thr Ser
225                 230                 235                 240

Leu Lys Pro Glu Asp Thr Ala Leu Tyr Tyr Cys Ala Ala Lys Ile Arg
                245                 250                 255

Pro Tyr Ile Phe Lys Ile Ala Gly Gln Tyr Asp Tyr Trp Gly Gln Gly
            260                 265                 270

Thr Leu Val Thr Val Ser Ser Gly Ala Ala Tyr Lys Asp His Asp
    275                 280                 285

Gly Asp Tyr Lys Asp His Asp Ile Asp Tyr Lys Asp Asp Asp Lys
    290                 295                 300

Gly Ala Ala His His His His His His
305                 310

<210> SEQ ID NO 282
<211> LENGTH: 313
<212> TYPE: PRT
<213> ORGANISM: Artificial Sequence
<220> FEATURE:
<223> OTHER INFORMATION: Nanobody sequence

<400> SEQUENCE: 282

Glu Val Gln Leu Val Glu Ser Gly Gly Gly Leu Val Gln Thr Gly Gly
1               5                   10                  15

Ser Leu Arg Leu Ser Cys Val Ala Ser Gly Arg Thr Tyr Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Glu Gly Asn Thr Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Pro Glu Asp Thr Ala Leu Tyr Tyr Cys
                85                  90                  95

Ala Ala Lys Ile Arg Pro Tyr Ile Phe Lys Ile Pro Gly Gln Tyr Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140
```

Gly Gly Gly Gly Ser Gly Gly Gly Ser Gly Gly Gly Ser Glu
145                 150                 155                 160

Val Gln Leu Val Glu Ser Gly Gly Leu Val Gln Pro Gly Gly Ser
            165                 170                 175

Leu Arg Leu Ser Cys Thr Phe Ser Gly Gly Thr Phe Ser Ser Tyr Thr
            180                 185                 190

Met Gly Trp Phe Arg Gln Ala Pro Gly Lys Glu Arg Glu Phe Val Ala
        195                 200                 205

Glu Val Arg Trp Gly Gly Val Thr Thr Tyr Ser Asn Ser Leu Lys Asp
210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Val Pro Asp Tyr Trp Gly Gln Gly
            260                 265                 270

Thr Leu Val Thr Val Ser Ser Gly Ala Ala Asp Tyr Lys Asp His Asp
            275                 280                 285

Gly Asp Tyr Lys Asp His Asp Ile Asp Tyr Lys Asp Asp Asp Asp Lys
        290                 295                 300

Gly Ala Ala His His His His His His
305                 310

<210> SEQ ID NO 283
<211> LENGTH: 280
<212> TYPE: PRT
<213> ORGANISM: Artificial Sequence
<220> FEATURE:
<223> OTHER INFORMATION: Nanobody sequence

<400> SEQUENCE: 283

Asp Val Gln Leu Val Glu Ser Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Pro Val Gln Ala Gly Gly Ser Leu Arg Leu Ser
                165                 170                 175

Cys Ala Ala Ser Gly Arg Thr Tyr Arg Gly Tyr Ser Met Gly Trp Phe
            180                 185                 190

```
Arg Gln Ala Pro Gly Lys Glu Arg Glu Phe Val Ala Ile Val Trp
    195                 200                 205

Ser Gly Gly Asn Thr Tyr Tyr Glu Asp Ser Val Lys Gly Arg Phe Thr
210                 215                 220

Ile Ser Arg Asp Asn Ala Lys Asn Thr Met Tyr Leu Gln Met Thr Ser
225                 230                 235                 240

Leu Lys Pro Glu Asp Ser Ala Thr Tyr Tyr Cys Ala Ala Lys Ile Arg
                245                 250                 255

Pro Tyr Ile Phe Lys Ile Ala Gly Gln Tyr Asp Tyr Trp Gly Gln Gly
                260                 265                 270

Thr Leu Val Thr Val Ser Ser Ala
            275                 280

<210> SEQ ID NO 284
<211> LENGTH: 320
<212> TYPE: PRT
<213> ORGANISM: Artificial Sequence
<220> FEATURE:
<223> OTHER INFORMATION: Nanobody sequence

<400> SEQUENCE: 284

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45

Ala Ala Ile Ser Trp Ser Asp Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Gly Gly Gly Ser Gly Gly
    130                 135                 140

Gly Gly Ser Gly Gly Gly Gly Ser Gly Gly Gly Ser Gly Gly Gly
145                 150                 155                 160

Gly Ser Glu Val Gln Leu Val Glu Ser Gly Gly Pro Val Gln Ala
                165                 170                 175

Gly Gly Ser Leu Arg Leu Ser Cys Ala Ala Ser Gly Arg Thr Tyr Arg
            180                 185                 190

Gly Tyr Ser Met Ala Trp Phe Arg Gln Ser Pro Gly Lys Glu Arg Glu
        195                 200                 205

Phe Val Ala Ala Ile Val Trp Ser Asp Gly Asn Thr Tyr Tyr Glu Asp
    210                 215                 220

Phe Val Lys Gly Arg Phe Thr Ile Ser Arg Asp Ser Ala Lys Asn Thr
225                 230                 235                 240

Leu Tyr Leu Gln Met Thr Asn Leu Lys Pro Glu Asp Thr Ala Leu Tyr
                245                 250                 255

Tyr Cys Ala Ala Lys Ile Arg Pro Tyr Ile Phe Lys Ile Ala Gly Gln
            260                 265                 270
```

Tyr Asp Tyr Trp Gly Gln Gly Thr Leu Val Thr Val Ser Ser Gly Ala
            275                 280                 285

Ala Asp Tyr Lys Asp His Asp Gly Asp Tyr Lys Asp His Asp Ile Asp
290                 295                 300

Tyr Lys Asp Asp Asp Asp Lys Gly Ala Ala His His His His His His
305                 310                 315                 320

<210> SEQ ID NO 285
<211> LENGTH: 320
<212> TYPE: PRT
<213> ORGANISM: Artificial Sequence
<220> FEATURE:
<223> OTHER INFORMATION: Nanobody sequence

<400> SEQUENCE: 285

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Asp Leu Thr Ser Thr Asn Pro Gly Ser Tyr Ile Tyr Ile Trp
        100                 105                 110

Ala Tyr Asp Tyr Trp Gly Gln Gly Thr Gln Val Thr Val Ser Ser Gly
    115                 120                 125

Gly Gly Gly Ser Gly Gly Gly Gly Ser Gly Gly Gly Gly Ser Gly Gly
130                 135                 140

Gly Gly Ser Gly Gly Gly Gly Ser Gly Gly Gly Gly Ser Gly Gly Gly
145                 150                 155                 160

Gly Ser Glu Val Gln Leu Val Glu Ser Gly Gly Gly Pro Val Gln Ala
            165                 170                 175

Gly Gly Ser Leu Arg Leu Ser Cys Ala Ala Ser Gly Arg Thr Tyr Arg
        180                 185                 190

Gly Tyr Ser Met Gly Trp Phe Arg Gln Ala Pro Gly Lys Glu Arg Glu
    195                 200                 205

Phe Val Ala Ala Ile Val Trp Ser Gly Gly Asn Thr Tyr Tyr Glu Asp
210                 215                 220

Ser Val Lys Gly Arg Phe Thr Ile Ser Arg Asp Asn Ala Lys Asn Thr
225                 230                 235                 240

Met Tyr Leu Gln Met Thr Ser Leu Lys Pro Glu Asp Ser Ala Thr Tyr
            245                 250                 255

Tyr Cys Ala Ala Lys Ile Arg Pro Tyr Ile Phe Lys Ile Ala Gly Gln
        260                 265                 270

Tyr Asp Tyr Trp Gly Gln Gly Thr Leu Val Thr Val Ser Ser Gly Ala
    275                 280                 285

Ala Asp Tyr Lys Asp His Asp Gly Asp Tyr Lys Asp His Asp Ile Asp
290                 295                 300

Tyr Lys Asp Asp Asp Asp Lys Gly Ala Ala His His His His His His
305                 310                 315                 320

<210> SEQ ID NO 286
<211> LENGTH: 463
<212> TYPE: PRT
<213> ORGANISM: Artificial Sequence
<220> FEATURE:
<223> OTHER INFORMATION: Nanobody sequence

<400> SEQUENCE: 286

```
Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Pro Val Gln Ala Gly Gly Ser Leu Arg Leu Ser
                165                 170                 175

Cys Ala Ala Ser Gly Arg Thr Tyr Arg Gly Tyr Ser Met Gly Trp Phe
            180                 185                 190

Arg Gln Ala Pro Gly Lys Glu Arg Glu Phe Val Ala Ala Ile Val Trp
        195                 200                 205

Ser Gly Gly Asn Thr Tyr Tyr Glu Asp Ser Val Lys Gly Arg Phe Thr
    210                 215                 220

Ile Ser Arg Asp Asn Ala Lys Asn Thr Met Tyr Leu Gln Met Thr Ser
225                 230                 235                 240

Leu Lys Pro Glu Asp Ser Ala Thr Tyr Tyr Cys Ala Ala Lys Ile Arg
                245                 250                 255

Pro Tyr Ile Phe Lys Ile Ala Gly Gln Tyr Asp Tyr Trp Gly Gln Gly
            260                 265                 270

Thr Leu Val Thr Val Ser Ser Gly Gly Gly Ser Gly Gly Gly Gly
        275                 280                 285

Ser Gly Gly Gly Gly Ser Gly Gly Gly Gly Ser Gly Gly Gly Gly Ser
    290                 295                 300

Gly Gly Gly Gly Ser Gly Gly Gly Gly Ser Glu Val Gln Leu Val Glu
305                 310                 315                 320

Ser Gly Gly Gly Leu Val Gln Pro Gly Asn Ser Leu Arg Leu Ser Cys
                325                 330                 335

Ala Ala Ser Gly Phe Thr Phe Ser Ser Phe Gly Met Ser Trp Val Arg
            340                 345                 350

Gln Ala Pro Gly Lys Gly Leu Glu Trp Val Ser Ser Ile Ser Gly Ser
        355                 360                 365
```

```
Gly Ser Asp Thr Leu Tyr Ala Asp Ser Val Lys Gly Arg Phe Thr Ile
        370                 375                 380
Ser Arg Asp Asn Ala Lys Thr Thr Leu Tyr Leu Gln Met Asn Ser Leu
385                 390                 395                 400
Arg Pro Glu Asp Thr Ala Val Tyr Tyr Cys Thr Ile Gly Gly Ser Leu
                405                 410                 415
Ser Arg Ser Ser Gln Gly Thr Leu Val Thr Val Ser Ser Gly Ala Ala
            420                 425                 430
Asp Tyr Lys Asp His Asp Gly Asp Tyr Lys Asp His Asp Ile Asp Tyr
        435                 440                 445
Lys Asp Asp Asp Asp Lys Gly Ala Ala His His His His His His
450                 455                 460
```

<210> SEQ ID NO 287
<211> LENGTH: 459
<212> TYPE: PRT
<213> ORGANISM: Artificial Sequence
<220> FEATURE:
<223> OTHER INFORMATION: Nanobody sequence

<400> SEQUENCE: 287

```
Glu Val Gln Leu Val Glu Ser Gly Gly Gly Leu Val Gln Pro Gly Gly
1               5                   10                  15
Ser Leu Arg Leu Ser Cys Thr Phe Ser Gly Thr Phe Ser Ser Tyr
            20                  25                  30
Thr Met Gly Trp Phe Arg Gln Ala Pro Gly Lys Glu Arg Glu Phe Val
            35                  40                  45
Ala Glu Val Arg Trp Gly Gly Val Thr Thr Tyr Ser Asn Ser Leu Lys
        50                  55                  60
Asp Arg Phe Ser Ile Ser Glu Asp Ser Val Lys Asn Ala Val Tyr Leu
65                  70                  75                  80
Gln Met Asn Ser Leu Lys Pro Glu Asp Thr Ala Val Tyr Tyr Cys Ala
                85                  90                  95
Ala Val Arg Gln Met Tyr Met Thr Val Val Pro Asp Tyr Trp Gly Gln
                100                 105                 110
Gly Thr Leu Val Thr Val Ser Ser Gly Gly Gly Ser Gly Gly Gly
            115                 120                 125
Gly Ser Gly Gly Gly Ser Gly Gly Gly Ser Gly Gly Gly Gly
        130                 135                 140
Ser Gly Gly Gly Ser Gly Gly Gly Ser Glu Val Gln Leu Val
145                 150                 155                 160
Glu Ser Gly Gly Gly Leu Val Gln Pro Gly Gly Ser Leu Arg Leu Ser
                165                 170                 175
Cys Ala Ala Ser Gly Asp Ile Tyr Lys Ser Phe Asp Met Gly Trp Tyr
                180                 185                 190
Arg Gln Ala Pro Gly Lys Gln Arg Asp Leu Val Ala Val Ile Gly Ser
            195                 200                 205
Arg Gly Asn Asn Arg Gly Arg Thr Asn Tyr Ala Asp Ser Val Lys Gly
        210                 215                 220
Arg Phe Thr Ile Ser Arg Asp Gly Thr Gly Asn Thr Val Tyr Leu Leu
225                 230                 235                 240
Met Asn Lys Leu Arg Pro Glu Asp Thr Ala Ile Tyr Tyr Cys Asn Thr
                245                 250                 255
Ala Pro Leu Val Ala Gly Arg Pro Trp Gly Arg Gly Thr Leu Val Thr
            260                 265                 270
```

```
Val Ser Ser Gly Gly Gly Ser Gly Gly Gly Ser Gly Gly
        275                 280                 285
Gly Ser Gly Gly Gly Ser Gly Gly Gly Ser Gly Gly Gly
        290                 295                 300
Ser Gly Gly Gly Ser Glu Val Gln Leu Val Glu Ser Gly Gly
305                 310                 315                 320
Leu Val Gln Pro Gly Asn Ser Leu Arg Leu Ser Cys Ala Ala Ser Gly
                325                 330                 335
Phe Thr Phe Ser Ser Phe Gly Met Ser Trp Val Arg Gln Ala Pro Gly
                340                 345                 350
Lys Gly Leu Glu Trp Val Ser Ser Ile Ser Gly Ser Gly Ser Asp Thr
                355                 360                 365
Leu Tyr Ala Asp Ser Val Lys Gly Arg Phe Thr Ile Ser Arg Asp Asn
        370                 375                 380
Ala Lys Thr Thr Leu Tyr Leu Gln Met Asn Ser Leu Arg Pro Glu Asp
385                 390                 395                 400
Thr Ala Val Tyr Tyr Cys Thr Ile Gly Gly Ser Leu Ser Arg Ser Ser
                405                 410                 415
Gln Gly Thr Leu Val Thr Val Ser Ser Gly Ala Ala Asp Tyr Lys Asp
                420                 425                 430
His Asp Gly Asp Tyr Lys Asp His Asp Ile Asp Tyr Lys Asp Asp Asp
        435                 440                 445
Asp Lys Gly Ala Ala His His His His His His
        450                 455

<210> SEQ ID NO 288
<211> LENGTH: 311
<212> TYPE: PRT
<213> ORGANISM: Artificial Sequence
<220> FEATURE:
<223> OTHER INFORMATION: Nanobody sequence

<400> SEQUENCE: 288

Glu Val Gln Leu Val Glu Ser Gly Gly Pro Val Gln Ala Gly Gly
1               5                   10                  15
Ser Leu Arg Leu Ser Cys Ala Ala Ser Gly Arg Thr Tyr Arg Gly Tyr
                20                  25                  30
Ser Met Gly Trp Phe Arg Gln Ala Pro Gly Lys Glu Arg Glu Phe Val
                35                  40                  45
Ala Ala Ile Val Trp Ser Gly Gly Asn Thr Tyr Tyr Glu Asp Ser Val
        50                  55                  60
Lys Gly Arg Phe Thr Ile Ser Arg Asp Asn Ala Lys Asn Thr Met Tyr
65                  70                  75                  80
Leu Gln Met Thr Ser Leu Lys Pro Glu Asp Ser Ala Thr Tyr Tyr Cys
                85                  90                  95
Ala Ala Lys Ile Arg Pro Tyr Ile Phe Lys Ile Ala Gly Gln Tyr Asp
                100                 105                 110
Tyr Trp Gly Gln Gly Thr Leu Val Thr Val Ser Ser Gly Gly Gly Gly
        115                 120                 125
Ser Gly Gly Gly Gly Ser Gly Gly Gly Ser Gly Gly Gly Gly Ser
        130                 135                 140
Gly Gly Gly Gly Ser Gly Gly Gly Ser Gly Gly Gly Gly Ser Glu
145                 150                 155                 160
Val Gln Leu Val Glu Ser Gly Gly Gly Leu Val Gln Ala Gly Gly Ser
                165                 170                 175
```

```
Leu Arg Leu Ser Cys Ala Ala Ser Gly Ile Thr Phe Ser Ile Asn Thr
            180                 185                 190

Met Gly Trp Tyr Arg Gln Ala Pro Gly Lys Gln Arg Glu Leu Val Ala
        195                 200                 205

Leu Ile Ser Ser Ile Gly Asp Thr Tyr Tyr Ala Asp Ser Val Lys Gly
210                 215                 220

Arg Phe Thr Ile Ser Arg Asp Asn Ala Lys Asn Thr Val Tyr Leu Gln
225                 230                 235                 240

Met Asn Ser Leu Lys Pro Glu Asp Thr Ala Val Tyr Tyr Cys Lys Arg
            245                 250                 255

Phe Arg Thr Ala Ala Gln Gly Thr Asp Tyr Trp Gly Gln Gly Thr Leu
        260                 265                 270

Val Thr Val Ser Ser Gly Ala Ala Asp Tyr Lys Asp His Asp Gly Asp
            275                 280                 285

Tyr Lys Asp His Asp Ile Asp Tyr Lys Asp Asp Asp Asp Lys Gly Ala
        290                 295                 300

Ala His His His His His His
305                 310

<210> SEQ ID NO 289
<211> LENGTH: 311
<212> TYPE: PRT
<213> ORGANISM: Artificial Sequence
<220> FEATURE:
<223> OTHER INFORMATION: Nanobody sequence

<400> SEQUENCE: 289

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Glu Val Gln Leu Val Glu Ser
145                 150                 155                 160

Gly Gly Gly Pro Val Gln Ala Gly Gly Ser Leu Arg Leu Ser Cys Ala
                165                 170                 175

Ala Ser Gly Arg Thr Tyr Arg Gly Tyr Ser Met Gly Trp Phe Arg Gln
            180                 185                 190

Ala Pro Gly Lys Glu Arg Glu Phe Val Ala Ala Ile Val Trp Ser Gly
        195                 200                 205

Gly Asn Thr Tyr Tyr Glu Asp Ser Val Lys Gly Arg Phe Thr Ile Ser
    210                 215                 220
```

Arg Asp Asn Ala Lys Asn Thr Met Tyr Leu Gln Met Thr Ser Leu Lys
225                 230                 235                 240

Pro Glu Asp Ser Ala Thr Tyr Tyr Cys Ala Ala Lys Ile Arg Pro Tyr
            245                 250                 255

Ile Phe Lys Ile Ala Gly Gln Tyr Asp Tyr Trp Gly Gln Gly Thr Leu
            260                 265                 270

Val Thr Val Ser Ser Gly Ala Ala Asp Tyr Lys Asp His Asp Gly Asp
        275                 280                 285

Tyr Lys Asp His Asp Ile Asp Tyr Lys Asp Asp Asp Lys Gly Ala
    290                 295                 300

Ala His His His His His His
305                 310

<210> SEQ ID NO 290
<211> LENGTH: 280
<212> TYPE: PRT
<213> ORGANISM: Artificial Sequence
<220> FEATURE:
<223> OTHER INFORMATION: Nanobody sequence

<400> SEQUENCE: 290

Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Asp Leu Thr Ser Thr Asn Pro Gly Ser Tyr Ile Tyr Ile Trp
        100                 105                 110

Ala Tyr Asp Tyr Trp Gly Gln Gly Thr Gln Val Thr Val Ser Ser Gly
    115                 120                 125

Gly Gly Gly Ser Gly Gly Gly Ser Gly Gly Gly Gly Ser Gly Gly
        130                 135                 140

Gly Gly Ser Gly Gly Gly Ser Gly Gly Gly Ser Gly Gly Gly
145                 150                 155                 160

Gly Ser Glu Val Gln Leu Val Glu Ser Gly Gly Gly Leu Val Gln Pro
            165                 170                 175

Gly Gly Ser Leu Arg Leu Ser Cys Ala Ala Ser Gly Asp Val His Lys
        180                 185                 190

Ile Asn Ile Leu Gly Trp Tyr Arg Gln Ala Pro Ala Lys Glu Arg Glu
    195                 200                 205

Met Val Ala His Ile Thr Ile Gly Asp Ala Thr Asp Tyr Ala Asp Ser
    210                 215                 220

Ala Lys Gly Arg Phe Thr Ile Ser Arg Asp Glu Ala Lys Asn Met Val
225                 230                 235                 240

Tyr Leu Gln Met Asn Ser Leu Lys Pro Glu Asp Thr Ala Val Tyr Phe
            245                 250                 255

Cys Arg Ala Tyr Ser Arg Ile Tyr Pro Tyr Asn Tyr Trp Gly Gln Gly
        260                 265                 270

```
Thr Leu Val Thr Val Ser Ser Ala
        275                 280

<210> SEQ ID NO 291
<211> LENGTH: 171
<212> TYPE: PRT
<213> ORGANISM: Homo sapiens

<400> SEQUENCE: 291

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 292
<211> LENGTH: 182
<212> TYPE: PRT
<213> ORGANISM: Homo sapiens

<400> SEQUENCE: 292

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Ala Glu
            100                 105                 110

Ile Val Ser Ile Phe Val Leu Ala Val Gly Val Tyr Phe Ile Ala Gly
        115                 120                 125

Gln Asp Gly Val Arg Gln Ser Arg Ala Ser Asp Lys Gln Thr Leu Leu
    130                 135                 140
```

Pro Asn Asp Gln Leu Tyr Gln Pro Leu Lys Asp Arg Glu Asp Gln
145                 150                 155                 160

Tyr Ser His Leu Gln Gly Asn Gln Leu Arg Asn Ala Ala Thr Ile Ser
            165                 170                 175

Gly Phe Leu Phe Arg Asn
            180

<210> SEQ ID NO 293
<211> LENGTH: 207
<212> TYPE: PRT
<213> ORGANISM: Homo sapiens

<400> SEQUENCE: 293

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Pro Val Pro Asn Pro Asp Tyr Glu Pro Ile Arg
            100                 105                 110

Lys Gly Gln Arg Asp Leu Tyr Ser Gly Leu Asn Gln Arg Arg Ile Arg
            115                 120                 125

Gly Ser Lys Pro Glu Asp Ala Asn Phe Asn Cys Met Glu Met Asp Val
130                 135                 140

Met Ser Val Ala Thr Ile Val Ile Val Asp Ile Cys Ile Thr Gly Gly
145                 150                 155                 160

Leu Leu Leu Leu Val Tyr Tyr Trp Ser Lys Asn Arg Lys Ala Lys Ala
                165                 170                 175

Lys Pro Val Thr Arg Gly Ala Gly Ala Gly Gly Arg Gln Arg Gly Gln
            180                 185                 190

Asn Lys Glu Arg Pro Tyr Leu Tyr Leu Arg Ala Arg Val Cys Glu
            195                 200                 205

<210> SEQ ID NO 294
<211> LENGTH: 164
<212> TYPE: PRT
<213> ORGANISM: Homo sapiens

<400> SEQUENCE: 294

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
50                  55                  60

Gln Gln Gly Gln Asn Gln Leu Tyr Asn Glu Leu Asn Leu Gly Arg Arg
65                  70                  75                  80

```
Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Glu Ala
            100                 105                 110

Tyr Ser Glu Ile Gly Met Lys Gly Glu Arg Arg Gly Lys Gly His
        115                 120                 125

Asp Gly Leu Tyr Gln Gly Leu Ser Thr Ala Thr Lys Asp Thr Tyr Asp
        130                 135                 140

Ala Leu His Met Gln Ala Leu Pro Pro Arg Tyr Asn Glu Leu Gln Lys
145                 150                 155                 160

Asp Lys Met Ala

<210> SEQ ID NO 295
<211> LENGTH: 142
<212> TYPE: PRT
<213> ORGANISM: Homo sapiens

<400> SEQUENCE: 295

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140

<210> SEQ ID NO 296
<211> LENGTH: 177
<212> TYPE: PRT
<213> ORGANISM: Homo sapiens

<400> SEQUENCE: 296

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95
```

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 297
<211> LENGTH: 118
<212> TYPE: PRT
<213> ORGANISM: Artificial Sequence
<220> FEATURE:
<223> OTHER INFORMATION: Nanobody sequence

<400> SEQUENCE: 297

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser
        115

<210> SEQ ID NO 298
<211> LENGTH: 119
<212> TYPE: PRT
<213> ORGANISM: Artificial Sequence
<220> FEATURE:
<223> OTHER INFORMATION: Nanobody sequence

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Gly Phe Asn
            20                  25                  30

Asp Met Ala Trp Tyr Arg Gln Ala Pro Gly Lys Gln Arg Glu Leu Val
        35                  40                  45

Ala Leu Ile Ser Arg Val Gly Val Thr Ser Ser Ala Asp Ser Val Lys
50                  55                  60

Gly Arg Phe Thr Ile Ser Arg Val Asn Ala Lys Asp Thr Val Tyr Leu
65                  70                  75                  80

Gln Met Asn Ser Leu Lys Pro Glu Asp Thr Ala Val Tyr Tyr Cys Tyr
                85                  90                  95

Met Asp Gln Arg Leu Asp Gly Ser Thr Leu Ala Tyr Trp Gly Gln Gly
                100                 105                 110

Thr Gln Val Thr Val Ser Ser
        115

<210> SEQ ID NO 299
<211> LENGTH: 127
<212> TYPE: PRT
<213> ORGANISM: Artificial Sequence
<220> FEATURE:
<223> OTHER INFORMATION: Nanobody sequence

<400> SEQUENCE: 299

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Val Ala Ile Asn Trp Ser Ser Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Gly Tyr Gln Ile Asn Ser Gly Asn Tyr Asn Phe Lys Asp Tyr
            100                 105                 110

Glu Tyr Asp Tyr Trp Gly Gln Gly Thr Gln Val Thr Val Ser Ser
        115                 120                 125

<210> SEQ ID NO 300
<211> LENGTH: 123
<212> TYPE: PRT
<213> ORGANISM: Artificial Sequence
<220> FEATURE:
<223> OTHER INFORMATION: Nanobody sequence

<400> SEQUENCE: 300

Glu Val Gln Leu Val Glu Ser Gly Gly Gly Ser Val Gln Ala Gly Gly
1               5                   10                  15

Ser Leu Arg Leu Ser Cys Ala Ala Ser Gly Asp Thr Tyr Gly Ser Tyr
            20                  25                  30

Trp Met Gly Trp Phe Arg Gln Ala Pro Gly Lys Glu Arg Glu Gly Val
        35                  40                  45

Ala Ala Ile Asn Arg Gly Gly Tyr Thr Val Tyr Ala Asp Ser Val
    50                  55                  60

Lys Gly Arg Phe Thr Ile Ser Arg Asp Thr Ala Lys Asn Thr Val Tyr
65                  70                  75                  80

Leu Gln Met Asn Ser Leu Arg Pro Asp Asp Thr Ala Asp Tyr Tyr Cys
                85                  90                  95

Ala Ala Ser Gly Val Leu Gly Gly Leu His Glu Asp Trp Phe Asn Tyr
            100                 105                 110

Trp Gly Gln Gly Thr Leu Val Thr Val Ser Ser
        115                 120

<210> SEQ ID NO 301
<211> LENGTH: 123
<212> TYPE: PRT
<213> ORGANISM: Artificial Sequence

```
<220> FEATURE:
<223> OTHER INFORMATION: Nanobody sequence

<400> SEQUENCE: 301

Glu Val Gln Leu Val Glu Ser Gly Gly Gly Ser Val Gln Ala Gly Gly
1               5                   10                  15

Ser Leu Arg Leu Ser Cys Ala Ala Ser Gly Asp Thr Tyr Gly Ser Tyr
            20                  25                  30

Trp Met Gly Trp Phe Arg Gln Ala Pro Gly Gln Glu Arg Glu Ala Val
        35                  40                  45

Ala Ala Ile Asn Arg Gly Gly Tyr Thr Val Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Asp Asp Thr Ala Asp Tyr Tyr Cys
                85                  90                  95

Ala Ala Ser Gly Val Leu Gly Gly Leu His Glu Asp Trp Phe Asn Tyr
            100                 105                 110

Trp Gly Gln Gly Thr Leu Val Thr Val Ser Ser
        115                 120

<210> SEQ ID NO 302
<211> LENGTH: 124
<212> TYPE: PRT
<213> ORGANISM: Artificial Sequence
<220> FEATURE:
<223> OTHER INFORMATION: Nanobody sequence

<400> SEQUENCE: 302

Glu Val Gln Leu Val Glu Ser Gly Gly Gly Ser Val Gln Thr Gly Gly
1               5                   10                  15

Ser Leu Arg Leu Thr Cys Ala Ala Ser Gly Arg Thr Ser Arg Ser Tyr
            20                  25                  30

Gly Met Gly Trp Phe Arg Gln Ala Pro Gly Lys Glu Arg Glu Phe Val
        35                  40                  45

Ser Gly Ile Ser Trp Arg Gly Asp Ser Thr Gly Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

Tyr Trp Gly Gln Gly Thr Leu Val Thr Val Ser Ser
        115                 120

<210> SEQ ID NO 303
<211> LENGTH: 124
<212> TYPE: PRT
<213> ORGANISM: Artificial Sequence
<220> FEATURE:
<223> OTHER INFORMATION: Nanobody sequence

<400> SEQUENCE: 303

Glu Val Gln Leu Val Glu Ser Gly Gly Gly Ser Val Gln Ala Gly Gly
1               5                   10                  15

Ser Leu Arg Leu Thr Cys Ala Ala Ser Gly Ser Thr Ser Arg Ser Tyr
            20                  25                  30
```

```
Gly Met Gly Trp Phe Arg Gln Ala Pro Gly Lys Glu Arg Glu Phe Val
        35                  40                  45

Ser Gly Ile Ser Trp Arg Gly Asp Ser Thr Gly Tyr Ala Asp Ser Val
 50                  55                  60

Lys Gly Arg Phe Thr Ile Ser Arg Asp Asn Ala Lys Asn Thr Val Asp
 65                  70                  75                  80

Leu Gln Met Asn Ser Leu Lys Pro Glu Asp Thr Ala Ile Tyr Tyr Cys
                 85                  90                  95

Ala Ala Ala Ala Gly Ser Thr Trp Tyr Gly Thr Leu Tyr Glu Tyr Asp
                100                 105                 110

Tyr Trp Gly Gln Gly Thr Leu Val Thr Val Ser Ser
            115                 120
```

<210> SEQ ID NO 304
<211> LENGTH: 120
<212> TYPE: PRT
<213> ORGANISM: Artificial Sequence
<220> FEATURE:
<223> OTHER INFORMATION: Nanobody sequence

<400> SEQUENCE: 304

```
Glu Val Gln Leu Val Glu Ser Gly Gly Gly Leu Val Gln Pro Gly Gly
 1               5                  10                  15

Ser Leu Arg Leu Ser Cys Thr Phe Ser Gly Gly Thr Phe Ser Ser Tyr
                 20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
 50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                 85                  90                  95

Ala Val Arg Gln Met Tyr Met Thr Val Val Pro Asp Tyr Trp Gly Gln
                100                 105                 110

Gly Thr Leu Val Thr Val Ser Ser
            115                 120
```

<210> SEQ ID NO 305
<211> LENGTH: 293
<212> TYPE: PRT
<213> ORGANISM: Artificial Sequence
<220> FEATURE:
<223> OTHER INFORMATION: Nanobody sequence

<400> SEQUENCE: 305

```
Glu Val Gln Leu Val Glu Ser Gly Gly Gly Leu Val Gln Gly Gly Gly
 1               5                  10                  15

Ser Leu Ser Leu Ser Cys Ala Ala Ser Gly Arg Thr Phe Ser Ser Tyr
                 20                  25                  30

Ala Met Ala Trp Phe Arg Gln Pro Pro Gly Lys Glu Arg Glu Phe Val
            35                  40                  45

Ala Ser Ile Ser Trp Ser Gly Glu Asn Thr Asn Tyr Arg Asn Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95
```

Ala Ala Lys Ile Ala Lys Thr Tyr Pro Asp Asn Trp Tyr Trp Thr Lys
                100                 105                 110

Ser Asn Asn Tyr Asn Tyr Trp Gly Gln Gly Thr Leu Val Thr Val Ser
                115                 120                 125

Ser Gly Gly Gly Ser Gly Gly Gly Ser Gly Gly Gly Ser
            130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Gly Leu Val
                165                 170                 175

Gln Gly Gly Gly Ser Leu Ser Leu Ser Cys Ala Ala Ser Gly Arg Thr
                180                 185                 190

Phe Ser Ser Tyr Ala Met Ala Trp Phe Arg Gln Pro Gly Lys Glu
                195                 200                 205

Arg Glu Phe Val Ala Ser Ile Ser Trp Ser Gly Glu Asn Thr Asn Tyr
                210                 215                 220

Arg Asn Ser Val Lys Gly Arg Phe Thr Ile Ser Arg Asp Asn Ala Lys
225                 230                 235                 240

Asn Thr Val Tyr Leu Gln Met Asn Ser Leu Lys Pro Glu Asp Thr Ala
                245                 250                 255

Val Tyr Tyr Cys Ala Ala Lys Ile Ala Lys Thr Tyr Pro Asp Asn Trp
                260                 265                 270

Tyr Trp Thr Lys Ser Asn Asn Tyr Asn Tyr Trp Gly Gln Gly Thr Leu
                275                 280                 285

Val Thr Val Ser Ser
            290

<210> SEQ ID NO 306
<211> LENGTH: 249
<212> TYPE: PRT
<213> ORGANISM: Artificial Sequence
<220> FEATURE:
<223> OTHER INFORMATION: Nanobody sequence

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Thr Phe Ser Gly Thr Phe Ser Ser Tyr
                20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
                100                 105                 110

Gly Thr Leu Val Thr Val Ser Ser Gly Gly Gly Ser Glu Val Gln
            115                 120                 125

Leu Val Glu Ser Gly Gly Gly Ser Val Gln Ala Gly Gly Ser Leu Arg
            130                 135                 140

Leu Ser Cys Ala Ala Ser Gly Arg Thr Phe Ser Thr Asn Pro Met Gly
145                 150                 155                 160

Trp Phe Arg Gln Val Pro Gly Lys Glu Arg Glu Leu Ile Ala Ala Val
            165                 170                 175

Arg Trp Ala Asp Gly Asn Thr Phe Tyr Ala Asp Ser Val Lys Gly Arg
            180                 185                 190

Phe Thr Ile Ser Arg Asp Asn Ala Lys Lys Thr Val Tyr Leu Gln Met
            195                 200                 205

Asn Ser Leu Lys Ser Glu Asp Thr Ala Thr Tyr Tyr Cys Ala Ala Gly
            210                 215                 220

Arg Pro Trp Ser Ala Tyr His Ser Pro Ala Glu Tyr Val His Trp Gly
225                 230                 235                 240

Gln Gly Thr Leu Val Thr Val Ser Ser
            245

<210> SEQ ID NO 307
<211> LENGTH: 254
<212> TYPE: PRT
<213> ORGANISM: Artificial Sequence
<220> FEATURE:
<223> OTHER INFORMATION: Nanobody sequence

<400> SEQUENCE: 307

Glu Val Gln Leu Val Glu Ser Gly Gly Gly Leu Val Gln Pro Gly Gly
1               5                   10                  15

Ser Leu Arg Leu Ser Cys Thr Phe Ser Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
        50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Glu Val Gln
            115                 120                 125

Leu Val Glu Ser Gly Gly Gly Leu Val Gln Gly Gly Ser Leu Ser
            130                 135                 140

Leu Ser Cys Ala Ala Ser Gly Arg Thr Phe Ser Ser Tyr Ala Met Ala
145                 150                 155                 160

Trp Phe Arg Gln Pro Pro Gly Lys Glu Arg Glu Phe Val Ala Ser Ile
            165                 170                 175

Ser Trp Ser Gly Glu Asn Thr Asn Tyr Arg Asn Ser Val Lys Gly Arg
            180                 185                 190

Phe Thr Ile Ser Arg Asp Asn Ala Lys Asn Thr Val Tyr Leu Gln Met
            195                 200                 205

Asn Ser Leu Lys Pro Glu Asp Thr Ala Val Tyr Tyr Cys Ala Ala Lys
            210                 215                 220

Ile Ala Lys Thr Tyr Pro Asp Asn Trp Tyr Trp Thr Lys Ser Asn Asn
225                 230                 235                 240

Tyr Asn Tyr Trp Gly Gln Gly Thr Leu Val Thr Val Ser Ser
            245                 250

<210> SEQ ID NO 308

```
<211> LENGTH: 258
<212> TYPE: PRT
<213> ORGANISM: Artificial Sequence
<220> FEATURE:
<223> OTHER INFORMATION: Nanobody sequence

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Asp Val Gln
        115                 120                 125

Leu Gln Ala Ser Gly Gly Gly Ser Val Gln Ala Gly Gly Ser Leu Arg
    130                 135                 140

Leu Ser Cys Ala Ala Ser Gly Tyr Thr Ile Gly Pro Tyr Cys Met Gly
145                 150                 155                 160

Trp Phe Arg Gln Ala Pro Gly Lys Glu Arg Glu Gly Val Ala Ala Ile
                165                 170                 175

Asn Met Gly Gly Gly Ile Thr Tyr Tyr Ala Asp Ser Val Lys Gly Arg
            180                 185                 190

Phe Thr Ile Ser Gln Asp Asn Ala Lys Asn Thr Val Tyr Leu Leu Met
        195                 200                 205

Asn Ser Leu Glu Pro Glu Asp Thr Ala Ile Tyr Tyr Cys Ala Ala Asp
    210                 215                 220

Ser Thr Ile Tyr Ala Ser Tyr Tyr Glu Cys Gly His Gly Leu Ser Thr
225                 230                 235                 240

Gly Gly Tyr Gly Tyr Asp Ser Trp Gly Gln Gly Thr Gln Val Thr Val
                245                 250                 255

Ser Ser

<210> SEQ ID NO 309
<211> LENGTH: 253
<212> TYPE: PRT
<213> ORGANISM: Artificial Sequence
<220> FEATURE:
<223> OTHER INFORMATION: Nanobody sequence

<400> SEQUENCE: 309

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60
```

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Ser Glu Val Gln Leu Val Glu Ser Gly Gly Ser Val Gln Ala Gly
    130                 135                 140

Gly Ser Leu Arg Leu Ser Cys Ala Ala Ser Gly Arg Thr Phe Ser Thr
145                 150                 155                 160

Asn Pro Met Gly Trp Phe Arg Gln Val Pro Gly Lys Glu Arg Glu Leu
                165                 170                 175

Ile Ala Ala Val Arg Trp Ala Asp Gly Asn Thr Phe Tyr Ala Asp Ser
            180                 185                 190

Val Lys Gly Arg Phe Thr Ile Ser Arg Asp Asn Ala Lys Lys Thr Val
        195                 200                 205

Tyr Leu Gln Met Asn Ser Leu Lys Ser Glu Asp Thr Ala Thr Tyr Tyr
    210                 215                 220

Cys Ala Ala Gly Arg Pro Trp Ser Ala Tyr His Ser Pro Ala Glu Tyr
225                 230                 235                 240

Val His Trp Gly Gln Gly Thr Leu Val Thr Val Ser Ser
                245                 250

<210> SEQ ID NO 310
<211> LENGTH: 258
<212> TYPE: PRT
<213> ORGANISM: Artificial Sequence
<220> FEATURE:
<223> OTHER INFORMATION: Nanobody sequence

<400> SEQUENCE: 310

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Ser Glu Val Gln Leu Val Glu Ser Gly Gly Gly Leu Val Gln Gly Gly
    130                 135                 140

Gly Ser Leu Ser Leu Ser Cys Ala Ala Ser Gly Arg Thr Phe Ser Ser
145                 150                 155                 160

Tyr Ala Met Ala Trp Phe Arg Gln Pro Pro Gly Lys Glu Arg Glu Phe
                165                 170                 175

```
Val Ala Ser Ile Ser Trp Ser Gly Glu Asn Thr Asn Tyr Arg Asn Ser
            180                 185                 190

Val Lys Gly Arg Phe Thr Ile Ser Arg Asp Asn Ala Lys Asn Thr Val
            195                 200                 205

Tyr Leu Gln Met Asn Ser Leu Lys Pro Glu Asp Thr Ala Val Tyr Tyr
            210                 215                 220

Cys Ala Ala Lys Ile Ala Lys Thr Tyr Pro Asp Asn Trp Tyr Trp Thr
225                 230                 235                 240

Lys Ser Asn Asn Tyr Asn Tyr Trp Gly Gln Gly Thr Leu Val Thr Val
            245                 250                 255

Ser Ser

<210> SEQ ID NO 311
<211> LENGTH: 262
<212> TYPE: PRT
<213> ORGANISM: Artificial Sequence
<220> FEATURE:
<223> OTHER INFORMATION: Nanobody sequence

<400> SEQUENCE: 311

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
            85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Ser Asp Val Gln Leu Gln Ala Ser Gly Gly Ser Val Gln Ala Gly
            130                 135                 140

Gly Ser Leu Arg Leu Ser Cys Ala Ala Ser Gly Tyr Thr Ile Gly Pro
145                 150                 155                 160

Tyr Cys Met Gly Trp Phe Arg Gln Ala Pro Gly Lys Glu Arg Glu Gly
            165                 170                 175

Val Ala Ala Ile Asn Met Gly Gly Ile Thr Tyr Tyr Ala Asp Ser
            180                 185                 190

Val Lys Gly Arg Phe Thr Ile Ser Gln Asp Asn Ala Lys Asn Thr Val
            195                 200                 205

Tyr Leu Leu Met Asn Ser Leu Glu Pro Glu Asp Thr Ala Ile Tyr Tyr
            210                 215                 220

Cys Ala Ala Asp Ser Thr Ile Tyr Ala Ser Tyr Tyr Glu Cys Gly His
225                 230                 235                 240

Gly Leu Ser Thr Gly Gly Tyr Gly Tyr Asp Ser Trp Gly Gln Gly Thr
            245                 250                 255

Gln Val Thr Val Ser Ser
            260
```

```
<210> SEQ ID NO 312
<211> LENGTH: 279
<212> TYPE: PRT
<213> ORGANISM: Artificial Sequence
<220> FEATURE:
<223> OTHER INFORMATION: Nanobody sequence

<400> SEQUENCE: 312

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Ser Val Gln Ala Gly Gly Ser Leu Arg Leu Ser
                165                 170                 175

Cys Ala Ala Ser Gly Arg Thr Phe Ser Thr Asn Pro Met Gly Trp Phe
            180                 185                 190

Arg Gln Val Pro Gly Lys Glu Arg Glu Leu Ile Ala Ala Val Arg Trp
        195                 200                 205

Ala Asp Gly Asn Thr Phe Tyr Ala Asp Ser Val Lys Gly Arg Phe Thr
    210                 215                 220

Ile Ser Arg Asp Asn Ala Lys Lys Thr Val Tyr Leu Gln Met Asn Ser
225                 230                 235                 240

Leu Lys Ser Glu Asp Thr Ala Thr Tyr Tyr Cys Ala Ala Gly Arg Pro
                245                 250                 255

Trp Ser Ala Tyr His Ser Pro Ala Glu Tyr Val His Trp Gly Gln Gly
            260                 265                 270

Thr Leu Val Thr Val Ser Ser
        275

<210> SEQ ID NO 313
<211> LENGTH: 284
<212> TYPE: PRT
<213> ORGANISM: Artificial Sequence
<220> FEATURE:
<223> OTHER INFORMATION: Nanobody sequence

<400> SEQUENCE: 313

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30
```

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Gly Gly Gly Ser Gly Gly Gly
        130                 135                 140

Ser Gly Gly Gly Ser Gly Gly Gly Ser Glu Val Gln Leu Val
145                 150                 155                 160

Glu Ser Gly Gly Gly Leu Val Gln Gly Gly Ser Leu Ser Leu Ser
                165                 170                 175

Cys Ala Ala Ser Gly Arg Thr Phe Ser Ser Tyr Ala Met Ala Trp Phe
            180                 185                 190

Arg Gln Pro Pro Gly Lys Glu Arg Glu Phe Val Ala Ser Ile Ser Trp
        195                 200                 205

Ser Gly Glu Asn Thr Asn Tyr Arg Asn Ser Val Lys Gly Arg Phe Thr
            210                 215                 220

Ile Ser Arg Asp Asn Ala Lys Asn Thr Val Tyr Leu Gln Met Asn Ser
225                 230                 235                 240

Leu Lys Pro Glu Asp Thr Ala Val Tyr Tyr Cys Ala Ala Lys Ile Ala
                245                 250                 255

Lys Thr Tyr Pro Asp Asn Trp Tyr Trp Thr Lys Ser Asn Asn Tyr Asn
            260                 265                 270

Tyr Trp Gly Gln Gly Thr Leu Val Thr Val Ser Ser
        275                 280

<210> SEQ ID NO 314
<211> LENGTH: 288
<212> TYPE: PRT
<213> ORGANISM: Artificial Sequence
<220> FEATURE:
<223> OTHER INFORMATION: Nanobody sequence

<400> SEQUENCE: 314

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
            35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

```
Gly Thr Leu Val Thr Val Ser Ser Gly Gly Gly Ser Gly Gly
            115                 120                 125

Gly Ser Gly Gly Gly Ser Gly Gly Gly Ser Gly Gly Gly Gly
    130                 135                 140

Ser Gly Gly Gly Ser Gly Gly Gly Ser Asp Val Gln Leu Gln
145                 150                 155                 160

Ala Ser Gly Gly Ser Val Gln Ala Gly Gly Ser Leu Arg Leu Ser
                165                 170                 175

Cys Ala Ala Ser Gly Tyr Thr Ile Gly Pro Tyr Cys Met Gly Trp Phe
                180                 185                 190

Arg Gln Ala Pro Gly Lys Glu Arg Glu Gly Val Ala Ala Ile Asn Met
            195                 200                 205

Gly Gly Gly Ile Thr Tyr Tyr Ala Asp Ser Val Lys Gly Arg Phe Thr
210                 215                 220

Ile Ser Gln Asp Asn Ala Lys Asn Thr Val Tyr Leu Leu Met Asn Ser
225                 230                 235                 240

Leu Glu Pro Glu Asp Thr Ala Ile Tyr Tyr Cys Ala Ala Asp Ser Thr
                245                 250                 255

Ile Tyr Ala Ser Tyr Tyr Glu Cys Gly His Gly Leu Ser Thr Gly Gly
                260                 265                 270

Tyr Gly Tyr Asp Ser Trp Gly Gln Gly Thr Gln Val Thr Val Ser Ser
            275                 280                 285

<210> SEQ ID NO 315
<211> LENGTH: 253
<212> TYPE: PRT
<213> ORGANISM: Artificial Sequence
<220> FEATURE:
<223> OTHER INFORMATION: Nanobody sequence

<400> SEQUENCE: 315

Glu Val Gln Leu Val Glu Ser Gly Gly Ser Val Gln Ala Gly Gly
1               5                   10                  15

Ser Leu Arg Leu Ser Cys Ala Ala Ser Gly Arg Thr Phe Ser Thr Asn
                20                  25                  30

Pro Met Gly Trp Phe Arg Gln Val Pro Gly Lys Glu Arg Glu Leu Ile
            35                  40                  45

Ala Ala Val Arg Trp Ala Asp Gly Asn Thr Phe Tyr Ala Asp Ser Val
        50                  55                  60

Lys Gly Arg Phe Thr Ile Ser Arg Asp Asn Ala Lys Lys Thr Val Tyr
65                  70                  75                  80

Leu Gln Met Asn Ser Leu Lys Ser Glu Asp Thr Ala Thr Tyr Tyr Cys
                85                  90                  95

Ala Ala Gly Arg Pro Trp Ser Ala Tyr His Ser Pro Ala Glu Tyr Val
            100                 105                 110

His Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Gly Ser Leu Arg Leu Ser Cys Thr Phe Ser Gly Gly
145                 150                 155                 160

Thr Phe Ser Ser Tyr Thr Met Gly Trp Phe Arg Gln Ala Pro Gly Lys
                165                 170                 175

Glu Arg Glu Phe Val Ala Glu Val Arg Trp Gly Gly Val Thr Thr Tyr
            180                 185                 190
```

```
Ser Asn Ser Leu Lys Asp Arg Phe Ser Ile Ser Glu Asp Ser Val Lys
        195                 200                 205

Asn Ala Val Tyr Leu Gln Met Asn Ser Leu Lys Pro Glu Asp Thr Ala
        210                 215                 220

Val Tyr Tyr Cys Ala Ala Val Arg Gln Met Tyr Met Thr Val Val Pro
225                 230                 235                 240

Asp Tyr Trp Gly Gln Gly Thr Leu Val Thr Val Ser Ser
                245                 250

<210> SEQ ID NO 316
<211> LENGTH: 279
<212> TYPE: PRT
<213> ORGANISM: Artificial Sequence
<220> FEATURE:
<223> OTHER INFORMATION: Nanobody sequence

<400> SEQUENCE: 316

Glu Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Phe Ser Thr Asn
            20                  25                  30

Pro Met Gly Trp Phe Arg Gln Val Pro Gly Lys Glu Arg Glu Leu Ile
        35                  40                  45

Ala Ala Val Arg Trp Ala Asp Gly Asn Thr Phe Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Ser Leu Lys Ser Glu Asp Thr Ala Thr Tyr Tyr Cys
                85                  90                  95

Ala Ala Gly Arg Pro Trp Ser Ala Tyr His Ser Pro Ala Glu Tyr Val
            100                 105                 110

His Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Thr Phe Ser Gly Gly Thr Phe Ser Ser Tyr Thr
            180                 185                 190

Met Gly Trp Phe Arg Gln Ala Pro Gly Lys Glu Arg Glu Phe Val Ala
        195                 200                 205

Glu Val Arg Trp Gly Gly Val Thr Thr Tyr Ser Asn Ser Leu Lys Asp
    210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Pro Asp Tyr Trp Gly Gln Gly
            260                 265                 270

Thr Leu Val Thr Val Ser Ser
        275

<210> SEQ ID NO 317
```

<211> LENGTH: 284
<212> TYPE: PRT
<213> ORGANISM: Artificial Sequence
<220> FEATURE:
<223> OTHER INFORMATION: Nanobody sequence

<400> SEQUENCE: 317

Glu Val Gln Leu Val Glu Ser Gly Gly Gly Leu Val Gln Gly Gly Gly
1               5                   10                  15

Ser Leu Ser Leu Ser Cys Ala Ala Ser Gly Arg Thr Phe Ser Ser Tyr
            20                  25                  30

Ala Met Ala Trp Phe Arg Gln Pro Pro Gly Lys Glu Arg Glu Phe Val
        35                  40                  45

Ala Ser Ile Ser Trp Ser Gly Glu Asn Thr Asn Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Lys Ile Ala Lys Thr Tyr Pro Asp Asn Trp Tyr Trp Thr Lys
            100                 105                 110

Ser Asn Asn Tyr Asn Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Gly Leu Val
                165                 170                 175

Gln Pro Gly Gly Ser Leu Arg Leu Ser Cys Thr Phe Ser Gly Gly Thr
            180                 185                 190

Phe Ser Ser Tyr Thr Met Gly Trp Phe Arg Gln Ala Pro Gly Lys Glu
        195                 200                 205

Arg Glu Phe Val Ala Glu Val Arg Trp Gly Gly Val Thr Thr Tyr Ser
210                 215                 220

Asn Ser Leu Lys Asp Arg Phe Ser Ile Ser Glu Asp Ser Val Lys Asn
225                 230                 235                 240

Ala Val Tyr Leu Gln Met Asn Ser Leu Lys Pro Glu Asp Thr Ala Val
                245                 250                 255

Tyr Tyr Cys Ala Ala Val Arg Gln Met Tyr Met Thr Val Val Pro Asp
            260                 265                 270

Tyr Trp Gly Gln Gly Thr Leu Val Thr Val Ser Ser
        275                 280

<210> SEQ ID NO 318
<211> LENGTH: 288
<212> TYPE: PRT
<213> ORGANISM: Artificial Sequence
<220> FEATURE:
<223> OTHER INFORMATION: Nanobody sequence

<400> SEQUENCE: 318

Glu Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val

```
                35                  40                  45
Ala Ala Ile Asn Met Gly Gly Gly Ile Thr Tyr Tyr Ala Asp Ser Val
 50                  55                  60
Lys Gly Arg Phe Thr Ile Ser Gln Asp Asn Ala Lys Asn Thr Val Tyr
 65                  70                  75                  80
Leu Leu Met Asn Ser Leu Glu Pro Glu Asp Thr Ala Ile Tyr Tyr Cys
                 85                  90                  95
Ala Ala Asp Ser Thr Ile Tyr Ala Ser Tyr Glu Cys Gly His Gly
                100                 105                 110
Leu Ser Thr Gly Gly Tyr Gly Tyr Asp Ser Trp Gly Gln Gly Thr Gln
                115                 120                 125
Val Thr Val Ser Ser Gly Gly Gly Ser Gly Gly Gly Ser Gly
                130                 135                 140
Gly Gly Gly Ser Gly Gly Gly Ser Gly Gly Gly Ser Gly Gly
145                 150                 155                 160
Gly Gly Ser Gly Gly Gly Ser Glu Val Gln Leu Val Glu Ser Gly
                165                 170                 175
Gly Gly Leu Val Gln Pro Gly Gly Ser Leu Arg Leu Ser Cys Thr Phe
                180                 185                 190
Ser Gly Gly Thr Phe Ser Ser Tyr Thr Met Gly Trp Phe Arg Gln Ala
                195                 200                 205
Pro Gly Lys Glu Arg Glu Phe Val Ala Glu Val Arg Trp Gly Val
                210                 215                 220
Thr Thr Tyr Ser Asn Ser Leu Lys Asp Arg Phe Ser Ile Ser Glu Asp
225                 230                 235                 240
Ser Val Lys Asn Ala Val Tyr Leu Gln Met Asn Ser Leu Lys Pro Glu
                245                 250                 255
Asp Thr Ala Val Tyr Tyr Cys Ala Ala Val Arg Gln Met Tyr Met Thr
                260                 265                 270
Val Val Pro Asp Tyr Trp Gly Gln Gly Thr Leu Val Thr Val Ser Ser
                275                 280                 285

<210> SEQ ID NO 319
<211> LENGTH: 292
<212> TYPE: PRT
<213> ORGANISM: Artificial Sequence
<220> FEATURE:
<223> OTHER INFORMATION: Nanobody sequence

<400> SEQUENCE: 319

Glu Val Gln Leu Val Glu Ser Gly Gly Gly Ser Val Gln Ala Gly Gly
 1                   5                  10                  15
Ser Leu Arg Leu Ser Cys Ala Ala Ser Gly Arg Thr Phe Ser Thr Asn
                 20                  25                  30
Pro Met Gly Trp Phe Arg Gln Val Pro Gly Lys Glu Arg Glu Leu Ile
                 35                  40                  45
Ala Ala Val Arg Trp Ala Asp Gly Asn Thr Phe Tyr Ala Asp Ser Val
 50                  55                  60
Lys Gly Arg Phe Thr Ile Ser Arg Asp Asn Ala Lys Lys Thr Val Tyr
 65                  70                  75                  80
Leu Gln Met Asn Ser Leu Lys Ser Glu Asp Thr Ala Thr Tyr Tyr Cys
                 85                  90                  95
Ala Ala Gly Arg Pro Trp Ser Ala Tyr His Ser Pro Ala Glu Tyr Val
                100                 105                 110
His Trp Gly Gln Gly Thr Leu Val Thr Val Ser Ser Gly Gly Gly Gly
```

```
            115                 120                 125
Ser Gly Gly Gly Ser Gly Gly Gly Ser Gly Gly Gly Ser
    130                 135                 140

Gly Gly Gly Gly Ser Gly Gly Gly Ser Gly Gly Gly Ser Asp
145                 150                 155                 160

Val Gln Leu Gln Ala Ser Gly Gly Ser Val Ala Gly Gly Ser
                    165                 170                 175

Leu Arg Leu Ser Cys Ala Ala Ser Gly Tyr Thr Ile Gly Pro Tyr Cys
                180                 185                 190

Met Gly Trp Phe Arg Gln Ala Pro Gly Lys Glu Arg Glu Gly Val Ala
            195                 200                 205

Ala Ile Asn Met Gly Gly Ile Thr Tyr Tyr Ala Asp Ser Val Lys
        210                 215                 220

Gly Arg Phe Thr Ile Ser Gln Asp Asn Ala Lys Asn Thr Val Tyr Leu
225                 230                 235                 240

Leu Met Asn Ser Leu Glu Pro Glu Asp Thr Ala Ile Tyr Tyr Cys Ala
                245                 250                 255

Ala Asp Ser Thr Ile Tyr Ala Ser Tyr Tyr Glu Cys Gly His Gly Leu
            260                 265                 270

Ser Thr Gly Gly Tyr Gly Tyr Asp Ser Trp Gly Gln Gly Thr Gln Val
        275                 280                 285

Thr Val Ser Ser
    290

<210> SEQ ID NO 320
<211> LENGTH: 258
<212> TYPE: PRT
<213> ORGANISM: Artificial Sequence
<220> FEATURE:
<223> OTHER INFORMATION: Nanobody sequence

<400> SEQUENCE: 320

Glu Val Gln Leu Val Glu Ser Gly Gly Gly Leu Val Gln Gly Gly Gly
1               5                   10                  15

Ser Leu Ser Leu Ser Cys Ala Ala Ser Gly Arg Thr Phe Ser Ser Tyr
                20                  25                  30

Ala Met Ala Trp Phe Arg Gln Pro Gly Lys Glu Arg Glu Phe Val
            35                  40                  45

Ala Ser Ile Ser Trp Ser Gly Glu Asn Thr Asn Tyr Arg Asn Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Lys Ile Ala Lys Thr Tyr Pro Asp Asn Trp Tyr Trp Thr Lys
            100                 105                 110

Ser Asn Asn Tyr Asn Tyr Trp Gly Gln Gly Thr Leu Val Thr Val Ser
        115                 120                 125

Ser Gly Gly Gly Gly Ser Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160

Thr Phe Ser Gly Gly Thr Phe Ser Ser Tyr Thr Met Gly Trp Phe Arg
                165                 170                 175

Gln Ala Pro Gly Lys Glu Arg Glu Phe Val Ala Glu Val Arg Trp Gly
```

```
              180                 185                 190
Gly Val Thr Thr Tyr Ser Asn Ser Leu Lys Asp Arg Phe Ser Ile Ser
                195                 200                 205
Glu Asp Ser Val Lys Asn Ala Val Tyr Leu Gln Met Asn Ser Leu Lys
            210                 215                 220
Pro Glu Asp Thr Ala Val Tyr Tyr Cys Ala Ala Val Arg Gln Met Tyr
225                 230                 235                 240
Met Thr Val Val Pro Asp Tyr Trp Gly Gln Gly Thr Leu Val Thr Val
                245                 250                 255
Ser Ser

<210> SEQ ID NO 321
<211> LENGTH: 297
<212> TYPE: PRT
<213> ORGANISM: Artificial Sequence
<220> FEATURE:
<223> OTHER INFORMATION: Nanobody sequence

<400> SEQUENCE: 321

Glu Val Gln Leu Val Glu Ser Gly Gly Gly Leu Val Gln Gly Gly Gly
1               5                   10                  15
Ser Leu Ser Leu Ser Cys Ala Ala Ser Gly Arg Thr Phe Ser Ser Tyr
                20                  25                  30
Ala Met Ala Trp Phe Arg Gln Pro Pro Gly Lys Glu Arg Glu Phe Val
            35                  40                  45
Ala Ser Ile Ser Trp Ser Gly Glu Asn Thr Asn Tyr Arg Asn Ser Val
        50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Asp Thr Ala Val Tyr Tyr Cys
                85                  90                  95
Ala Ala Lys Ile Ala Lys Thr Tyr Pro Asp Asn Trp Tyr Trp Thr Lys
            100                 105                 110
Ser Asn Asn Tyr Asn Tyr Trp Gly Gln Gly Thr Leu Val Thr Val Ser
        115                 120                 125
Ser Gly Gly Gly Gly Ser Gly Gly Gly Ser Gly Gly Gly Gly Ser
130                 135                 140
Gly Gly Gly Gly Ser Gly Gly Gly Ser Gly Gly Gly Gly Ser Gly
145                 150                 155                 160
Gly Gly Ser Asp Val Gln Leu Gln Ala Ser Gly Gly Gly Ser Val
                165                 170                 175
Gln Ala Gly Gly Ser Leu Arg Leu Ser Cys Ala Ala Ser Gly Tyr Thr
                180                 185                 190
Ile Gly Pro Tyr Cys Met Gly Trp Phe Arg Gln Ala Pro Gly Lys Glu
            195                 200                 205
Arg Glu Gly Val Ala Ala Ile Asn Met Gly Gly Ile Thr Tyr Tyr
            210                 215                 220
Ala Asp Ser Val Lys Gly Arg Phe Thr Ile Ser Gln Asp Asn Ala Lys
225                 230                 235                 240
Asn Thr Val Tyr Leu Leu Met Asn Ser Leu Glu Pro Glu Asp Thr Ala
                245                 250                 255
Ile Tyr Tyr Cys Ala Ala Asp Ser Thr Ile Tyr Ala Ser Tyr Glu
            260                 265                 270
Cys Gly His Gly Leu Ser Thr Gly Gly Tyr Gly Tyr Asp Ser Trp Gly
            275                 280                 285
```

-continued

```
Gln Gly Thr Gln Val Thr Val Ser Ser
    290             295

<210> SEQ ID NO 322
<211> LENGTH: 279
<212> TYPE: PRT
<213> ORGANISM: Artificial Sequence
<220> FEATURE:
<223> OTHER INFORMATION: Nanobody sequence

<400> SEQUENCE: 322

Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Phe Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Glu Gly Asn Thr Tyr Tyr Glu Asp Phe Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Pro Glu Asp Thr Ala Leu Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Thr Phe Ser Gly Thr Phe Ser Ser Tyr Thr
            180                 185                 190

Met Gly Trp Phe Arg Gln Ala Pro Gly Lys Glu Arg Glu Phe Val Ala
        195                 200                 205

Glu Val Arg Trp Gly Gly Val Thr Thr Tyr Ser Asn Ser Leu Lys Asp
    210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Val Pro Asp Tyr Trp Gly Gln Gly
            260                 265                 270

Thr Leu Val Thr Val Ser Ser
        275

<210> SEQ ID NO 323
<211> LENGTH: 279
<212> TYPE: PRT
<213> ORGANISM: Artificial Sequence
<220> FEATURE:
<223> OTHER INFORMATION: Nanobody sequence

<400> SEQUENCE: 323

Glu Val Gln Leu Val Glu Ser Gly Gly Gly Pro Val Gln Ala Gly Gly
```

```
            1               5                  10                 15
        Ser Leu Arg Leu Ser Cys Ala Ala Ser Gly Arg Thr Tyr Arg Gly Tyr
                        20                  25                  30

Ser Met Gly Trp Phe Arg Gln Ala Pro Gly Lys Glu Arg Glu Phe Val
                        35                  40                  45

Ala Ala Ile Val Trp Ser Gly Gly Asn Thr Tyr Tyr Glu Asp Ser Val
                        50                  55                  60

Lys Gly Arg Phe Thr Ile Ser Arg Asp Asn Ala Lys Asn Thr Met Tyr
         65                  70                  75                  80

Leu Gln Met Thr Ser Leu Lys Pro Glu Asp Ser Ala Thr Tyr Tyr Cys
                        85                  90                  95

Ala Ala Lys Ile Arg Pro Tyr Ile Phe Lys Ile Ala Gly Gln Tyr Asp
                       100                 105                 110

Tyr Trp Gly Gln Gly Thr Leu Val Thr Val Ser Ser Gly Gly Gly Gly
                       115                 120                 125

Ser Gly Gly Gly Gly Ser Gly Gly Gly Gly Ser Gly Gly Gly Gly Ser
                       130                 135                 140

Gly Gly Gly Gly Ser Gly Gly Gly Ser Gly Gly Gly Ser Glu
        145                 150                 155                 160

Val Gln Leu Val Glu Ser Gly Gly Leu Val Gln Pro Gly Gly Ser
                       165                 170                 175

Leu Arg Leu Ser Cys Thr Phe Ser Gly Thr Phe Ser Ser Tyr Thr
                       180                 185                 190

Met Gly Trp Phe Arg Gln Ala Pro Gly Lys Glu Arg Glu Phe Val Ala
                       195                 200                 205

Glu Val Arg Trp Gly Gly Val Thr Thr Tyr Ser Asn Ser Leu Lys Asp
                       210                 215                 220

Arg Phe Ser Ile Ser Glu Asp Ser Val Lys Asn Ala Val Tyr Leu Gln
        225                 230                 235                 240

Met Asn Ser Leu Lys Pro Glu Asp Thr Ala Val Tyr Tyr Cys Ala Ala
                       245                 250                 255

Val Arg Gln Met Tyr Met Thr Val Val Pro Asp Tyr Trp Gly Gln Gly
                       260                 265                 270

Thr Leu Val Thr Val Ser Ser
                       275

<210> SEQ ID NO 324
<211> LENGTH: 279
<212> TYPE: PRT
<213> ORGANISM: Artificial Sequence
<220> FEATURE:
<223> OTHER INFORMATION: Nanobody sequence

<400> SEQUENCE: 324

Glu Val Gln Leu Val Glu Ser Gly Gly Gly Pro Val Gln Ala Gly Gly
         1               5                  10                  15

Ser Leu Arg Leu Ser Cys Ala Ala Ser Gly Arg Thr Tyr Arg Gly Tyr
                        20                  25                  30

Ser Met Ala Trp Phe Arg Gln Ser Pro Gly Lys Glu Arg Glu Phe Val
                        35                  40                  45

Ala Ala Ile Val Trp Ser Asp Gly Asn Thr Tyr Tyr Glu Asp Phe Val
                        50                  55                  60

Lys Gly Arg Phe Thr Ile Ser Arg Asp Ser Ala Lys Asn Thr Leu Tyr
         65                  70                  75                  80

Leu Gln Met Thr Asn Leu Lys Pro Glu Asp Thr Ala Leu Tyr Tyr Cys
```

-continued

```
                85                  90                  95
Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser Gly Gly Gly Gly
        115                 120                 125

Ser Gly Gly Gly Ser Gly Gly Gly Ser Gly Gly Gly Ser
    130                 135                 140

Gly Gly Gly Gly Ser Gly Gly Gly Ser Gly Gly Gly Ser Glu
145                 150                 155                 160

Val Gln Leu Val Glu Ser Gly Gly Leu Val Gln Pro Gly Gly Ser
                165                 170                 175

Leu Arg Leu Ser Cys Thr Phe Ser Gly Thr Phe Ser Ser Tyr Thr
                180                 185                 190

Met Gly Trp Phe Arg Gln Ala Pro Gly Lys Glu Arg Glu Phe Val Ala
        195                 200                 205

Glu Val Arg Trp Gly Val Thr Thr Tyr Ser Asn Ser Leu Lys Asp
    210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Pro Asp Tyr Trp Gly Gln Gly
                260                 265                 270

Thr Leu Val Thr Val Ser Ser
            275

<210> SEQ ID NO 325
<211> LENGTH: 275
<212> TYPE: PRT
<213> ORGANISM: Artificial Sequence
<220> FEATURE:
<223> OTHER INFORMATION: Nanobody sequence

<400> SEQUENCE: 325

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Ile Tyr Lys Ser Phe
            20                  25                  30

Asp Met Gly Trp Tyr Arg Gln Ala Pro Gly Lys Gln Arg Asp Leu Val
        35                  40                  45

Ala Val Ile Gly Ser Arg Gly Asn Asn Arg Gly Arg Thr Asn Tyr Ala
    50                  55                  60

Asp Ser Val Lys Gly Arg Phe Thr Ile Ser Arg Asp Gly Thr Gly Asn
65                  70                  75                  80

Thr Val Tyr Leu Leu Met Asn Lys Leu Arg Pro Glu Asp Thr Ala Ile
                85                  90                  95

Tyr Tyr Cys Asn Thr Ala Pro Leu Val Ala Gly Arg Pro Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
```

```
                 165                 170                 175
Cys Thr Phe Ser Gly Gly Thr Phe Ser Ser Tyr Thr Met Gly Trp Phe
                180                 185                 190

Arg Gln Ala Pro Gly Lys Glu Arg Glu Phe Val Ala Glu Val Arg Trp
                195                 200                 205

Gly Gly Val Thr Thr Tyr Ser Asn Ser Leu Lys Asp Arg Phe Ser Ile
            210                 215                 220

Ser Glu Asp Ser Val Lys Asn Ala Val Tyr Leu Gln Met Asn Ser Leu
225                 230                 235                 240

Lys Pro Glu Asp Thr Ala Val Tyr Tyr Cys Ala Ala Val Arg Gln Met
                245                 250                 255

Tyr Met Thr Val Val Pro Asp Tyr Trp Gly Gln Gly Thr Leu Val Thr
                260                 265                 270

Val Ser Ser
        275

<210> SEQ ID NO 326
<211> LENGTH: 279
<212> TYPE: PRT
<213> ORGANISM: Artificial Sequence
<220> FEATURE:
<223> OTHER INFORMATION: Nanobody sequence

<400> SEQUENCE: 326

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Asn Met Asn
                20                  25                  30

Pro Leu Gly Trp Phe Arg Gln Ser Pro Gly Lys Glu Arg Glu Phe Val
            35                  40                  45

Ala Ala His Arg Trp Ser Asp Gly Asn Thr Tyr Tyr Val Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ala Gly Arg Pro Trp Ser Ala Phe Arg Ser Pro Gly Glu Tyr Val
                100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Ser Gly Gly Gly Gly Ser
130                 135                 140

Gly Gly Gly Gly Ser Gly Gly Gly Ser Gly Gly Gly Gly Ser Glu
145                 150                 155                 160

Val Gln Leu Val Glu Ser Gly Gly Leu Val Gln Pro Gly Gly Ser
                165                 170                 175

Leu Arg Leu Ser Cys Thr Phe Ser Gly Thr Phe Ser Ser Tyr Thr
                180                 185                 190

Met Gly Trp Phe Arg Gln Ala Pro Gly Lys Glu Arg Glu Phe Val Ala
            195                 200                 205

Glu Val Arg Trp Gly Gly Val Thr Thr Tyr Ser Asn Ser Leu Lys Asp
        210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
```

245                 250                 255
Val Arg Gln Met Tyr Met Thr Val Val Pro Asp Tyr Trp Gly Gln Gly
            260                 265                 270

Thr Leu Val Thr Val Ser Ser
            275

<210> SEQ ID NO 327
<211> LENGTH: 279
<212> TYPE: PRT
<213> ORGANISM: Artificial Sequence
<220> FEATURE:
<223> OTHER INFORMATION: Nanobody sequence

<400> SEQUENCE: 327

Glu Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Phe Ser Thr Asn
            20                  25                  30

Pro Met Gly Trp Phe Arg Gln Val Pro Gly Lys Glu Arg Glu Leu Ile
        35                  40                  45

Ala Ala Val Arg Trp Ala Asp Gly Asn Thr Phe Tyr Ala Asp Ser Val
50                  55                  60

Lys Gly Arg Phe Thr Ile Ser Arg Asp Asn Ala Lys Lys Thr Val Tyr
65                  70                  75                  80

Leu Gln Met Asn Ser Leu Lys Ser Glu Asp Thr Ala Thr Tyr Tyr Cys
                85                  90                  95

Ala Ala Gly Arg Pro Trp Ser Ala Tyr His Ser Pro Ala Glu Tyr Val
            100                 105                 110

His Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Thr Phe Ser Gly Thr Phe Ser Ser Tyr Thr
            180                 185                 190

Met Gly Trp Phe Arg Gln Ala Pro Gly Lys Glu Arg Glu Phe Val Ala
        195                 200                 205

Glu Val Arg Trp Gly Gly Val Thr Thr Tyr Ser Asn Ser Leu Lys Asp
    210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Val Pro Asp Tyr Trp Gly Gln Gly
            260                 265                 270

Thr Leu Val Thr Val Ser Ser
            275

<210> SEQ ID NO 328
<211> LENGTH: 284
<212> TYPE: PRT
<213> ORGANISM: Artificial Sequence
<220> FEATURE:
<223> OTHER INFORMATION: Nanobody sequence

```
<400> SEQUENCE: 328

Glu Val Gln Leu Val Glu Ser Gly Gly Gly Leu Val Gln Gly Gly
1               5                   10                  15

Ser Leu Ser Leu Ser Cys Ala Ala Ser Gly Arg Thr Phe Ser Ser Tyr
            20                  25                  30

Ala Met Ala Trp Phe Arg Gln Pro Pro Gly Lys Glu Arg Glu Phe Val
            35                  40                  45

Ala Ser Ile Ser Trp Ser Gly Glu Asn Thr Asn Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Lys Ile Ala Lys Thr Tyr Pro Asp Asn Trp Tyr Trp Thr Lys
            100                 105                 110

Ser Asn Asn Tyr Asn Tyr Trp Gly Gln Gly Thr Leu Val Thr Val Ser
            115                 120                 125

Ser Gly Gly Gly Gly Ser Gly Gly Gly Ser Gly Gly Gly Gly Ser
        130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Gly Leu Val
                165                 170                 175

Gln Pro Gly Gly Ser Leu Arg Leu Ser Cys Thr Phe Ser Gly Gly Thr
            180                 185                 190

Phe Ser Ser Tyr Thr Met Gly Trp Phe Arg Gln Ala Pro Gly Lys Glu
            195                 200                 205

Arg Glu Phe Val Ala Glu Val Arg Trp Gly Gly Val Thr Thr Tyr Ser
            210                 215                 220

Asn Ser Leu Lys Asp Arg Phe Ser Ile Ser Glu Asp Ser Val Lys Asn
225                 230                 235                 240

Ala Val Tyr Leu Gln Met Asn Ser Leu Lys Pro Glu Asp Thr Ala Val
                245                 250                 255

Tyr Tyr Cys Ala Ala Val Arg Gln Met Tyr Met Thr Val Val Pro Asp
            260                 265                 270

Tyr Trp Gly Gln Gly Thr Leu Val Thr Val Ser Ser
            275                 280

<210> SEQ ID NO 329
<211> LENGTH: 269
<212> TYPE: PRT
<213> ORGANISM: Artificial Sequence
<220> FEATURE:
<223> OTHER INFORMATION: Nanobody sequence

<400> SEQUENCE: 329

Glu Val Gln Leu Val Glu Ser Gly Gly Gly Ala Val Gln Pro Gly Gly
1               5                   10                  15

Ser Leu Arg Leu Ser Cys Ala Ala Ser Gly Ile Arg Ile Ser Arg Asn
            20                  25                  30

Met Met Gly Trp Phe Arg Gln Ala Pro Gly Lys Gln Arg Asp Leu Val
            35                  40                  45

Ala Arg Ile Thr Pro Gly Gly Asp Thr Tyr Tyr Val Asp Ser Val Lys
    50                  55                  60
```

-continued

Gly Arg Phe Ser Ile Ser Lys Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ser Tyr Ser Thr Leu Gly Ser Trp Gly Gln Gly Thr Leu Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Thr Phe Ser Gly Gly
            165                 170                 175

Thr Phe Ser Ser Tyr Thr Met Gly Trp Phe Arg Gln Ala Pro Gly Lys
            180                 185                 190

Glu Arg Glu Phe Val Ala Glu Val Arg Trp Gly Gly Val Thr Thr Tyr
            195                 200                 205

Ser Asn Ser Leu Lys Asp Arg Phe Ser Ile Ser Glu Asp Ser Val Lys
210                 215                 220

Asn Ala Val Tyr Leu Gln Met Asn Ser Leu Lys Pro Glu Asp Thr Ala
225                 230                 235                 240

Val Tyr Tyr Cys Ala Ala Val Arg Gln Met Tyr Met Thr Val Val Pro
            245                 250                 255

Asp Tyr Trp Gly Gln Gly Thr Leu Val Thr Val Ser Ser
            260                 265

<210> SEQ ID NO 330
<211> LENGTH: 279
<212> TYPE: PRT
<213> ORGANISM: Artificial Sequence
<220> FEATURE:
<223> OTHER INFORMATION: Nanobody sequence

<400> SEQUENCE: 330

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Pro Val Gln Ala Gly Ser Leu Arg Leu Ser
                165                 170                 175

Cys Ala Ala Ser Gly Arg Thr Tyr Arg Gly Tyr Ser Met Ala Trp Phe
            180                 185                 190

Arg Gln Ser Pro Gly Lys Glu Arg Glu Phe Val Ala Ala Ile Val Trp
        195                 200                 205

Ser Asp Gly Asn Thr Tyr Tyr Glu Asp Phe Val Lys Gly Arg Phe Thr
    210                 215                 220

Ile Ser Arg Asp Ser Ala Lys Asn Thr Leu Tyr Leu Gln Met Thr Asn
225                 230                 235                 240

Leu Lys Pro Glu Asp Thr Ala Leu Tyr Tyr Cys Ala Ala Lys Ile Arg
                245                 250                 255

Pro Tyr Ile Phe Lys Ile Ala Gly Gln Tyr Asp Tyr Trp Gly Gln Gly
                260                 265                 270

Thr Leu Val Thr Val Ser Ser
            275

<210> SEQ ID NO 331
<211> LENGTH: 275
<212> TYPE: PRT
<213> ORGANISM: Artificial Sequence
<220> FEATURE:
<223> OTHER INFORMATION: Nanobody sequence

<400> SEQUENCE: 331

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Asp Ile Tyr Lys Ser Phe Asp Met Gly Trp Tyr
            180                 185                 190

Arg Gln Ala Pro Gly Lys Gln Arg Asp Leu Val Ala Val Ile Gly Ser
        195                 200                 205

Arg Gly Asn Asn Arg Gly Arg Thr Asn Tyr Ala Asp Ser Val Lys Gly
    210                 215                 220

Arg Phe Thr Ile Ser Arg Asp Gly Thr Gly Asn Thr Val Tyr Leu Leu
225                 230                 235                 240

Met Asn Lys Leu Arg Pro Glu Asp Thr Ala Ile Tyr Tyr Cys Asn Thr
                245                 250                 255

Ala Pro Leu Val Ala Gly Arg Pro Trp Gly Arg Gly Thr Leu Val Thr
            260                 265                 270

Val Ser Ser
        275

<210> SEQ ID NO 332
<211> LENGTH: 269
<212> TYPE: PRT
<213> ORGANISM: Artificial Sequence
<220> FEATURE:
<223> OTHER INFORMATION: Nanobody sequence

<400> SEQUENCE: 332

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Ala Val Gln Pro Gly Gly Ser Leu Arg Leu Ser
                165                 170                 175

Cys Ala Ala Ser Gly Ile Arg Ile Ser Arg Asn Met Met Gly Trp Phe
            180                 185                 190

Arg Gln Ala Pro Gly Lys Gln Arg Asp Leu Val Ala Arg Ile Thr Pro
        195                 200                 205

Gly Gly Asp Thr Tyr Tyr Val Asp Ser Val Lys Gly Arg Phe Ser Ile
    210                 215                 220

Ser Lys Asp Asn Ala Lys Asn Thr Val Tyr Leu Gln Met Asn Ser Leu
225                 230                 235                 240

Lys Pro Glu Asp Thr Ala Val Tyr Tyr Cys Asn Ser Tyr Ser Thr Leu
                245                 250                 255

Gly Ser Trp Gly Gln Gly Thr Leu Val Thr Val Ser Ser
            260                 265

<210> SEQ ID NO 333
<211> LENGTH: 279
<212> TYPE: PRT
<213> ORGANISM: Artificial Sequence
<220> FEATURE:
<223> OTHER INFORMATION: Nanobody sequence

<400> SEQUENCE: 333

```
Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

Cys Ala Ala Ser Gly Arg Ser Phe Asn Met Asn Pro Leu Gly Trp Phe
            180                 185                 190

Arg Gln Ser Pro Gly Lys Glu Arg Glu Phe Val Ala Ala His Arg Trp
        195                 200                 205

Ser Asp Gly Asn Thr Tyr Tyr Val Asp Ser Val Lys Gly Arg Phe Thr
    210                 215                 220

Ile Ser Arg Asp Asn Ala Lys Asn Thr Val Tyr Leu Gln Met Asn Ser
225                 230                 235                 240

Leu Lys Ser Glu Asp Thr Ala Val Tyr Tyr Cys Ala Ala Gly Arg Pro
                245                 250                 255

Trp Ser Ala Phe Arg Ser Pro Gly Glu Tyr Val Tyr Trp Gly Gln Gly
            260                 265                 270

Thr Leu Val Thr Val Ser Ser
        275

<210> SEQ ID NO 334
<211> LENGTH: 279
<212> TYPE: PRT
<213> ORGANISM: Artificial Sequence
<220> FEATURE:
<223> OTHER INFORMATION: Nanobody sequence

<400> SEQUENCE: 334

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80
```

```
Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

Glu Ser Gly Gly Ser Val Gln Ala Gly Ser Leu Arg Leu Ser
                165                 170                 175

Cys Ala Ala Ser Gly Arg Thr Phe Ser Thr Asn Pro Met Gly Trp Phe
            180                 185                 190

Arg Gln Val Pro Gly Lys Glu Arg Glu Leu Ile Ala Ala Val Arg Trp
            195                 200                 205

Ala Asp Gly Asn Thr Phe Tyr Ala Asp Ser Val Lys Gly Arg Phe Thr
210                 215                 220

Ile Ser Arg Asp Asn Ala Lys Lys Thr Val Tyr Leu Gln Met Asn Ser
225                 230                 235                 240

Leu Lys Ser Glu Asp Thr Ala Thr Tyr Tyr Cys Ala Ala Gly Arg Pro
                245                 250                 255

Trp Ser Ala Tyr His Ser Pro Ala Glu Tyr Val His Trp Gly Gln Gly
            260                 265                 270

Thr Leu Val Thr Val Ser Ser
            275

<210> SEQ ID NO 335
<211> LENGTH: 284
<212> TYPE: PRT
<213> ORGANISM: Artificial Sequence
<220> FEATURE:
<223> OTHER INFORMATION: Nanobody sequence

<400> SEQUENCE: 335

Glu Val Gln Leu Val Glu Ser Gly Gly Gly Leu Val Gln Pro Gly Gly
1               5                   10                  15

Ser Leu Arg Leu Ser Cys Thr Phe Ser Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160
```

```
Glu Ser Gly Gly Gly Leu Val Gln Gly Gly Ser Leu Ser Leu Ser
            165                 170                 175

Cys Ala Ala Ser Gly Arg Thr Phe Ser Ser Tyr Ala Met Ala Trp Phe
            180                 185                 190

Arg Gln Pro Pro Gly Lys Glu Arg Glu Phe Val Ala Ser Ile Ser Trp
            195                 200                 205

Ser Gly Glu Asn Thr Asn Tyr Arg Asn Ser Val Lys Gly Arg Phe Thr
        210                 215                 220

Ile Ser Arg Asp Asn Ala Lys Asn Thr Val Tyr Leu Gln Met Asn Ser
225                 230                 235                 240

Leu Lys Pro Glu Asp Thr Ala Val Tyr Tyr Cys Ala Ala Lys Ile Ala
            245                 250                 255

Lys Thr Tyr Pro Asp Asn Trp Tyr Trp Thr Lys Ser Asn Asn Tyr Asn
            260                 265                 270

Tyr Trp Gly Gln Gly Thr Leu Val Thr Val Ser Ser
            275                 280

<210> SEQ ID NO 336
<211> LENGTH: 279
<212> TYPE: PRT
<213> ORGANISM: Artificial Sequence
<220> FEATURE:
<223> OTHER INFORMATION: Nanobody sequence

<400> SEQUENCE: 336

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Gly Ser Gly Gly Gly Ser Gly Gly Gly Gly
        130                 135                 140

Ser Gly Gly Gly Gly Ser Gly Gly Gly Ser Glu Val Gln Leu Val
145                 150                 155                 160

Glu Ser Gly Gly Gly Pro Val Gln Ala Gly Ser Leu Arg Leu Ser
            165                 170                 175

Cys Ala Ala Ser Gly Arg Thr Tyr Arg Gly Tyr Ser Met Gly Trp Phe
            180                 185                 190

Arg Gln Ala Pro Gly Lys Glu Arg Glu Phe Val Ala Ala Ile Val Trp
            195                 200                 205

Ser Gly Gly Asn Thr Tyr Tyr Glu Asp Ser Val Lys Gly Arg Phe Thr
        210                 215                 220

Ile Ser Arg Asp Asn Ala Lys Asn Thr Met Tyr Leu Gln Met Thr Ser
225                 230                 235                 240
```

Leu Lys Pro Glu Asp Ser Ala Thr Tyr Tyr Cys Ala Ala Lys Ile Arg
                245                 250                 255

Pro Tyr Ile Phe Lys Ile Ala Gly Gln Tyr Asp Tyr Trp Gly Gln Gly
            260                 265                 270

Thr Leu Val Thr Val Ser Ser
        275

<210> SEQ ID NO 337
<211> LENGTH: 279
<212> TYPE: PRT
<213> ORGANISM: Artificial Sequence
<220> FEATURE:
<223> OTHER INFORMATION: Nanobody sequence

<400> SEQUENCE: 337

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Ser Gly Gly Gly Gly
        115                 120                 125

Gly Ser Gly Gly Gly Gly Ser Gly Gly Gly Ser Gly Gly Gly Gly
        130                 135                 140

Ser Gly Gly Gly Gly Ser Gly Gly Gly Ser Glu Val Gln Leu Val
145                 150                 155                 160

Glu Ser Gly Gly Gly Leu Val Gln Thr Gly Gly Ser Leu Arg Leu Ser
                165                 170                 175

Cys Val Ala Ser Gly Arg Thr Tyr Arg Gly Tyr Ser Met Ala Trp Phe
            180                 185                 190

Arg Gln Pro Pro Gly Lys Glu Arg Glu Phe Val Ala Ala Ile Thr Trp
        195                 200                 205

Ser Glu Gly Asn Thr Tyr Tyr Glu Asp Phe Val Lys Gly Arg Phe Thr
    210                 215                 220

Ile Ser Arg Asp Asn Ala Lys Asn Thr Leu Tyr Leu Gln Met Thr Ser
225                 230                 235                 240

Leu Lys Pro Glu Asp Thr Ala Leu Tyr Tyr Cys Ala Ala Lys Ile Arg
                245                 250                 255

Pro Tyr Ile Phe Lys Ile Pro Gly Gln Tyr Asp Tyr Trp Gly Gln Gly
            260                 265                 270

Thr Leu Val Thr Val Ser Ser
        275

<210> SEQ ID NO 338
<211> LENGTH: 279
<212> TYPE: PRT
<213> ORGANISM: Artificial Sequence
<220> FEATURE:
<223> OTHER INFORMATION: Nanobody sequence

<400> SEQUENCE: 338

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Pro Val Gln Ala Gly Gly Ser Leu Arg Leu Ser
                165                 170                 175

Cys Ala Ala Ser Gly Arg Thr Phe Arg Gly Tyr Ser Met Ala Trp Phe
            180                 185                 190

Arg Gln Pro Pro Gly Lys Glu Arg Glu Phe Val Ala Ala Ile Thr Trp
        195                 200                 205

Ser Glu Gly Asn Thr Tyr Tyr Glu Asp Phe Val Lys Gly Arg Phe Thr
    210                 215                 220

Ile Ser Arg Asp Asn Ala Lys Asn Thr Leu Tyr Leu Gln Met Thr Ser
225                 230                 235                 240

Leu Lys Pro Glu Asp Thr Ala Leu Tyr Tyr Cys Ala Ala Lys Ile Arg
                245                 250                 255

Pro Tyr Ile Phe Lys Ile Ala Gly Gln Tyr Asp Tyr Trp Gly Gln Gly
            260                 265                 270

Thr Leu Val Thr Val Ser Ser
        275

<210> SEQ ID NO 339
<211> LENGTH: 279
<212> TYPE: PRT
<213> ORGANISM: Artificial Sequence
<220> FEATURE:
<223> OTHER INFORMATION: Nanobody sequence

<400> SEQUENCE: 339

Glu Val Gln Leu Val Glu Ser Gly Gly Gly Leu Val Gln Thr Gly Gly
1               5                   10                  15

Ser Leu Arg Leu Ser Cys Val Ala Ser Gly Arg Thr Tyr Arg Gly Tyr
            20                  25                  30

Ser Met Ala Trp Phe Arg Gln Pro Pro Gly Lys Glu Arg Glu Phe Val
        35                  40                  45

Ala Ala Ile Thr Trp Ser Glu Gly Asn Thr Tyr Tyr Glu Asp Phe Val

```
                 50                  55                  60
Lys Gly Arg Phe Thr Ile Ser Arg Asp Asn Ala Lys Asn Thr Leu Tyr
 65                  70                  75                  80

Leu Gln Met Thr Ser Leu Lys Pro Glu Asp Thr Ala Leu Tyr Tyr Cys
                     85                  90                  95

Ala Ala Lys Ile Arg Pro Tyr Ile Phe Lys Ile Pro Gly Gln Tyr Asp
                100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Ser Glu
145                 150                 155                 160

Val Gln Leu Val Glu Ser Gly Gly Leu Val Gln Pro Gly Gly Ser
                165                 170                 175

Leu Arg Leu Ser Cys Thr Phe Ser Gly Gly Thr Phe Ser Ser Tyr Thr
                180                 185                 190

Met Gly Trp Phe Arg Gln Ala Pro Gly Lys Glu Arg Glu Phe Val Ala
            195                 200                 205

Glu Val Arg Trp Gly Gly Val Thr Thr Tyr Ser Asn Ser Leu Lys Asp
            210                 215                 220

Arg Phe Ser Ile Ser Glu Asp Ser Val Lys Asn Ala Val Tyr Leu Gln
225                 230                 235                 240

Met Asn Ser Leu Lys Pro Glu Asp Thr Ala Val Tyr Tyr Cys Ala Ala
                245                 250                 255

Val Arg Gln Met Tyr Met Thr Val Val Pro Asp Tyr Trp Gly Gln Gly
            260                 265                 270

Thr Leu Val Thr Val Ser Ser
            275

<210> SEQ ID NO 340
<211> LENGTH: 279
<212> TYPE: PRT
<213> ORGANISM: Artificial Sequence
<220> FEATURE:
<223> OTHER INFORMATION: Nanobody sequence

<400> SEQUENCE: 340

Asp Val Gln Leu Val Glu Ser Gly Gly Gly Leu Val Gln Pro Gly Gly
 1                   5                  10                  15

Ser Leu Arg Leu Ser Cys Thr Phe Ser Gly Gly Thr Phe Ser Ser Tyr
                 20                  25                  30

Thr Met Gly Trp Phe Arg Gln Ala Pro Gly Lys Glu Arg Glu Phe Val
             35                  40                  45

Ala Glu Val Arg Trp Gly Gly Val Thr Thr Tyr Ser Asn Ser Leu Lys
 50                  55                  60

Asp Arg Phe Ser Ile Ser Glu Asp Ser Val Lys Asn Ala Val Tyr Leu
 65                  70                  75                  80

Gln Met Asn Ser Leu Lys Pro Glu Asp Thr Ala Val Tyr Tyr Cys Ala
                 85                  90                  95

Ala Val Arg Gln Met Tyr Met Thr Val Val Pro Asp Tyr Trp Gln Gly
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Gly Gly Gly Gly
```

```
                130                 135                 140
Ser Gly Gly Gly Ser Gly Gly Gly Ser Glu Val Gln Leu Val
145                 150                 155                 160

Glu Ser Gly Gly Gly Pro Val Gln Ala Gly Gly Ser Leu Arg Leu Ser
                165                 170                 175

Cys Ala Ala Ser Gly Arg Thr Tyr Arg Gly Tyr Ser Met Gly Trp Phe
                180                 185                 190

Arg Gln Ala Pro Gly Lys Glu Arg Glu Phe Val Ala Ala Ile Val Trp
                195                 200                 205

Ser Gly Gly Asn Thr Tyr Tyr Glu Asp Ser Val Lys Gly Arg Phe Thr
210                 215                 220

Ile Ser Arg Asp Asn Ala Lys Asn Thr Met Tyr Leu Gln Met Thr Ser
225                 230                 235                 240

Leu Lys Pro Glu Asp Ser Ala Thr Tyr Tyr Cys Ala Ala Lys Ile Arg
                245                 250                 255

Pro Tyr Ile Phe Lys Ile Ala Gly Gln Tyr Asp Tyr Trp Gly Gln Gly
                260                 265                 270

Thr Leu Val Thr Val Ser Ser
        275

<210> SEQ ID NO 341
<211> LENGTH: 286
<212> TYPE: PRT
<213> ORGANISM: Artificial Sequence
<220> FEATURE:
<223> OTHER INFORMATION: Nanobody sequence

<400> SEQUENCE: 341

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
                35                  40                  45

Ala Ala Ile Ser Trp Ser Asp Gly Ser Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
                100                 105                 110

Ala Tyr Asp Tyr Trp Gly Gln Gly Thr Gln Val Thr Val Ser Ser Gly
            115                 120                 125

Gly Gly Gly Ser Gly Gly Gly Gly Ser Gly Gly Gly Gly Ser Gly Gly
            130                 135                 140

Gly Gly Ser Gly Gly Gly Gly Ser Gly Gly Gly Gly Ser Gly Gly Gly
145                 150                 155                 160

Gly Ser Glu Val Gln Leu Val Glu Ser Gly Gly Gly Pro Val Gln Ala
                165                 170                 175

Gly Gly Ser Leu Arg Leu Ser Cys Ala Ala Ser Gly Arg Thr Tyr Arg
                180                 185                 190

Gly Tyr Ser Met Ala Trp Phe Arg Gln Ser Pro Gly Lys Glu Arg Glu
                195                 200                 205

Phe Val Ala Ala Ile Val Trp Ser Asp Gly Asn Thr Tyr Tyr Glu Asp
```

```
                 210                 215                 220

Phe Val Lys Gly Arg Phe Thr Ile Ser Arg Asp Ser Ala Lys Asn Thr
225                 230                 235                 240

Leu Tyr Leu Gln Met Thr Asn Leu Lys Pro Glu Asp Thr Ala Leu Tyr
                245                 250                 255

Tyr Cys Ala Ala Lys Ile Arg Pro Tyr Ile Phe Lys Ile Ala Gly Gln
            260                 265                 270

Tyr Asp Tyr Trp Gly Gln Gly Thr Leu Val Thr Val Ser Ser
            275                 280                 285

<210> SEQ ID NO 342
<211> LENGTH: 286
<212> TYPE: PRT
<213> ORGANISM: Artificial Sequence
<220> FEATURE:
<223> OTHER INFORMATION: Nanobody sequence

<400> SEQUENCE: 342

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45

Ala Ala Ile Ser Trp Ser Asp Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
            115                 120                 125

Gly Gly Ser Gly Gly Gly Gly Ser Gly Gly Gly Gly Ser Gly Gly Gly
130                 135                 140

Gly Gly Ser Gly Gly Gly Gly Ser Gly Gly Gly Ser Gly Gly Gly Gly
145                 150                 155                 160

Gly Ser Glu Val Gln Leu Val Glu Ser Gly Gly Pro Val Gln Ala
            165                 170                 175

Gly Gly Ser Leu Arg Leu Ser Cys Ala Ala Ser Gly Arg Thr Tyr Arg
            180                 185                 190

Gly Tyr Ser Met Gly Trp Phe Arg Gln Ala Pro Gly Lys Glu Arg Glu
            195                 200                 205

Phe Val Ala Ala Ile Val Trp Ser Gly Gly Asn Thr Tyr Tyr Glu Asp
            210                 215                 220

Ser Val Lys Gly Arg Phe Thr Ile Ser Arg Asp Asn Ala Lys Asn Thr
225                 230                 235                 240

Met Tyr Leu Gln Met Thr Ser Leu Lys Pro Glu Asp Ser Ala Thr Tyr
                245                 250                 255

Tyr Cys Ala Ala Lys Ile Arg Pro Tyr Ile Phe Lys Ile Ala Gly Gln
            260                 265                 270

Tyr Asp Tyr Trp Gly Gln Gly Thr Leu Val Thr Val Ser Ser
            275                 280                 285
```

-continued

```
<210> SEQ ID NO 343
<211> LENGTH: 429
<212> TYPE: PRT
<213> ORGANISM: Artificial Sequence
<220> FEATURE:
<223> OTHER INFORMATION: Nanobody sequence

<400> SEQUENCE: 343
```

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Pro Val Gln Ala Gly Gly Ser Leu Arg Leu Ser
                165                 170                 175

Cys Ala Ala Ser Gly Arg Thr Tyr Arg Gly Tyr Ser Met Gly Trp Phe
            180                 185                 190

Arg Gln Ala Pro Gly Lys Glu Arg Glu Phe Val Ala Ala Ile Val Trp
        195                 200                 205

Ser Gly Gly Asn Thr Tyr Tyr Glu Asp Ser Val Lys Gly Arg Phe Thr
    210                 215                 220

Ile Ser Arg Asp Asn Ala Lys Asn Thr Met Tyr Leu Gln Met Thr Ser
225                 230                 235                 240

Leu Lys Pro Glu Asp Ser Ala Thr Tyr Tyr Cys Ala Ala Lys Ile Arg
                245                 250                 255

Pro Tyr Ile Phe Lys Ile Ala Gly Gln Tyr Asp Tyr Trp Gly Gln Gly
            260                 265                 270

Thr Leu Val Thr Val Ser Ser Gly Gly Gly Gly Ser Gly Gly Gly Gly
        275                 280                 285

Ser Gly Gly Gly Gly Ser Gly Gly Gly Gly Ser Gly Gly Gly Gly Ser
    290                 295                 300

Gly Gly Gly Gly Ser Gly Gly Gly Gly Ser Glu Val Gln Leu Val Glu
305                 310                 315                 320

Ser Gly Gly Gly Leu Val Gln Pro Gly Asn Ser Leu Arg Leu Ser Cys
                325                 330                 335

Ala Ala Ser Gly Phe Thr Phe Ser Ser Phe Gly Met Ser Trp Val Arg
            340                 345                 350

Gln Ala Pro Gly Lys Gly Leu Glu Trp Val Ser Ser Ile Ser Gly Ser
        355                 360                 365

Gly Ser Asp Thr Leu Tyr Ala Asp Ser Val Lys Gly Arg Phe Thr Ile

```
                370                 375                 380
Ser Arg Asp Asn Ala Lys Thr Thr Leu Tyr Leu Gln Met Asn Ser Leu
385                 390                 395                 400

Arg Pro Glu Asp Thr Ala Val Tyr Tyr Cys Thr Ile Gly Gly Ser Leu
            405                 410                 415

Ser Arg Ser Ser Gln Gly Thr Leu Val Thr Val Ser Ser
            420                 425

<210> SEQ ID NO 344
<211> LENGTH: 425
<212> TYPE: PRT
<213> ORGANISM: Artificial Sequence
<220> FEATURE:
<223> OTHER INFORMATION: Nanobody sequence

<400> SEQUENCE: 344

Glu Val Gln Leu Val Glu Ser Gly Gly Gly Leu Val Gln Pro Gly Gly
1               5                   10                  15

Ser Leu Arg Leu Ser Cys Thr Phe Ser Gly Gly Thr Phe Ser Ser Tyr
            20                  25                  30

Thr Met Gly Trp Phe Arg Gln Ala Pro Gly Lys Glu Arg Glu Phe Val
        35                  40                  45

Ala Glu Val Arg Trp Gly Gly Val Thr Thr Tyr Ser Asn Ser Leu Lys
    50                  55                  60

Asp Arg Phe Ser Ile Ser Glu Asp Ser Val Lys Asn Ala Val Tyr Leu
65                  70                  75                  80

Gln Met Asn Ser Leu Lys Pro Glu Asp Thr Ala Val Tyr Tyr Cys Ala
                85                  90                  95

Ala Val Arg Gln Met Tyr Met Thr Val Val Pro Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Asp Ile Tyr Lys Ser Phe Asp Met Gly Trp Tyr
            180                 185                 190

Arg Gln Ala Pro Gly Lys Gln Arg Asp Leu Val Ala Val Ile Gly Ser
        195                 200                 205

Arg Gly Asn Asn Arg Gly Arg Thr Asn Tyr Ala Asp Ser Val Lys Gly
    210                 215                 220

Arg Phe Thr Ile Ser Arg Asp Gly Thr Gly Asn Thr Val Tyr Leu Leu
225                 230                 235                 240

Met Asn Lys Leu Arg Pro Glu Asp Thr Ala Ile Tyr Tyr Cys Asn Thr
                245                 250                 255

Ala Pro Leu Val Ala Gly Arg Pro Trp Gly Arg Gly Thr Leu Val Thr
            260                 265                 270

Val Ser Ser Gly Gly Gly Gly Ser Gly Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Ser Gly Gly Gly Gly Ser Glu Val Gln Leu Val Glu Ser Gly Gly Gly
```

```
                305                 310                 315                 320
Leu Val Gln Pro Gly Asn Ser Leu Arg Leu Ser Cys Ala Ala Ser Gly
                    325                 330                 335

Phe Thr Phe Ser Ser Phe Gly Met Ser Trp Val Arg Gln Ala Pro Gly
                    340                 345                 350

Lys Gly Leu Glu Trp Val Ser Ile Ser Gly Ser Gly Ser Asp Thr
                355                 360                 365

Leu Tyr Ala Asp Ser Val Lys Gly Arg Phe Thr Ile Ser Arg Asp Asn
            370                 375                 380

Ala Lys Thr Thr Leu Tyr Leu Gln Met Asn Ser Leu Arg Pro Glu Asp
385                 390                 395                 400

Thr Ala Val Tyr Tyr Cys Thr Ile Gly Gly Ser Leu Ser Arg Ser Ser
                    405                 410                 415

Gln Gly Thr Leu Val Thr Val Ser Ser
                    420                 425

<210> SEQ ID NO 345
<211> LENGTH: 277
<212> TYPE: PRT
<213> ORGANISM: Artificial Sequence
<220> FEATURE:
<223> OTHER INFORMATION: Nanobody sequence

<400> SEQUENCE: 345

Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
                20                  25                  30

Ser Met Gly Trp Phe Arg Gln Ala Pro Gly Lys Glu Arg Glu Phe Val
            35                  40                  45

Ala Ala Ile Val Trp Ser Gly Gly Asn Thr Tyr Tyr Glu Asp Ser Val
        50                  55                  60

Lys Gly Arg Phe Thr Ile Ser Arg Asp Asn Ala Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
                100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Ala Gly Gly Ser
                165                 170                 175

Leu Arg Leu Ser Cys Ala Ala Ser Gly Ile Thr Phe Ser Ile Asn Thr
                180                 185                 190

Met Gly Trp Tyr Arg Gln Ala Pro Gly Lys Gln Arg Glu Leu Val Ala
            195                 200                 205

Leu Ile Ser Ser Ile Gly Asp Thr Tyr Tyr Ala Asp Ser Val Lys Gly
        210                 215                 220

Arg Phe Thr Ile Ser Arg Asp Asn Ala Lys Asn Thr Val Tyr Leu Gln
225                 230                 235                 240

Met Asn Ser Leu Lys Pro Glu Asp Thr Ala Val Tyr Tyr Cys Lys Arg
```

```
                        245                 250                 255
Phe Arg Thr Ala Ala Gln Gly Thr Asp Tyr Trp Gly Gln Gly Thr Leu
            260                 265                 270

Val Thr Val Ser Ser
        275

<210> SEQ ID NO 346
<211> LENGTH: 277
<212> TYPE: PRT
<213> ORGANISM: Artificial Sequence
<220> FEATURE:
<223> OTHER INFORMATION: Nanobody sequence

<400> SEQUENCE: 346

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Glu Val Gln Leu Val Glu Ser
145                 150                 155                 160

Gly Gly Gly Pro Val Gln Ala Gly Gly Ser Leu Arg Leu Ser Cys Ala
                165                 170                 175

Ala Ser Gly Arg Thr Tyr Arg Gly Tyr Ser Met Gly Trp Phe Arg Gln
            180                 185                 190

Ala Pro Gly Lys Glu Arg Glu Phe Val Ala Ala Ile Val Trp Ser Gly
        195                 200                 205

Gly Asn Thr Tyr Tyr Glu Asp Ser Val Lys Gly Arg Phe Thr Ile Ser
    210                 215                 220

Arg Asp Asn Ala Lys Asn Thr Met Tyr Leu Gln Met Thr Ser Leu Lys
225                 230                 235                 240

Pro Glu Asp Ser Ala Thr Tyr Tyr Cys Ala Ala Lys Ile Arg Pro Tyr
                245                 250                 255

Ile Phe Lys Ile Ala Gly Gln Tyr Asp Tyr Trp Gly Gln Gly Thr Leu
            260                 265                 270

Val Thr Val Ser Ser
        275

<210> SEQ ID NO 347
<211> LENGTH: 279
<212> TYPE: PRT
<213> ORGANISM: Artificial Sequence
<220> FEATURE:
<223> OTHER INFORMATION: Nanobody sequence
```

```
<400> SEQUENCE: 347

Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Gly Ser Gly Gly Gly Gly Ser Gly Gly
130                 135                 140

Gly Gly Ser Gly Gly Gly Gly Ser Gly Gly Gly Gly Ser Gly Gly Gly
145                 150                 155                 160

Gly Ser Glu Val Gln Leu Val Glu Ser Gly Gly Gly Leu Val Gln Pro
        165                 170                 175

Gly Gly Ser Leu Arg Leu Ser Cys Ala Ala Ser Gly Asp Val His Lys
        180                 185                 190

Ile Asn Ile Leu Gly Trp Tyr Arg Gln Ala Pro Ala Lys Glu Arg Glu
            195                 200                 205

Met Val Ala His Ile Thr Ile Gly Asp Ala Thr Asp Tyr Ala Asp Ser
        210                 215                 220

Ala Lys Gly Arg Phe Thr Ile Ser Arg Asp Glu Ala Lys Asn Met Val
225                 230                 235                 240

Tyr Leu Gln Met Asn Ser Leu Lys Pro Glu Asp Thr Ala Val Tyr Phe
                245                 250                 255

Cys Arg Ala Tyr Ser Arg Ile Tyr Pro Tyr Asn Tyr Trp Gly Gln Gly
            260                 265                 270

Thr Leu Val Thr Val Ser Ser
            275

<210> SEQ ID NO 348
<211> LENGTH: 115
<212> TYPE: PRT
<213> ORGANISM: Artificial Sequence
<220> FEATURE:
<223> OTHER INFORMATION: Nanobody sequence

<400> SEQUENCE: 348

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 349
<211> LENGTH: 115
<212> TYPE: PRT
<213> ORGANISM: Artificial Sequence
<220> FEATURE:
<223> OTHER INFORMATION: Nanobody sequence

<400> SEQUENCE: 349

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Phe
             20                  25                  30

Gly Met Ser Trp Val Arg Gln Ala Pro Gly Lys Gly Pro Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 350
<211> LENGTH: 116
<212> TYPE: PRT
<213> ORGANISM: Artificial Sequence
<220> FEATURE:
<223> OTHER INFORMATION: Nanobody sequence

<400> SEQUENCE: 350

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala
        115
```

<210> SEQ ID NO 351
<211> LENGTH: 116
<212> TYPE: PRT
<213> ORGANISM: Artificial Sequence
<220> FEATURE:
<223> OTHER INFORMATION: Nanobody sequence

<400> SEQUENCE: 351

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 352
<211> LENGTH: 115
<212> TYPE: PRT
<213> ORGANISM: Artificial Sequence
<220> FEATURE:
<223> OTHER INFORMATION: Nanobody sequence

<400> SEQUENCE: 352

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 353
<211> LENGTH: 116
<212> TYPE: PRT
<213> ORGANISM: Artificial Sequence
<220> FEATURE:
<223> OTHER INFORMATION: Nanobody sequence

<400> SEQUENCE: 353

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 354
<211> LENGTH: 115
<212> TYPE: PRT
<213> ORGANISM: Artificial Sequence
<220> FEATURE:
<223> OTHER INFORMATION: Nanobody sequence

<400> SEQUENCE: 354

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 355
<211> LENGTH: 116
<212> TYPE: PRT
<213> ORGANISM: Artificial Sequence
<220> FEATURE:
<223> OTHER INFORMATION: Nanobody sequence

<400> SEQUENCE: 355

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Gln Gly Thr Leu Val Thr
            100                 105                 110

Val Ser Ser Ala
        115

<210> SEQ ID NO 356
<211> LENGTH: 117
<212> TYPE: PRT
<213> ORGANISM: Artificial Sequence
<220> FEATURE:
<223> OTHER INFORMATION: Nanobody sequence

<400> SEQUENCE: 356

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Gln Gly Thr Leu Val Thr
            100                 105                 110

Val Ser Ser Ala Ala
        115

<210> SEQ ID NO 357
<211> LENGTH: 118
<212> TYPE: PRT
<213> ORGANISM: Artificial Sequence
<220> FEATURE:
<223> OTHER INFORMATION: Nanobody sequence

<400> SEQUENCE: 357

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Gln Gly Thr Leu Val Thr
            100                 105                 110

Val Ser Ser Ala Ala Ala
```

```
<210> SEQ ID NO 358
<211> LENGTH: 116
<212> TYPE: PRT
<213> ORGANISM: Artificial Sequence
<220> FEATURE:
<223> OTHER INFORMATION: Nanobody sequence

<400> SEQUENCE: 358
```

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
            115

```
<210> SEQ ID NO 359
<211> LENGTH: 117
<212> TYPE: PRT
<213> ORGANISM: Artificial Sequence
<220> FEATURE:
<223> OTHER INFORMATION: Nanobody sequence

<400> SEQUENCE: 359
```

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
            115

```
<210> SEQ ID NO 360
<211> LENGTH: 118
<212> TYPE: PRT
<213> ORGANISM: Artificial Sequence
<220> FEATURE:
<223> OTHER INFORMATION: Nanobody sequence

<400> SEQUENCE: 360
```

-continued

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
            115

<210> SEQ ID NO 361
<211> LENGTH: 98
<212> TYPE: PRT
<213> ORGANISM: Artificial Sequence
<220> FEATURE:
<223> OTHER INFORMATION: Nanobody sequence

<400> SEQUENCE: 361

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
            35                  40                  45

Ser Cys Ile Ser Ser Ser Asp Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala

<210> SEQ ID NO 362
<211> LENGTH: 5
<212> TYPE: PRT
<213> ORGANISM: Artificial Sequence
<220> FEATURE:
<223> OTHER INFORMATION: Linker

<400> SEQUENCE: 362

Gly Gly Gly Gly Ser
1               5

<210> SEQ ID NO 363
<211> LENGTH: 7
<212> TYPE: PRT
<213> ORGANISM: Artificial Sequence
<220> FEATURE:
<223> OTHER INFORMATION: Linker

<400> SEQUENCE: 363

Ser Gly Gly Ser Gly Gly Ser

```
1               5

<210> SEQ ID NO 364
<211> LENGTH: 9
<212> TYPE: PRT
<213> ORGANISM: Artificial Sequence
<220> FEATURE:
<223> OTHER INFORMATION: Linker

<400> SEQUENCE: 364

Gly Gly Gly Gly Ser Gly Gly Gly Ser
1               5

<210> SEQ ID NO 365
<211> LENGTH: 10
<212> TYPE: PRT
<213> ORGANISM: Artificial Sequence
<220> FEATURE:
<223> OTHER INFORMATION: Linker

<400> SEQUENCE: 365

Gly Gly Gly Gly Ser Gly Gly Gly Gly Ser
1               5                   10

<210> SEQ ID NO 366
<211> LENGTH: 15
<212> TYPE: PRT
<213> ORGANISM: Artificial Sequence
<220> FEATURE:
<223> OTHER INFORMATION: Linker

<400> SEQUENCE: 366

Gly Gly Gly Gly Ser Gly Gly Gly Gly Ser Gly Gly Gly Gly Ser
1               5                   10                  15

<210> SEQ ID NO 367
<211> LENGTH: 18
<212> TYPE: PRT
<213> ORGANISM: Artificial Sequence
<220> FEATURE:
<223> OTHER INFORMATION: Linker

<400> SEQUENCE: 367

Gly Gly Gly Gly Ser Gly Gly Gly Gly Ser Gly Gly Gly Gly Gly
1               5                   10                  15

Gly Ser

<210> SEQ ID NO 368
<211> LENGTH: 20
<212> TYPE: PRT
<213> ORGANISM: Artificial Sequence
<220> FEATURE:
<223> OTHER INFORMATION: Linker

<400> SEQUENCE: 368

Gly Gly Gly Gly Ser Gly Gly Gly Gly Ser Gly Gly Gly Gly Ser Gly
1               5                   10                  15

Gly Gly Gly Ser
            20

<210> SEQ ID NO 369
<211> LENGTH: 25
<212> TYPE: PRT
<213> ORGANISM: Artificial Sequence
<220> FEATURE:
<223> OTHER INFORMATION: Linker
```

```
<400> SEQUENCE: 369

Gly Gly Gly Gly Ser Gly Gly Gly Gly Ser Gly Gly Gly Gly Ser Gly
1               5                   10                  15
Gly Gly Gly Ser Gly Gly Gly Gly Ser
            20                  25

<210> SEQ ID NO 370
<211> LENGTH: 30
<212> TYPE: PRT
<213> ORGANISM: Artificial Sequence
<220> FEATURE:
<223> OTHER INFORMATION: Linker

<400> SEQUENCE: 370

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser
            20                  25                  30

<210> SEQ ID NO 371
<211> LENGTH: 35
<212> TYPE: PRT
<213> ORGANISM: Artificial Sequence
<220> FEATURE:
<223> OTHER INFORMATION: Linker

<400> SEQUENCE: 371

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser
        35

<210> SEQ ID NO 372
<211> LENGTH: 3
<212> TYPE: PRT
<213> ORGANISM: Artificial Sequence
<220> FEATURE:
<223> OTHER INFORMATION: Linker

<400> SEQUENCE: 372

Ala Ala Ala
1

<210> SEQ ID NO 373
<211> LENGTH: 5
<212> TYPE: PRT
<213> ORGANISM: Artificial Sequence
<220> FEATURE:
<223> OTHER INFORMATION: CDR1

<400> SEQUENCE: 373

Ser Phe Gly Met Ser
1               5

<210> SEQ ID NO 374
<211> LENGTH: 17
<212> TYPE: PRT
<213> ORGANISM: Artificial Sequence
<220> FEATURE:
<223> OTHER INFORMATION: CDR2

<400> SEQUENCE: 374
```

Ser Ile Ser Gly Ser Gly Ser Asp Thr Leu Tyr Ala Asp Ser Val Lys
1               5                   10                  15

Gly

<210> SEQ ID NO 375
<211> LENGTH: 6
<212> TYPE: PRT
<213> ORGANISM: Artificial Sequence
<220> FEATURE:
<223> OTHER INFORMATION: CDR3

<400> SEQUENCE: 375

Gly Gly Ser Leu Ser Arg
1               5

<210> SEQ ID NO 376
<211> LENGTH: 10
<212> TYPE: PRT
<213> ORGANISM: Artificial Sequence
<220> FEATURE:
<223> OTHER INFORMATION: CDR1

<400> SEQUENCE: 376

Gly Phe Thr Phe Ser Ser Phe Gly Met Ser
1               5                   10

<210> SEQ ID NO 377
<211> LENGTH: 10
<212> TYPE: PRT
<213> ORGANISM: Artificial Sequence
<220> FEATURE:
<223> OTHER INFORMATION: CDR1

<400> SEQUENCE: 377

Gly Phe Thr Phe Arg Ser Phe Gly Met Ser
1               5                   10

<210> SEQ ID NO 378
<211> LENGTH: 10
<212> TYPE: PRT
<213> ORGANISM: Artificial Sequence
<220> FEATURE:
<223> OTHER INFORMATION: CDR2

<400> SEQUENCE: 378

Ser Ile Ser Gly Ser Gly Ser Asp Thr Leu
1               5                   10

<210> SEQ ID NO 379
<211> LENGTH: 182
<212> TYPE: PRT
<213> ORGANISM: Homo sapiens

<400> SEQUENCE: 379

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
            35                  40                  45

Glu Ala Lys Asn Ile Thr Trp Phe Lys Asp Gly Lys Met Ile Gly Phe
        50                  55                  60

Leu Thr Glu Asp Lys Lys Lys Trp Asn Leu Gly Ser Asn Ala Lys Asp

```
                65                  70                  75                  80
Pro Arg Gly Met Tyr Gln Cys Lys Gly Ser Gln Asn Lys Ser Lys Pro
                    85                  90                  95

Leu Gln Val Tyr Tyr Arg Met Cys Gln Asn Cys Ile Glu Leu Asn Ala
                100                 105                 110

Ala Thr Ile Ser Gly Phe Leu Phe Ala Glu Ile Val Ser Ile Phe Val
                115                 120                 125

Leu Ala Val Gly Val Tyr Phe Ile Ala Gly Gln Asp Gly Val Arg Gln
            130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 380
<211> LENGTH: 207
<212> TYPE: PRT
<213> ORGANISM: Homo sapiens

<400> SEQUENCE: 380

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
        50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 381
<211> LENGTH: 107
<212> TYPE: PRT
<213> ORGANISM: Homo sapiens

<400> SEQUENCE: 381

Ile Gln Val Glu Gln Ser Pro Pro Asp Leu Ile Leu Gln Glu Gly Ala
```

```
1               5                   10                  15
Asn Ser Thr Leu Arg Cys Asn Phe Ser Asp Ser Val Asn Asn Leu Gln
                20                  25                  30

Trp Phe His Gln Asn Pro Trp Gly Gln Leu Ile Asn Leu Phe Tyr Ile
                35                  40                  45

Pro Ser Gly Thr Lys Gln Asn Gly Arg Leu Ser Ala Thr Thr Val Ala
                50                  55                  60

Thr Glu Arg Tyr Ser Leu Leu Tyr Ile Ser Ser Gln Thr Thr Asp
65                  70                  75                  80

Ser Gly Val Tyr Phe Cys Ala Ala Leu Ile Gln Gly Ala Gln Lys Leu
                85                  90                  95

Val Phe Gly Gln Gly Thr Arg Leu Thr Ile Asn
                100                 105
```

<210> SEQ ID NO 382
<211> LENGTH: 110
<212> TYPE: PRT
<213> ORGANISM: Homo sapiens

<400> SEQUENCE: 382

```
Asn Ala Gly Val Thr Gln Thr Pro Lys Phe Arg Ile Leu Lys Ile Gly
1               5                   10                  15

Gln Ser Met Thr Leu Gln Cys Thr Gln Asp Met Asn His Asn Tyr Met
                20                  25                  30

Tyr Trp Tyr Arg Gln Asp Pro Gly Met Gly Leu Lys Leu Ile Tyr Tyr
                35                  40                  45

Ser Val Gly Ala Gly Ile Thr Asp Lys Gly Glu Val Pro Asn Gly Tyr
                50                  55                  60

Asn Val Ser Arg Ser Thr Thr Glu Asp Phe Pro Leu Arg Leu Glu Leu
65                  70                  75                  80

Ala Ala Pro Ser Gln Thr Ser Val Tyr Phe Cys Ala Ser Thr Tyr His
                85                  90                  95

Gly Thr Gly Tyr Phe Gly Glu Gly Ser Trp Leu Thr Val Val
                100                 105                 110
```

<210> SEQ ID NO 383
<211> LENGTH: 108
<212> TYPE: PRT
<213> ORGANISM: Homo sapiens

<400> SEQUENCE: 383

```
Gln Leu Leu Glu Gln Ser Pro Gln Phe Leu Ser Ile Gln Glu Gly Glu
1               5                   10                  15

Asn Leu Thr Val Tyr Cys Asn Ser Ser Ser Val Phe Ser Ser Leu Gln
                20                  25                  30

Trp Tyr Arg Gln Glu Pro Gly Glu Gly Pro Val Leu Leu Val Thr Val
                35                  40                  45

Val Thr Gly Gly Glu Val Lys Lys Leu Lys Arg Leu Thr Phe Gln Phe
                50                  55                  60

Gly Asp Ala Arg Lys Asp Ser Ser Leu His Ile Thr Ala Ala Gln Pro
65                  70                  75                  80

Gly Asp Thr Gly Leu Tyr Leu Cys Ala Gly Ala Gly Ser Gln Gly Asn
                85                  90                  95

Leu Ile Phe Gly Lys Gly Thr Lys Leu Ser Val Lys
                100                 105
```

```
<210> SEQ ID NO 384
<211> LENGTH: 112
<212> TYPE: PRT
<213> ORGANISM: Homo sapiens

<400> SEQUENCE: 384

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ser Arg
                85                  90                  95

Ser Ser Tyr Glu Gln Tyr Phe Gly Pro Gly Thr Arg Leu Thr Val Thr
            100                 105                 110

<210> SEQ ID NO 385
<211> LENGTH: 110
<212> TYPE: PRT
<213> ORGANISM: Homo sapiens

<400> SEQUENCE: 385

Gly Asp Ala Lys Thr Thr Gln Pro Asn Ser Met Glu Ser Asn Glu Glu
1               5                   10                  15

Glu Pro Val His Leu Pro Cys Asn His Ser Thr Ile Ser Gly Thr Asp
            20                  25                  30

Tyr Ile His Trp Tyr Arg Gln Leu Pro Ser Gln Gly Pro Glu Tyr Val
        35                  40                  45

Ile His Gly Leu Thr Ser Asn Val Asn Asn Arg Met Ala Ser Leu Ala
    50                  55                  60

Ile Ala Glu Asp Arg Lys Ser Ser Thr Leu Ile Leu His Arg Ala Thr
65                  70                  75                  80

Leu Arg Asp Ala Ala Val Tyr Tyr Cys Thr Val Tyr Gly Gly Ala Thr
                85                  90                  95

Asn Lys Leu Ile Phe Gly Thr Gly Thr Leu Leu Ala Val Gln
            100                 105                 110

<210> SEQ ID NO 386
<211> LENGTH: 114
<212> TYPE: PRT
<213> ORGANISM: Homo sapiens

<400> SEQUENCE: 386

Val Val Ser Gln His Pro Ser Trp Val Ile Ala Lys Ser Gly Thr Ser
1               5                   10                  15

Val Lys Ile Glu Cys Arg Ser Leu Asp Phe Gln Ala Thr Thr Met Phe
            20                  25                  30

Trp Tyr Arg Gln Phe Pro Lys Gln Ser Leu Met Leu Met Ala Thr Ser
        35                  40                  45

Asn Glu Gly Ser Lys Ala Thr Tyr Glu Gln Gly Val Glu Lys Asp Lys
    50                  55                  60

Phe Leu Ile Asn His Ala Ser Leu Thr Leu Ser Thr Leu Thr Val Thr
65                  70                  75                  80
```

```
Ser Ala His Pro Glu Asp Ser Phe Tyr Ile Cys Ser Ala Arg Gly
            85                  90                  95

Gly Ser Tyr Asn Ser Pro Leu His Phe Gly Asn Gly Thr Arg Leu Thr
            100                 105                 110

Val Thr

<210> SEQ ID NO 387
<211> LENGTH: 133
<212> TYPE: PRT
<213> ORGANISM: Artificial Sequence
<220> FEATURE:
<223> OTHER INFORMATION: Nanobody sequence

<400> SEQUENCE: 387

Asp Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
        115                 120                 125

Val Thr Val Ser Ser
    130

<210> SEQ ID NO 388
<211> LENGTH: 127
<212> TYPE: PRT
<213> ORGANISM: Artificial Sequence
<220> FEATURE:
<223> OTHER INFORMATION: Nanobody sequence

<400> SEQUENCE: 388

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80
```

-continued

```
Leu Gln Met Asn Ser Leu Lys Pro Glu Asp Thr Ala Val Tyr Tyr Cys
                85              90                  95

Ala Ala Asp Leu Thr Ser Thr Asn Pro Gly Ser Tyr Ile Tyr Ile Trp
            100             105             110

Ala Tyr Asp Tyr Trp Gly Gln Gly Thr Gln Val Thr Val Ser Ser
        115             120             125
```

T CELL RECRUITING POLYPEPTIDES BASED ON CD3 REACTIVITY

RELATED APPLICATIONS

This application is a continuation of U.S. application Ser. No. 15/573,298, filed Nov. 10, 2017, which is a national stage filing under 35 U.S.C. § 371 of International Application No. PCT/EP2016/060919, filed May 13, 2016, and claims the benefit under 35 U.S.C. § 119(e) of U.S. provisional application Ser. No. 62/160,794, filed May 13, 2015, the entire contents of each of which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 29, 2021, is named A084870181US02-SEQ-JRV, and is 419,203 bytes in size.

FIELD OF THE INVENTION

The present invention provides multispecific T cell recruiting polypeptides binding CD3 on a T cell and at least one antigen on a target cell. The present invention also relates to the monovalent T cell recruiting polypeptides for use in these multispecific polypeptides. The invention also provides methods for treatment and kits providing the same.

BACKGROUND

Cancer takes an enormous human toll around the world. It is nowadays the world's leading cause of death, followed by heart disease and stroke. Cancers figure among the leading causes of morbidity and mortality worldwide, with approximately 14 million new cases and 8.2 million cancer related deaths in 2012. The number of new cases is expected to rise by about 70% over the next 2 decades (source: WHO Cancer). The total economic impact of premature death and disability from cancer worldwide was about $900 billion in 2008, representing 1.5% of the world's gross domestic product.

Available treatment regimens for solid tumours typically include a combination of surgical resection chemotherapy and radiotherapy. In 40 years of clinical experience little progress has been achieved, especially in advanced stages of cancer.

New therapies combatting cancer are eagerly awaited.

Antibody therapy is now an important part of the physician's armamentarium to battle diseases and especially cancer. Monoclonal antibodies have been established as a key therapeutic approach for a range of diseases already for several years. All of the contemporaneously approved antibody therapies rely on monospecific monoclonal antibodies (mAbs). Until today, most of the targets of the mAbs require either an agonistic or an antagonistic approach. Whereas targeting of cell-surface antigens themselves can mediate antitumor activity through the induction of apoptosis, most mAb-based activity against hematologic malignancies is reliant on either Fc-mediated effector functions such as complement dependent cytotoxicity (CDC) and antibody-dependent cell-mediated cytotoxicity (ADCC).

Immunotherapy has emerged as a rapidly growing area of cancer research. Immunotherapy is directing the body's immune surveillance system, and in particular T cells, to cancer cells.

Cytotoxic T cells (CTL) are T lymphocytes that kill cancer cells, cells that are infected (particularly with viruses), or cells that are damaged in other ways. T lymphocytes (or T cells) express the T cell receptor or TCR molecule and the CD3 receptor on the cell surface. The αβ TCR-CD3 complex (or "TCR complex") is composed of six different type I single-spanning transmembrane proteins: the TCRα and TCRβ chains that form the TCR heterodimer responsible for ligand recognition, and the non-covalently associated CD3γ, CD3δ, CD3ε and ζ chains, which bear cytoplasmic sequence motifs that are phosphorylated upon receptor activation and recruit a large number of signalling components (Call et al. 2004, Molecular Immunology 40: 1295-1305).

Both α and β chains of the T cell receptor consist of a constant domain and a variable domain. Physiologically, the αβ chains of the T cell receptor recognize the peptide loaded MHC complex and couple upon engagement to the CD3 chains. These CD3 chains subsequently transduce the engagement signal to the intracellular environment.

Considering the potential of naturally occurring Cytotoxic T lymphocytes (CTLs) to mediate cell lysis, various strategies have been explored to recruit CTLs to mediate tumour cell killing. Since T lymphocytes lack the expression of Fc receptors, they are not recruited to a tumour site through the Fc tail of an anti-tumour monoclonal. As an alternative, the patient's T cells were modified with a second TCR of known specificity for a defined tumour antigen. This adoptive cell transfer is by nature highly personalized and labour intensive. However, the main problem of T cell therapies remains the large number of immune escape mechanisms know to occur in cancer patients (Nagorsen et al. 2012, Pharmacology & Therapeutics 136: 334-342).

Rather than eliciting specific T cell responses, which rely on expression by cancer cells of MHC molecules and the presence, generation, transport and display of specific peptide antigens, more recent developments have attempted to combine the advantages of immunotherapy with antibody therapy by engaging all cytotoxic T cells of a patient in a polyclonal fashion via recombinant antibody based technologies: "bispecifics".

Bispecific antibodies have been engineered that have a tumour recognition part on the one arm (target-binding arm) whereas the other arm of the molecule has specificity for a T cell antigen (effector-binding arm), mostly CD3. Through the simultaneous binding of the two arms to their respective target antigens, T lymphocytes are directed towards and activated at the tumour cell where they can exert their cytolytic function.

The concept of using bispecific antibodies to activate T cells against tumour cells was described more than 20 years ago, but manufacturing problems and clinical failures sent the field into stagnation. Smaller format bispecifics were developed, which more easily penetrate tissues and tumours than conventional antibodies. In addition, the smaller format is better at creating the cytotoxic synapses, which kill the target cell. It was thought that the smaller format bispecifics would be easier to manufacture and less immunogenic than conventional antibodies. However, the smaller bispecific BiTE molecules, consisting of two single chain variable fragments (scFvs) joined by a 5 amino acid peptide linker, present a lack of stability (scFvs tend to aggregate), low expression titres and poor solubility. Moreover, the first clinical trials of Blinatumomab (a BiTE molecule), which recognizes CD3 chains, were prematurely stopped due to neurologic adverse events, cytokine release syndrome and infections on the one hand and the absence of objective clinical responses or robust signs of biological activity on the other hand. Efficacy aside, BiTEs must be continuously infused—probably due to the lack of an Fc domain—which does not contribute to a patient compliance. The same problem holds true for DARTs (dual affinity retargeting molecules developed by MacroGenics), in which the heavy variable domain from one antibody (Ab) is linked with the light variable domain of another Ab. MacroGenics now attempts to solve this problem by fusing an Fc domain onto its next generation DARTs, which makes the molecule not only bigger, but also results in manufacturing problems and importation of other Fc functions. The larger format with Fc will have a better PK, but re-introduces the risk of off-target activity. (Garber 2014, Nature reviews 13: 799-801) There remains the need for alternative bispecific formats.

SUMMARY OF THE INVENTION

The invention solves this problem by providing multispecific polypeptides comprising a first and at least one further immunoglobulin single variable domain (ISV), wherein said first ISV has high affinity for/binds to CD3; said at least one further ISV has high affinity for/binds to an antigen present on a target cell. In a particular aspect, the binding of the first ISV will activate the inherent cytolytic potential of the T cell against the target cell independently of MHC1.

Thus, in a first aspect the present invention provides a polypeptide comprising a first and a second immunoglobulin single variable domain (ISV), wherein
- said first ISV has high affinity for/binds to cluster of differentiation 3 (CD3) present on a T cell;
- said second ISV has high affinity for/binds to a first antigen on a target cell;
- wherein said first antigen is different from said CD3; and
- wherein said target cell is different from said T cell.

In a further aspect, the present invention provides a polypeptide as described herein, wherein said polypeptide directs the T-cell to the target cell.

In a further aspect, the present invention provides a polypeptide as described herein, wherein said polypeptide induces T cell activation.

In a further aspect, the present invention provides a polypeptide as described herein, wherein said T cell activation is independent from MHC recognition.

In a further aspect, the present invention provides a polypeptide as described herein, wherein said T cell activation depends on presenting said polypeptide bound to said first antigen on a target cell to a T cell.

In a further aspect, the present invention provides a polypeptide as described herein, wherein said T cell activation causes one or more cellular response of said T cell, wherein said cellular response is selected from the group consisting of proliferation, differentiation, cytokine secretion, cytotoxic effector molecule release, cytotoxic activity, expression of activation markers and redirected target cell lysis.

In a further aspect, the present invention provides a polypeptide as described herein, wherein said T cell activation causes inhibition of an activity of said target cell by more than about 10%, such as 20%, 30%, or 40% or even more than 50%, such as more than 60%, such as 70%, 80%, or even more than 90%, such as 100%.

In a further aspect, the present invention provides a polypeptide as described herein, wherein said first ISV binds to CD3γ (SEQ ID NO: 292), to CD3δ (SEQ ID NO: 291) and/or CD3ε (SEQ ID NO: 293) of the TCR complex, or polymorphic variants or isoforms thereof.

Alternatively, the present invention provides a polypeptide as described herein, wherein said first ISV binds to CD3γ (SEQ ID NO: 379), to CD3δ (SEQ ID NO: 291) and/or CD3ε (SEQ ID NO: 380) of the TCR complex, or polymorphic variants or isoforms thereof.

In a further aspect, the present invention provides a polypeptide as described herein, wherein said polypeptide and/or first ISV has an on rate constant (Kon) for binding to said CD3 selected from the group consisting of at least about $10^2$ $M^{-1}s^{-1}$, at least about $10^3$ $M^{-1}s^{-1}$, at least about $10^4$ $M^{-1}s^{-1}$, at least about $10^5$ $M^{-1}s^{-1}$, at least about $10^6$ $M^{-1}s^{-1}$, $10^7$ $M^{-1}s^{-1}$, at least about $10^8$ $M^{-1}s^{-1}$, at least about $10^9$ $M^{-1}s^{-1}$, and at least about $10^{10}$ $M^{-1}s^{-1}$, preferably as measured by surface plasmon resonance.

In a further aspect, the present invention provides a polypeptide as described herein, wherein said polypeptide and/or first ISV has an off rate constant (Koff) for binding to said CD3 selected from the group consisting of at most about $10^{-3}$ $s^{-1}$, at most about $10^{-4}$ $s^{-1}$, at most about $10^{-5}$ $s^{-1}$, at most about $10^{-6}$ $s^{-1}$, at most about $10^{-7}$ $s^{-1}$, at most about $10^{-8}$ $s^{-1}$, at most about $10^{-9}$ $s^{-1}$, and at most about $10^{-10}$ $s^{-1}$, preferably as measured by surface plasmon resonance.

In a further aspect, the present invention provides a polypeptide as described herein, wherein said first ISV binds to said CD3 with an EC50 value of between 100 nM and 1 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less, such as less than 500, 400, 300, 200, 100, 90, 80, 70, 60, 50, 40, 30, 20, 10, 5 pM, or even less, such as less than 4 pM, preferably as measured by flow cytometry.

In a further aspect, the present invention provides a polypeptide as described herein, wherein said first ISV binds to said CD3 with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less such, as less than 10 pM. Preferably, the KD is determined by SPR, for instance as determined by Proteon.

In a further aspect, the present invention provides a polypeptide as described herein, wherein said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 81-100; and
    (b) amino acid sequences that have 4, 3, 2, or 1 amino acid(s) difference with the amino acid sequence of SEQ ID NO: 81; and/or
  (ii) CDR2 is chosen from the group consisting of:
    (c) SEQ ID NOs: 101-122; and
    (d) amino acid sequences that have 4, 3, 2, or 1 amino acid(s) difference with the amino acid sequence of SEQ ID NO: 101; and/or
  (iii) CDR3 is chosen from the group consisting of:
    (e) SEQ ID NOs: 123-143; and
    (f) amino acid sequences that have 3, 2, or 1 amino acid(s) difference with the amino acid sequence of SEQ ID NO: 123.

In a further aspect, the present invention provides a polypeptide as described herein, wherein said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 81-100; or (b) amino acid sequences that have 4, 3, 2, or 1 amino acid(s) difference with the amino acid sequence of SEQ ID NO: 81 or with any of SEQ ID NOs: 81-100, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
  (ii) CDR2 is chosen from the group consisting of:
    (c) SEQ ID NOs: 101-122; or (d) amino acid sequences that have 4, 3, 2, or 1 amino acid(s) difference with the amino acid sequence of SEQ ID NO: 101 or with any of SEQ ID NOs: 101-122, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
  (e) SEQ ID NOs: 123-143; or (f) amino acid sequences that have 4, 3, 2, or 1 amino acid(s) difference with the amino acid sequence of SEQ ID NO: 123 or with any of SEQ ID NOs: 123-143, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of
  (a) SEQ ID NO: 81; and
  (b) amino acid sequences that have 1 or 2 amino acid difference(s) with SEQ ID NO: 81, wherein
    at position 1 the G has been changed into R;
    at position 3 the T has been changed into A;
    at position 4 the Y has been changed into F;
    at position 8 the S has been changed into G; and/or
    at position 10 the G has been changed into A.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 101; and
  (b) amino acid sequences that have 1, 2 or 3 amino acid difference(s) with SEQ ID NO: 101, wherein
    at position 3 the V has been changed into T or A;
    at position 5 the S has been changed into T;
    at position 6 the G has been changed into D or E; and/or
    at position 9 the T has been changed into S, A or P.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
  (a) SEQ ID NO: 123; and
  (b) amino acid sequences that have 1 or 2 amino acid difference(s) with SEQ ID NO: 123, wherein
    at position 2 the I has been changed into T;
    at position 9 the I has been changed into V; and/or
    at position 10 the A has been changed into P.

Preferably, the polypeptide comprising the one or more CDRs with 3, 2, or 1 amino acid(s) difference binds CD3 with about the same or a higher affinity compared to the binding by the polypeptide comprising the CDRs without the 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of
    (a) SEQ ID NO: 81; and
    (b) amino acid sequences that have 1 or 2 amino acid difference(s) with SEQ ID NO: 81, wherein
      at position 1 the G has been changed into R;
      at position 3 the T has been changed into A;
      at position 4 the Y has been changed into F;
      at position 8 the S has been changed into G; and/or
      at position 10 the G has been changed into A,
    provided that the polypeptide comprising the CDR1 with 2, or 1 amino acid(s) difference binds CD3 with about the same or a higher affinity compared to the binding by the polypeptide comprising the CDR1 without the 2, or 1 amino acid(s) difference, said affinity as measured by surface plasmon resonance;
  and in which
  (ii) CDR2 is chosen from the group consisting of
    (a) SEQ ID NO: 101; and
    (b) amino acid sequences that have 1, 2 or 3 amino acid difference(s) with SEQ ID NO: 101, wherein
      at position 3 the V has been changed into T or A;
      at position 5 the S has been changed into T;
      at position 6 the G has been changed into D or E; and/or
      at position 9 the T has been changed into S, A or P,
    provided that the polypeptide comprising the CDR2 with 3, 2, or 1 amino acid(s) difference binds CD3 with about the same or a higher affinity compared to the binding by the polypeptide comprising the CDR2 without the 3, 2, or 1 amino acid(s) difference, said affinity as measured by surface plasmon resonance;
  and in which
  (iii) CDR3 is chosen from the group consisting of
    (a) SEQ ID NO: 123; and
    (b) amino acid sequences that have 1, or 2 amino acid difference(s) with SEQ ID NO: 123, wherein
      at position 2 the I has been changed into T;
      at position 9 the I has been changed into V; and/or
      at position 10 the A has been changed into P,
    provided that the polypeptide comprising the CDR3 with 2, or 1 amino acid(s) difference binds CD3 with about the same or a higher affinity compared to the binding by the polypeptide comprising the CDR3 without the 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 81-87; and
    (b) amino acid sequences that have 4, 3, 2, or 1 amino acid(s) difference with the amino acid sequence of SEQ ID NO: 81; and/or
  (ii) CDR2 is chosen from the group consisting of:
    (c) SEQ ID NOs: 101-109; and
    (d) amino acid sequences that have 4, 3, 2, or 1 amino acid(s) difference with the amino acid sequence of SEQ ID NO: 101; and/or
  (iii) CDR3 is chosen from the group consisting of:
    (e) SEQ ID NOs: 123-127; and
    (f) amino acid sequences that have 4, 3, 2, or 1 amino acid(s) difference with the amino acid sequence of SEQ ID NO: 123.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 81-87; and
    (b) amino acid sequences that have 4, 3, 2, or 1 amino acid(s) difference with the amino acid sequence of SEQ ID NO: 81, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
  (ii) CDR2 is chosen from the group consisting of:
    (c) SEQ ID NOs: 101-109; and
    (d) amino acid sequences that have 4, 3, 2, or 1 amino acid(s) difference with the amino acid sequence of SEQ ID NO: 101, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
  (iii) CDR3 is chosen from the group consisting of:
    (e) SEQ ID NOs: 123-127; and
    (f) amino acid sequences that have 4, 3, 2, or 1 amino acid(s) difference with the amino acid sequence of SEQ ID NO: 123, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 81, CDR2 is represented by SEQ ID NO: 101, and CDR3 is represented by SEQ ID NO: 123.

In a further aspect, the present invention provides a polypeptide as described herein, in which said first ISV is chosen from the group consisting of SEQ ID NOs: 1-50.

In a further aspect, the present invention provides a polypeptide as described herein, in which said first ISV cross-blocks the binding to CD3 by at least one of the polypeptides with SEQ ID NOs: 1-50.

In a further aspect, the present invention provides a polypeptide as described herein in which said first ISV is cross-blocked from binding to CD3 by at least one of the polypeptides with SEQ ID NOs: 1-50.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is SEQ ID NO: 88.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR2 is SEQ ID NO: 110.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR3 is SEQ ID NO: 128.

In a further aspect, the present invention provides a polypeptide as described herein, wherein said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 88; and
    (b) amino acid sequences that have 1, 2, 3, or 4 amino acid(s) difference with the amino acid sequence of SEQ ID NO: 88; and/or
  (ii) CDR2 is chosen from the group consisting of:
    (c) SEQ ID NO: 110; and
    (d) amino acid sequences that have 1, 2, 3, or 4 amino acid(s) difference with the amino acid sequence of SEQ ID NO: 110; and/or
  (iii) CDR3 is chosen from the group consisting of:
    (e) SEQ ID NO: 128; and
    (f) amino acid sequences that have 1, 2, 3, or 4 amino acid(s) difference with the amino acid sequence of SEQ ID NO: 128.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 88; and
    (b) amino acid sequences that have 4, 3, 2, or 1 amino acid(s) difference with the amino acid sequence of SEQ ID NO: 88, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
  (ii) CDR2 is chosen from the group consisting of:
    (c) SEQ ID NOs: 110; and
    (d) amino acid sequences that have 4, 3, 2, or 1 amino acid(s) difference with the amino acid sequence of SEQ ID NO: 110, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
  (iii) CDR3 is chosen from the group consisting of:
    (e) SEQ ID NOs: 128; and
    (f) amino acid sequences that have 4, 3, 2, or 1 amino acid(s) difference with the amino acid sequence of SEQ ID NO: 128, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 88, CDR2 is represented by SEQ ID NO: 110, and CDR3 is represented by SEQ ID NO: 128.

In a further aspect, the present invention provides a polypeptide as described herein, in which said first ISV is SEQ ID NOs: 51.

In a further aspect, the present invention provides a polypeptide as described herein, in which said first ISV cross-blocks the binding to CD3 by the polypeptide with SEQ ID NOs: 51.

In a further aspect, the present invention provides a polypeptide as described herein in which said first ISV is cross-blocked from binding to CD3 by the polypeptide with SEQ ID NOs: 51.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is SEQ ID NO: 90.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 112; and
  (b) amino acid sequence that has 1 amino acid difference with SEQ ID NO: 112, wherein
    at position 2 the V has been changed into A.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR3 is SEQ ID NO: 130.

Preferably, the polypeptide comprising the one or more CDRs with 1 amino acid difference binds CD3 with about the same or a higher affinity compared to the binding by the polypeptide comprising the CDRs without the 1 amino acid difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
  (i) CDR1 is SEQ ID NO: 90; and and in which
  (ii) CDR2 is chosen from the group consisting of
    (a) SEQ ID NO: 112; and
    (b) amino acid sequences that have 1 amino acid difference with SEQ ID NO: 112, wherein
      at position 2 the V has been changed into A,
    provided that the polypeptide comprising the CDR2 with 1 amino acid difference binds CD3 with about the same or a higher affinity compared to the binding by the polypeptide comprising the CDR2 without the 1 amino acid difference, said affinity as measured by surface plasmon resonance;
  and in which
  (iii) CDR3 is SEQ ID NO: 130.

In a further aspect, the present invention provides a polypeptide as described herein, wherein said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 90; and
    (b) amino acid sequences that have 1, 2, 3, or 4 amino acid(s) difference with the amino acid sequence of SEQ ID NO: 90; and/or
  (ii) CDR2 is chosen from the group consisting of:
    (c) SEQ ID NOs: 112-113; and
    (d) amino acid sequences that have 1, 2, 3, or 4 amino acid(s) difference with the amino acid sequence of SEQ ID NO: 112; and/or
  (iii) CDR3 is chosen from the group consisting of:
    (e) SEQ ID NO: 130; and
    (f) amino acid sequences that have 1, 2, 3, or 4 amino acid(s) difference with the amino acid sequence of SEQ ID NO: 130.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 90; and
    (b) amino acid sequences that have 4, 3, 2, or 1 amino acid(s) difference with the amino acid sequence of SEQ ID NO: 90, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
  (ii) CDR2 is chosen from the group consisting of:
    (c) SEQ ID NOs: 112-113; and
    (d) amino acid sequences that have 4, 3, 2, or 1 amino acid(s) difference with the amino acid sequence of SEQ ID NO: 112, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
  (iii) CDR3 is chosen from the group consisting of:
    (e) SEQ ID NOs: 130; and
    (f) amino acid sequences that have 4, 3, 2, or 1 amino acid(s) difference with the amino acid sequence of SEQ ID NO: 130, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 90, CDR2 is represented by SEQ ID NO: 112, and CDR3 is represented by SEQ ID NO: 130.

In a further aspect, the present invention provides a polypeptide as described herein, in which said first ISV is chosen from the group consisting of SEQ ID NOs: 53-56.

In a further aspect, the present invention provides a polypeptide as described herein, in which said first ISV cross-blocks the binding to CD3 by at least one of the polypeptides with SEQ ID NOs: 53-56.

In a further aspect, the present invention provides a polypeptide as described herein in which said first ISV is cross-blocked from binding to CD3 by at least one of the polypeptides with SEQ ID NOs: 53-56.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is SEQ ID NO: 89.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR2 is SEQ ID NO: 111.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR3 is SEQ ID NO: 129.

In a further aspect, the present invention provides a polypeptide as described herein, wherein said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 89; and
    (b) amino acid sequences that have 1, 2, 3, or 4 amino acid(s) difference with the amino acid sequence of SEQ ID NO: 89; and/or
  (ii) CDR2 is chosen from the group consisting of:
    (c) SEQ ID NO: 111; and
    (d) amino acid sequences that have 1, 2, 3, or 4 amino acid(s) difference with the amino acid sequence of SEQ ID NO: 111; and/or
  (iii) CDR3 is chosen from the group consisting of:
    (e) SEQ ID NO: 129; and
    (f) amino acid sequences that have 1, 2 3, or 4 amino acid(s) difference with the amino acid sequence of SEQ ID NO: 129.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 89; and
    (b) amino acid sequences that have 4, 3, 2, or 1 amino acid(s) difference with the amino acid sequence of SEQ ID NO: 89, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
  (ii) CDR2 is chosen from the group consisting of:
    (c) SEQ ID NOs: 111; and
    (d) amino acid sequences that have 4, 3, 2, or 1 amino acid(s) difference with the amino acid sequence of SEQ ID NO: 111, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
  (iii) CDR3 is chosen from the group consisting of:
    (e) SEQ ID NOs: 129; and
    (f) amino acid sequences that have 4, 3, 2, or 1 amino acid(s) difference with the amino acid sequence of SEQ ID NO: 129, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 89, CDR2 is represented by SEQ ID NO: 111, and CDR3 is represented by SEQ ID NO: 129.

In a further aspect, the present invention provides a polypeptide as described herein, in which said first ISV is SEQ ID NOs: 52.

In a further aspect, the present invention provides a polypeptide as described herein, in which said first ISV cross-blocks the binding to CD3 by the polypeptide with SEQ ID NOs: 52.

In a further aspect, the present invention provides a polypeptide as described herein in which said first ISV is cross-blocked from binding to CD3 by the polypeptides with SEQ ID NOs: 52.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of
  (a) SEQ ID NO: 91; and
  (b) amino acid sequences that have 1, 2 or 3 amino acid(s) difference with SEQ ID NO: 91, wherein
    at position 6 the R has been changed into N or T;
    at position 7 the N has been changed into H; and/or
    at position 8 the M has been changed into T.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 114; and
  (b) amino acid sequences that have 1, 2 or 3 amino acid(s) difference with SEQ ID NO: 114, wherein
    at position 1 the R has been changed into Q;
    at position 3 the T has been changed into S; and/or
    at position 7 the D has been changed into A or K.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
  (a) SEQ ID NO: 131; and
  (b) amino acid sequences that have 1 amino acid difference with SEQ ID NO: 131, wherein
    at position 2 the S has been changed into R; and/or
    at position 6 the S has been changed into V.

Preferably, the polypeptide comprising the one or more CDRs with 3, 2, or 1 amino acid(s) difference binds CD3 with about the same or a higher affinity compared to the binding by the polypeptide comprising the CDRs without the 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of
  (a) SEQ ID NO: 91; and
  (b) amino acid sequences that have 1, 2 or 3 amino acid difference(s) with SEQ ID NO: 91, wherein
    at position 6 the R has been changed into N or T;
    at position 7 the N has been changed into H; and/or
    at position 8 the M has been changed into T,
  provided that the polypeptide comprising the CDR1 with 3, 2, or 1 amino acid(s) difference binds CD3 with about the same or a higher affinity compared to the binding by the polypeptide comprising the CDR1 without the 3, 2, or 1 amino acid(s) difference, said affinity as measured by surface plasmon resonance;
and in which
(ii) CDR2 is chosen from the group consisting of
  (a) SEQ ID NO: 114; and
  (b) amino acid sequences that have 1, 2 or 3 amino acid difference(s) with SEQ ID NO: 114, wherein
    at position 1 the R has been changed into Q;
    at position 3 the T has been changed into S; and/or
    at position 7 the D has been changed into A or K,
  provided that the polypeptide comprising the CDR2 with 3, 2, or 1 amino acid(s) difference binds CD3 with about the same or a higher affinity compared to the binding by the polypeptide comprising the CDR2 without the 3, 2, or 1 amino acid(s) difference, said affinity as measured by surface plasmon resonance;
and in which
(iii) CDR3 is chosen from the group consisting of
  (a) SEQ ID NO: 131; and
  (b) amino acid sequences that have 1 amino acid difference with SEQ ID NO: 131, wherein
    at position 2 the S has been changed into R; and/or
    at position 6 the S has been changed into V,
  provided that the polypeptide comprising the CDR3 with 1 amino acid difference binds CD3 with about the same or a higher affinity compared to the binding by the polypeptide comprising the CDR3 without the 1 amino acid difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 91-93; and
  (b) amino acid sequences that have 4, 3, 2, or 1 amino acid(s) difference with the amino acid sequence of SEQ ID NO: 91; and/or
(ii) CDR2 is chosen from the group consisting of:
  (c) SEQ ID NOs: 114-117; and
  (d) amino acid sequences that have 4, 3, 2, or 1 amino acid(s) difference with the amino acid sequence of SEQ ID NO: 114; and/or
(iii) CDR3 is chosen from the group consisting of:
  (e) SEQ ID NOs: 131-133; and
  (f) amino acid sequences that have 4, 3, 2, or 1 amino acid(s) difference with the amino acid sequence of SEQ ID NO: 131.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 91-93; and
  (b) amino acid sequences that have 4, 3, 2, or 1 amino acid(s) difference with the amino acid sequence of SEQ ID NO: 91, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
  (c) SEQ ID NOs: 114-117; and
  (d) amino acid sequences that have 4, 3, 2, or 1 amino acid(s) difference with the amino acid sequence of SEQ ID NO: 114, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
  (e) SEQ ID NOs: 131-133; and
  (f) amino acid sequences that have 4, 3, 2, or 1 amino acid(s) difference with the amino acid sequence of SEQ ID NO: 131, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 91, CDR2 is represented by SEQ ID NO: 114, and CDR3 is represented by SEQ ID NO: 131.

In a further aspect, the present invention provides a polypeptide as described herein, in which said first ISV is chosen from the group consisting of SEQ ID NOs: 57-65.

In a further aspect, the present invention provides a polypeptide as described herein, in which said first ISV cross-blocks the binding to CD3 by at least one of the polypeptides with SEQ ID NOs: 57-65.

In a further aspect, the present invention provides a polypeptide as described herein in which said first ISV is cross-blocked from binding to CD3 by at least one of the polypeptides with SEQ ID NOs: 57-65.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of
 (a) SEQ ID NO: 94; and
 (b) amino acid sequences that have 1, 2, 3 or 4 amino acid(s) difference with SEQ ID NO: 94, wherein
  at position 3 the S has been changed into T, A or G;
  at position 5 the N has been changed into S;

at position 6 the M has been changed into T or A; and/or
at position 9 the L has been changed into M.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
(a) SEQ ID NO: 118; and
(b) amino acid sequences that have 1, 2 or 3 amino acid(s) difference with SEQ ID NO: 118, wherein
at position 2 the H has been changed into V;
at position 5 the S has been changed into H or A;
at position 8 the N has been changed into S; and/or
at position 10 the Y has been changed into F.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
(a) SEQ ID NO: 134; and
(b) amino acid sequences that have 1, 2, 3, 4 or 5 amino acid(s) difference with SEQ ID NO: 134, wherein
at position 6 the A has been changed into S or D;
at position 7 the F has been changed into Y or A;
at position 8 the R has been changed into H;
at position 9 the S has been changed into A;
at position 11 the G has been changed into D, T, N, S, K or R; and/or
at position 14 the V has been changed into I.

Preferably, the polypeptide comprising the one or more CDRs with 5, 4, 3, 2, or 1 amino acid(s) difference binds CD3 with about the same or a higher affinity compared to the binding by the polypeptide comprising the CDRs without the 5, 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which
(i) CDR1 is chosen from the group consisting of
(a) SEQ ID NO: 94; and
(b) amino acid sequences that have 1, 2, 3 or 4 amino acid difference(s) with SEQ ID NO: 94, wherein
at position 3 the S has been changed into T, A or G;
at position 5 the N has been changed into S;
at position 6 the M has been changed into T or A; and/or
at position 9 the L has been changed into M,
provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance;
and in which
(ii) CDR2 is chosen from the group consisting of
(a) SEQ ID NO: 118; and
(b) amino acid sequences that have 1, 2 or 3 amino acid difference(s) with SEQ ID NO: 118, wherein
at position 2 the H has been changed into V;
at position 5 the S has been changed into H or A;
at position 8 the N has been changed into S; and/or
at position 10 the Y has been changed into F,
provided that the polypeptide comprising the CDR2 with 3, 2, or 1 amino acid(s) difference binds CD3 with about the same or a higher affinity compared to the binding by the polypeptide comprising the CDR2 without the 3, 2, or 1 amino acid(s) difference, said affinity as measured by surface plasmon resonance;
and in which
(iii) CDR3 is chosen from the group consisting of
(a) SEQ ID NO: 134; and
(b) amino acid sequences that have 1, 2, 3, 4 or 5 amino acid difference(s) with SEQ ID NO: 134, wherein
at position 6 the A has been changed into S or D;
at position 7 the F has been changed into Y or A;
at position 8 the R has been changed into H;
at position 9 the S has been changed into A;
at position 11 the G has been changed into D, T, N, S, K or R; and/or
at position 14 the V has been changed into I,
provided that the polypeptide comprising the CDR3 with 5, 4, 3, 2, or 1 amino acid(s) difference binds CD3 with about the same or a higher affinity compared to the binding by the polypeptide comprising the CDR3 without the 5, 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 94-100; and
(b) amino acid sequences that have 4, 3, 2, or 1 amino acid(s) difference with the amino acid sequence of SEQ ID NO: 94; and/or
(ii) CDR2 is chosen from the group consisting of:
(c) SEQ ID NOs: 118-122; and
(d) amino acid sequences that have 4, 3, 2, or 1 amino acid(s) difference with the amino acid sequence of SEQ ID NO: 118; and/or
(iii) CDR3 is chosen from the group consisting of:
(e) SEQ ID NOs: 134-143; and
(f) amino acid sequences that have 4, 3, 2, or 1 amino acid(s) difference with the amino acid sequence of SEQ ID NO: 134.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which:
(i) CDR1 is chosen from the group consisting of:
(a) SEQ ID NOs: 94-100; and
(b) amino acid sequences that have 4, 3, 2, or 1 amino acid(s) difference with the amino acid sequence of SEQ ID NO: 94, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
(c) SEQ ID NOs: 118-122; and
(d) amino acid sequences that have 4, 3, 2, or 1 amino acid(s) difference with the amino acid sequence of SEQ ID NO: 118, provided that the polypeptide comprising the CDR2 with 4, 3, 2, or 1 amino acid(s)

difference binds CD3 with about the same or a higher affinity compared to the binding by the polypeptide comprising the CDR2 without the 4, 3, 2, or 1 amino acid(s) difference, said affinity as measured by surface plasmon resonance; and/or (iii) CDR3 is chosen from the group consisting of:
  (e) SEQ ID NOs: 134-143; and
  (f) amino acid sequences that have 4, 3, 2, or 1 amino acid(s) difference with the amino acid sequence of SEQ ID NO: 134, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 94, CDR2 is represented by SEQ ID NO: 118, and CDR3 is represented by SEQ ID NO: 134.

In a further aspect, the present invention provides a polypeptide as described herein, in which said first ISV is chosen from the group consisting of SEQ ID NOs: 66-80.

In a further aspect, the present invention provides a polypeptide as described herein, in which said first ISV cross-blocks the binding to CD3 by at least one of the polypeptides with SEQ ID NOs: 66-80.

In a further aspect, the present invention provides a polypeptide as described herein in which said first ISV is cross-blocked from binding to CD3 by at least one of the polypeptides with SEQ ID NOs: 66-80.

In a further aspect, the present invention provides a polypeptide as described herein, wherein said first antigen on a target cell is a tumour antigen, preferably a tumour associated antigen (TAA).

In a further aspect, the present invention provides a polypeptide as described herein, further comprising a third ISV, which has high affinity for/binds to a second antigen on a target cell, wherein said second antigen is different from said first antigen.

In a further aspect, the present invention provides a polypeptide as described herein, wherein said second antigen on a target cell is a tumour antigen, preferably a tumour associated antigen (TAA).

In a further aspect, the present invention provides a polypeptide as described herein, wherein said first antigen and said second antigen are present on the same target cells.

In a further aspect, the present invention provides a polypeptide as described herein, wherein said first antigen and said second antigen are present on different target cells.

In a further aspect, the present invention provides a polypeptide as described herein, wherein said TAA's are independently chosen from the group consisting of Melanoma-associated Chondroitin Sulfate Proteoglycan (MCSP), Epidermal Growth Factor Receptor (EGFR), Fibroblast Activation Protein (FAP), MART-1, carcinoembryonic antigen (CEA), gp100, MAGE-1, HER-2, Lewis$^Y$ antigens, CD123, CD44, CLL-1, CD96, CD47, CD32, CXCR4, Tim-3, CD25, TAG-72, Ep-CAM, PSMA, PSA, GD2, GD3, CD4, CD5, CD19, CD20, CD22, CD33, CD36, CD45, CD52, CD147, growth factor receptors including ErbB3 and ErbB4, Cytokine receptors including Interleukin-2 receptor gamma chain (CD132 antigen), Interleukin-10 receptor alpha chain (IL-10R-A), Interleukin-10 receptor beta chain (IL-10R-B), Interleukin-12 receptor beta-1 chain (IL-12R-beta1), Interleukin-12 receptor beta-2 chain (IL-12 receptor beta-2), Interleukin-13 receptor alpha-1 chain (IL-13R-alpha-1) (CD213a1 antigen), Interleukin-13 receptor alpha-2 chain (Interleukin-13 binding protein), Interleukin-17 receptor (IL-17 receptor), Interleukin-17B receptor (IL-17B receptor), Interleukin 21 receptor precursor (IL-21R), Interleukin-1 receptor type I (IL-1R-1) (CD121a), Interleukin-1 receptor type II (IL-1R-beta) (CDw121b), Interleukin-1 receptor antagonist protein (IL-1ra), Interleukin-2 receptor alpha chain (CD25 antigen), Interleukin-2 receptor beta chain (CD122 antigen), Interleukin-3 receptor alpha chain (IL-3R-alpha) (CD123 antigen), CD30, IL23R, IGF-1R, IL5R, IgE, CD248 (endosialin), CD44v6, gpA33, Ron, Trop2, PSCA, claudin 6, claudin 18.2, CLEC12A, CD38, ephA2, c-Met, CD56, MUC16, EGFRvIII, AGS-16, CD27L, Nectin-4, SLITRK6, mesothelin, folate receptor, tissue factor, axl, glypican-3, CA9, Cripto, CD138, CD37, MUC1, CD70, gastrin releasing peptide receptor, PAP, CEACAM5, CEACAM6, CXCR7, N-cadherin, FXYD2 gamma a, CD21, CD133, Na/K-ATPase, mIgM (membrane-bound IgM), mIgA (membrane-bound IgA), Mer, Tyro2, CD120, CD95, CA 195, DR5, DR6, DcR3 and CAIX, including related polymorphic variants and isoforms.

In a further aspect, the present invention provides a polypeptide as described herein, wherein said TAA is CD20 (UniProt 11836), HER2 (Uniprot P04626), polymorphic variants or isoforms thereof.

In a further aspect, the present invention provides a polypeptide as described herein, wherein said first antigen and said second antigen are chosen from the group consisting of:
  EGFR as a first antigen and CEA as a second antigen;
  CD19 as a first antigen and CD20 as a second antigen;
  CD19 as a first antigen and CD22 as a second antigen;
  CD123 as a first antigen and Tim-3 as a second antigen; and
  CD132 as a first antigen and CD69 as a second antigen.

In a further aspect, the present invention provides a polypeptide as described herein, further comprising a serum protein binding moiety.

In a further aspect, the present invention provides a polypeptide as described herein, wherein said serum protein binding moiety binds serum albumin.

In a further aspect, the present invention provides a polypeptide as described herein, wherein said serum protein binding moiety is an ISV binding serum albumin.

In a further aspect, the present invention provides a polypeptide as described herein, wherein said ISV binding serum albumin essentially consists of 4 framework regions (FR1 to FR4, respectively) and 3 complementarity determining regions (CDR1 to CDR3 respectively), in which CDR1 is SFGMS (SEQ ID NO: 373), CDR2 is SISGSGSDTLYADSVKG (SEQ ID NO: 374) and CDR3 is GGSLSR (SEQ ID NO: 375), CDR determined according to Kabat definition; and/or in which CDR1 is GFTFSSFGMS (SEQ ID NO: 376) or GFTFRSFGMS (SEQ ID NO: 377), CDR2 is SISGSGSDTL (SEQ ID NO: 378) and CDR3 is GGSLSR (SEQ ID NO: 375), CDR determined according to Kontermann 2010.

In a further aspect, the present invention provides a polypeptide as described herein, wherein said ISV binding serum albumin is selected from Alb8, Alb23, Alb129, Alb132, Alb11, Alb11 (S112K)-A, Alb82, Alb82-A, Alb82-AA, Alb82-AAA, Alb82-G, Alb82-GG, and Alb82-GGG (SEQ ID NOs: 348 to 360).

In a further aspect, the present invention provides a polypeptide as described herein, wherein said ISVs are directly linked to each other or are linked via a linker.

In a further aspect, the present invention provides a polypeptide as described herein, wherein said first ISV and/or said second ISV and/or possibly said third ISV and/or possibly said ISV binding serum albumin are linked via a linker.

In a further aspect, the present invention provides a polypeptide as described herein, wherein said linker is chosen from the group consisting of linkers of 5GS, 7GS, 9GS, 10GS, 15GS, 18GS, 20GS, 25GS, 30GS and 35GS (SEQ ID NOs: 362 to 372).

In a further aspect, the present invention provides a polypeptide as described herein, wherein said serum protein binding moiety is a non-antibody based polypeptide.

In a further aspect, the present invention provides a polypeptide as described herein, further comprising PEG.

In a further aspect, the present invention provides a polypeptide as described herein, wherein said ISV is a Nanobody®, a $V_{HH}$, a humanized $V_{HH}$, or a camelized $V_H$.

In a further aspect, the present invention provides a polypeptide wherein said first ISV is chosen from the group consisting of SEQ ID NOs: 1 to 80.

In a further aspect, the present invention provides a polypeptide as described herein, wherein said first ISV is chosen from the group consisting of SEQ ID NOs: 1 to 80, and wherein said second ISV is chosen from the group consisting of SEQ ID NOs: 297 to 304.

In a further aspect, the present invention provides a polypeptide chosen from the group consisting of SEQ ID NOs: 249-250, 252-253, 255-256, 258-260, 263, 265-283, 286-289, 306-307, 309-310, 312-313, 315-317, 320, 322-340 and 343-346.

In a further aspect, the present invention provides a polypeptide that specifically binds CD3 and that comprises or essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 81-100; or
  (b) amino acid sequences that have 4, 3, 2, or 1 amino acid(s) difference with the amino acid sequence of any of SEQ ID NOs: 81-100, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
  (c) SEQ ID NOs: 101-122; or
  (d) amino acid sequences that have 4, 3, 2, or 1 amino acid(s) difference with the amino acid sequence of any of SEQ ID NOs: 101-122, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
  (e) SEQ ID NOs: 123-143; or
  (f) amino acid sequences that have 4, 3, 2, or 1 amino acid(s) difference with the amino acid sequence of any of SEQ ID NOs: 123-143, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

The present invention also provides a polypeptide as described herein, in which:
(i) CDR1 is chosen from the group consisting of:
  (a) SEQ ID NOs: 81-87; and
  (b) amino acid sequences that have 4, 3, 2, or 1 amino acid(s) difference with the amino acid sequence of SEQ ID NO: 81, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
  (c) SEQ ID NOs: 101-109; and
  (d) amino acid sequences that have 4, 3, 2, or 1 amino acid(s) difference with the amino acid sequence of SEQ ID NO: 101, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
  (e) SEQ ID NOs: 123-127; and
  (f) amino acid sequences that have 4, 3, 2, or 1 amino acid(s) difference with the amino acid sequence of SEQ ID NO: 123, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which CDR1 is chosen from the group consisting of
  (a) SEQ ID NO: 81; and
  (b) amino acid sequences that have 1 or 2 amino acid difference(s) with SEQ ID NO: 81, wherein
    at position 1 the G has been changed into R;
    at position 3 the T has been changed into A;
    at position 4 the Y has been changed into F;
    at position 8 the S has been changed into G; and/or
    at position 10 the G has been changed into A.

In a further aspect, the present invention provides a polypeptide as described herein, in which CDR2 is chosen from the group consisting of
  (a) SEQ ID NO: 101; and
  (b) amino acid sequences that have 1, 2 or 3 amino acid difference(s) with SEQ ID NO: 101, wherein
    at position 3 the V has been changed into T or A;
    at position 5 the S has been changed into T;
    at position 6 the G has been changed into D or E; and/or
    at position 9 the T has been changed into S, A or P.

In a further aspect, the present invention provides a polypeptide as described herein, in which CDR3 is chosen from the group consisting of
  (a) SEQ ID NO: 123; and
  (b) amino acid sequences that have 1 or 2 amino acid difference(s) with SEQ ID NO: 123, wherein at position 2 the I has been changed into T;
at position 9 the I has been changed into V; and/or
at position 10 the A has been changed into P.

In a further aspect, the present invention provides a polypeptide as described herein, in which: CDR1 is represented by SEQ ID NO: 81, CDR2 is represented by SEQ ID NO: 101, and CDR3 is represented by SEQ ID NO: 123.

In a further aspect, the present invention provides a polypeptide as described herein, in which:
(i) CDR1 is chosen from the group consisting of:
 (a) SEQ ID NOs: 88; and
 (b) amino acid sequences that have 4, 3, 2, or 1 amino acid(s) difference with the amino acid sequence of SEQ ID NO: 88, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
 (c) SEQ ID NOs: 110; and
 (d) amino acid sequences that have 4, 3, 2, or 1 amino acid(s) difference with the amino acid sequence of SEQ ID NO: 110, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
 (e) SEQ ID NOs: 128; and
 (f) amino acid sequences that have 4, 3, 2, or 1 amino acid(s) difference with the amino acid sequence of SEQ ID NO: 128, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which: CDR1 is SEQ ID NO: 88.

In a further aspect, the present invention provides a polypeptide as described herein, in which: CDR2 is SEQ ID NO: 110.

In a further aspect, the present invention provides a polypeptide as described herein, in which: CDR3 is SEQ ID NO: 128.

In a further aspect, the present invention provides a polypeptide as described herein, in which: CDR1 is represented by SEQ ID NO: 88, CDR2 is represented by SEQ ID NO: 110, and CDR3 is represented by SEQ ID NO: 128.

In a further aspect, the present invention provides a polypeptide as described herein, in which:
(i) CDR1 is chosen from the group consisting of
 (a) SEQ ID NO: 90; and
 (b) amino acid sequences that have 4, 3, 2, or 1 amino acid(s) difference with the amino acid sequence of SEQ ID NO: 90, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
 (c) SEQ ID NOs: 112-113; and
 (d) amino acid sequences that have 4, 3, 2, or 1 amino acid(s) difference with the amino acid sequence of SEQ ID NO: 112, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
 (e) SEQ ID NO: 130; and
 (f) amino acid sequences that have 4, 3, 2, or 1 amino acid(s) difference with the amino acid sequence of SEQ ID NO: 130, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which: CDR1 is SEQ ID NO: 90.

In a further aspect, the present invention provides a polypeptide as described herein, in which: CDR2 is chosen from the group consisting of
 (a) SEQ ID NO: 112; and
 (b) amino acid sequence that has 1 amino acid difference with SEQ ID NO: 112, wherein
 at position 2 the V has been changed into A.

In a further aspect, the present invention provides a polypeptide as described herein, in which: CDR3 is SEQ ID NO: 130.

In a further aspect, the present invention provides a polypeptide as described herein, in which: CDR1 is represented by SEQ ID NO: 90, CDR2 is represented by SEQ ID NO: 112, and CDR3 is represented by SEQ ID NO: 130.

In a further aspect, the present invention provides a polypeptide as described herein, in which:
(i) CDR1 is chosen from the group consisting of:
 (a) SEQ ID NOs: 89; and
 (b) amino acid sequences that have 4, 3, 2, or 1 amino acid(s) difference with the amino acid sequence of SEQ ID NO: 89, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
 (c) SEQ ID NOs: 111; and
 (d) amino acid sequences that have 4, 3, 2, or 1 amino acid(s) difference with the amino acid sequence of SEQ ID NO: 111, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or (iii) CDR3 is chosen from the group consisting of:
  (e) SEQ ID NOs: 129; and
  (f) amino acid sequences that have 4, 3, 2, or 1 amino acid(s) difference with the amino acid sequence of SEQ ID NO: 129, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which: CDR1 is SEQ ID NO: 89.

In a further aspect, the present invention provides a polypeptide as described herein, in which: CDR2 is SEQ ID NO: 111.

In a further aspect, the present invention provides a polypeptide as described herein, in which: CDR3 is SEQ ID NO: 129.

In a further aspect, the present invention provides a polypeptide as described herein, in which: CDR1 is represented by SEQ ID NO: 89, CDR2 is represented by SEQ ID NO: 111, and CDR3 is represented by SEQ ID NO: 129.

The present invention also provides a polypeptide as described herein, in which:
  (i) CDR1 is chosen from the group consisting of:
    (a) SEQ ID NOs: 91-93; and
    (b) amino acid sequences that have 4, 3, 2, or 1 amino acid(s) difference with the amino acid sequence of SEQ ID NO: 91, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
  (ii) CDR2 is chosen from the group consisting of:
    (c) SEQ ID NOs: 114-117; and
    (d) amino acid sequences that have 4, 3, 2, or 1 amino acid(s) difference with the amino acid sequence of SEQ ID NO: 114, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
  (iii) CDR3 is chosen from the group consisting of:
    (e) SEQ ID NOs: 131-133; and
    (f) amino acid sequences that have 4, 3, 2, or 1 amino acid(s) difference with the amino acid sequence of SEQ ID NO: 131, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which CDR1 is chosen from the group consisting of
  (a) SEQ ID NO: 91; and
  (b) amino acid sequences that have 1, 2 or 3 amino acid(s) difference with SEQ ID NO: 91, wherein
    at position 6 the R has been changed into N or T;
    at position 7 the N has been changed into H; and/or
    at position 8 the M has been changed into T.

In a further aspect, the present invention provides a polypeptide as described herein, in which CDR2 is chosen from the group consisting of
  (a) SEQ ID NO: 114; and
  (b) amino acid sequences that have 1, 2 or 3 amino acid(s) difference with SEQ ID NO: 114, wherein
    at position 1 the R has been changed into Q;
    at position 3 the T has been changed into S; and/or
    at position 7 the D has been changed into A or K.

In a further aspect, the present invention provides a polypeptide as described herein, in which CDR3 is chosen from the group consisting of
  (a) SEQ ID NO: 131; and
  (b) amino acid sequences that have 1 amino acid difference with SEQ ID NO: 131, wherein
    at position 2 the S has been changed into R; and/or
    at position 6 the S has been changed into V.

In a further aspect, the present invention provides a polypeptide as described herein, in which: CDR1 is represented by SEQ ID NO: 91, CDR2 is represented by SEQ ID NO: 114, and CDR3 is represented by SEQ ID NO: 131.

The present invention also provides a polypeptide as described herein, in which:
  (i) CDR1 is chosen from the group consisting of:
    (a) SEQ ID NOs: 94-100; and
    (b) amino acid sequences that have 4, 3, 2, or 1 amino acid(s) difference with the amino acid sequence of SEQ ID NO: 94, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
  (ii) CDR2 is chosen from the group consisting of:
    (c) SEQ ID NOs: 118-122; and
    (d) amino acid sequences that have 4, 3, 2, or 1 amino acid(s) difference with the amino acid sequence of SEQ ID NO: 118, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
  (iii) CDR3 is chosen from the group consisting of:
    (e) SEQ ID NOs: 134-143; and
    (f) amino acid sequences that have 4, 3, 2, or 1 amino acid(s) difference with the amino acid sequence of SEQ ID NO: 134, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In a further aspect, the present invention provides a polypeptide as described herein, in which CDR1 is chosen from the group consisting of
  (a) SEQ ID NO: 94; and
  (b) amino acid sequences that have 1, 2, 3 or 4 amino acid(s) difference with SEQ ID NO: 94, wherein
    at position 3 the S has been changed into T, A or G;
    at position 5 the N has been changed into S;
    at position 6 the M has been changed into T or A; and/or
    at position 9 the L has been changed into M.

In a further aspect, the present invention provides a polypeptide as described herein, in which CDR2 is chosen from the group consisting of
(a) SEQ ID NO: 118; and
(b) amino acid sequences that have 1, 2 or 3 amino acid(s) difference with SEQ ID NO: 118, wherein
at position 2 the H has been changed into V;
at position 5 the S has been changed into H or A;
at position 8 the N has been changed into S; and/or
at position 10 the Y has been changed into F.

In a further aspect, the present invention provides a polypeptide as described herein, in which CDR3 is chosen from the group consisting of
(a) SEQ ID NO: 134; and
(b) amino acid sequences that have 1, 2, 3, 4 or 5 amino acid(s) difference with SEQ ID NO: 134, wherein
at position 6 the A has been changed into S or D;
at position 7 the F has been changed into Y or A;
at position 8 the R has been changed into H;
at position 9 the S has been changed into A;
at position 11 the G has been changed into D, T, N, S, K or R; and/or
at position 14 the V has been changed into I.

In a further aspect, the present invention provides a polypeptide as described herein, in which: CDR1 is represented by SEQ ID NO: 94, CDR2 is represented by SEQ ID NO: 118, and CDR3 is represented by SEQ ID NO: 134.

In a further aspect, the present invention provides a polypeptide as described herein, which is a Nanobody, a $V_{HH}$, a humanized $V_{HH}$, or a camelized $V_H$.

In a further aspect, the present invention provides a polypeptide as described herein, further comprising a serum protein binding moiety.

In a further aspect, the present invention provides a polypeptide as described herein, wherein said serum protein binding moiety binds serum albumin.

In a further aspect, the present invention provides a polypeptide as described herein, wherein said serum protein binding moiety is an ISV that binds serum albumin.

In a further aspect, the present invention provides a polypeptide as described herein, wherein said ISV that binds serum albumin essentially consists of 4 framework regions (FR1 to FR4, respectively) and 3 complementarity determining regions (CDR1 to CDR3 respectively), in which CDR1 is SFGMS (SEQ ID NO: 373), CDR2 is SISGSGSDTLYADSVKG (SEQ ID NO: 374) and CDR3 is GGSLSR (SEQ ID NO: 375), CDR as determined according to Kabat definition; and/or in which CDR1 is GFTFSSFGMS (SEQ ID NO: 376) or GFTFRSFGMS (SEQ ID NO: 377), CDR2 is SISGSGSDTL (SEQ ID NO: 378) and CDR3 is GGSLSR (SEQ ID NO: 375), CDR as determined according to Kontermann 2010.

In a further aspect, the present invention provides a polypeptide as described herein, wherein said ISV that binds serum albumin is selected from Alb8, Alb23, Alb129, Alb132, Alb11, Alb11 (S112K)-A, Alb82, Alb82-A, Alb82-AA, Alb82-AAA, Alb82-G, Alb82-GG, and Alb82-GGG (SEQ ID NOs: 348 to 360).

In a further aspect, the present invention provides a polypeptide as described herein, wherein said ISV is directly linked or is linked via a linker.

In a further aspect, the present invention provides a polypeptide as described herein, wherein said linker is chosen from the group consisting of linkers of 5GS, 7GS, 9GS, 10GS, 15GS, 18GS, 20GS, 25GS, 30GS and 35GS (SEQ ID NOs: 362 to 372).

In a further aspect, the present invention provides a polypeptide as described herein, further comprising a PEG moiety.

In a further aspect, the present invention provides a nucleic acid or nucleic acid sequence encoding a polypeptide as defined herein.

In a further aspect, the present invention provides vector comprising a nucleic acid or nucleic acid sequence as defined herein.

In a further aspect, the present invention provides a host cell transformed or transfected with the nucleic acid or nucleic acid sequence as defined herein or with the vector as defined herein.

In a further aspect, the present invention provides a process for the production of the polypeptide as defined herein, said process comprising culturing a host cell as defined herein under conditions allowing the expression of the polypeptide as defined herein and recovering the produced polypeptide from the culture.

In a further aspect, the present invention provides a pharmaceutical composition comprising the polypeptide as described herein, or the polypeptide produced according to the process as described herein.

In a further aspect, the present invention provides a polypeptide as described herein, or produced as described herein, for use in treating a subject in need thereof.

In a further aspect, the present invention provides a method for delivering a prophylactic or therapeutic polypeptide to a specific location, tissue or cell type in the body, the method comprising the steps of administering to a subject a polypeptide as described herein, or produced as described herein.

In a further aspect, the present invention provides a polypeptide as described herein, or produced as described herein for use in the prevention, treatment or amelioration of a disease selected from the group consisting of a proliferative disease, an inflammatory disease, an infectious disease and an autoimmune disease.

In a further aspect, the present invention provides a method for the prevention, treatment or amelioration of a disease selected from the group consisting of a proliferative disease, an inflammatory disease, an infectious disease and an autoimmune disease, comprising the step of administering to a subject in need thereof the polypeptide as described herein, or produced as described herein.

In a further aspect, the present invention provides a polypeptide for use in or a method for the prevention, treatment or amelioration of a disease as described herein, wherein said proliferative disease is cancer.

In a further aspect, the present invention provides a polypeptide for use in or a method for the prevention, treatment or amelioration of a disease as described herein, wherein said cancer is chosen from the group consisting of carcinomas, gliomas, mesotheliomas, melanomas, lymphomas, leukemias, adenocarcinomas: breast cancer, ovarian cancer, cervical cancer, glioblastoma, multiple myeloma (including monoclonal gammopathy of undetermined significance, asymptomatic and symptomatic myeloma), prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease or AIDS-associated primary effusion lymphoma, neuroectodermal tumors, rhabdomyosarcoma; as well as any metastasis of any of the above cancers, as well as non-cancer indications such as nasal polyposis.

In a further aspect, the present invention provides a polypeptide for use in or a method for the prevention, treatment or amelioration of a disease as described herein, wherein the treatment is a combination treatment.

In a further aspect, the present invention provides a kit comprising a polypeptide as defined herein, a nucleic acid or nucleic acid sequence as defined herein, a vector as defined herein, or a host cell as defined herein.

FIGURE LEGENDS

FIG. 1: QC of human TCR/CD3 and human CD3 transfected cell lines using 100 nM of anti-human TCR α/β antibody (clone BW242/412) (black) and 100 nM anti-human CD3 antibody (clone OKT-3) (grey). The MCF value (mean channel fluorescence) is plotted for each cell line.

FIGS. 2A and 2B: Dose dependent binding of monovalent CD3 Nanobodies to human TCR/CD3 expressed on CHO-K1 cells (FIG. 2A) and to purified primary human T cells (FIG. 2B). The MCF value (mean channel fluorescence) is plotted against the concentration of the Nanobody.

Figure 3:
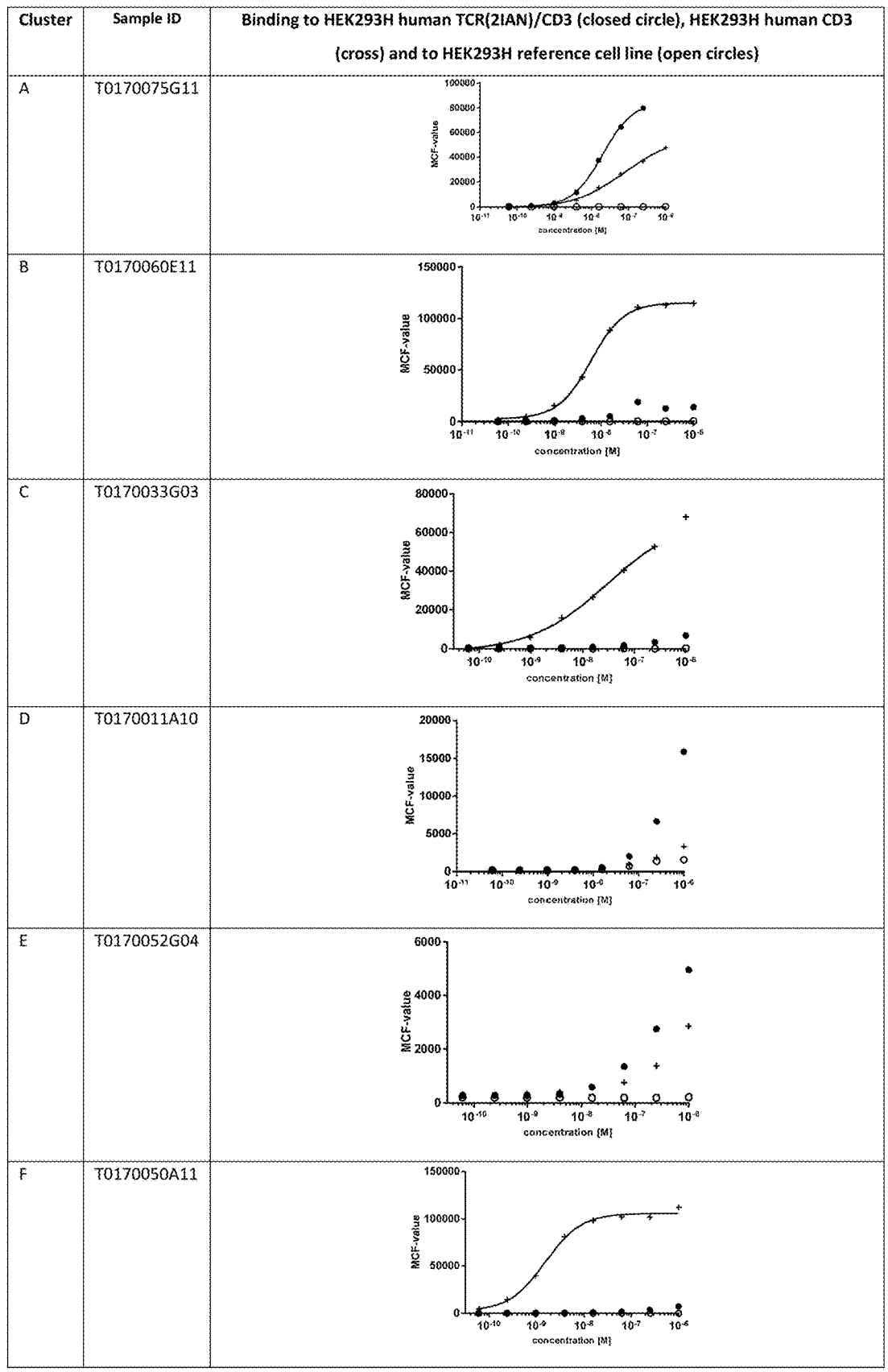

FIG. 3: Dose dependent binding of monovalent CD3 Nanobodies to HEK293H human TCR(2IAL)/CD3 (closed circle), HEK293H human CD3 (cross) and to HEK293H parental cell line (open circles). The MCF value (mean channel fluorescence) is plotted against the concentration of the Nanobody.

Figure 4A:
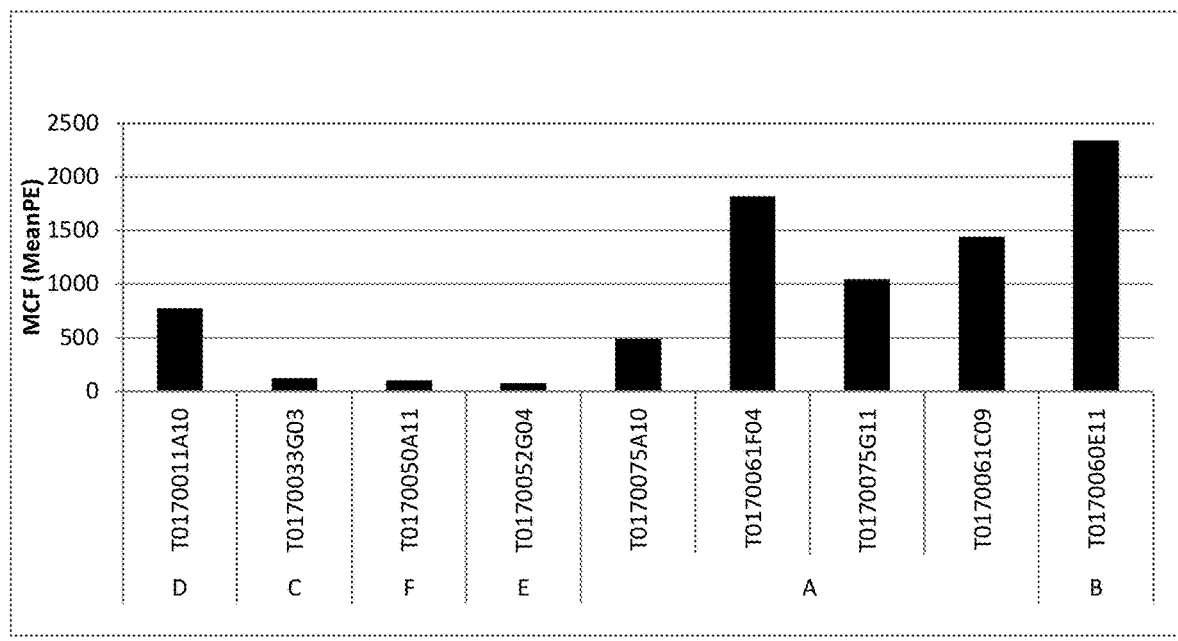
Figure 4B:
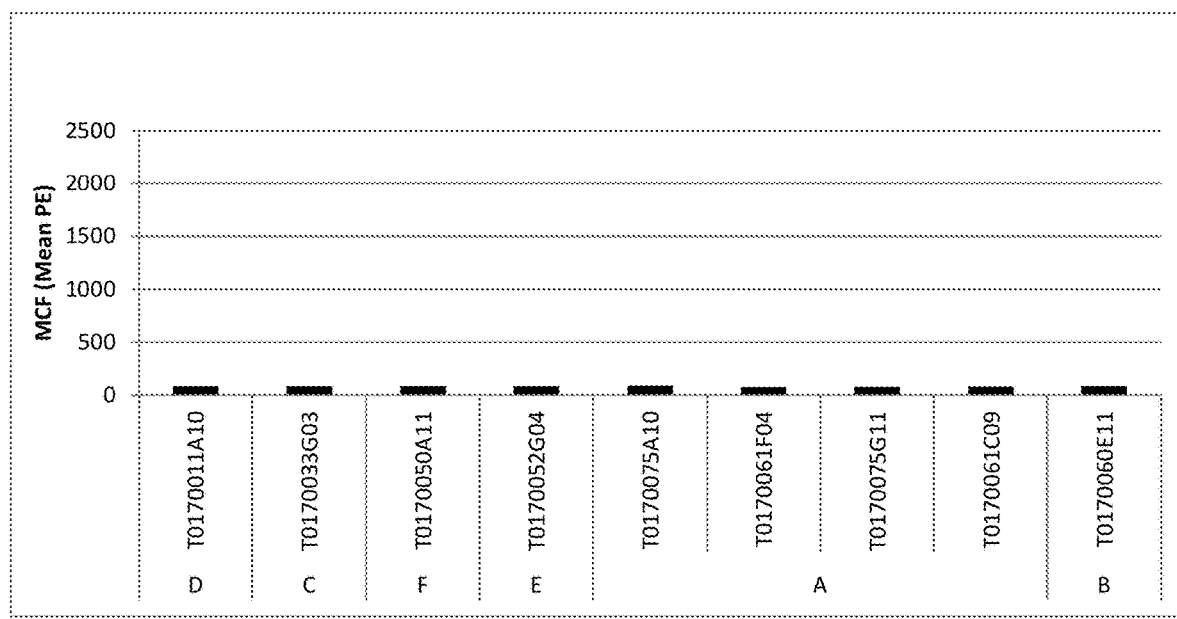

FIGS. 4A and 4B: T cell activation data of bead coupled monovalent CD3 Nanobodies (FIG. 4A). T cell activation data of monovalent CD3 Nanobodies presented in solution (FIG. 4B). Activation is measured by monitoring the CD69 upregulation on primary human T cells. The MCF value (mean channel fluorescence) is plotted for each Nanobody.

FIGS. 5A-5C: Binding of a dilution series of CD20×CD3 (full line) and CD3×CD20 (dotted line) bispecific Nanobodies to human TCR/CD3 expressed on CHO-K1 cells (FIG. 5A), primary human T cells (FIG. 5B) and Ramos cells (FIG. 5C). The MCF value (mean channel fluorescence) is plotted against the concentration of the Nanobody.

Figures 6A, 6B:
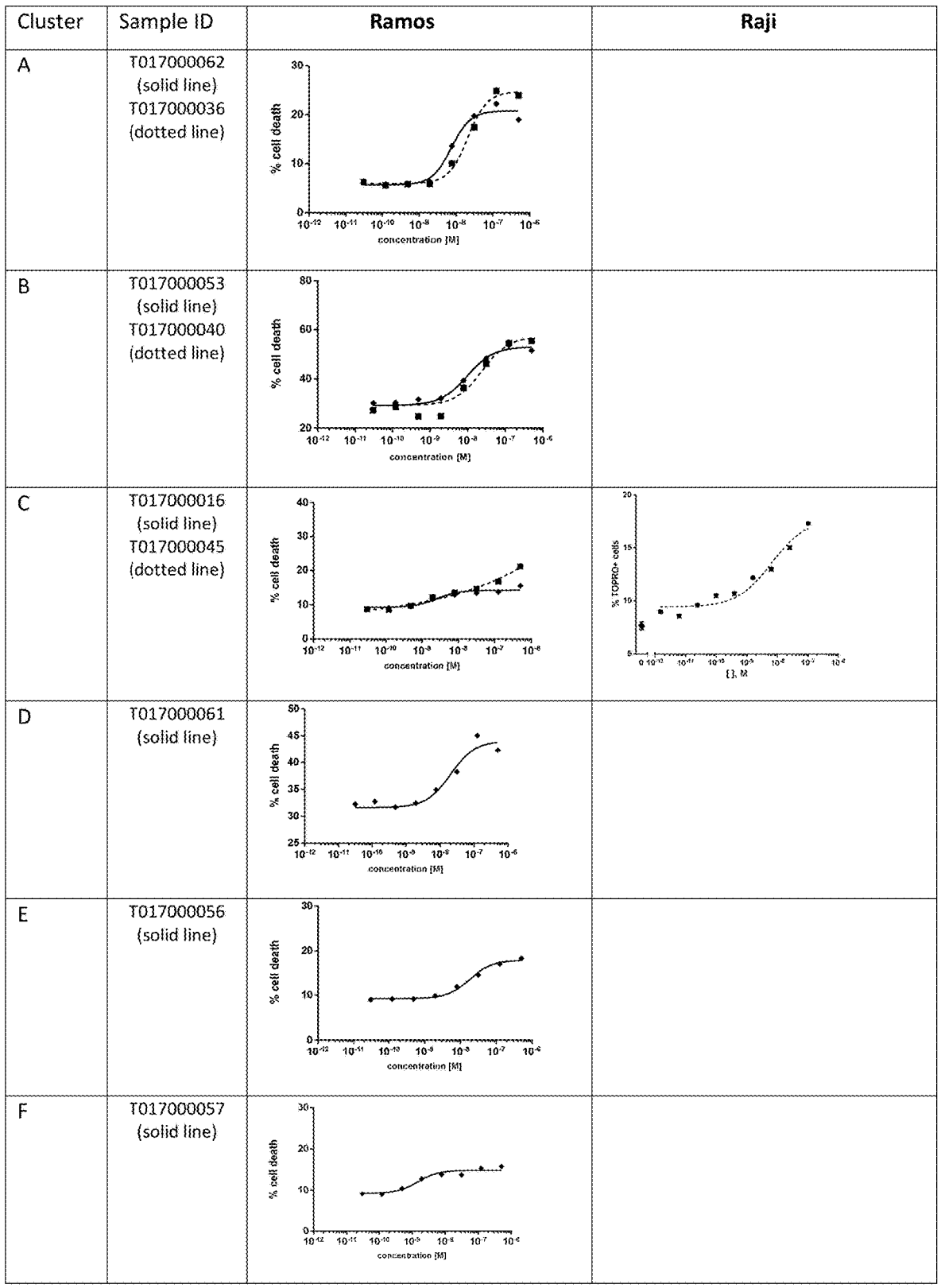

FIGS. 6A and 6B: Dose-dependent killing effect of CD20×CD3 (full line) and CD3×CD20 (dotted line) bispecific Nanobodies in a flow cytometry based human T cells mediated Ramos (FIG. 6A) and Raji (FIG. 6B) B cell killing assay. The % cell death (% of TOPRO positive cells) is plotted against the concentration of the Nanobody.

Figure 7:
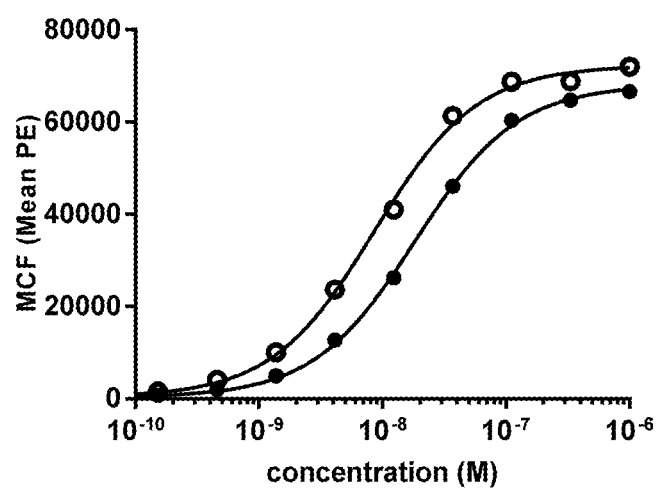

FIG. 7: Dose-dependent binding of the anti-CD20 Nanobody on human CD20 Ramos (open symbols) and Raji (closed symbols) cells. The MCF value (mean channel fluorescence) is plotted against the concentration of the Nanobody.

Figure 8:
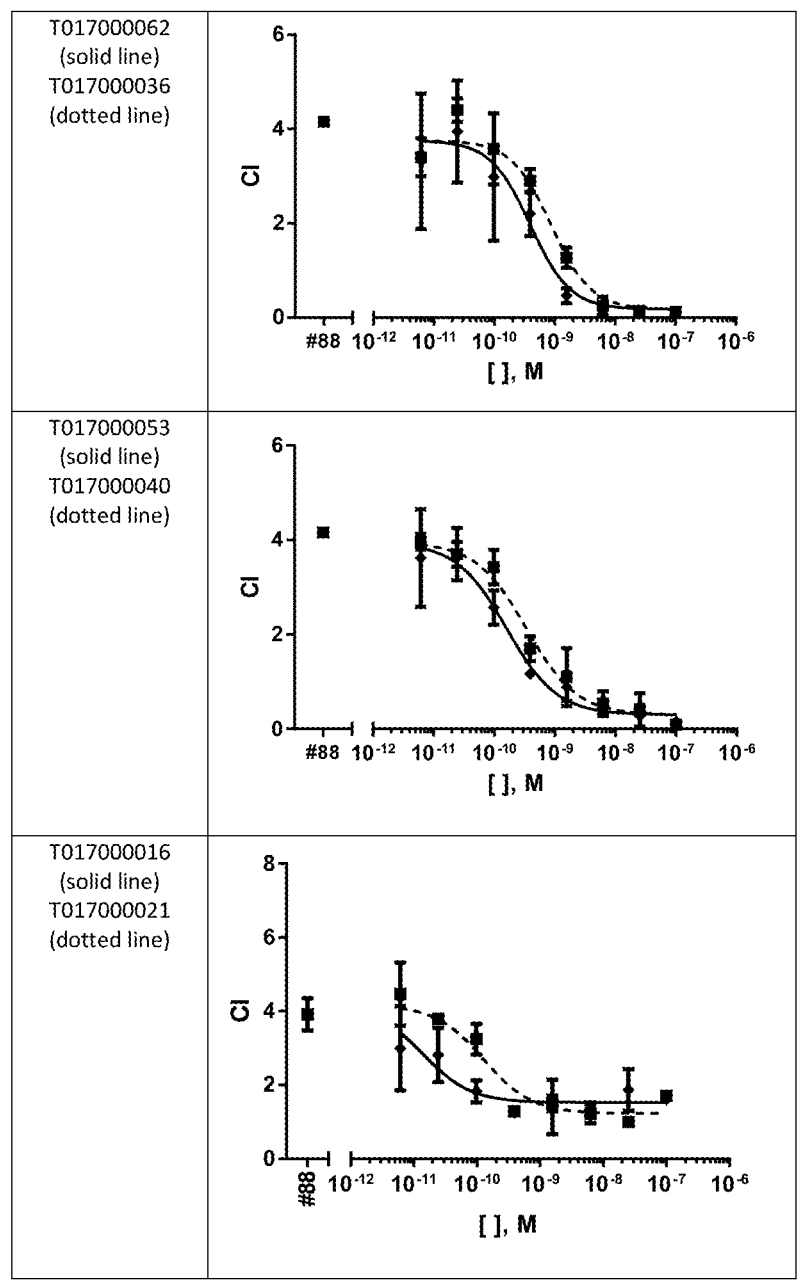

FIG. 8: Dose-dependent killing effect of CD20×CD3 (full line) and CD3×CD20 (dotted line) bispecific Nanobodies in the xCELLigence based human T cells mediated CHO-K1 human CD20 killing assay assay. The CI is plotted against the concentration of Nanobody.

Figure 9:
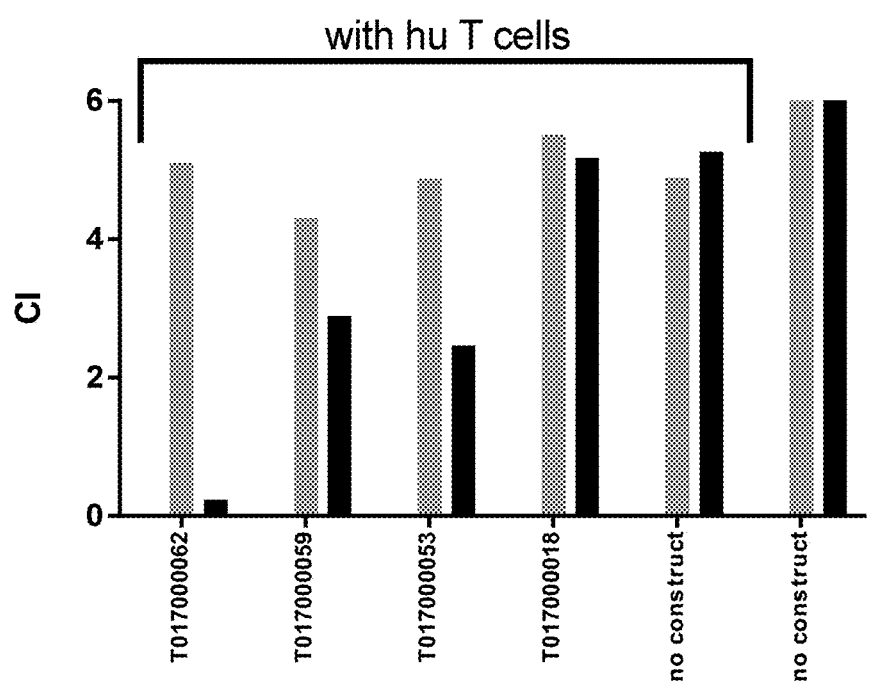

FIG. 9: Killing effect of 1 µM of CD20×CD3 and an irrelevant construct in a xCELLigence based killing assay using CHO-K1 human CD20 cells (black bars) and using CHO-K1 parental cell line (grey bars) to illustrate TAA dependent killing. The cell index (CI) is plotted against the concentration of the Nanobody.

Figure 10:
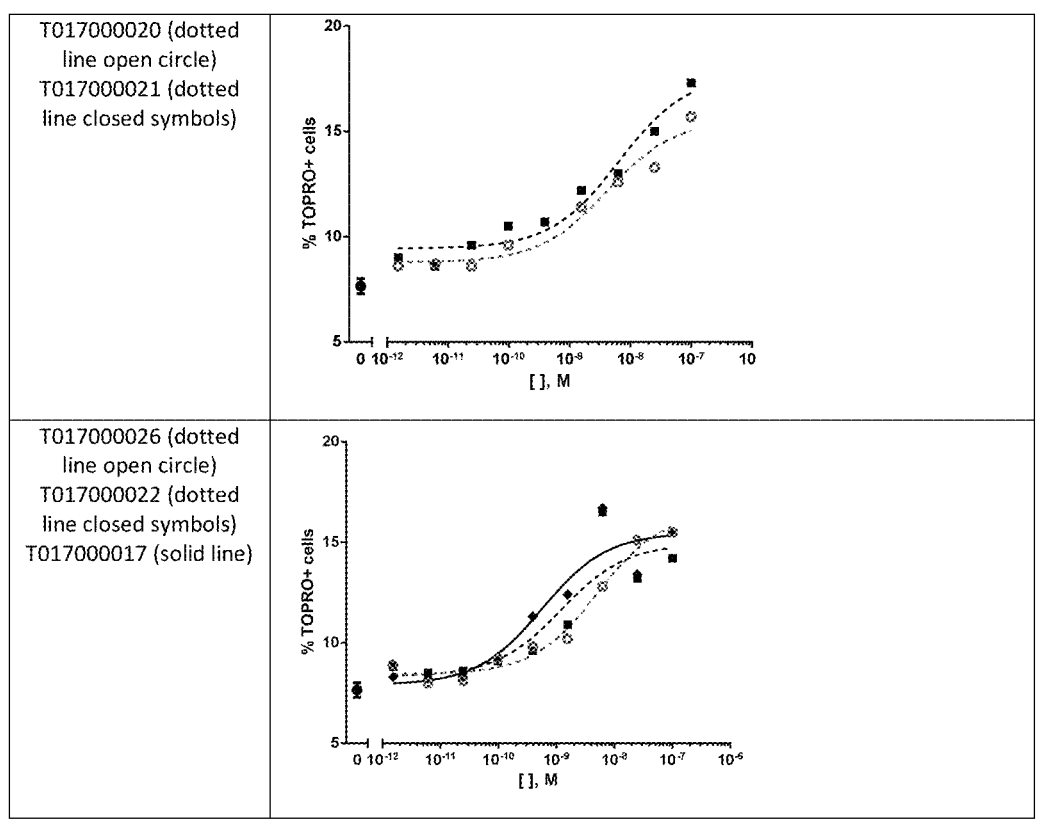

FIG. 10: Dose-dependent killing effect of CD20×CD3 Nanobodies with 9GS linker (open circles—dotted line) and a 35GS linker (closed squares—dotted line) and the CD3×CD20 Nanobody with a 35GS linker (closed diamonds—solid line) in a flow cytometry based killing assay using Ramos. The % cell death (TORPRO positive cells) is plotted against the concentration of Nanobody.

Figure 11:
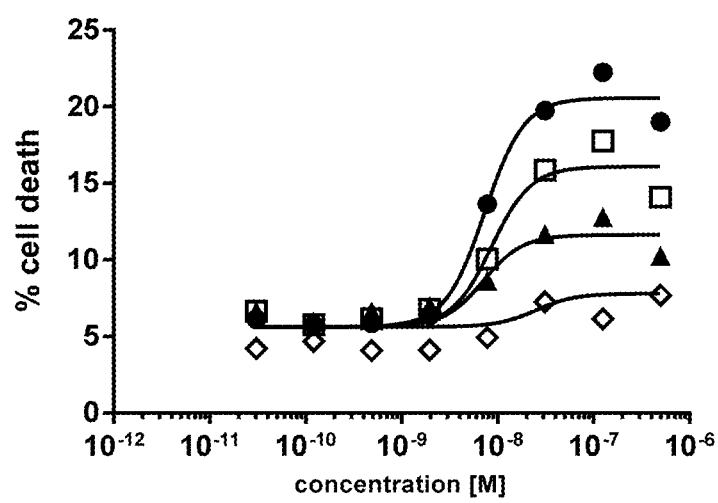

FIG. 11: Dose-dependent killing of T017000062 in a flow cytometry based human T cells mediated Ramos B cell killing assay using different effector (E) to target (T) ratio's (E:T ratio 10:1—closed circles, E:T ratio 5:1—open squares, E:T ratio 2:1—closed triangles and E:T ratio 1:1—open diamonds. The % cell death (% of TOPRO positive cells) is plotted against the concentration of the Nanobody.

Figure 12:
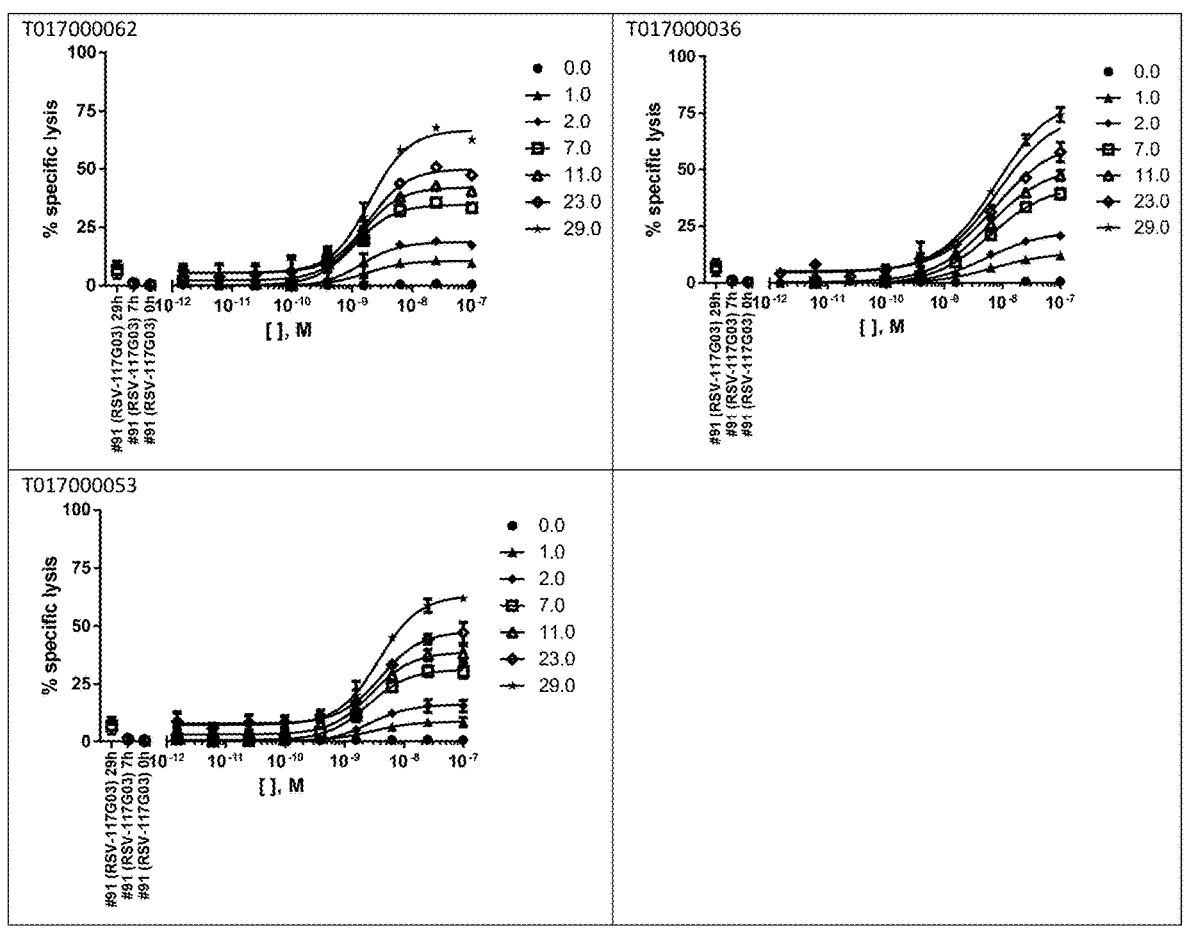

FIG. 12: Time-dependent cytolytic activity of CD20/CD3 in the purified primary human T cells mediated killing assay in xCELLigence using CHO-K1 human CD20 target cells. The % specific lysis is plotted against the concentration of the construct. The different curves represent the analysis time after addition of the T cells.

FIGS. 13A-13C: Binding of a serial dilution of HLE constructs to human TCR/CD3 expressed on CHO-K1 cells (FIG. 13A), primary human T cells (FIG. 13B) and Ramos cells (FIG. 13C). The MCF value (mean channel fluorescence) is plotted against the concentration of the Nanobody.

Figure 14A:
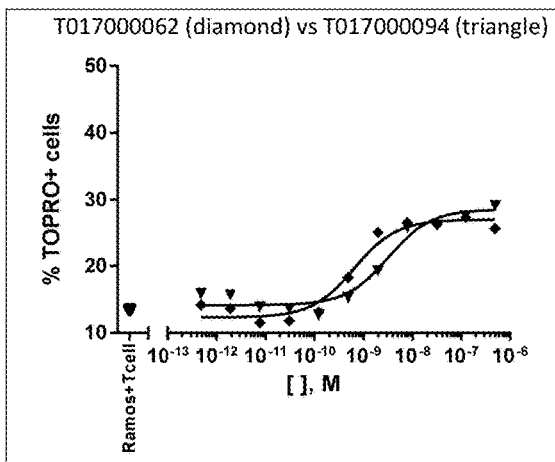
Figure 14B:
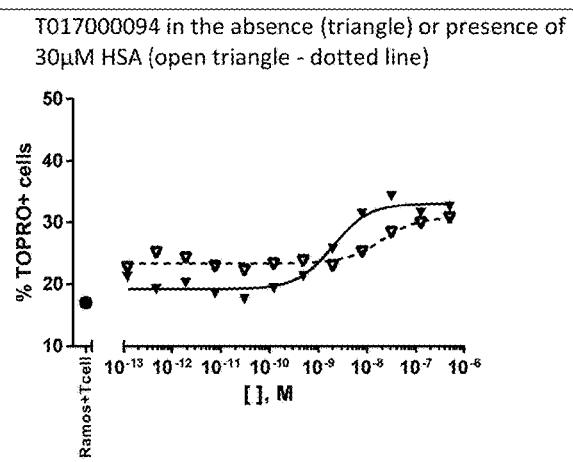
Figure 14C:
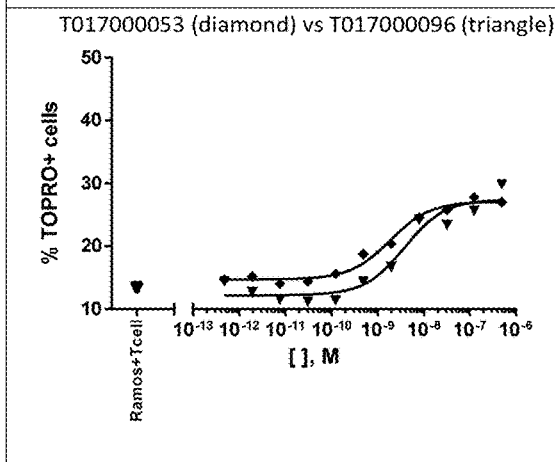
Figure 14D:
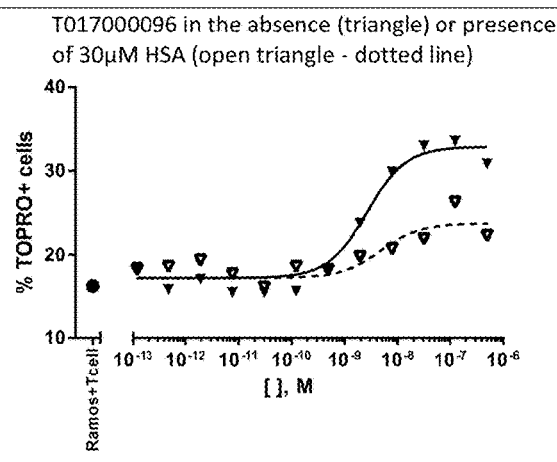

FIGS. 14A-14D: Dose-dependent killing of CD20×CD3 bispecific Nanobody (solid line-diamonds) versus CD20×CD3×ALB11 constructs (solid line—closed triangle) (FIG. 14A, FIG. 14C) and dose-dependent killing effect of CD20×CD3×ALB11 constructs in the absence (solid line—closed triangle) or presence of 30 µM HSA (dotted line—open triangle) in a flow cytometry based human T cells mediated Ramos B cell killing assay (FIG. 14B, FIG. 14D). The % cell death (% of TOPRO positive cells) is plotted against the concentration of the Nanobody.

Figure 15:
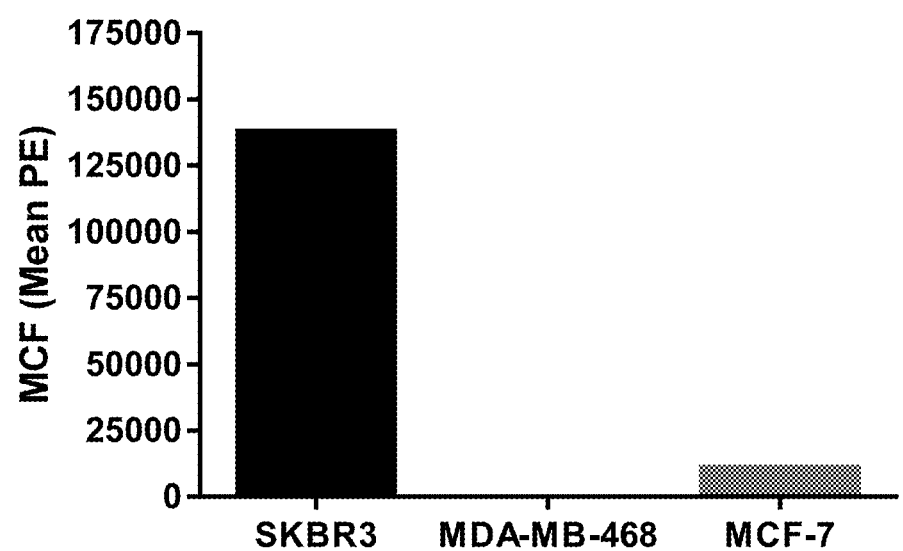

FIG. 15: Binding of 100 nM monovalent anti-HER2 Nanobody (5F07) to SK-BR-3, MCF-7 and MDA-MB-468 cell lines in flow cytometry to compare HER2 expression levels. The MCF value (mean channel fluorescence) is plotted for each cell line.

Figure 16:
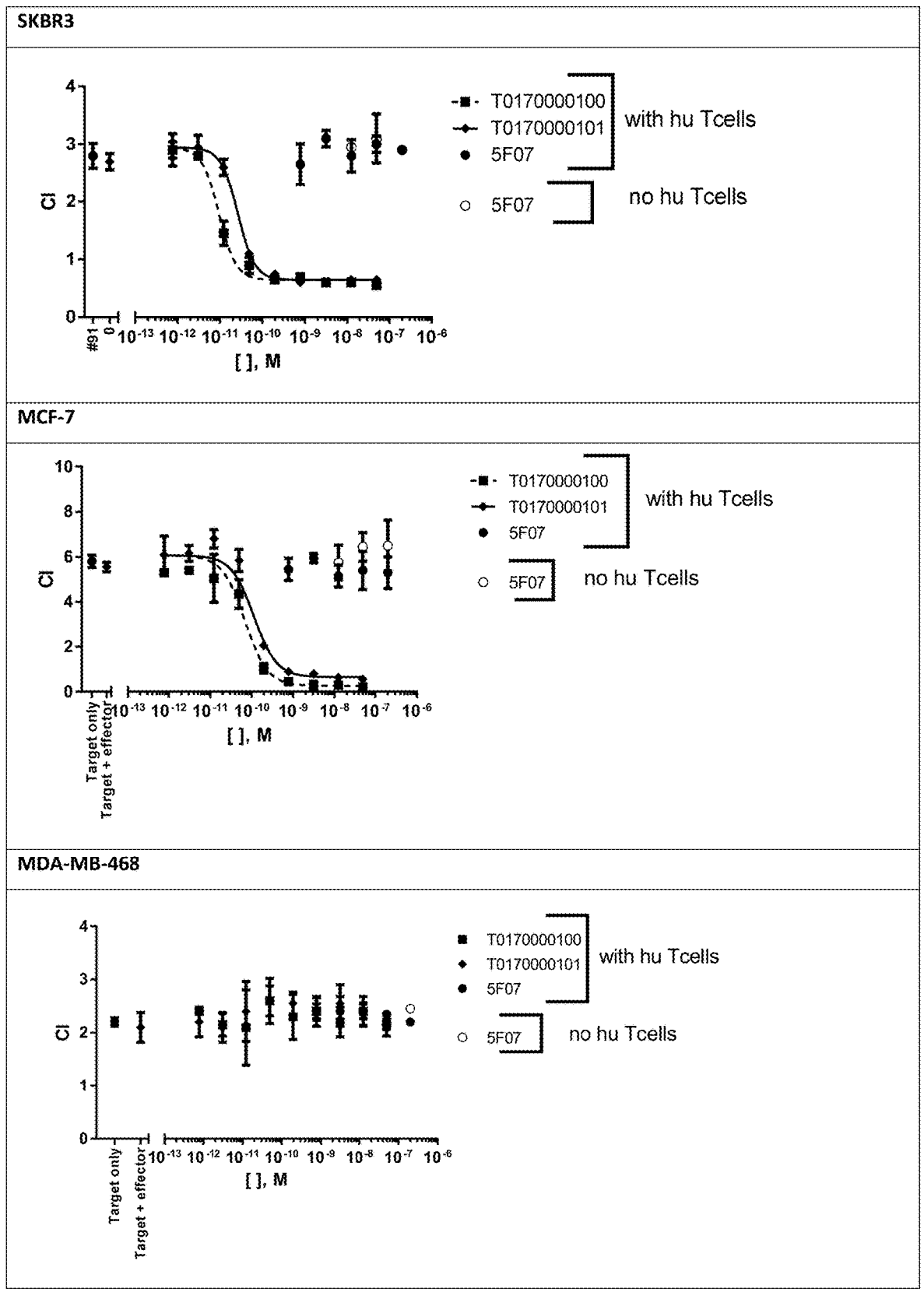

FIG. 16: Dose-dependent killing effect of bispecific CD3×HER2 Nanobodies (dotted line) and bispecific HER2×CD3 (full line) in an xCELLigence based human T cells mediated cell killing assay. Data were analysed using at 18 h. The Cell index (CI) was plotted against the concentration of the Nanobody.

Figure 17:
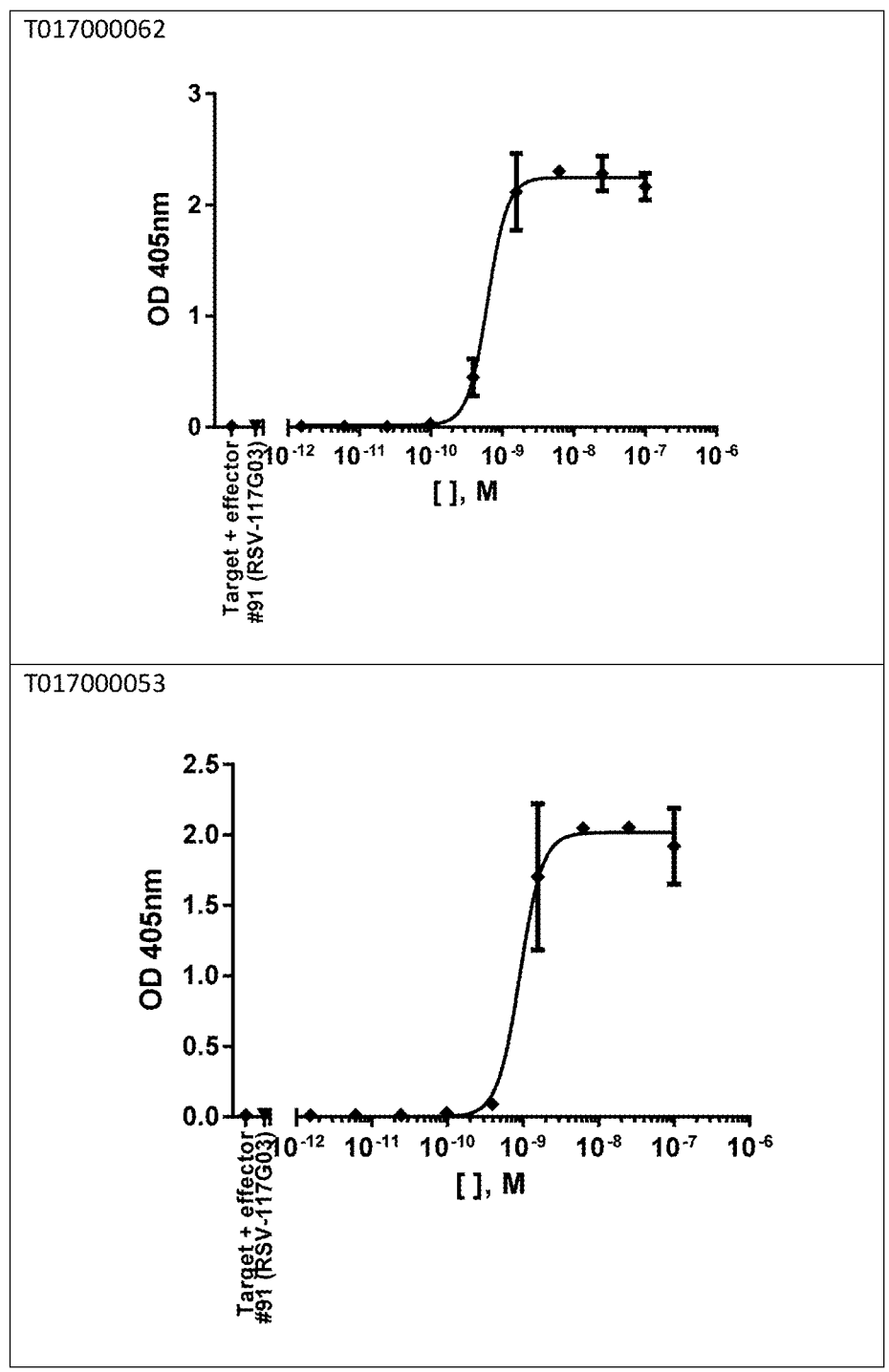

FIG. 17: Dose-dependent INF-7 production by human T cells after incubation of human CD20 positive CHO-K1 cells with bispecific CD20×CD3 Nanobodies in flow cytometry based killing assay. Data were analysed after 72 h incubation. The OD at 405 nm was plotted against the concentration of the Nanobody.

Figure 18:
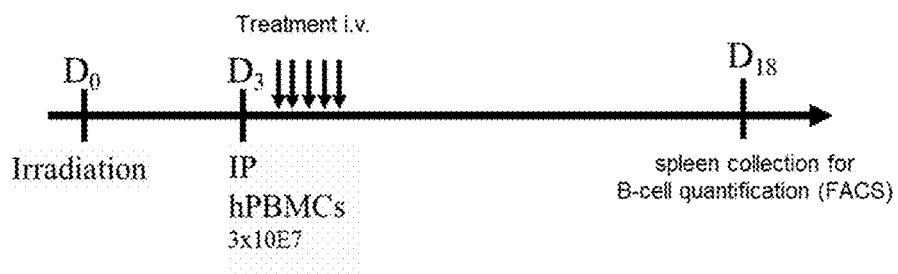

FIG. 18: Study design PBMC B cell depletion model. PBMCs were injected intraperitoneally to animals on day 3 (D3). Mice were treated from D3 to D7 with T017000084 (CD3/CD20) IV Q1Dx5 or T017000088 IV Q1Dx5 (irrelevant Nanobody).

Figure 19:
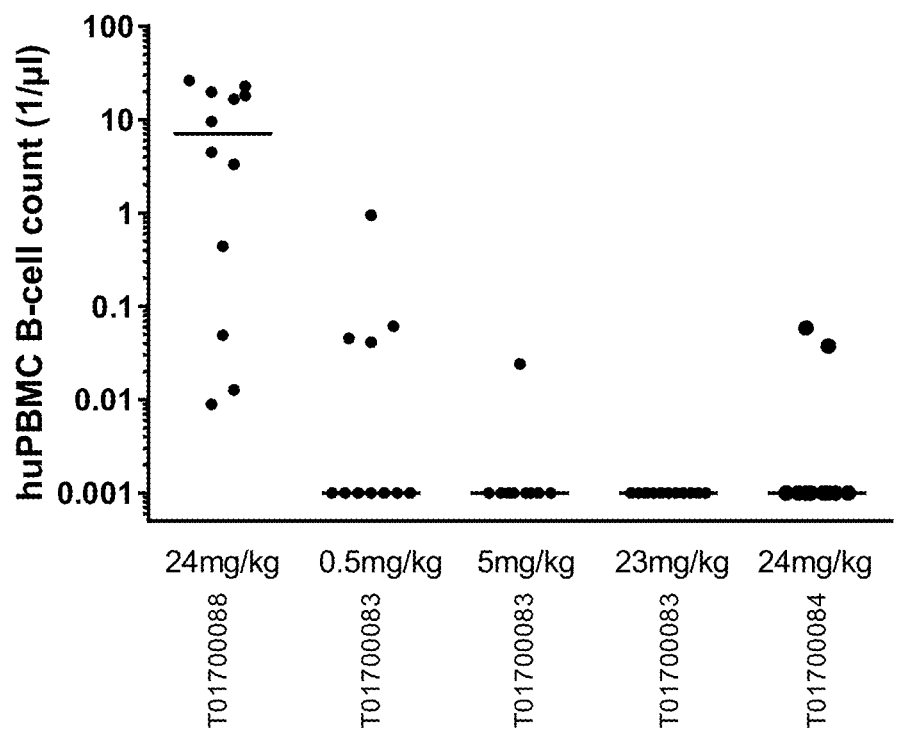

FIG. 19: Absolute PBMC-derived B cell count on log scale. Individual animal results are depicted. The number of B-cells is shown in function of the different treatment groups.

Figure 20:
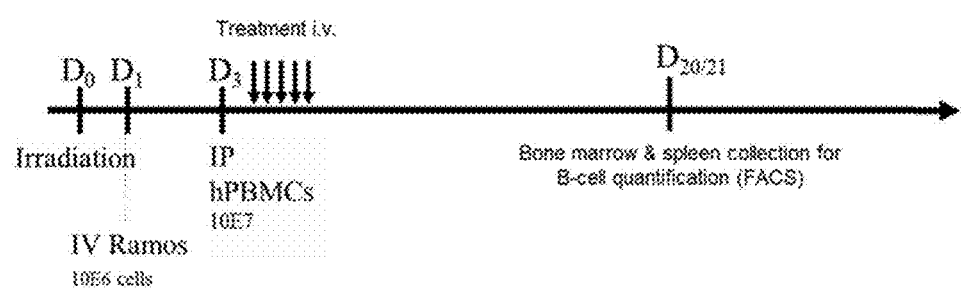

FIG. 20: Study design Ramos model. Ramos cells were injected intravenously to mice on D1. PBMCs were injected intraperitoneally to animals on D3. Mice were treated from D3 to D7 with T017000084 (CD3/CD20) IV Q1Dx5 or T017000088 IV Q1Dx5 (irrelevant Nanobody).

FIG. 21: Absolute Ramos B cell count on log scale. Individual animal results are depicted. The open circles on top of the graph show which active doses were statistically significant different from the irrelevant NB (T017000088) based on the F-tests from the mixed-effects ANOVA analysis. All effects are statistically significant at the 5% level of significance.

FIG. 22: Absolute PBMC-derived B cell count on log scale. Individual animal results are depicted. The open circles on top of the graph show which active doses were statistically significant different from the irrelevant NB (T017000088) based on the F-tests from the mixed-effects ANOVA analysis. All effects are statistically significant at the 5% level of significance.

Figure 23A:
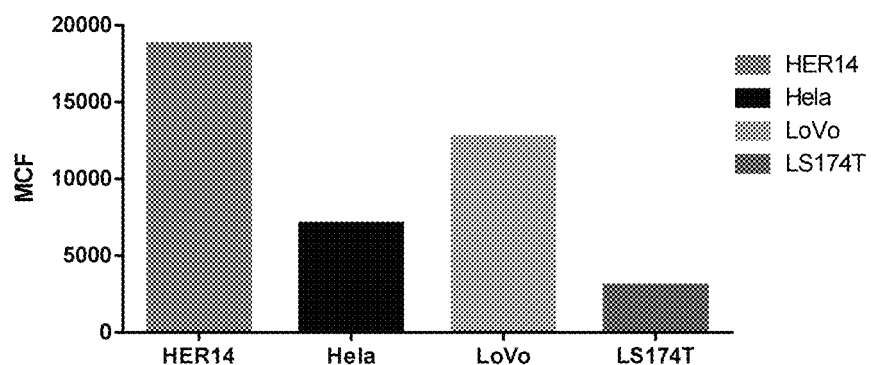
Figure 23B:
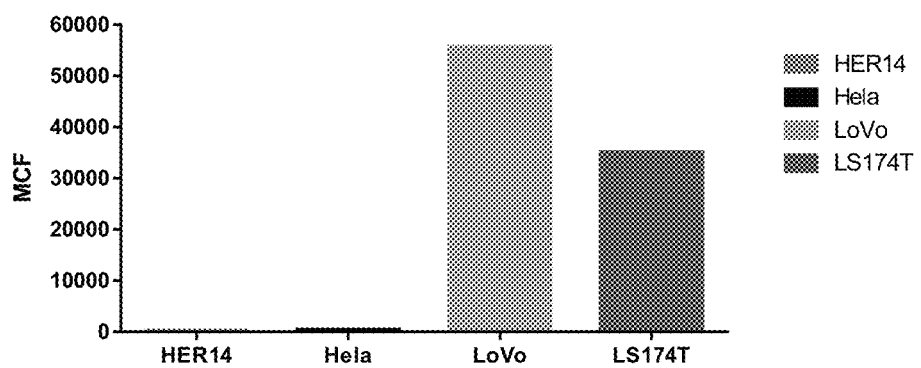

FIGS. 23A and 23B: Determination of EGFR (FIG. 23A; Santa Cruz, sc-120 PE) or CEACAM5 (FIG. 23B; Sino Biological, 11077-MM02-P) expression level on HER14, Hela, LoVo and LS174-T cell lines in flow cytometry. The MCF value (mean channel fluorescence) is plotted for each cell line.

DETAILED DESCRIPTION OF THE INVENTION

The present inventors realized that formats bringing T cells and tumour cells together to induce an immune response should comply with various and frequently opposing requirements. The format should be broadly applicable. In particular, the format should preferably be useful in a broad range of patients and preferably also against a broad range of tumours. The format should preferably be safe and only target the intended cells. In addition, the format should preferably be small enough to easily penetrate tissues and tumours, while on the other hand the format should be patient friendly. For instance, the format should have an extended half-life, such that the format is not removed instantaneously upon administration by renal clearance. However, extending the half-life should preferably not introduce off-target activity and side effects or limit the penetration into tissues and tumours. Additionally, it was recognized that tumour cells often create escape mechanisms by the down-regulation of targeted antigens within a therapy. Accordingly, in a further preferred version, the format should target simultaneously multiple antigens.

The present invention realizes at least one of these requirements.

In particular, it was hypothesized that immunoglobulin single variable domains (ISVs) would in principle be ideal candidates, since they are small enough to easily penetrate (tumour) tissue and can be combined with other ISVs as building blocks. Next, ISVs directed against CD3, and in particular CD3ε, should have broad applicability.

Six clusters of related ISVs were identified, which had an unexpected range of advantageous features. First, the ISVs were unexpectedly broadly applicable, i.e. the CD3 ISVs were able to bind to T cells from different donors with high affinity. Formatted in a multispecific polypeptide, the CD3 ISVs enabled tumour cell killing with different tumour associated antigens. Hence, the CD3 ISVs can be used against a multitude of cancers. In addition, the multispecific polypeptides comprising the CD3 ISVs remained active when bound to albumin. This contributes to a favourable PK profile and patient compliance, while minimizing side effects. The polypeptides of the invention only showed effects when bound both to the T cell and the target cell, which is indicative of its safety.

The present inventors considered that the simultaneous targeting of multiple antigens reduces the probability of generating tumour escape variants, because of which the therapeutic activity of T cell engaging strategy is improved. Multispecific polypeptides are provided which comprise a CD3 ISV combined with immunoglobulin single variable domains against different target antigens and/or different epitopes on a particular antigen (biparatopic).

Immunoglobulin sequences, such as antibodies and antigen binding fragments derived there from (e.g., immunoglobulin single variable domains or ISVs) are used to specifically target their respective antigens in research and therapeutic applications. The generation of immunoglobulin single variable domains such as e.g., VHHs or Nanobodies may involve the immunization of an experimental animal such as a Llama, construction of phage libraries from immune tissue, selection of phage displaying antigen binding immunoglobulin single variable domains and screening of said domains and engineered constructs thereof for the desired specificities (WO 94/04678). Alternatively, similar immunoglobulin single variable domains such as e.g., dAbs can be generated by selecting phage displaying antigen binding immunoglobulin single variable domains directly from naive or synthetic libraries and subsequent screening of said domains and engineered constructs thereof for the desired specificities (Ward et al., Nature, 1989, 341: 544-6; Holt et al., Trends Biotechnol., 2003, 21(11):484-490; as well as for example WO 06/030220, WO 06/003388 and other published patent applications of Domantis Ltd.). Unfortunately, the use of monoclonal and/or heavily engineered antibodies also carries a high manufacturing cost and may result in suboptimal tumor penetration compared to other strategies.

The present invention provides multispecific polypeptides that specifically bind to CD3 of the T cell receptor complex, with an unexpected range of advantageous features. First, the polypeptides are easy to manufacture. Moreover, the ISVs are unexpectedly broad applicable, i.e. the CD3 ISVs were able to bind to T cells from different donors with high affinity. Formatted in a multispecific polypeptide, the CD3 ISVs enabled tumour cell killing with different tumour associated antigens. In contrast, no killing was observed when the polypeptides were not bound to T cells and target cell which underscores the safety of the polypeptides of the invention. Hence, the CD3 ISVs can be used against a multitude of cancers. Moreover, the CD3 ISVs can be considered as safe. In addition, the multispecific polypeptides comprising the CD3 ISVs remained active when bound to albumin. This will contribute to a favourable PK profile and patient compliance, while minimizing side effects.

Accordingly, the present invention relates to a polypeptide comprising a first and a second immunoglobulin single variable domain (ISV), wherein the first ISV has high affinity for/binds to CD3 and the second ISV has high affinity for/binds to an antigen on a cell (target cell), preferably a tumour cell. The antigen is preferably specific for said target cell, such as e.g. a tumour associated antigen (TAA). The multispecific polypeptide of the invention directs the T cell to the cell, e.g. a tumour cell and induces T cell activation in order to allow said T cell to inhibit or kill said target cell, e.g. said tumour cell.

Definitions a) Unless indicated or defined otherwise, all terms used have their usual meaning in the art, which will be clear to the skilled person. Reference is for example made to the standard handbooks mentioned in paragraph a) on page 46 of WO 08/020079.

b) The term "immunoglobulin single variable domain", interchangeably used with "single variable domain" and "ISV", defines molecules wherein the antigen binding site is present on, and formed by, a single immunoglobulin domain. This sets immunoglobulin single variable domains apart from "conventional" immunoglobulins or their fragments (such as Fabs, scFvs, etc.), wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation. In contrast, the binding site of an immunoglobulin single variable domain is formed by a single VH or VL domain. Hence, the antigen binding site of an immunoglobulin single variable domain is formed by no more than three CDRs.

The terms "immunoglobulin single variable domain", "single variable domain", and "ISV" hence do not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

The term "immunoglobulin single variable domain" or "ISV" includes (without being limiting) antigen-binding domains or fragments such as $V_{HH}$ domains or $V_H$ or $V_L$ domains, respectively.

The terms antigen-binding molecules or antigen-binding protein are used interchangeably and include also the term Nanobodies. The immunoglobulin single variable domains can be light chain variable domain sequences (e.g., a $V_L$-sequence), or heavy chain variable domain sequences (e.g., a $V_H$-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences, humanized VHH sequences or camelized VH sequences. The invention includes immunoglobulin sequences of different origin, comprising mouse, rat, rabbit, donkey, human and camelid immunoglobulin sequences. The immunoglobulin single variable domain includes fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. It is noted that the terms Nanobody or Nanobodies are registered trademarks of Ablynx N.V. and thus may also be referred to as Nanobody® or Nanobodies®, respectively.

c) Unless indicated otherwise, the terms "immunoglobulin sequence", "sequence", "nucleotide sequence" and "nucleic acid" are as described in paragraph b) on page 46 of WO 08/020079.

d) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta 2006 (Adv. Drug Deliv. Rev. 58 (5-6):640-656), Levin and Weiss 2006 (Mol. Biosyst. 2(1):49-57), Irving et al. 2005 (J. Immunol. Methods 248(1-2):31-45), Schmitz et al. 2000 (Placenta 21 Suppl. A: 5106-112, Gonzales et al. 2005 (Tumour Biol. 26(1):31-43), which describe techniques for protein engineering, such as affinity maturation and other techniques for improving the specificity and other desired properties of proteins such as immunoglobulins.

e) Amino acid residues will be indicated according to the standard three-letter or one-letter amino acid code. Reference is made to Table A-2 on page 48 of the International application WO 08/020079 of Ablynx N.V. entitled "Immunoglobulin single variable domains directed against IL-6R and polypeptides comprising the same for the treatment of diseases and disorders associated with 11-6 mediated signalling".

f) For the purposes of comparing two or more nucleotide sequences, the percentage of "sequence identity" between a first nucleotide sequence and a second nucleotide sequence may be calculated or determined as described in paragraph e) on page 49 of WO 08/020079 (incorporated herein by reference), such as by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique, again as described in paragraph e) on pages 49 of WO 08/020079 (incorporated herein by reference).

g) For the purposes of comparing two or more immunoglobulin single variable domains or other amino acid sequences such e.g. the polypeptides of the invention etc., the percentage of "sequence identity" between a first amino acid sequence and a second amino acid sequence (also referred to herein as "amino acid identity") may be calculated or determined as described in paragraph f) on pages 49 and 50 of WO 08/020079 (incorporated herein by reference), such as by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein; or using a suitable computer algorithm or technique, again as described in paragraph f) on pages 49 and 50 of WO 08/020079 (incorporated herein by reference).

Also, in determining the degree of sequence identity between two immunoglobulin single variable domains, the skilled person may take into account so-called "conservative" amino acid substitutions, as described on page 50 of WO 08/020079.

Any amino acid substitutions applied to the polypeptides described herein may also be based on the analysis of the frequencies of amino acid variations between homologous proteins of different species developed by Schulz et al. 1978 (Principles of Protein Structure, Springer-Verlag), on the analyses of structure forming potentials developed by Chou and Fasman 1975 (Biochemistry 13: 211) and 1978 (Adv. Enzymol. 47: 45-149), and on the analysis of hydrophobicity patterns in proteins developed by Eisenberg et al. 1984 (Proc. Natl. Acad. Sci. USA 81: 140-144), Kyte & Doolittle 1981 (J Molec. Biol. 157: 105-132), and Goldman et al. 1986 (Ann. Rev. Biophys. Chem. 15: 321-353), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. 1996 (Nature Structural Biology, 3: 803), Spinelli et al. 1996 (Natural Structural Biology 3: 752-757), and Decanniere et al. 1999 (Structure, 7: 361). Further information about some of the amino acid residues that in conventional $V_H$ domains form the $V_H/V_L$ interface and potential camelizing substitutions on these positions can be found in the prior art cited above.

h) Immunoglobulin single variable domains and nucleic acid sequences are said to be "exactly the same" if they have 100% sequence identity (as defined herein) over their entire length.

i) When comparing two immunoglobulin single variable domains, the term "amino acid difference" refers to an insertion, deletion or substitution of a single amino acid residue on a position of the first sequence, compared to the second sequence; it being understood that two immunoglobulin single variable domains can contain one, two or more such amino acid differences.

j) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020079.

k) The term "in essentially isolated form" has the meaning given to it in paragraph j) on pages 52 and 53 of WO 08/020079.

l) The terms "domain" and "binding domain" have the meanings given to it in paragraph k) on page 53 of WO 08/020079.

m) The terms "antigenic determinant" and "epitope", which may also be used interchangeably herein, have the meanings given to it in paragraph l) on page 53 of WO 08/020079.

n) As further described in paragraph m) on page 53 of WO 08/020079, an amino acid sequence (such as an antibody, a polypeptide of the invention, or generally an antigen-binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

o) The term "specificity" refers to the number of different types of antigens or antigenic determinants to which a particular antigen-binding molecule or antigen-binding protein (such as an ISV, Nanobody or a polypeptide of the invention) can bind. The specificity of an antigen-binding protein can be determined based on affinity and/or avidity.

The affinity, represented by the equilibrium constant for the dissociation of an antigen with an antigen-binding protein ($K_D$ or KD), is a measure for the binding strength between an antigenic determinant, i.e. the target, and an antigen-binding site on the antigen-binding protein, i.e. the ISV or Nanobody: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest.

Avidity is the affinity of the polypeptide, i.e. the ligand is able to bind via two (or more) pharmacophores (ISV) in which the multiple interactions synergize to enhance the "apparent" affinity. Avidity is the measure of the strength of binding between the polypeptide of the invention and the pertinent antigens. The polypeptide of the invention is able to bind via its two (or more) building blocks, such as ISVs or Nanobodies, to the at least two targets, in which the multiple interactions, e.g. the first building block, ISV or Nanobody binding to the first target and the second building block, ISV, or Nanobody binding to the second target, synergize to enhance the "apparent" affinity. Avidity is related to both the affinity between an antigenic determinant and its antigen binding site on the antigen-binding molecule and the number of pertinent binding sites present on the antigen-binding molecules. For example, and without limitation, polypeptides that contain two or more building blocks, such as ISVs or Nanobodies directed against different targets on a cell may (and usually will) bind with higher avidity than each of the individual monomers or individual building blocks, such as, for instance, the monovalent ISVs or Nanobodies, comprised in the polypeptides of the invention.

Any $K_D$ value greater than $10^{-4}$ mol/liter (or any $K_A$ value lower than $10^4$ $M^{-1}$) liters/mol is generally considered to indicate non-specific binding.

The polypeptides of the invention comprise a first and a second building block, e.g. a first and a second ISV, or a first and a second Nanobody. Preferably the affinity of each building block, e.g. ISV or Nanobody, is determined individually. In other words, the affinity is determined for the monovalent building block, ISV or Nanobody, independent of avidity effects due to the other building block, ISV or Nanobody, which might or might not be present. The affinity for a monovalent building block, ISV or Nanobody can be determined on the monovalent building block, ISV or Nanobody per se, i.e. when said monovalent building block, ISV or Nanobody is not comprised in the polypeptide of the invention. In the alternative or in addition, the affinity for a monovalent building block, ISV or Nanobody can be determined on one target while the other target is absent.

The binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship $[K_D=1/K_A]$.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or $M^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well-known relation $DG=RT \cdot \ln(K_D)$ (equivalently $DG=-RT \cdot \ln(K_A)$), where R equals the gas constant, T equals the absolute temperature and ln denotes the natural logarithm.

The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units $M^{-1}s^{-1}$. The on-rate may vary between $10^2$ $M^{-1}s^{-1}$ to about $10^7$ $M^{-1}s^{-1}$, approaching the diffusion-limited association rate constant for biomolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}=0.69$ s).

The affinity of a molecular interaction between two molecules can be measured via different techniques known per se, such as the well-known surface plasmon resonance (SPR) biosensor technique (see for example Ober et al. 2001, Intern. Immunology, 13: 1551-1559). The term "surface plasmon resonance", as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIAcore® system (BIAcore International AB, a GE Healthcare company, Uppsala, Sweden and Piscataway, NJ.). For further descriptions, see Jonsson et al. 1993 (Ann. Biol. Clin. 51: 19-26), Jonsson et al. 1991 (Biotechniques 11: 620-627), Johnsson, et al. 1995 (J. Mol. Recognit. 8: 125-131), and Johnnson, et al. 1991 (Anal. Biochem. 198: 268-277).

Alternatively, affinities can be measured in Kinetic Exclusion Assay (KinExA) (see for example Drake et al. 2004, Anal. Biochem., 328: 35-43), using the KinExA® platform (Sapidyne Instruments Inc, Boise, USA). The term "KinExA", as used herein, refers to a solution-based method to measure true equilibrium binding affinity and kinetics of unmodified molecules. Equilibrated solutions of an antibody/antigen complex are passed over a column with beads precoated with antigen (or antibody), allowing the free antibody (or antigen) to bind to the coated molecule. Detection of the antibody (or antigen) thus captured is accomplished with a fluorescently labeled protein binding the antibody (or antigen).

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition site for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. 1985 (J. Immunol. Methods, 77: 305-19). This method establishes a solution phase binding equilibrium measurement and avoids possible artefacts relating to adsorption of one of the molecules on a support such as plastic.

However, the accurate measurement of $K_D$ may be quite labour-intensive and, as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence, in the present document, $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D = IC_{50}/(1+c_{ref}/K_{D\ ref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

p) The half-life of an amino acid sequence, compound or polypeptide of the invention can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). Reference is for example made to the Experimental Part below, as well as to the standard handbooks, such as Kenneth et al. 1996 (Chemical Stability of Pharmaceuticals: A Handbook for Pharmacists) and Peters et al. 1996 (Pharmacokinete analysis: A Practical Approach). Reference is also made to Gibaldi & Perron 1982 (Pharmacokinetics, Dekker M, 2nd Rev. edition). The terms "increase in half-life" or "increased half-life" are as defined in paragraph o) on page 57 of WO 08/020079 and in particular refer to an increase in the t½-beta, either with or without an increase in the t½-alpha and/or the AUC or both.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated.

r) An immunoglobulin single variable domain or polypeptide is said to be "specific for" a first target or antigen compared to a second target or antigen when it binds to the first antigen with an affinity/avidity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10.000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or polypeptide. Preferably, when an immunoglobulin single variable domain or polypeptide is "specific for" a first target or antigen compared to a second target or antigen, it is directed against (as defined herein) said first target or antigen, but not directed against said second target or antigen.

s) The terms "cross-block", "cross-blocked" and "cross-blocking" are used interchangeably herein to mean the ability of an immunoglobulin single variable domain or polypeptide to interfere with the binding of the natural ligand to its receptor(s). The extent to which an immunoglobulin single variable domain or polypeptide of the invention is able to interfere with the binding of another compound such as the natural ligand to its target and therefore whether it can be said to cross-block according to the invention, can be determined using competition binding assays. One particularly suitable quantitative cross-blocking assay uses a FACS- or an ELISA-based approach or Alphascreen to measure competition between the labelled (e.g., His tagged or biotinylated) immunoglobulin single variable domain or polypeptide according to the invention and the other binding agent in terms of their binding to the target. The experimental part generally describes suitable FACS-, ELISA- or Alphascreen-displacement-based assays for determining whether a binding molecule cross-blocks or is capable of cross-blocking an immunoglobulin single variable domain or polypeptide according to the invention. It will be appreciated that the assay can be used with any of the immunoglobulin single variable domains or other binding agents described herein. Thus, in general, a cross-blocking amino acid sequence or other binding agent according to the invention is for example one which will bind to the target in the above cross-blocking assay such that, during the assay and in the presence of a second amino acid sequence or other binding agent of the invention, the recorded displacement of the immunoglobulin single variable domain or polypeptide according to the invention is between 60% and 100% (e.g., in ELISA/Alphascreen based competition assay) or between 80% to 100% (e.g., in FACS based competition assay) of the maximum theoretical displacement (e.g. displacement by cold (e.g., unlabeled) immunoglobulin single variable domain or polypeptide that needs to be cross-blocked) by the to be tested potentially cross-blocking agent that is present in an amount of 0.01 mM or less (cross-blocking agent may be another conventional monoclonal antibody such as IgG, classic monovalent antibody fragments (Fab, scFv) and engineered variants (e.g., diabodies, triabodies, minibodies, VHHs, dAbs, VHs, VLs)).

t) An amino acid sequence such as e.g. an immunoglobulin single variable domain or polypeptide according to the invention is said to be a "VHH1 type immunoglobulin single variable domain" or "VHH type 1 sequence", if said VHH1 type immunoglobulin single variable domain or VHH type 1 sequence has 85% identity (using the VHH1 consensus sequence as the query sequence and use the blast algorithm with standard setting, i.e., blosom62 scoring matrix) to the VHH1 consensus sequence (QVQLVESGG-GLVQPGGSLRLS-CAASGFTLDYYAIGWFRQAPGKEREGVSCISSSD GSTYYADSVKGRFTISRD-NAKNTVYLQMNSLKPEDTAVYYCAA) (SEQ ID NO: 361), and mandatorily has a cysteine in position 50, i.e., C50 (using Kabat numbering).

u) An amino acid sequence such as e.g., an immunoglobulin single variable domain or polypeptide according to the invention is said to be "cross-reactive" for two different antigens or antigenic determinants (such as serum albumin from two different species of mammal, such as human serum albumin and cynomolgus monkey serum albumin) if it is specific for (as defined herein) both these different antigens or antigenic determinants.

v) As further described in paragraph q) on pages 58 and 59 of WO 08/020079 (incorporated herein by reference), the amino acid residues of an immunoglobulin single variable domain are numbered according to the general numbering for $V_H$ domains given by Kabat et al. ("Sequence of proteins of immunological interest", US Public Health Services, NIH Bethesda, MD, Publication No. 91), as applied to $V_{HH}$ domains from Camelids in the article of Riechmann and Muyldermans, 2000 (J. Immunol. Methods 240 (1-2): 185-195; see for example FIG. 2 of this publication). It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

In the present application, however, unless indicated otherwise, CDR sequences were determined according to Kontermann and Dübel (Eds. 2010, Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

w) The Figures, Sequence Listing and the Experimental Part/Examples are only given to further illustrate the invention and should not be interpreted or construed as limiting the scope of the invention and/or of the appended claims in any way, unless explicitly indicated otherwise herein.

x) The half maximal inhibitory concentration (IC50) is a measure of the effectiveness of a compound in inhibiting a biological or biochemical function, e.g. a pharmacological effect. This quantitative measure indicates how much of the ISV or Nanobody (inhibitor) is needed to inhibit a given biological process (or component of a process, i.e. an enzyme, cell, cell receptor, chemotaxis, anaplasia, metastasis, invasiveness, etc) by half. In other words, it is the half maximal (50%) inhibitory concentration (IC) of a substance (50% IC, or IC50). The IC50 of a drug can be determined by constructing a dose-response curve and examining the effect of different concentrations of antagonist such as the ISV or Nanobody of the invention on reversing agonist activity. IC50 values can be calculated for a given antagonist such as the ISV or Nanobody of the invention by determining the concentration needed to inhibit half of the maximum biological response of the agonist.

The term half maximal effective concentration (EC50) refers to the concentration of a compound which induces a response halfway between the baseline and maximum after a specified exposure time. In the present context it is used as a measure of a polypeptide's, ISV's or Nanobody's potency. The EC50 of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the EC50. This can be determined mathematically by derivation of the best-fit line. Relying on a graph for estimation is convenient in most cases. In case the EC50 is provided in the examples section, the experiments were designed to reflect the $K_D$ as accurate as possible. In other words, the EC50 values may then be considered as $K_D$ values. The term "average $K_D$" relates to the average $K_D$ value obtained in at least 1, but preferably more than 1, such as at least 2 experiments. The term "average" refers to the mathematical term "average" (sums of data divided by the number of items in the data).

It is also related to IC50 which is a measure of a compound's inhibition (50% inhibition). For competition binding assays and functional antagonist assays, IC50 is the most common summary measure of the dose-response curve. For agonist/stimulator assays the most common summary measure is the EC50.

y) It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The present invention relates to a polypeptide comprising at least a first and at least one further immunoglobulin single variable domain (ISV), wherein said at least first ISV has high affinity for/binds to cluster of differentiation 3 (CD3) and said at least one further ISV has high affinity for/binds to an antigen on a target cell.

Typically, the multispecific polypeptides of the invention combine high affinity antigen recognition on the target cell with T cell activation, resulting in an activation that is independent of the T cells' natural specificity. The mode of action of the binding molecules that binds both to a cell surface molecule on a target cell such as a tumour antigen and to the T cell co-receptor CD3 is commonly known. Bringing a T cell in close vicinity to a target cell, i.e., engaging said T cell results in killing of the target cell by the T cell. In the present invention this process is exploited in fighting against proliferative disease, inflammatory disease, infectious disease and autoimmune disease. Generally T cells are equipped with granules containing a deadly combination of pore-forming proteins, called perforins, and cell death-inducing proteases, called granzymes. Preferably, these proteins are delivered into target cells via a cytolytic synapse that forms if T cells are in close vicinity with a target cell that is aimed to be killed. Normally, close vicinity between a T cell and a target cell is achieved by the T cell binding to an MHC/peptide complex using its matching T cell receptor. The polypeptides of the invention bring a T cell into such close vicinity to a target cell in the absence of T cell receptor/MHC interaction.

Accordingly, the present invention relates to a polypeptide as described herein, wherein said polypeptide directs the T cell to the target cell.

With one arm (first ISV), the multispecific polypeptide has high affinity for/binds to CD3, a protein component of the signal-transducing complex of the T cell receptor on T-cells. With another arm (second ISV and/or third ISV, etc.), the multispecific polypeptide recognizes, has high affinity for/binds an antigen(s) on target cells. Preferably, T cell activation is only seen when the multispecific polypeptides are presented to T cells on the surface of target cells. Antigen dependence on target cells for activation results in a favourable safety profile. In an embodiment, the multispecific polypeptides transiently tether T cells and target cells. Preferably, the multispecific polypeptide can induce resting polyclonal T cells, such as $CD4^+$ and/or $CD8^+$ T cells into activation, for highly potent redirected lysis of target cells. Preferably, the T cell is directed to a next target cell after lysis of the first target cell.

Proteins and polypeptides that comprise or essentially consist of two or more immunoglobulin single variable domains (such as at least two immunoglobulin single variable domains of the invention) will be referred to herein as "multivalent" proteins or polypeptides or as "multivalent constructs". Some non-limiting examples of such multivalent constructs will become clear from the further description herein. The polypeptides of the invention are "multivalent", i.e. comprising two or more building blocks or ISVs of which at least the first building block, ISV or Nanobody and the second building block, ISV or Nanobody are different, and directed against different targets, such as antigens or antigenic determinants. Polypeptides of the invention that contain at least two building blocks, ISVs or Nanobodies, in which at least one building block, ISV or Nanobody is directed against a first antigen (i.e., against the first target, such as e.g. CD3) and at least one building block, ISV or Nanobody is directed against a second antigen (i.e., against the second target which is different from the first target, such as e.g. a TAA, e.g. CD20 or HER2), will also be referred to as "multispecific" polypeptides of the invention, and the building blocks, ISVs or Nanobodies present in such polypeptides will also be referred to herein as being in a "multivalent format" or "multispecific format". Thus, for example, a "bispecific" polypeptide of the invention is a polypeptide that comprises at least one building block, ISV or Nanobody directed against a first target (e.g. CD3) and at least one further building block, ISV or Nanobody directed against a second target (i.e., directed against a second target different from said first target, such as e.g. a TAA, e.g. CD20 or HER2), whereas a "trispecific" polypeptide of the invention is a polypeptide that comprises at least one building block, ISV or Nanobody directed against a first target (e.g., CD3), a second building block, ISV or Nanobody directed against a second target different from said first target (e.g. a TAA, such as CD20 or HER2) and at least one further building block, ISV or Nanobody directed against a third antigen (i.e., different from both the first and the second target, such as another TAA); etc. As will be clear from the description, the invention is not limited to bispecific polypeptides, in the sense that a multispecific polypeptide of the invention may comprise at least a first building block, ISV or Nanobody against a first target, a second building block, ISV or Nanobody against a second target and any number of building blocks, ISVs or Nanobodies directed against one or more targets, which may be the same or different from the first and/or second target, respectively. The building blocks, ISVs or Nanobodies can optionally be linked via linker sequences.

The terms bispecific polypeptide, bispecific format, bispecific construct, bispecific Nanobody construct, bispecific and bispecific antibody are used interchangeably herein.

As will be clear from the further description above and herein, the immunoglobulin single variable domains of the invention can be used as "building blocks" to form polypeptides of the invention, e.g., by suitably combining them with other groups, residues, moieties or binding units, in order to form compounds or constructs as described herein (such as, without limitations, the bi-/tri-/tetra-/multivalent and bi-/tri-/tetra-/multispecific polypeptides of the invention described herein) which combine within one molecule one or more desired properties or biological functions.

It will be appreciated (as is also demonstrated in the Example section) that the ISV binding CD3 and the ISV binding the antigen on a target cell can be positioned in any order in the polypeptide of the invention. More particularly, in one embodiment, the ISV binding CD3 is positioned N-terminally and the ISV binding the antigen on a target cell is positioned C-terminally. In another embodiment, the ISV binding the antigen on a target cell is positioned N-terminally and the ISV binding CD3 is positioned C-terminally.

In a preferred aspect, the polypeptide of the invention comprises at least a first, at least a second and at least a third immunoglobulin single variable domain (ISV), wherein said at least a first ISV has high affinity for/binds to CD3; said at least a second ISV has high affinity for/binds to a first antigen on a target cell, and said at least a third ISV has high affinity for/binds to a second antigen on a target cell, wherein said second antigen is different from said first antigen. Said first antigen and said second antigen can be on the same or on different target cells.

It will be appreciated (as is also demonstrated in the Example section) that the ISV binding CD3 and the ISVs binding the first and second antigen on a target cell can be positioned in any order in the polypeptide of the invention. More particularly, in one embodiment, the ISV binding CD3 is positioned N-terminally, the ISV binding the first antigen on a target cell is positioned centrally and the ISV binding the second antigen on a target cell is positioned C-terminally. In another embodiment, the ISV binding CD3 is positioned N-terminally, the ISV binding the second antigen on a target cell is positioned centrally and the ISV binding the first antigen on a target cell is positioned C-terminally. In another embodiment, the ISV binding the first antigen on a target cell is positioned N-terminally, the ISV binding the second antigen on a target cell is positioned centrally and the ISV binding CD3 is positioned C-terminally. In another embodiment, the ISV binding the first antigen on a target cell is positioned N-terminally, the ISV binding CD3 is positioned centrally and the ISV binding the second antigen on a target cell is positioned C-terminally. In another embodiment, the ISV binding the second antigen on a target cell is positioned N-terminally, the ISV binding CD3 is positioned centrally and the ISV binding the first antigen on a target cell is positioned C-terminally. In another embodiment, the ISV binding the second antigen on a target cell is positioned N-terminally, the ISV binding the first antigen on a target cell is positioned centrally and the ISV binding CD3 is positioned C-terminally.

The invention further relates to compounds or constructs, and in particular proteins or polypeptides that comprise or essentially consist of one or more ISVs or polypeptides of the invention, and optionally further comprise one or more other groups, residues, moieties or binding units. As will become clear to the skilled person from the further disclosure herein, such further groups, residues, moieties, binding units or amino acid sequences may or may not provide further functionality to the polypeptide of the invention (and/or to the compound or construct in which it is present) and may or may not modify the properties of the polypeptide of the invention.

The compounds, constructs or polypeptides of the invention can generally be prepared by a method which comprises at least one step of suitably linking the one or more immunoglobulin single variable domains of the invention to the one or more further groups, residues, moieties or binding units, optionally via one or more suitable linkers, so as to provide the compound, construct or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound, construct or polypeptide of the invention, starting from an amino acid sequence of the invention, is also referred to herein as "formatting" said amino acid sequence of the invention; and an amino acid of the invention that is made part of a compound, construct or polypeptide of the invention is said to be "formatted" or to be "in the format of" said compound, construct or polypeptide of the invention. Examples of ways in which an amino acid sequence of the invention can be formatted and examples of such formats will be clear to the skilled person based on the disclosure herein; and such formatted immunoglobulin single variable domains or polypeptides form a further aspect of the invention.

For example, such further groups, residues, moieties or binding units may be one or more additional immunoglobulin single variable domains, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, immunoglobulin single variable domains that are suitable for use as a domain antibody, single domain antibodies, immunoglobulin single variable domains (ISVs) that are suitable for use as a single domain antibody, "dAb"'s, immunoglobulin single variable domains that are suitable for use as a dAb, or Nanobodies. Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domains or polypeptides of the invention so as to provide a "derivative" of an ISV or polypeptide of the invention, as further described herein.

Also within the scope of the present invention are compounds or constructs, which comprise or essentially consist of one or more derivatives as described herein, and optionally further comprise one or more other groups, residues, moieties or binding units, optionally linked via one or more linkers. Preferably, said one or more other groups, residues, moieties or binding units are immunoglobulin single variable domains. In the compounds or constructs described above, the one or more immunoglobulin single variable domains of the invention and the one or more groups, residues, moieties or binding units may be linked directly to each other and/or via one or more suitable linkers or spacers. For example, when the one or more groups, residues, moieties or binding units are immunoglobulin single variable domains, the linkers may also be immunoglobulin single variable domains, so that the resulting compound or construct is a fusion protein or fusion polypeptide.

In some embodiments, the polypeptides comprise at least two or more immunoglobulin single variable domains disclosed herein. In some embodiments, the polypeptides essentially consist of two or more immunoglobulin single variable domains disclosed herein. A polypeptide that "essentially consists of" two or more immunoglobulin single variable domains, is a polypeptide that in addition to the two or more immunoglobulin single variable domains disclosed herein does not have additional immunoglobulin single variable domains. For instance, a polypeptide that essentially consists of two immunoglobulin single variable domains does not include any additional immunoglobulin single variable domains. However, it should be appreciated that a polypeptide that essentially consists of two or more immunoglobulin single variable domains may include additional functionalities, such as a label, a toxin, one or more linkers, a binding sequence, etc. These additional functionalities include both amino acid based and non-amino acid based groups. In some embodiments, the polypeptides consist of one or more immunoglobulin single variable domains disclosed herein. It should be appreciated that the terms "polypeptide construct" and "polypeptide" can be used interchangeably herein (unless the context clearly dictates otherwise).

In some embodiments, the polypeptides include multivalent or multispecific constructs comprising immunoglobulin single variable domains disclosed herein. In some embodiments, the polypeptides comprise one or more antibody based-scaffolds and/or non-antibody based scaffolds disclosed herein. In some embodiments, the polypeptides comprise a serum binding protein moiety. In some embodiments, the serum binding protein moiety is an immunoglobulin single variable domain. In some embodiments, the immunoglobulin single variable domain is a Nanobody®.

It will be appreciated that the order of the building blocks, such as e.g. a first building block, a second building block, a third building block etc., on the polypeptide (orientation) can be chosen according to the needs of the person skilled in the art, as well as the relative affinities which may depend on the location of these building blocks in the polypeptide. Whether the polypeptide comprises a linker, is a matter of design choice. However, some orientations, with or without linkers, may provide preferred binding characteristics in comparison to other orientations. For instance, the order of a first and a second building block in the polypeptide of the invention can be (from N-terminus to C-terminus): (i) first building block (e.g. a first ISV such as a first Nanobody)—[linker]—second building block (e.g. a second ISV such as a second Nanobody); or (ii) second building block (e.g. a second ISV such as a second Nanobody)—[linker]—first building block (e.g. a first ISV such as a first Nanobody); (wherein the linker is optional). All orientations are encompassed by the invention. Polypeptides that contain an orientation of building blocks that provides desired (binding) characteristics can be easily identified by routine screening, for instance as exemplified in the experimental section.

The first immunoglobulin single variable domain (ISV) of the polypeptide of the invention has high affinity for/binds to an effector cell, preferably the TCR complex of said effector cell, and even more preferably CD3.

An effector cell is a cell comprising a TCR complex, preferably an immune cell, such as a T-helper cell, monocyte, macrophage, or dendritic cell, preferably a CD4$^+$ T-helper cell (also known as CD4 cell, T-helper cell or T4 cell), more preferably a Cytotoxic T cell (also known as Tc cell, CTL or CD8$^+$ T cells), Natural Killer T cells (NKT cells) or Natural Killer cells (NK cells). In some embodiments, the cell is present in vivo. In some embodiments, the cell is present in vitro. The effector cell of the invention relates in particular to mammalian cells, preferably to primate cells, and even more preferably to human cells.

As used herein, the terms "TCR complex" or "αβ TCR-CD3 complex" refers to the T cell receptor complex presented on the surface of T cells (see Kuhns et al. 2006, Immunity 24:133-139). The TCR complex is composed of six different type I single-spanning transmembrane proteins: the TCRα and TCRβ chains that form the TCR heterodimer responsible for ligand recognition, and the non-covalently associated CD3γ, CD3δ, CD3ε and ζ chains, which bear cytoplasmic sequence motifs that are phosphorylated upon receptor activation and recruit a large number of signalling components. Both α and β chains of the T cell receptor consist of a constant domain and a variable domain. The sequences for the human CD3 and the human TCRα/β constant domains are provided in Table A-10 (SEQ ID NOs: 291-296; cf. UniProtKB: CD3 delta: P04234, CD3 gamma: P09693, CD3 epsilon: P07766, CD3 zeta: P20963, TCR alpha: P01848 and TCR beta: P01850).

In an embodiment, the present invention relates to a polypeptide as described herein, wherein said first ISV binds to CD3γ (SEQ ID NO: 292), to CD3δ (SEQ ID NO: 291) and/or CD3ε (SEQ ID NO: 293) of the TCR complex, or polymorphic variants or isoforms thereof.

Alternatively, the present invention provides a polypeptide as described herein, wherein said first ISV binds to CD3γ (SEQ ID NO: 379), to CD3δ (SEQ ID NO: 291) and/or CD3ε (SEQ ID NO: 380) of the TCR complex, or polymorphic variants or isoforms thereof.

Isoforms are alternative protein sequences that can be generated from the same gene by a single or by the combination of biological events such as alternative promoter usage, alternative splicing, alternative initiation and ribosomal frameshifting, all as known in the art.

"T cell activation" as used herein refers to one or more cellular response(s) of a T cell, e.g. a cytotoxic T cell, such as selected from: proliferation, differentiation, cytokine secretion, cytotoxic effector molecule release, cytotoxic activity, expression of activation markers, and redirected target cell lysis. The polypeptides of the invention are capable of inducing T cell activation. Suitable assays to measure T cell activation are known in the art described herein, for instance as described in WO 99/54440 or by Schlereth et al. 2005 (Cancer Immunol. Immunother. 20: 1-12), or as exemplified in the examples or below.

In an embodiment, the present invention relates to a polypeptide as described herein, wherein said polypeptide induces T cell activation. Preferably, the polypeptide of the invention induces T cell activation only when said second and/or further ISV is bound to an antigen on a target cell.

In an embodiment, the present invention relates to a polypeptide as described herein, wherein said T cell activation depends on presenting said polypeptide bound to said first antigen on a target cell to a T cell.

T cell activation by the polypeptides of the invention can be monitored by upregulation of CD69, CD25 and various cell adhesion molecules, de novo expression and/or release of cytokines (e.g., IFN-γ, TNF-α, IL-6, IL-2, IL-4 and IL-10), upregulation of granzyme and perforin expression, and/or cell proliferation, membrane blebbing, activation of procaspases 3 and/or 7, fragmentation of nuclear DNA and/or cleavage of caspase substrate poly (ADPribose) polymerase. Preferably, redirected lysis of target cells by multispecific polypeptides is independent of T cell receptor specificity, presence of MHC class I and/or β2 microglobulin, and/or of any co-stimulatory stimuli.

In an embodiment, the present invention relates to a polypeptide as described herein, wherein said T cell activation is independent from MHC recognition.

The polypeptides of the invention show redirected lysis in vitro with previously unstimulated peripheral polyclonal $CD8^+$- and $CD4^+$-positive T cells. The redirected lysis of target cells via the recruitment of T cells by the polypeptides of the invention involves cytolytic synapse formation and delivery of perforin and granzymes. Cell lysis by T cells has been described, e.g. by Atkinson and Bleackley 1995 (Crit. Rev. Immunol 15(3-4):359-384). Preferably, the engaged T cells are capable of serial target cell lysis, and are not affected by immune escape mechanisms interfering with peptide antigen processing and presentation, or clonal T cell differentiation (see, for example, WO 2007/042261). In vitro, redirected lysis is seen at low picomolar concentrations, suggesting that very low numbers of the polypeptides of the invention need to be bound to target cells for triggering T cells. As demonstrated in the examples, the low effector to target ratio might be indicative for serial target cell lysis. Accordingly, the present invention relates to potent polypeptides. Preferably, the polypeptide of the invention mediates killing of target cells, e.g. cancer cells, such as stimulating T cells in pore-forming and delivering pro-apoptotic components of cytotoxic T cell granules.

In an embodiment, the present invention relates to a polypeptide as described herein, wherein said T cell activation causes one or more cellular response of said T cell, wherein said cellular response is selected from the group consisting of proliferation, differentiation, cytokine secretion, cytotoxic effector molecule release, cytotoxic activity, expression of activation markers and redirected target cell lysis.

As used herein, the term "potency" is a measure of the biological activity of an agent, such as a polypeptide, ISV or Nanobody. Potency of an agent can be determined by any suitable method known in the art, such as for instance as described in the experimental section. Cell culture based potency assays are often the preferred format for determining biological activity since they measure the physiological response elicited by the agent and can generate results within a relatively short period of time. Various types of cell based assays, based on the mechanism of action of the product, can be used, including but not limited to proliferation assays, cytotoxicity assays, cell killing assays, reporter gene assays, cell surface receptor binding assays, and assays to measure induction/inhibition of functionally essential protein or other signal molecules (such as phosphorylated proteins, enzymes, cytokines, cAMP and the like), Ramos B-cell depletion model, T cell mediated tumour cell killing assay (for instance as set out in the Examples section), all well known in the art. Results from cell based potency assays can be expressed as "relative potency" as determined by comparison of the multispecific polypeptide of the invention to the response obtained for the corresponding reference monovalent ISV, e.g. a polypeptide comprising only one ISV or one Nanobody, optionally further comprising an irrelevant Nanobody (cf. experimental section).

In an embodiment, the present invention relates to a polypeptide as described herein, wherein said T cell activation causes inhibition of an activity of said target cell, such as to delay or minimize the spread of the target cell, to inhibit or delay growth and/or proliferation of the target cell, and/or to kill the target cell (e.g., cause regression of the disorder and/or symptoms) by more than about 10%, such as 20%, 30%, or 40% or even more than 50%, such as more than 60%, such as 70%, 80%, or even more than 90%, such as 100%.

The first building block, ISV, Nanobody or VHH of the invention has a high affinity for its target, i.e. CD3. The first building block, ISV or Nanobody of the invention may for example be directed against an antigenic determinant, epitope, part, domain, subunit or confirmation (where applicable) of said first target. The first building block, e.g. the first ISV, Nanobody or VHH, is preferably chosen for its high affinity for its target per se, disregarding the influence of any avidity effects.

Accordingly, the present invention relates to a polypeptide as described herein, wherein said first ISV binds to CD3 with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less, such as less than 10 pM. Preferably, the KD is determined by Kinexa or SPR, for instance as determined by a Proteon. For instance, said KD is determined as set out in the Examples section.

Accordingly, the present invention relates to a polypeptide as described herein, wherein said first ISV has a high affinity when measured as a monovalent. Preferably said average KD is measured by surface plasmon resonance (SPR) on recombinant protein.

Accordingly, the present invention relates to a polypeptide as described herein, wherein said polypeptide has a dissociation constant ($K_D$) to (or for binding) said CD3 selected from the group consisting of: at most about $10^{-5}$ M, at most about $10^{-6}$ M, at most about $10^{-7}$ M, at most about $10^{-8}$ M, at most about $10^{-9}$ M, at most about $10^{-10}$ M, at most about $10^{-11}$ M, and at most about $10^{-12}$ M, preferably as measured by surface plasmon resonance.

The present invention also relates to a polypeptide as described herein, wherein said first ISV binds to said CD3 with an EC50 value of between 100 nM and 1 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less, such as less than 500, 400, 300, 200, 100, 90, 80, 70, 60, 50, 40, 30, 20, 10, 5 pM, or even less, such as less than 4 pM.

Accordingly, the present invention relates to a polypeptide as described herein, wherein said average KD is determined by FACS, Biacore, ELISA, on a monovalent first ISV, such as a Nanobody, or a polypeptide comprising a monovalent first ISV, such as a Nanobody, for instance said EC50 is determined as set out in the Examples section.

It has been shown in the examples that the KD correlates well with the EC50.

In an embodiment, the present invention relates to a polypeptide as described herein, wherein said polypeptide has an on rate constant (Kon) to (or for binding) said CD3 selected from the group consisting of at least about $10^2$ $M^{-1}s^{-1}$, at least about $103$ $M^{-1}s^{-1}$, at least about $10^4$ $M^{-1}s^{-1}$, at least about $10^5$ $M^{-1}s^{-1}$, at least about $10^6$ $M^{-1}s^{-1}$, $10^7$ $M^{-1}s^{-1}$, at least about $10^8$ $M^{-1}s^{-1}$, at least about $109$ $M^{-1}s^{-1}$, and at least about $10^{10}$ $M^{-1}s^{-1}$, preferably as measured by surface plasmon resonance or as performed in the examples section.

In an embodiment the present invention relates to a polypeptide as described herein, wherein said polypeptide has an off rate constant (Koff) to (or for binding) said CD3 selected from the group consisting of at most about $10^{-3}$ $s^{-1}$, at most about $10^{-4}$ $s^{-1}$, at most about $10^{-5}$ $s^{-1}$, at most about $10^{-6}$ $s^{-1}$, at most about $10^{-7}$ $s^{-1}$, at most about $10^{-8}$ $s^{-1}$, at most about $10^{-9}$ $s^{-1}$, and at most about $10^{-10}$ $s^{-1}$, preferably as measured by surface plasmon resonance or as performed in the examples section.

Amino acid sequence modifications of the binding molecules, ISVs, or polypeptides described herein are contemplated. For example, it may be desirable to improve the binding affinity and/or other biological properties of the antibody or ISV. Amino acid sequence variants of the binding molecules, ISVs, or polypeptides are prepared by introducing appropriate nucleotide changes into the binding molecules, ISVs, or polypeptides nucleic acid, or by peptide synthesis.

Such modifications include, for example, deletions from, and/or insertions into, and/or substitutions of, residues within the amino acid sequences of the binding molecules, ISVs, or polypeptides. Any combination of deletion, insertion, and substitution is made to arrive at the final construct, provided that the final construct possesses the desired characteristics. The amino acid changes also may alter post-translational processes of the binding molecules, such as changing the number or position of glycosylation sites. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs). The substitutions are preferably conservative substitutions as described herein. Additionally or alternatively, 1, 2, 3, 4, 5, or 6 amino acids may be inserted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted or deleted in each of the FRs.

A useful method for identification of certain residues or regions of the binding molecules, ISVs or polypeptides, that are preferred locations for mutagenesis is called "alanine scanning mutagenesis" as described by Cunningham and Wells 1989 (Science 244: 1081-1085). Here, a residue or group of target residues within the binding molecule is/are identified (e.g. charged residues such as Arg, Asp, His, Lys, and Glu) and replaced by a neutral or negatively charged amino acid (most preferably alanine or polyalanine) to affect the interaction of the amino acids with the epitope. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se needs not to be predetermined. For example, to analyze the performance of a mutation at a given site, ala scanning or random mutagenesis is conducted at a target codon or region and the expressed binding molecule variants are screened for the desired activity.

Preferably, amino acid sequence insertions include amino- and/or carboxyl-terminal fusions ranging in length from 1, 2, 3, 4, 5, 6, 7, 8, 9 or 10 residues to polypeptides containing a hundred or more residues.

Another type of variant is an amino acid substitution variant. These variants have preferably at least 1, 2, 3, 4, 5, 6, 7, 8, 9 or 10 amino acid residues in the binding molecule, ISV or polypeptide replaced by a different residue. The sites of greatest interest for substitution mutagenesis include the CDRs, in particular the hypervariable regions, but FR alterations are also contemplated. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

Generally, if amino acids are substituted in one or more or all of the CDRs, it is preferred that the then-obtained "substituted" sequence is at least 60%, more preferably 65%, even more preferably 70%, particularly preferably 75%, more particularly preferably 80% or even more than 90% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the binding molecule may have different degrees of identity to their substituted sequences, e.g., CDR1 may have 80%, while CDR3 may have 90%.

Preferred substitutions (or replacements) are conservative substitutions. However, any substitution (including non-conservative substitution or one or more from the "exemplary substitutions" listed in Table B-1 below) is envisaged as long as the polypeptide retains its capability to bind to CD3 present on a T cell via the first ISV and to a first antigen on a target cell via the second ISV and/or its CDRs have an identity to the then substituted sequence (at least 60%, more preferably 65%, even more preferably 70%, particularly preferably 75%, more particularly preferably 80% identical to the "original" CDR sequence).

Conservative substitutions are shown in Table B-1 below.

TABLE B-1

Amino Acid Substitutions

| Original | Exemplary Substitutions | Preferred Substitutions |
| --- | --- | --- |
| Ala (A) | val, leu, ile | val |
| Arg (R) | lys, gln, asn | lys |
| Asn (N) | gln, his, asp, lys, arg | gln |
| Asp (D) | glu, asn | glu |
| Cys (C) | ser, ala | ser |
| Gln (Q) | asn, glu | asn |
| Glu (E) | asp, gln | asp |
| Gly (G) | ala | ala |
| His (H) | asn, gln, lys, arg | arg |

TABLE B-1-continued

Amino Acid Substitutions

| Original | Exemplary Substitutions | Preferred Substitutions |
|---|---|---|
| Ile (I) | leu, val, met, ala, phe | leu |
| Leu (L) | norleucine, ile, val, met, ala | ile |
| Lys (K) | arg, gln, asn | arg |
| Met (M) | leu, phe, ile | leu |
| Phe (F) | leu, val, ile, ala, tyr | tyr |
| Pro (P) | ala | ala |
| Ser (S) | thr | thr |
| Thr (T) | ser | ser |
| Trp (W) | tyr, phe | tyr |
| Tyr (Y) | trp, phe, thr, ser | phe |
| Val (V) | ile, leu, met, phe, ala | leu |

Sequence analysis further revealed that there are only a limited number of sequence variations in the CDRs (cf. Example 4.2 and Tables A-1 to A-6).

Accordingly, the present invention relates to a polypeptide as described herein, wherein said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 81-100; and
    (b) amino acid sequences that have 4, 3, 2, or 1 amino acid(s) difference with the amino acid sequence of SEQ ID NO: 81 or with any of SEQ ID NOs: 81-100; and/or
  (ii) CDR2 is chosen from the group consisting of:
    (c) SEQ ID NOs: 101-122; and
    (d) amino acid sequences that have 4, 3, 2, or 1 amino acid(s) difference with the amino acid sequence of SEQ ID NO: 101 or with any of SEQ ID NOs: 101-122; and/or
  (iii) CDR3 is chosen from the group consisting of:
    (e) SEQ ID NOs: 123-143; and
    (f) amino acid sequences that have 3, 2, or 1 amino acid(s) difference with the amino acid sequence of SEQ ID NO: 123 or with any of SEQ ID NOs: 123-143.

Further preferred CDR sequences are depicted in Table A-8.

Generally, the combinations of CDR's listed in Table A-8 (i.e. those mentioned on the same line in Table A-4) are preferred. Thus, it is generally preferred that, when a CDR in an ISV is a CDR sequence mentioned in Table A-8 or suitably chosen from the group consisting of CDR sequences that have 4, 3, 2 or only 1 amino acid difference(s) with a CDR sequence listed in Table A-8, that at least one and preferably both of the other CDR's are suitably chosen from the CDR sequences that belong to the same combination in Table A-8 (i.e. mentioned on the same line in Table A-8) or are suitably chosen from the group consisting of CDR sequences that have 4, 3, 2 or only 1 amino acid difference(s) with the CDR sequence(s) belonging to the same combination.

Sequence analysis of the resulting binders further resulted in the identification of 6 distinct clusters. Corresponding alignments are provided (see Table A-1, Table A-2, Table A-3, Table A-4, Table A-5 and Table A-6). Clustering was based on sequence similarities and differences in CDR2 and CDR3. Cluster A is the most prominent comprising 50 clones (SEQ ID NO:s 1-50), cluster B and cluster D are each represented by only 1 clone (SEQ ID NO: 51 and SEQ ID NO: 52, respectively), cluster C comprises 4 clones (SEQ ID NO:s 53-56), cluster E comprises 9 clones (SEQ ID NO:s 57-65) and cluster F comprises clones (SEQ ID NO:s 66-80). The clustering based on the structural similarities and differences in the amino acid sequence translated into functional similarities and differences as revealed by the examples. Representatives of all clusters were isolated based on high affinity binding to CD3 (Examples 3 & 4) and human T cell activation (Example 4.2). In general cluster A representatives demonstrated the best EC50 values. Although cluster C representatives had somewhat less favourable EC50 values than cluster B representatives, cluster C representatives had lower IC50 values in a flow cytometry based T cell mediated Ramos killing assay (cf. Example 10).

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of
  (a) SEQ ID NO: 81; and
  (b) amino acid sequences that have 1, 2, 3 or 4 amino acid difference(s) with SEQ ID NO: 81, wherein
    at position 1 the G has been changed into R;
    at position 3 the T has been changed into A;
    at position 4 the Y has been changed into F;
    at position 8 the S has been changed into G; and/or
    at position 10 the G has been changed into A.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 101; and
  (b) amino acid sequences that have 1, 2, 3 or 4 amino acid difference(s) with SEQ ID NO: 101, wherein
    at position 3 the V has been changed into T or A;
    at position 5 the S has been changed into T;
    at position 6 the G has been changed into D or E; and/or
    at position 9 the T has been changed into S, A or P.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
  (a) SEQ ID NO: 123; and
  (b) amino acid sequences that have 1, 2 or 3 amino acid difference(s) with SEQ ID NO: 123, wherein
    at position 2 the I has been changed into T;
    at position 9 the I has been changed into V; and/or
    at position 10 the A has been changed into P.

In an embodiment, the invention relates to a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 81-87; and
    (b) amino acid sequences that have 4, 3, 2, or 1 amino acid(s) difference with the amino acid sequence of SEQ ID NO: 81; and/or
  (ii) CDR2 is chosen from the group consisting of:
    (c) SEQ ID NOs: 101-109; and
    (d) amino acid sequences that have 4, 3, 2, or 1 amino acid(s) difference with the amino acid sequence of SEQ ID NO: 101; and/or (iii) CDR3 is chosen from the group consisting of:
  (e) SEQ ID NOs: 123-127; and
  (f) amino acid sequences that have 3, 2, or 1 amino acid(s) difference with the amino acid sequence of SEQ ID NO: 123.

In an embodiment, the invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 81, CDR2 is represented by SEQ ID NO: 101, and CDR3 is represented by SEQ ID NO: 123.

Nanobodies belonging to cluster B are represented by 1 clone.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 88; and
    (b) amino acid sequences that have 1, 2, 3, or 4 amino acid(s) difference with the amino acid sequence of SEQ ID NO: 88; and/or
  (ii) CDR2 is chosen from the group consisting of:
    (c) SEQ ID NO: 110; and
    (d) amino acid sequences that have 1, 2, 3, or 4 amino acid(s) difference with the amino acid sequence of SEQ ID NO: 110; and/or
  (iii) CDR3 is chosen from the group consisting of:
    (e) SEQ ID NO: 128; and
    (f) amino acid sequences that have 1, 2, or 3 amino acid(s) difference with the amino acid sequence of SEQ ID NO: 128.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 88, CDR2 is represented by SEQ ID NO: 110, and CDR3 is represented by SEQ ID NO: 128.

Nanobodies of cluster C show very limited sequence variability in the CDRs.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 112; and
  (b) amino acid sequence that has 1 amino acid difference with SEQ ID NO: 112, wherein
    at position 2 the V has been changed into A.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 90; and
    (b) amino acid sequences that have 1, 2, 3, or 4 amino acid(s) difference with the amino acid sequence of SEQ ID NO: 90; and/or
  (ii) CDR2 is chosen from the group consisting of:
    (c) SEQ ID NOs: 112-113; and
    (d) amino acid sequences that have 1, 2, 3, or 4 amino acid(s) difference with the amino acid sequence of SEQ ID NO: 112; and/or
  (iii) CDR3 is chosen from the group consisting of:
    (e) SEQ ID NO: 130; and
    (f) amino acid sequences that have 1, 2, or 3 amino acid(s) difference with the amino acid sequence of SEQ ID NO: 130.

In an aspect, the present invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 90, CDR2 is represented by SEQ ID NO: 112, and CDR3 is represented by SEQ ID NO: 130.

Nanobodies belonging to cluster D are represented by 1 clone.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 89; and
    (b) amino acid sequences that have 1, 2, 3, or 4 amino acid(s) difference with the amino acid sequence of SEQ ID NO: 89; and/or
  (ii) CDR2 is chosen from the group consisting of:
    (c) SEQ ID NO: 111; and
    (d) amino acid sequences that have 1, 2, 3, or 4 amino acid(s) difference with the amino acid sequence of SEQ ID NO: 111; and/or
  (iii) CDR3 is chosen from the group consisting of:
    (e) SEQ ID NO: 129; and
    (f) amino acid sequences that have 1, 2, or 3 amino acid(s) difference with the amino acid sequence of SEQ ID NO: 129.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 89, CDR2 is represented by SEQ ID NO: 111, and CDR3 is represented by SEQ ID NO: 129.

Cluster E comprises 9 clones.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of
  (a) SEQ ID NO: 91; and
  (b) amino acid sequences that have 1, 2 or 3 amino acid(s) difference with SEQ ID NO: 91, wherein
    at position 6 the R has been changed into N or T;
    at position 7 the N has been changed into H; and/or
    at position 8 the M has been changed into T.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 114; and
  (b) amino acid sequences that have 1, 2 or 3 amino acid(s) difference with SEQ ID NO: 114, wherein
    at position 1 the R has been changed into Q;
    at position 3 the T has been changed into S; and/or
    at position 7 the D has been changed into A or K.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
  (a) SEQ ID NO: 131; and
  (b) amino acid sequences that have 1 or 2 amino acid(s) difference with SEQ ID NO: 131, wherein
    at position 2 the S has been changed into R; and/or
    at position 6 the S has been changed into V.

In an embodiment, the invention relates to a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 91-93; and
    (b) amino acid sequences that have 4, 3, 2, or 1 amino acid(s) difference with the amino acid sequence of SEQ ID NO: 91; and/or
  (ii) CDR2 is chosen from the group consisting of:
    (c) SEQ ID NOs: 114-117; and
    (d) amino acid sequences that have 4, 3, 2, or 1 amino acid(s) difference with the amino acid sequence of SEQ ID NO: 114; and/or
  (iii) CDR3 is chosen from the group consisting of:
    (e) SEQ ID NOs: 131-133; and
    (f) amino acid sequences that have 3, 2, or 1 amino acid(s) difference with the amino acid sequence of SEQ ID NO: 131.

In an embodiment, the invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 91, CDR2 is represented by SEQ ID NO: 114, and CDR3 is represented by SEQ ID NO: 131.

Nanobodies belonging to cluster F are represented by 15 clones.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR1 is chosen from the group consisting of
  (a) SEQ ID NO: 94; and
  (b) amino acid sequences that have 1, 2, 3 or 4 amino acid(s) difference with SEQ ID NO: 94, wherein
    at position 3 the S has been changed into T, A or G;
    at position 5 the N has been changed into S;
    at position 6 the M has been changed into T or A; and/or
    at position 9 the L has been changed into M.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR2 is chosen from the group consisting of
  (a) SEQ ID NO: 118; and
  (b) amino acid sequences that have 1, 2, 3 or 4 amino acid(s) difference with SEQ ID NO: 118, wherein
    at position 2 the H has been changed into V;
    at position 5 the S has been changed into H or A;
    at position 8 the N has been changed into S; and/or
    at position 10 the Y has been changed into F.

Accordingly, the present invention relates to a polypeptide as described herein, in which said first ISV essentially consists of 4 framework regions (FR1 to FR4, respectively) and 3 complementarity determining regions (CDR1 to CDR3, respectively), in which CDR3 is chosen from the group consisting of
  (a) SEQ ID NO: 134; and
  (b) amino acid sequences that have 1, 2, 3 or 4 amino acid(s) difference with SEQ ID NO: 134, wherein
    at position 6 the A has been changed into S or D;
    at position 7 the F has been changed into Y or A;
    at position 8 the R has been changed into H;
    at position 9 the S has been changed into A;
    at position 11 the G has been changed into D, T, N, S, K or R; and/or
    at position 14 the V has been changed into I.

In an embodiment, the invention relates to a polypeptide as described herein, in which said first ISV essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 94-100; and
    (b) amino acid sequences that have 4, 3, 2, or 1 amino acid(s) difference with the amino acid sequence of SEQ ID NO: 94; and/or
  (ii) CDR2 is chosen from the group consisting of:
    (c) SEQ ID NOs: 118-122; and
    (d) amino acid sequences that have 4, 3, 2, or 1 amino acid(s) difference with the amino acid sequence of SEQ ID NO: 118; and/or
  (iii) CDR3 is chosen from the group consisting of:
    (e) SEQ ID NOs: 134-143; and
    (f) amino acid sequences that have 3, 2, or 1 amino acid(s) difference with the amino acid sequence of SEQ ID NO: 134.

In an embodiment, the invention relates to a polypeptide as described herein, in which said first ISV essentially consists of 4 framework regions (FR1 to FR4, respectively) and 3 complementarity determining regions (CDR1 to CDR3, respectively), in which: CDR1 is represented by SEQ ID NO: 94, CDR2 is represented by SEQ ID NO: 118, and CDR3 is represented by SEQ ID NO: 134.

The second immunoglobulin single variable domain (ISV) of the polypeptide of the invention has a high affinity for/binds to an antigen on a target cell, preferably a cancer cell. A "target cell" as referred to herein, is a cell that presents a particular antigen on its surface. In a preferred aspect, the "target cell" is a cancer cell.

The membrane (also called plasma membrane or phospholipid bilayer) surrounds the cytoplasm of a cell, which is the outer boundary of the cell, i.e. the membrane is the surface of the cell. This membrane serves to separate and protect a cell from its surrounding environment and is made mostly from a double layer of phospholipids. Embedded within this membrane is a variety of protein molecules, such as channels, pumps and cellular receptors. Since the membrane is fluid, the protein molecules can travel within the membrane. The term "antigen on a target cell" as used herein denotes a molecule, which is displayed on the surface of a cell. In most cases, this molecule will be located in or on the plasma membrane of the cell such that at least part of this molecule remains accessible from outside the cell in tertiary form. A non-limiting example of a cell surface molecule, which is located in the plasma membrane, is a transmembrane protein comprising, in its tertiary conformation, regions of hydrophilicity and hydrophobicity. Here, at least one hydrophobic region allows the cell surface molecule to be embedded, or inserted in the hydrophobic plasma membrane of the cell while the hydrophilic regions extend on either side of the plasma membrane into the cytoplasm and extracellular space, respectively.

Said antigen can be any target on a cell, e.g. a tumour antigen. In a preferred embodiment, said antigen is specific for said target cell, e.g. cancer cell, such as a tumour associated antigen (TAA) on said cancer cell.

The term "tumour antigen" as used herein may be understood as those antigens that are presented on tumour cells. These antigens can be presented on the cell surface with an extracellular part, which is often combined with a transmembrane and cytoplasmic part of the molecule. These antigens can sometimes be presented only by tumour cells and never by a normal or healthy cell. Tumour antigens can be exclusively expressed on tumour cells or might represent a tumour specific mutation compared to normal cells. In this case, they are called tumour-specific antigens. However, this will not be the case generally. More common are antigens that are presented by tumour cells and normal cells, and they are called "tumour-associated antigens (TAA)". These tumour-associated antigens can be overexpressed on tumour cells compared to normal cells or are better accessible for antibody binding in tumour cells due to the less compact structure of the tumour tissue compared to normal tissue. TAA are preferably antigens that are expressed on cells of particular tumours, but that are preferably not expressed in normal cells. Often, TAA are antigens that are normally expressed in cells only at particular points in an organism's development (such as during fetal development) and that are being inappropriately expressed in the organism at the present point of development, or are antigens not expressed in normal tissues or cells of an organ now expressing the antigen.

In an embodiment, said first antigen on a target cell is a tumour antigen, preferably a tumour associated antigen (TAA).

In an embodiment, said second antigen on a target cell is a tumour antigen, preferably a tumour associated antigen (TAA).

In an embodiment, said antigen is present more abundantly on a cancer cell than on a normal cell. The antigen on a target cell is preferably a tumor-associated antigen (TAA). Preferred TAA include MART-1, carcinoembryonic antigen ("CEA"), gp100, MAGE-1, HER-2, CD20, Lewis' antigens, Melanoma-associated Chondroitin Sulfate Proteoglycan (MCSP), Epidermal Growth Factor Receptor (EGFR), Fibroblast Activation Protein (FAP), CD19 and CD33.

Cell surface antigens that are preferentially expressed on AML LSC compared with normal hematopoietic stem cells, and thus preferred as TAA, include CD123, CD44, CLL-1, CD96, CD47, CD32, CXCR4, Tim-3 and CD25.

Other tumor-associated antigens suitable as an antigen on a target cell for binding by the second ISV within the polypeptides of the invention include: TAG-72, Ep-CAM, PSMA, PSA, glycolipids such as GD2 and GD3.

The TAA of the invention include also hematopoietic differentiation antigens, i.e. glycoproteins usually associated with cluster differentiation (CD) grouping, such as CD4, CD5, CD19, CD20, CD22, CD33, CD36, CD45, CD52, CD69 and CD147; growth factor receptors, including HER2, ErbB3 and ErbB4; Cytokine receptors, including Interleukin-2 receptor gamma chain (CD132 antigen), Interleukin-10 receptor alpha chain (IL-10R-A), Interleukin-10 receptor beta chain (IL-10R-B), Interleukin-12 receptor beta-1 chain (IL-12R-beta1), Interleukin-12 receptor beta-2 chain (IL-12 receptor beta-2), Interleukin-13 receptor alpha-1 chain (IL-13R-alpha-1) (CD213a1 antigen), Interleukin-13 receptor alpha-2 chain (Interleukin-13 binding protein), Interleukin-17 receptor (IL-17 receptor), Interleukin-17B receptor (IL-17B receptor), Interleukin 21 receptor precursor (IL-21R), Interleukin-1 receptor type I (IL-1R-1) (CD121a), Interleukin-1 receptor type II (IL-1R-beta) (CDw121b), Interleukin-1 receptor antagonist protein (IL-1ra), Interleukin-2 receptor alpha chain (CD25 antigen), Interleukin-2 receptor beta chain (CD122 antigen), Interleukin-3 receptor alpha chain (IL-3R-alpha) (CD123 antigen); as well as others, such as CD30, IL23R, IGF-1R, IL5R, IgE, CD248 (endosialin), CD44v6, gpA33, Ron, Trop2, PSCA, claudin 6, claudin 18.2, CLEC12A, CD38, ephA2, c-Met, CD56, MUC16, EGFRvIII, AGS-16, CD27L, Nectin-4, SLITRK6, mesothelin, folate receptor, tissue factor, axl, glypican-3, CA9, Cripto, CD138, CD37, MUC1, CD70, gastrin releasing peptide receptor, PAP, CEACAM5, CEACAM6, CXCR7, N-cadherin, FXYD2 gamma a, CD21, CD133, Na/K-ATPase, mIgM (membrane-bound IgM), mIgA (membrane-bound IgA), Mer, Tyro2, CD120, CD95, CA 195, DR5, DR6, DcR3 and CAIX.

Accordingly the present invention relates to a polypeptide as described herein, wherein said TAA is chosen from the group consisting of Melanoma-associated Chondroitin Sulfate Proteoglycan (MCSP), Epidermal Growth Factor Receptor (EGFR), Fibroblast Activation Protein (FAP), MART-1, carcinoembryonic antigen ("CEA"), gp100, MAGE-1, HER-2, Lewis' antigens, CD123, CD44, CLL-1, CD96, CD47, CD32, CXCR4, Tim-3, CD25, TAG-72, Ep-CAM, PSMA, PSA, GD2, GD3, CD4, CD5, CD19, CD20, CD22, CD33, CD36, CD45, CD52, CD147; growth factor receptors, including ErbB3 and ErbB4; Cytokine receptors, including Interleukin-2 receptor gamma chain (CD132 antigen), Interleukin-10 receptor alpha chain (IL-10R-A), Interleukin-10 receptor beta chain (IL-10R-B), Interleukin-12 receptor beta-1 chain (IL-12R-beta1), Interleukin-12 receptor beta-2 chain (IL-12 receptor beta-2), Interleukin-13 receptor alpha-1 chain (IL-13R-alpha-1) (CD213a1 antigen), Interleukin-13 receptor alpha-2 chain (Interleukin-13 binding protein), Interleukin-17 receptor (IL-17 receptor), Interleukin-17B receptor (IL-17B receptor), Interleukin 21 receptor precursor (IL-21R), Interleukin-1 receptor type I (IL-1R-1) (CD121a), Interleukin-1 receptor type II (IL-1R-beta) (CDw121b), Interleukin-1 receptor antagonist protein (IL-1ra), Interleukin-2 receptor alpha chain (CD25 antigen), Interleukin-2 receptor beta chain (CD122 antigen), Interleukin-3 receptor alpha chain (IL-3R-alpha) (CD123 antigen), CD30, IL23R, IGF-1R, IL5R, IgE, CD248 (endosialin), CD44v6, gpA33, Ron, Trop2, PSCA, claudin 6, claudin 18.2, CLEC12A, CD38, ephA2, c-Met, CD56, MUC16, EGFRvIII, AGS-16, CD27L, Nectin-4, SLITRK6, mesothelin, folate receptor, tissue factor, axl, glypican-3, CA9, Cripto, CD138, CD37, MUC1, CD70, gastrin releasing peptide receptor, PAP, CEACAM5, CEACAM6, CXCR7, N-cadherin, FXYD2 gamma a, CD21, CD133, Na/K-ATPase, mIgM (membrane-bound IgM), mIgA (membrane-bound IgA), Mer, Tyro2, CD120, CD95, CA 195, DR5, DR6, DcR3 and CAIX, and related polymorphic variants and isoforms, preferably said TAA is CD20 (UniProt 11836), HER2 (Uniprot P04626), polymorphic variants and/or isoforms thereof.

The second building block, ISV, Nanobody or VHH of the invention has a high affinity for its antigen. The second building block, ISV or Nanobody of the invention may, for example, be directed against an antigenic determinant, epitope, part, domain, subunit or confirmation (where applicable) of said antigen on a target cell.

The target cell of the invention relates in particular to mammalian cells, and preferably to primate cells and even more preferably to human cells. The target cell is preferably a hyperproliferative cell such as e.g. a cancer cell.

The present invention relates to a polypeptide as described herein, wherein said second or further ISV binds to an antigen on a target cell with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less such as less than 10 pM. Preferably, the KD is determined by KinExA or SPR, for instance as determined or Proteon.

Accordingly, the present invention relates to a polypeptide as described herein, wherein said second or further ISV has a high affinity for its antigen when measured as a monovalent.

Accordingly, the present invention relates to a polypeptide as described herein, wherein said average KD is measured by surface plasmon resonance (SPR) and/or KinExA or Proteon, for instance on recombinant protein, such as described in the Examples section.

The present invention also relates to a polypeptide as described herein, wherein said second or further ISV binds to an antigen on a target cell with an EC50 value of between 100 nM and 1 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less such as less than 500, 400, 300, 200, 100, 90, 80, 70, 60, 50, 40, 30, 20, 10, 5 pM, or even less such as less than 4 pM.

Accordingly, the present invention relates to a polypeptide as described herein, wherein said average EC50 is determined by FACS, or ELISA, on a monovalent second ISV, such as a Nanobody, or a polypeptide comprising a monovalent second ISV, such as a Nanobody.

It has been shown in the examples that the KD correlates well with the EC50.

Simultaneous targeting of multiple antigens can reduce the probability of generating tumour escape variants, because of which the therapeutic activity of T cell engaging strategy is improved. The present invention provides multispecific polypeptides which comprise a CD3 ISV combined with immunoglobulin single variable domains against different (target) antigens (on a target cell) (cf. Example 19). Preferred combinations of first and second antigens are provided below (it will be appreciated that the ISVs binding said antigens can be positioned in any order in the polypeptide of the invention):

| first antigen | second antigen |
| --- | --- |
| EGFR (OMIM: 131550) | CD20 (OMIM: 112210) |
| EGFR (OMIM: 131550) | CEA (OMIM: 114890) |
| EGFR (OMIM: 131550) | HER2 (OMIM: 164870) |
| HER2 (OMIM: 164870) | CD20 (OMIM: 112210) |
| HER2 (OMIM: 164870) | CEA (OMIM: 114890) |
| CD20 (OMIM: 112210) | CEA (OMIM: 114890) |

Similarly, simultaneous targeting of multiple epitopes, antigenic determinants, parts, domains, subunit or conformation of a protein or antigen on a target cell can reduce the probability of generating tumour escape variants, because of which the therapeutic activity of T cell engaging strategy is improved (cf. Example 20). The present invention provides polypeptides which comprise a anti-CD3 ISV combined with immunoglobulin single variable domains against different epitopes, antigenic determinants, parts, domains, subunit or conformation of an antigen on a target cell (also referred to as biparatopic constructs). Preferred combinations of first and second TAA ISVs are provided below (it will be appreciated that the ISVs binding said antigens can be positioned in any order in the polypeptide of the invention):

| TAA1 ISV | name | SEQ ID NO: | TAA2 ISV | name | SEQ ID NO: |
| --- | --- | --- | --- | --- | --- |
| EGFR-1 | 7D12 | 302 | EGFR-2 | 9G08 | 299 |
| HER2-1 | 5F07 | 297 | HER2-2 | 47D05 | 298 |
| CEA-1 | CEA#1 | 300 | CEA-2 | CEA#5 | 301 |

The polypeptides and compositions of the present invention can be used for the prevention and/or treatment of diseases and disorders of the present invention (herein also "diseases and disorders of the present invention") which include, but are not limited to cancer. The term "cancer" refers to the pathological condition in mammals that is typically characterized by dysregulated cellular proliferation or survival. Examples of cancer include, but are not limited to, carcinomas, gliomas, mesotheliomas, melanomas, lymphomas, leukemias, adenocarcinomas: breast cancer, ovarian cancer, cervical cancer, glioblastoma, multiple myeloma (including monoclonal gammopathy of undetermined significance, asymptomatic and symptomatic myeloma), prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease or AIDS-associated primary effusion lymphoma, neuroectodermal tumors, rhabdomyosarcoma (see e.g., Cancer, Principles and practice (DeVita, et al. eds 1997) for additional cancers); as well as any metastasis of any of the above cancers, as well as non-cancer indications such as nasal polyposis; as well as other disorders and diseases described herein.

For a general description of immunoglobulin single variable domains, reference is made to the further description below, as well as to the prior art cited herein. In this respect, it should however be noted that this description and the prior art mainly describes immunoglobulin single variable domains of the so-called "$V_H3$ class" (i.e., immunoglobulin single variable domains with a high degree of sequence homology to human germline sequences of the $V_H3$ class such as DP-47, DP-51 or DP-29), which form a preferred aspect of this invention. It should, however, be noted that the invention in its broadest sense generally covers any type of immunoglobulin single variable domains and for example also covers the immunoglobulin single variable domains belonging to the so-called "$V_H4$ class" (i.e., immunoglobulin single variable domains with a high degree of sequence homology to human germline sequences of the $V_H4$ class such as DP-78), as for example described in WO 07/118670.

Generally, immunoglobulin single variable domains (in particular $V_{HH}$ sequences and sequence optimized immunoglobulin single variable domains) can in particular be characterized by the presence of one or more "Hallmark residues" (as described for example in Table B-2) in one or more of the framework sequences (again as further described herein).

globulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. As mentioned herein, a particularly preferred class of immunoglobulin single variable domains of the invention comprises immunoglobulin single variable domains with an

TABLE B-2

Hallmark Residues in VHHs

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | $F^{(1)}$, Y, V, L, A, H, S, I, W, C, N, G, D, T, P, preferably $F^{(1)}$ or Y |
| 44$^{(8)}$ | G | $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$. |
| 45$^{(8)}$ | L | $L^{(2)}$, $R^{(3)}$, P, H, F, G, Q, S, E, T, Y, C, I, D, V; preferably $L^{(2)}$ or $R^{(3)}$ |
| 47$^{(8)}$ | W, Y | $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ |
| 83 | R or K; usually R | R, $K^{(5)}$, T, $E^{(5)}$, Q N, S, I, V, G, M, L, A, D, Y, H; preferably K or R; most preferably K |
| 84 | A, T, D; predominantly A | $P^{(5)}$, S, H, L, A, V, I, T, F, D, R, Y, N, Q, G, E; preferably P |
| 103 | W | $W^{(4)}$, $R^{(6)}$, G, S, K, A, M, Y, L, F, T, N, V, Q, $P^{(6)}$, E, C; preferably W |
| 104 | G | G, A, S, T, D, P, N, E, C, L; preferably G |
| 108 | L, M or T; predominantly L | Q, $L^{(7)}$, R, P, E, K, S, T, M, A, H; preferably Q or $L^{(7)}$ |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREL, QQREL or QQREF), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring $V_{HH}$ domains.
$^{(6)}$In particular, but not exclusively, in combination with GLEW at positions 44-47.
$^{(7)}$With the proviso that when positions 44-47 are GLEW, position 108 is always Q in (non-humanized) $V_{HH}$ sequences that also contain a W at 103.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

The immunoglobulins of the invention may also contain a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is made to WO 12/175741 and WO 15/060643.

Apart from this and/or in addition, the immunoglobulin of the invention may have certain preferred amino acid residues at positions 11, 89, 110 and/or 112 as is described in further detail in WO 15/060643 (which is incorporated herein as reference).

Again, such immunoglobulin single variable domains may be derived in any suitable manner and from any suitable source, and may for example be naturally occurring $V_{HH}$ sequences (i.e., from a suitable species of Camelid, e.g., llama) or synthetic or semi-synthetic VHs or VLs (e.g., from human). Such immunoglobulin single variable domains may include "humanized" or otherwise "sequence optimized" VHHs, "camelized" immunoglobulin sequences (and in particular camelized heavy chain variable domain sequences, i.e., camelized VHs), as well as human VHs, human VLs, camelid VHHs that have been altered by techniques such as affinity maturation (for example, starting from synthetic, random or naturally occurring immunoamino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized immunoglobulin single variable domains of the invention can be obtained in any suitable manner known per se and thus are not strictly limited to polypeptides that have been obtained using a polypeptide that comprises a naturally occurring $V_{HH}$ domain as a starting material.

Another particularly preferred class of immunoglobulin single variable domains of the invention comprises immunoglobulin single variable domains with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a V$_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the V$_H$—V$_L$ interface, and/or at the so-called Camelidae hallmark as defined herein (see also for example WO 94/04678 and Davies and Riechmann 1994 (FEBS letters 339: 285-290) and 1996 (Protein Engineering 9: 531-537)). Preferably, the V$_H$ sequence that is used as a starting material or starting point for generating or designing the camelized immunoglobulin single variable domains is preferably a V$_H$ sequence from a mammal, more preferably the V$_H$ sequence of a human being, such as a V$_H$3 sequence. However, it should be noted that such camelized immunoglobulin single variable domains of the invention can be obtained in any suitable manner known per se and thus are not strictly limited to polypeptides that have been obtained using a polypeptide that comprises a naturally occurring V$_H$ domain as a starting material.

For example, again as further described herein, both "humanization" and "camelization" can be performed by providing a nucleotide sequence that encodes a naturally occurring V$_{HH}$ domain or V$_H$ domain, respectively, and then changing, in a manner known per se, one or more codons in said nucleotide sequence in such a way that the new nucleotide sequence encodes a "humanized" or "camelized" immunoglobulin single variable domain of the invention, respectively. This nucleic acid can then be expressed in a manner known per se, so as to provide the desired immunoglobulin single variable domains of the invention. Alternatively, based on the amino acid sequence of a naturally occurring V$_{HH}$ domain or V$_H$ domain, respectively, the amino acid sequence of the desired humanized or camelized immunoglobulin single variable domains of the invention, respectively, can be designed and then synthesized de novo using techniques for peptide synthesis known per se. Also, based on the amino acid sequence or nucleotide sequence of a naturally occurring V$_{HH}$ domain or V$_H$ domain, respectively, a nucleotide sequence encoding the desired humanized or camelized immunoglobulin single variable domains of the invention, respectively, can be designed and then synthesized de novo using techniques for nucleic acid synthesis known per se, after which the nucleic acid thus obtained can be expressed in a manner known per se, so as to provide the desired immunoglobulin single variable domains of the invention.

Accordingly, the present invention relates to a polypeptide as described herein, wherein said ISV is a Nanobody, a V$_{HH}$, a humanized V$_{HH}$, or a camelized V$_H$.

Generally, proteins or polypeptides that comprise or essentially consist of a single building block, single immunoglobulin single variable domain or single Nanobody will be referred to herein as "monovalent" proteins or polypeptides, as "monovalent constructs", as "monovalent building block", as "monovalent immunoglobulin single variable domain", or as "monovalent Nanobody", respectively.

In this respect, the present invention also relates to the monovalent building blocks that make up the polypeptides of the invention.

Accordingly, the present invention relates to an ISV or polypeptide that specifically binds the constant domain of the CD3 and that comprises or essentially consists of 4 framework regions (FR1 to FR4, respectively) and 3 complementarity determining regions (CDR1 to CDR3, respectively), in which:

(i) CDR1 is chosen from the group consisting of:
  (a) SEQ ID NOs: 81-100; or
  (b) amino acid sequences that have 4, 3, 2, or 1 amino acid(s) difference with the amino acid sequence of any of SEQ ID NOs: 81-100, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or (ii) CDR2 is chosen from the group consisting of:
  (c) SEQ ID NOs: 101-122; or
  (d) amino acid sequences that have 4, 3, 2, or 1 amino acid(s) difference with the amino acid sequence of any of SEQ ID NOs: 101-122, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or (iii) CDR3 is chosen from the group consisting of:
  (e) SEQ ID NOs: 123-143; or
  (f) amino acid sequences that have 4, 3, 2, or 1 amino acid(s) difference with the amino acid sequence of any of SEQ ID NOs: 123-143, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

As discussed above, ISVs were isolated that belong to different clusters, based on structural similarities and differences in CDR2 and CDR3.

Immunoglobulin single variable domains belonging to cluster A are represented by polypeptides according in which:

(i) CDR1 is chosen from the group consisting of:
  (a) SEQ ID NOs: 81-87; and
  (b) amino acid sequences that have 4, 3, 2, or 1 amino acid(s) difference with the amino acid sequence of SEQ ID NO: 81, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or (ii) CDR2 is chosen from the group consisting of:
  (c) SEQ ID NOs: 101-109; and
  (d) amino acid sequences that have 4, 3, 2, or 1 amino acid(s) difference with the amino acid sequence of SEQ ID NO: 101, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or (iii) CDR3 is chosen from the group consisting of:
  (e) SEQ ID NOs: 123-127; and
  (f) amino acid sequences that have 4, 3, 2, or 1 amino acid(s) difference with the amino acid sequence of SEQ ID NO: 123, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster A, CDR1 is chosen from the group consisting of
(a) SEQ ID NO: 81; and
(b) amino acid sequences that have 1 or 2 amino acid difference(s) with SEQ ID NO: 81, wherein
at position 1 the G has been changed into R;
at position 3 the T has been changed into A;
at position 4 the Y has been changed into F;
at position 8 the S has been changed into G; and/or
at position 10 the G has been changed into A.

In another aspect, in the polypeptides belonging to cluster A, CDR2 is chosen from the group consisting of
(a) SEQ ID NO: 101; and
(b) amino acid sequences that have 1, 2 or 3 amino acid difference(s) with SEQ ID NO: 101, wherein
at position 3 the V has been changed into T or A;
at position 5 the S has been changed into T;
at position 6 the G has been changed into D or E; and/or
at position 9 the T has been changed into S, A or P.

In another aspect, in the polypeptides belonging to cluster A, CDR3 is chosen from the group consisting of
(a) SEQ ID NO: 123; and
(b) amino acid sequences that have 1 or 2 amino acid difference(s) with SEQ ID NO: 123, wherein
at position 2 the I has been changed into T;
at position 9 the I has been changed into V; and/or
at position 10 the A has been changed into P.

Accordingly, the present invention relates to an ISV or polypeptide that specifically binds CD3 and that comprises or essentially consists of 4 framework regions (FR1 to FR4, respectively) and 3 complementarity determining regions (CDR1 to CDR3, respectively), in which:
(i) CDR1 is chosen from the group consisting of
(a) SEQ ID NO: 81; and
(b) amino acid sequences that have 1 or 2 amino acid difference(s) with SEQ ID NO: 81, wherein
at position 1 the G has been changed into R;
at position 3 the T has been changed into A;
at position 4 the Y has been changed into F;
at position 8 the S has been changed into G; and/or
at position 10 the G has been changed into A,
and in which
(ii) CDR2 is chosen from the group consisting of
(a) SEQ ID NO: 101; and
(b) amino acid sequences that have 1, 2 or 3 amino acid difference(s) with SEQ ID NO: 101, wherein
at position 3 the V has been changed into T or A;
at position 5 the S has been changed into T;
at position 6 the G has been changed into D or E; and/or
at position 9 the T has been changed into S, A or P,
and in which
(iii) CDR3 is chosen from the group consisting of
(a) SEQ ID NO: 123; and
(b) amino acid sequences that have 1, or 2 amino acid difference(s) with SEQ ID NO: 123, wherein
at position 2 the I has been changed into T;
at position 9 the I has been changed into V; and/or
at position 10 the A has been changed into P.

In another aspect, the present invention provides a polypeptide as described herein, in which: CDR1 is represented by SEQ ID NO: 81, CDR2 is represented by SEQ ID NO: 101, and CDR3 is represented by SEQ ID NO: 123. Preferably the polypeptide is selected from any of SEQ ID NOs: 1 to 50.

Immunoglobulin single variable domains belonging to cluster B are represented by polypeptides according in which:
(i) CDR1 is chosen from the group consisting of:
(a) SEQ ID NOs: 88; and
(b) amino acid sequences that have 4, 3, 2, or 1 amino acid(s) difference with the amino acid sequence of SEQ ID NO: 88, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
(c) SEQ ID NOs: 110; and
(d) amino acid sequences that have 4, 3, 2, or 1 amino acid(s) difference with the amino acid sequence of SEQ ID NO: 110, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
(e) SEQ ID NOs: 128; and
(f) amino acid sequences that have 4, 3, 2, or 1 amino acid(s) difference with the amino acid sequence of SEQ ID NO: 128, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster B, CDR1 is SEQ ID NO: 88.
In another aspect, in the polypeptides belonging to cluster B, CDR2 is SEQ ID NO: 110.
In another aspect, in the polypeptides belonging to cluster B, CDR3 is SEQ ID NO: 128.
In another aspect, the invention relates to a polypeptide in which: CDR1 is represented by SEQ ID NO: 88, CDR2 is represented by SEQ ID NO: 110, and CDR3 is represented by SEQ ID NO: 128. Preferably the polypeptide is SEQ ID NOs: 51.

Immunoglobulin single variable domains belonging to cluster C are represented by polypeptides according in which:
(i) CDR1 is chosen from the group consisting of:
(a) SEQ ID NO: 90; and
(b) amino acid sequences that have 4, 3, 2, or 1 amino acid(s) difference with the amino acid sequence of SEQ ID NO: 90, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
(c) SEQ ID NOs: 112-113; and
(d) amino acid sequences that have 4, 3, 2, or 1 amino acid(s) difference with the amino acid sequence of SEQ ID NO: 112, provided that the polypeptide comprising the CDR2 with 4, 3, 2, or 1 amino acid(s)

difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
 (e) SEQ ID NO: 130; and
 (f) amino acid sequences that have 4, 3, 2, or 1 amino acid(s) difference with the amino acid sequence of SEQ ID NO: 130, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster C, CDR1 is SEQ ID NO: 90.

In another aspect, in the polypeptides belonging to cluster C, CDR2 is chosen from the group consisting of
(a) SEQ ID NO: 112; and
(b) amino acid sequence that has 1 amino acid difference with SEQ ID NO: 112, wherein
 at position 2 the V has been changed into A.

In another aspect, in the polypeptides belonging to cluster C, CDR3 is SEQ ID NO: 130.

Accordingly, the present invention relates to an ISV or polypeptide that specifically binds CD3 and that comprises or essentially consists of 4 framework regions (FR1 to FR4, respectively) and 3 complementarity determining regions (CDR1 to CDR3, respectively), in which:
(i) CDR1 is SEQ ID NO: 90; and
and in which
(ii) CDR2 is chosen from the group consisting of
 (a) SEQ ID NO: 112; and
 (b) amino acid sequences that have 1 amino acid difference with SEQ ID NO: 112, wherein
  at position 2 the V has been changed into A, and in which
(iii) CDR3 is SEQ ID NO: 130.

In another aspect, the invention relates to a polypeptide in which: CDR1 is represented by SEQ ID NO: 90, CDR2 is represented by SEQ ID NO: 112, and CDR3 is represented by SEQ ID NO: 130. Preferably the polypeptide is selected from any of SEQ ID NOs: 53-56.

Immunoglobulin single variable domains belonging to cluster D are represented by polypeptides according in which:
(i) CDR1 is chosen from the group consisting of:
 (a) SEQ ID NOs: 89; and
 (b) amino acid sequences that have 4, 3, 2, or 1 amino acid(s) difference with the amino acid sequence of SEQ ID NO: 89, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
 (c) SEQ ID NOs: 111; and
 (d) amino acid sequences that have 4, 3, 2, or 1 amino acid(s) difference with the amino acid sequence of SEQ ID NO: 111, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
 (e) SEQ ID NOs: 129; and
 (f) amino acid sequences that have 4, 3, 2, or 1 amino acid(s) difference with the amino acid sequence of SEQ ID NO: 129, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster D, CDR1 is SEQ ID NO: 89.

In another aspect, in the polypeptides belonging to cluster D, CDR2 is SEQ ID NO: 111.

In another aspect, in the polypeptides belonging to cluster D, CDR3 is SEQ ID NO: 129.

In another aspect, the invention relates to a polypeptide in which: CDR1 is represented by SEQ ID NO: 89, CDR2 is represented by SEQ ID NO: 111, and CDR3 is represented by SEQ ID NO: 129. Preferably the polypeptide is SEQ ID NOs: 52.

Immunoglobulin single variable domains belonging to cluster E are represented by polypeptides according in which:
(i) CDR1 is chosen from the group consisting of:
 (a) SEQ ID NOs: 91-93; and
 (b) amino acid sequences that have 4, 3, 2, or 1 amino acid(s) difference with the amino acid sequence of SEQ ID NO: 91, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
 (c) SEQ ID NOs: 114-117; and
 (d) amino acid sequences that have 4, 3, 2, or 1 amino acid(s) difference with the amino acid sequence of SEQ ID NO: 114, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
 (e) SEQ ID NOs: 131-133; and
 (f) amino acid sequences that have 4, 3, 2, or 1 amino acid(s) difference with the amino acid sequence of SEQ ID NO: 131, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster E, CDR1 is chosen from the group consisting of
(a) SEQ ID NO: 91; and
(b) amino acid sequences that have 1, 2 or 3 amino acid(s) difference with SEQ ID NO: 91, wherein
 at position 6 the R has been changed into N or T;
 at position 7 the N has been changed into H; and/or
 at position 8 the M has been changed into T.

In another aspect, in the polypeptides belonging to cluster E, CDR2 is chosen from the group consisting of
(a) SEQ ID NO: 114; and
(b) amino acid sequences that have 1, 2 or 3 amino acid(s) difference with SEQ ID NO: 114, wherein
at position 1 the R has been changed into Q;
at position 3 the T has been changed into S; and/or
at position 7 the D has been changed into A or K.

In another aspect, in the polypeptides belonging to cluster E, CDR3 is chosen from the group consisting of
(a) SEQ ID NO: 131; and
(b) amino acid sequences that have 1 amino acid difference with SEQ ID NO: 131, wherein
at position 2 the S has been changed into R; and/or
at position 6 the S has been changed into V.

Accordingly, the present invention relates to an ISV or polypeptide that specifically binds CD3 and that comprises or essentially consists of 4 framework regions (FR1 to FR4, respectively) and 3 complementarity determining regions (CDR1 to CDR3, respectively), in which:
(i) CDR1 is chosen from the group consisting of
(a) SEQ ID NO: 91; and
(b) amino acid sequences that have 1, 2 or 3 amino acid difference(s) with SEQ ID NO: 91, wherein
at position 6 the R has been changed into N or T;
at position 7 the N has been changed into H; and/or
at position 8 the M has been changed into T,
and in which
(ii) CDR2 is chosen from the group consisting of
(a) SEQ ID NO: 114; and
(b) amino acid sequences that have 1, 2 or 3 amino acid difference(s) with SEQ ID NO: 114, wherein
at position 1 the R has been changed into Q;
at position 3 the T has been changed into S; and/or
at position 7 the D has been changed into A or K,
and in which
(iii) CDR3 is chosen from the group consisting of
(a) SEQ ID NO: 131; and
(b) amino acid sequences that have 1 amino acid difference with SEQ ID NO: 131, wherein
at position 2 the S has been changed into R; and/or
at position 6 the S has been changed into V.

In another aspect, the present invention provides a polypeptide as described herein, in which: CDR1 is represented by SEQ ID NO: 91, CDR2 is represented by SEQ ID NO: 114, and CDR3 is represented by SEQ ID NO: 131. Preferably the polypeptide is selected from any of SEQ ID NOs: 57-65.

Immunoglobulin single variable domains belonging to cluster F are represented by polypeptides according in which:
(i) CDR1 is chosen from the group consisting of:
(a) SEQ ID NOs: 94-100; and
(b) amino acid sequences that have 4, 3, 2, or 1 amino acid(s) difference with the amino acid sequence of SEQ ID NO: 94, provided that the polypeptide comprising the CDR1 with 4, 3, 2, or 1 amino acid(s) difference binds CD3 with about the same or a higher affinity compared to the binding by the polypeptide comprising the CDR1 without the 4, 3, 2, or 1 amino acid(s) difference, said affinity as measured by surface plasmon resonance; and/or
(ii) CDR2 is chosen from the group consisting of:
(c) SEQ ID NOs: 118-122; and
(d) amino acid sequences that have 4, 3, 2, or 1 amino acid(s) difference with the amino acid sequence of SEQ ID NO: 118, provided that the polypeptide comprising the CDR2 with 4, 3, 2, or 1 amino acid(s) difference binds CD3 with about the same or a higher affinity compared to the binding by the polypeptide comprising the CDR2 without the 4, 3, 2, or 1 amino acid(s) difference, said affinity as measured by surface plasmon resonance; and/or
(iii) CDR3 is chosen from the group consisting of:
(e) SEQ ID NOs: 134-143; and
(f) amino acid sequences that have 4, 3, 2, or 1 amino acid(s) difference with the amino acid sequence of SEQ ID NO: 134, provided that the polypeptide comprising the CDR3 with 4, 3, 2, or 1 amino acid(s) difference binds CD3 with about the same or a higher affinity compared to the binding by the polypeptide comprising the CDR3 without the 4, 3, 2, or 1 amino acid(s) difference, said affinity as measured by surface plasmon resonance.

In another aspect, in the polypeptides belonging to cluster F, CDR1 is chosen from the group consisting of
(a) SEQ ID NO: 94; and
(b) amino acid sequences that have 1, 2, 3 or 4 amino acid(s) difference with SEQ ID NO: 94, wherein
at position 3 the S has been changed into T, A or G;
at position 5 the N has been changed into S;
at position 6 the M has been changed into T or A; and/or
at position 9 the L has been changed into M.

In another aspect, in the polypeptides belonging to cluster F, CDR2 is chosen from the group consisting of
(a) SEQ ID NO: 118; and
(b) amino acid sequences that have 1, 2 or 3 amino acid(s) difference with SEQ ID NO: 118, wherein
at position 2 the H has been changed into V;
at position 5 the S has been changed into H or A;
at position 8 the N has been changed into S; and/or
at position 10 the Y has been changed into F.

In another aspect, in the polypeptides belonging to cluster F, CDR3 is chosen from the group consisting of
(a) SEQ ID NO: 134; and
(b) amino acid sequences that have 1, 2, 3, 4 or 5 amino acid(s) difference with SEQ ID NO: 134, wherein
at position 6 the A has been changed into S or D;
at position 7 the F has been changed into Y or A;
at position 8 the R has been changed into H;
at position 9 the S has been changed into A;
at position 11 the G has been changed into D, T, N, S, K or R; and/or
at position 14 the V has been changed into I.

Accordingly, the present invention relates to an ISV or polypeptide that specifically binds CD3 and that comprises or essentially consists of 4 framework regions (FR1 to FR4, respectively) and 3 complementarity determining regions (CDR1 to CDR3, respectively), in which:
(i) CDR1 is chosen from the group consisting of
(a) SEQ ID NO: 94; and
(b) amino acid sequences that have 1, 2, 3 or 4 amino acid difference(s) with SEQ ID NO: 94, wherein
at position 3 the S has been changed into T, A or G;
at position 5 the N has been changed into S;
at position 6 the M has been changed into T or A; and/or
at position 9 the L has been changed into M,
and in which
(ii) CDR2 is chosen from the group consisting of
(a) SEQ ID NO: 118; and
(b) amino acid sequences that have 1, 2 or 3 amino acid difference(s) with SEQ ID NO: 118, wherein
at position 2 the H has been changed into V;
at position 5 the S has been changed into H or A;

at position 8 the N has been changed into S; and/or at position 10 the Y has been changed into F, and in which (iii) CDR3 is chosen from the group consisting of
  (a) SEQ ID NO: 134; and
  (b) amino acid sequences that have 1, 2, 3, 4 or 5 amino acid difference(s) with SEQ ID NO: 134, wherein
    at position 6 the A has been changed into S or D;
    at position 7 the F has been changed into Y or A;
    at position 8 the R has been changed into H;
    at position 9 the S has been changed into A;
    at position 11 the G has been changed into D, T, N, S, K or R; and/or
    at position 14 the V has been changed into I.

In another aspect, the present invention provides a polypeptide as described herein, in which: CDR1 is represented by SEQ ID NO: 94, CDR2 is represented by SEQ ID NO: 118, and CDR3 is represented by SEQ ID NO: 134. Preferably the polypeptide is selected from any of SEQ ID NOs: 66-80.

In a further aspect, the invention relates to polypeptides that cross-block the binding to CD3 by at least one of the ISVs or polypeptides belonging to Cluster A, B, C, D, E or F.

Accordingly, the present invention relates to polypeptides that cross-block the binding to CD3 by at least one of the ISVs or polypeptides with SEQ ID NOs: 1-50.

Accordingly, the present invention relates to polypeptides that cross-block the binding to CD3 by the ISV or polypeptide with SEQ ID NO: 51.

Accordingly, the present invention relates to polypeptides that cross-block the binding to CD3 by at least one of the ISVs or polypeptides with SEQ ID NOs: 53-56.

Accordingly, the present invention relates to polypeptides that cross-block the binding to CD3 by the ISV or polypeptide with SEQ ID NO: 52.

Accordingly, the present invention relates to polypeptides that cross-block the binding to CD3 by at least one of the ISVs or polypeptides with SEQ ID NOs: 57-65.

Accordingly, the present invention relates to polypeptides that cross-block the binding to CD3 by at least one of the ISVs or polypeptides with SEQ ID NOs: 66-80.

In a further aspect, the invention relates to polypeptides that are cross-blocked from binding to CD3 by at least one of the ISVs or polypeptides belonging to Cluster A, B, C, D, E or F.

Accordingly, the present invention relates to polypeptides that are cross-blocked from binding to CD3 by at least one of the ISVs or polypeptides belonging to SEQ ID NOs: 1-50.

Accordingly, the present invention relates to polypeptides that are cross-blocked from binding to CD3 by the ISV or polypeptide with SEQ ID NO: 51.

Accordingly, the present invention relates to polypeptides that are cross-blocked from binding to CD3 by at least one of the ISVs or polypeptides belonging to SEQ ID NOs: 53-56.

Accordingly, the present invention relates to polypeptides that are cross-blocked from binding to CD3 by the ISV or polypeptide with SEQ ID NO: 52.

Accordingly, the present invention relates to polypeptides that are cross-blocked from binding to CD3 by at least one of the ISVs or polypeptides belonging to SEQ ID NOs: 57-65.

Accordingly, the present invention relates to polypeptides that are cross-blocked from binding to CD3 by at least one of the ISVs or polypeptides belonging to SEQ ID NOs: 66-80.

The invention further relates to compounds or constructs, and in particular proteins or polypeptides that comprise or essentially consist of one or more ISVs or polypeptides of the invention, and optionally further comprise one or more other groups, residues, moieties or binding units. As will become clear to the skilled person from the further disclosure herein, such further groups, residues, moieties, binding units or amino acid sequences may or may not provide further functionality to the polypeptide of the invention (and/or to the compound or construct in which it is present) and may or may not modify the properties of the polypeptide of the invention.

In a specific, but non-limiting aspect of the invention, which will be further described herein, the ISVs and polypeptides of the invention may have an increased half-life in serum (as further described herein) compared to the immunoglobulin single variable domain or polypeptide from which they have been derived. For example, an immunoglobulin single variable domain or polypeptide of the invention may be linked (chemically or otherwise) to one or more groups or moieties that extend the half-life (such as PEG), so as to provide a derivative of the ISV or polypeptide of the invention with increased half-life.

In a specific aspect of the invention, a compound or construct of the invention or a polypeptide of the invention may have an increased half-life, compared to the corresponding ISV or polypeptide of the invention. Some preferred, but non-limiting examples of such compounds, constructs and polypeptides will become clear to the skilled person based on the further disclosure herein, and for example comprise immunoglobulin single variable domains or polypeptides of the invention that have been chemically modified to increase the half-life thereof (for example, by means of pegylation); immunoglobulin single variable domains or polypeptides of the invention that comprise at least one additional binding site for binding to a serum protein (such as serum albumin); or constructs or polypeptides of the invention which comprise at least ISV or polypeptide of the invention that is linked to at least one moiety (and in particular at least one amino acid sequence) which increases the half-life of the ISV or polypeptide of the invention. Examples of ISVs or polypeptides of the invention which comprise such half-life extending moieties or immunoglobulin single variable domains will become clear to the skilled person based on the further disclosure herein; and for example include, without limitation, polypeptides in which the one or more immunoglobulin single variable domains or polypeptide of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, "dAb" 's, immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); ISVs or polypeptides in which an ISV or polypeptide of the invention is linked to an Fc portion (such as a human Fc) or a suitable part or fragment thereof; or polypeptides in which the one or more immunoglobulin single variable domains or polypeptide of the invention are suitable linked to one or more small proteins or peptides that can bind to serum proteins, such as, without limitation, the proteins and peptides described in WO 91/01743, WO 01/45746, WO 02/076489, WO 08/068280, WO 09/127691 and WO 11/095545.

Generally, the compounds, constructs or polypeptides of the invention with increased half-life preferably have a half-life that is at least 1.5 times, preferably at least 2 times, such as at least 5 times, for example at least 10 times or more than 20 times, greater than the half-life of the corresponding ISV or polypeptide of the invention per se. For example, the compounds, constructs or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding ISV or polypeptide of the invention per se.

In a preferred, but non-limiting aspect of the invention, such compounds, constructs or polypeptides of the invention have a serum half-life e.g. in humans that is increased with more than 1 hours, preferably more than 2 hours, more preferably more than 6 hours, such as more than 12 hours, or even more than 24, 48 or 72 hours, compared to the corresponding ISV or polypeptide of the invention per se.

In another preferred, but non-limiting aspect of the invention, such compounds, constructs or polypeptides of the invention exhibit a serum half-life in human of at least about 12 hours, preferably at least 24 hours, more preferably at least 48 hours, even more preferably at least 72 hours or more.

For example, compounds, constructs or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In the present invention it was demonstrated that the inclusion of the albumin targeting binding unit in the construct as such did not have an essential impact on the obtained potency or efficacy. Although a minor loss of efficacy/potency was observed in the presence of HSA, the half-life extended CD3 multispecific polypeptides were still potent in tumour cell killing. Albumin-based drug delivery has been demonstrated to be useful for achieving improved cancer therapy, largely due to its passive target toward tumour via the enhanced permeability and retention effect and the increased demand for albumin by tumour cells as source of energy and amino acids. However, albumin lacks not only the active mechanism to overcome the cell membrane barrier, but also the ability to penetrate into tumour tissues (Qianqian Guo et al. Polym. Chem., 2013, 4, 4584-4587).

In a particularly preferred but non-limiting aspect of the invention, the invention provides a polypeptide of the invention comprising a first and a second immunoglobulin single variable domain (ISV); and further comprising one or more (preferably one) serum albumin binding immunoglobulin single variable domain as described herein, e.g. the serum albumin binding immunoglobulin single variable domain referred to as Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG (Table B-3).

TABLE B-3

Immunoglobulin single variable domains for use in HLE of the ISVs and polypeptides of the invention

| | |
|---|---|
| Alb8 | EVQLVESGGGLVQPGNSLRLSCAASGFTFSSFGMSWVRQAPGKGLEWVSSISGSGSDTLYADSV KGRFTISRDNAKTTLYLQMNSLRPEDTAVYYCTIGGSLSRSSQGTLVTVSS |
| Alb23 | EVQLLESGGGLVQPGGSLRLSCAASGFTFRSFGMSWVRQAPGKGPEWVSSISGSGSDTLYADSV KGRFTISRDNSKNTLYLQMNSLRPEDTAVYYCTIGGSLSRSSQGTLVTVSS |
| Alb129 | EVQLVESGGGVVQPGNSLRLSCAASGFTFSSFGMSWVRQAPGKGLEWVSSISGSGSDTLYADSV KGRFTISRDNAKTTLYLQMNSLRPEDTATYYCTIGGSLSRSSQGTLVTVSSA |
| Alb132 | EVQLVESGGGVVQPGGSLRLSCAASGFTFRSFGMSWVRQAPGKGPEWVSSISGSGSDTLYADS VKGRFTISRDNSKNTLYLQMNSLRPEDTATYYCTIGGSLSRSSQGTLVTVSSA |
| Alb11 | EVQLVESGGGLVQPGNSLRLSCAASGFTFSSFGMSWVRQAPGKGLEWVSSISGSGSDTLYADSV KGRFTISRDNAKTTLYLQMNSLRPEDTAVYYCTIGGSLSRSSQGTLVTVSS |
| Alb11 (S112K)-A | EVQLVESGGGLVQPGNSLRLSCAASGFTFSSFGMSWVRQAPGKGLEWVSSISGSGSDTLYADSV KGRFTISRDNAKTTLYLQMNSLRPEDTAVYYCTIGGSLSRSSQGTLVKVSSA |
| Alb82 | EVQLVESGGGVVQPGNSLRLSCAASGFTFSSFGMSWVRQAPGKGLEWVSSISGSGSDTLYADSV KGRFTISRDNAKTTLYLQMNSLRPEDTALYYCTIGGSLSRSSQGTLVTVSS |
| Alb82-A | EVQLVESGGGVVQPGNSLRLSCAASGFTFSSFGMSWVRQAPGKGLEWVSSISGSGSDTLYADSV KGRFTISRDNAKTTLYLQMNSLRPEDTALYYCTIGGSLSRSSQGTLVTVSSA |
| Alb82-AA | EVQLVESGGGVVQPGNSLRLSCAASGFTFSSFGMSWVRQAPGKGLEWVSSISGSGSDTLYADSV KGRFTISRDNAKTTLYLQMNSLRPEDTALYYCTIGGSLSRSSQGTLVTVSSAA |
| Alb82-AAA | EVQLVESGGGVVQPGNSLRLSCAASGFTFSSFGMSWVRQAPGKGLEWVSSISGSGSDTLYADSV KGRFTISRDNAKTTLYLQMNSLRPEDTALYYCTIGGSLSRSSQGTLVTVSSAAA |

TABLE B-3-continued

Immunoglobulin single variable domains for use in HLE of the ISVs and polypeptides of the invention

| | |
|---|---|
| Alb82-G | EVQLVESGGGVVQPGNSLRLSCAASGFTFSSFGMSWVRQAPGKGLEWVSSISGSGSDTLYADSV<br>KGRFTISRDNAKTTLYLQMNSLRPEDTALYYCTIGGSLSRSSQGTLVTVSSG |
| Alb82-GG | EVQLVESGGGVVQPGNSLRLSCAASGFTFSSFGMSWVRQAPGKGLEWVSSISGSGSDTLYADSV<br>KGRFTISRDNAKTTLYLQMNSLRPEDTALYYCTIGGSLSRSSQGTLVTVSSGG |
| Alb82-GGG | EVQLVESGGGVVQPGNSLRLSCAASGFTFSSFGMSWVRQAPGKGLEWVSSISGSGSDTLYADSV<br>KGRFTISRDNAKTTLYLQMNSLRPEDTALYYCTIGGSLSRSSQGTLVTVSSGGG |

Accordingly, the present invention relates to a polypeptide as described herein, further comprising a serum protein binding moiety.

The present invention relates to a polypeptide as described herein, wherein said serum protein binding moiety binds serum albumin.

The present invention relates to a polypeptide as described herein, wherein said serum protein binding moiety is an immunoglobulin single variable domain binding serum albumin.

The present invention relates to a polypeptide as described herein, wherein said ISV binding serum albumin essentially consists of 4 framework regions (FR1 to FR4, respectively) and 3 complementarity determining regions (CDR1 to CDR3 respectively), in which CDR1 is SFGMS (SEQ ID NO: 373), CDR2 is SISGSGSDTLYADSVKG (SEQ ID NO: 374), and in which CDR3 is GGSLSR (SEQ ID NO: 375), CDR determined according to Kabat definition; and/or in which CDR1 is GFTFSSFGMS (SEQ ID NO: 376) or GFTFRSFGMS (SEQ ID NO: 377), CDR2 is SISGSGSDTL (SEQ ID NO: 378) and CDR3 is GGSLSR (SEQ ID NO: 375), CDR determined according to Kontermann 2010.

The present invention relates to a polypeptide as described herein, wherein said ISV binding serum albumin comprises Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG (Table B-3).

In the polypeptides of the invention, the two or more building blocks, ISVs or Nanobodies and the optionally one or more polypeptides, one or more other groups, drugs, agents, residues, moieties or binding units may be directly linked to each other (as for example described in WO 99/23221) and/or may be linked to each other via one or more suitable spacers or linkers, or any combination thereof.

Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISV or Nanobody by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4ser)_3$ or $(gly_3ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table B-4.

TABLE B-4

| | Linkers |
|---|---|
| 5GS | GGGGS |
| 7GS | SGGSGGS |
| 9GS | GGGGSGGGS |
| 10GS | GGGGSGGGGS |
| 15GS | GGGGSGGGGSGGGGS |
| 18GS | GGGGSGGGSGGGGGGGS |
| 20GS | GGGGSGGGGSGGGGSGGGGS |
| 25GS | GGGGSGGGGSGGGGSGGGGSGGGGS |
| 30GS | GGGGSGGGGSGGGGSGGGGSGGGGSGGGGS |
| 35GS | GGGGSGGGGSGGGGSGGGGSGGGGSGGGGSGGGGS |
| Poly-A | AAA |

Some other particularly preferred linkers are poly-alanine (such as AAA), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for CD3, or for one or more of the other antigens. Based on the disclosure herein, the skilled person will be able to determine the optimal linker(s) for use in a specific polypeptide of the invention, optionally after some limited routine experiments.

For example, in multivalent polypeptides of the invention that comprise building blocks, ISVs or Nanobodies directed against a first and second target, the length and flexibility of the linker are preferably such that it allows each building block, ISV or Nanobody of the invention present in the polypeptide to bind to its cognate target, e.g. the antigenic determinant on each of the targets. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the ISV, Nanobodies, or polypeptide of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thereto. For example, when a polypeptide of the invention comprises three of more building blocks, ISV or Nanobodies, it is possible to link them by use of a linker with three or more "arms", which each "arm" being linked to a building block, ISV or Nanobody, so as to provide a "star-shaped" construct. It is also possible, although usually less preferred, to use circular constructs.

Accordingly, the present invention relates to a polypeptide as described herein, wherein said first ISV and said second ISV and possibly said third ISV and/or said ISV binding serum albumin are directly linked to each other or are linked via a linker.

The present invention relates to a polypeptide as described herein, wherein said linker is chosen from the group consisting of linkers of 5GS, 7GS, 9GS, 10GS, 15GS, 18GS, 20GS, 25GS, 30GS and 35GS.

The present invention relates to a polypeptide as described herein, wherein said serum protein binding moiety is a non-antibody based polypeptide (e.g. PEG).

The invention also relates to methods for preparing the ISVs, polypeptides and constructs described herein. The ISVs, polypeptides and constructs of the invention can be prepared in a manner known per se, as will be clear to the skilled person from the further description herein. For example, the ISVs, polypeptides and constructs of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and constructs include the methods and techniques described herein.

The method for producing an ISV, polypeptide or protein construct of the invention may comprise the following steps:
the expression, in a suitable host cell or host organism (also referred to herein as a "host of the invention") or in another suitable expression system of a nucleic acid that encodes said IVS, polypeptide or protein construct of the invention,
optionally followed by:
isolating and/or purifying the ISVs, polypeptide or protein construct of the invention thus obtained.

In particular, such a method may comprise the steps of:
cultivating and/or maintaining a host of the invention under conditions that are such that said host of the invention expresses and/or produces at least one ISVs, polypeptide or protein construct of the invention;
optionally followed by:
isolating and/or purifying the ISVs, polypeptide or protein construct of the invention thus obtained.

Accordingly, the present invention also relates to a nucleic acid or nucleotide sequence that encodes an ISV, polypeptide or protein construct of the invention (also referred to as "nucleic acid of the invention" or "nucleotide sequence of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the polypeptides or protein constructs of the invention given herein, and/or can be isolated from a suitable natural source. Also, as will be clear to the skilled person, to prepare a nucleic acid of the invention, also several nucleotide sequences, such as at least one nucleotide sequence encoding an immunoglobulin single variable domain of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned herein, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
 a) at least one nucleic acid of the invention; operably connected to
 b) one or more regulatory elements, such as a promoter and optionally a suitable terminator;
and optionally also
 c) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

The nucleic acids of the invention and/or the genetic constructs of the invention may be used to transform a host cell or host organism, i.e. for expression and/or production of the polypeptide or protein construct of the invention. The host is preferably a non-human host. Suitable hosts or host cells will be clear to the skilled person, and may for example be any suitable fungal, prokaryotic or eukaryotic cell or cell line or any suitable fungal, prokaryotic or eukaryotic organism, for example:

a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;

a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;

a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;

an amphibian cell or cell line, such as *Xenopus* oocytes;

an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;

a plant or plant cell, for example in tobacco plants; and/or a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. 1998 (Res. Immunol. 149: 589-99); Riechmann and Muyldermans 1999 (J. Immunol. Met. 231: 25-38); van der Linden 2000 (J. Biotechnol. 80: 261-70); Joosten et al. 2003 (Microb. Cell Fact. 2: 1); Joosten et al. 2005 (Appl. Microbiol. Biotechnol. 66: 384-92); and the further references cited herein.

For expression of the ISVs, polypeptides or constructs in a cell, they may also be expressed as so-called "intrabodies", as for example described in WO 94/02610, WO 95/22618 and U.S. Pat. No. 7,004,940; WO 03/014960; in Cattaneo and Biocca 1997 (Intracellular Antibodies: Development and Applications. Landes and Springer-Verlag); and in Kontermann 2004 (Methods 34: 163-170).

According to one preferred, but non-limiting embodiment of the invention, the ISV, polypeptide or protein construct of the invention is produced in a bacterial cell, in particular a bacterial cell suitable for large scale pharmaceutical production, such as cells of the strains mentioned above.

According to another preferred, but non-limiting embodiment of the invention, the ISV, polypeptide or protein construct of the invention is produced in a yeast cell, in particular a yeast cell suitable for large scale pharmaceutical production, such as cells of the species mentioned above.

According to yet another preferred, but non-limiting embodiment of the invention, the ISV, polypeptide or construct of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the polypeptide of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an ISV, polypeptide or protein construct of the invention (and in case of a host organism: in at least one cell, part, tissue or organ thereof). The invention also includes further generations, progeny and/or offspring of the host cell or host organism of the invention, for instance obtained by cell division or by sexual or asexual reproduction.

Accordingly, in another aspect, the invention relates to a host or host cell that expresses (or that under suitable circumstances is capable of expressing) an ISV, polypeptide or protein construct of the invention; and/or that contains a nucleic acid encoding the same. Some preferred but non-limiting examples of such hosts or host cells can be as generally described in WO 04/041867, WO 04/041865 or WO 09/068627. For example, ISVs, polypeptides and protein constructs of the invention may with advantage be expressed, produced or manufactured in a yeast strain, such as a strain of *Pichia pastoris*. Reference is also made to WO 04/25591, WO 10/125187, WO 11/003622, and WO 12/056000 which also describes the expression/production in *Pichia* and other hosts/host cells of immunoglobulin single variable domains and polypeptides comprising the same.

To produce/obtain expression of the ISVs, polypeptides or protein constructs of the invention, the transformed host cell or transformed host organism may generally be kept, maintained and/or cultured under conditions such that the (desired) ISV, polypeptide or protein construct of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the ISVs, polypeptides or protein constructs of the invention may be expressed in a constitutive manner, in a transient manner, or only when suitably induced.

It will also be clear to the skilled person that the ISV, polypeptide or protein construct of the invention may (first) be generated in an immature form (as mentioned above), which may then be subjected to post-translational modification, depending on the host cell/host organism used. Also, the ISV, polypeptide or protein construct of the invention may be glycosylated, again depending on the host cell/host organism used.

The ISV, polypeptide or protein construct of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide or construct of the invention) and/or preparative immunological techniques (i.e. using antibodies against the amino acid sequence to be isolated).

The constructs of the invention can generally be prepared by a method which comprises at least the step of suitably linking ISVs or polypeptides of the invention to the one or more further groups, residues, moieties or binding units, optionally via the one or more suitable linkers, so as to provide the constructs of the invention. The ISVs, polypeptides and constructs of the invention can then further be modified, and in particular by chemical and/or biological (e.g. enzymatical) modification, of one or more of the amino acid residues that form the polypeptides or constructs of the invention, to obtain derivatives of the polypeptides or constructs of the invention.

The invention also relates to a pharmaceutical composition comprising the ISV, polypeptide, compound or construct of the invention.

In the above methods, the amino acid sequences, ISVs, Nanobodies, polypeptides, compounds or constructs of the invention and/or the compositions comprising the same can be administered in any suitable manner, depending on the specific pharmaceutical formulation or composition to be used. Thus, the amino acid sequences, ISVs, Nanobodies, polypeptides, compounds or constructs of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

As used herein, the term "therapeutic agent" refers to any agent that can be used in the treatment and/or management of a hyperproliferative cell disorder, e.g., cancer, or one or more symptoms thereof. In certain embodiments, the term "therapeutic agent" refers to a multispecific polypeptide of the invention. Preferably, a therapeutic agent is an agent which is known to be useful for, or has been or is currently being used for the treatment, prevention and/or management of a hyperproliferative cell disorder, e.g., cancer, or one or more symptoms thereof.

As used herein, a "therapeutically effective amount" in the context of cancer refers to the amount of a therapy alone, or in combination with other therapies, that provides a therapeutic benefit in the treatment and/or management of cancers. In one aspect, a therapeutically effective amount refers to the amount of a therapy sufficient to destroy, modify, control or remove primary, regional or metastatic cancer tissue. In another aspect, a therapeutically effective amount refers to the amount of a therapy sufficient to reduce the symptoms of a cancer. In another aspect, a therapeutically effective amount refers to the amount of a therapy sufficient to delay or minimize the spread of cancer. In a specific embodiment, a therapeutically effective amount of a therapy is an amount of a therapy sufficient to inhibit growth or proliferation of cancer cells, kill existing cancer cells (e.g., cause regression of the cancer), and/or prevent the spread of cancer cells to other tissues or areas (e.g., prevent metastasis). In another specific embodiment, a therapeutically effective amount of a therapy is the amount of a therapy sufficient to inhibit the growth of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% as measured by a standard method known in the art. Used in connection with an amount of a multispecific polypeptide of the invention, the term can encompass an amount that improves overall therapy, reduces or avoids unwanted effects, or enhances the therapeutic efficacy of or synergies with another therapy. In one embodiment, a therapeutically effective amount of a therapy reduces or avoids unwanted effects, or enhances the therapeutic efficacy of or synergies with another therapy by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control (e.g., a negative control such as phosphate buffered saline) in an assay known in the art or described herein.

As used herein, a "therapeutically effective amount" in the context of a non-cancer hyperproliferative cell disorder refers to the amount of a therapy alone, or in combination with other therapies, that provides a therapeutic benefit in the treatment and/or management of said disorder. In one aspect, a therapeutically effective amount refers to the amount of a therapy sufficient to destroy, modify, control or remove cells affected by a non-cancer hyperproliferative cell disorder. In another aspect, a therapeutically effective amount refers to the amount of a therapy sufficient to reduce the symptoms of a non-cancer hyperproliferative cell disorder. In another aspect, a therapeutically effective amount refers to the amount of a therapy sufficient to delay or minimize the spread of the non-cancer hyperproliferative cell disorder. In a specific embodiment, a therapeutically effective amount of a therapy is an amount of a therapy sufficient to inhibit growth or proliferation of the non-cancer hyperproliferative cell disorder, kill existing non-cancer hyperproliferative cells (e.g., cause regression of the disorder). In another specific embodiment, a therapeutically effective amount of a therapy is the amount of a therapy sufficient to inhibit the growth of the non-cancer hyperproliferative cells by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% as measured by a standard method known in the art. Used in connection with an amount of a multispecific polypeptide of the invention, the term can encompass an amount that improves overall therapy, reduces or avoids unwanted effects, or enhances the therapeutic efficacy of or synergies with another therapy. In one embodiment, a therapeutically effective amount of a therapy reduces or avoids unwanted effects, or enhances the therapeutic efficacy of or synergies with another therapy by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control (e.g., a negative control such as phosphate buffered saline) in an assay known in the art.

As used herein, the term "therapy" refers to any protocol, method and/or agent that can be used in the treatment, prevention and/or management of a hyperproliferative cell disorder, e.g., cancer. In certain embodiments, the terms "therapies" and "therapy" refer to a biological therapy, supportive therapy, and/or other therapies useful in the treatment, prevention and/or management of a hyperproliferative cell disorder, e.g., cancer, or one or more symptoms thereof known to one of skill in the art such as medical personnel.

As used herein, the terms "treat", "treatment" and "treating" in the context of administering a therapy(ies) to a subject refer to the reduction or amelioration of the progression, severity, and/or duration of a disorder associated with a hyperproliferative cell disorder, e.g., cancer, and/or the amelioration of one or more symptoms thereof resulting from the administration of one or more therapies (including, but not limited to, the administration of one or more prophylactic or therapeutic agents). In specific embodiments, the terms "treat", "treatment" and "treating" in the context of administering (a) therapy(ies) to a subject refer to the reduction or amelioration of the progression, severity, and/or duration of a hyperproliferative cell disorder, e.g., cancer, refers to a reduction in cancer cells by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control (e.g., a negative control such as phosphate buffered saline). In other embodiments, the terms "treat", "treatment" and "treating" in the context of administering (a) therapy(ies) to a subject refer to the reduction or amelioration of the progression, severity, and/or duration of a hyperproliferative cell disorder, e.g., cancer, refers to no change in cancer cell number, a reduction in hospitalization time, a reduction in mortality, or an increase in survival time of the subject with cancer.

The amino acid sequences, ISVs, Nanobodies, polypeptides, compounds and/or constructs of the invention and/or the compositions comprising the same are administered according to a regime of treatment that is suitable for preventing and/or treating the hyperproliferative cell disorder, e.g., cancer, to be prevented or treated. The clinician will generally be able to determine a suitable treatment regimen, depending on factors such as the stage of the hyperproliferative cell disorder, e.g., cancer, to be treated, the severity of the hyperproliferative cell disorder, e.g., cancer, to be treated and/or the severity of the symptoms thereof, the specific amino acid sequence, ISV, Nanobody, polypeptide, compound and/or construct of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, ISVs, Nanobodies, polypeptides, compounds and/or constructs of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of a hyperproliferative cell disorder, e.g., cancer, mentioned herein and depending on the type of hyperproliferative cell disorder, e.g., cancer, and stage of the disease to be treated, the potency of the specific amino acid sequence, ISV, Nanobody, polypeptide, compound or construct of the invention to be used, the specific route of administration and the specific pharmaceutical formulation or composition used, the amino acid sequences, ISVs, Nanobodies, polypeptides, compounds or constructs of the invention will generally be administered in an amount between 1 gram and 0.01 milligram per kg body weight per day, preferably between 0.1 gram and 0.01 milligram per kg body weight per day, such as about 0.1, 1, 10, 100 or 1000 milligram per kg body weight per day, e.g. from 0.1 mg per kg to 25 mg per kg of the subject's body weight; either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgement. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, ISV, Nanobody, polypeptide, compound or construct of the invention will be used. It is however within the scope of the invention to use two or more amino acid sequences, ISVs, Nanobodies, polypeptides compounds and/or constructs of the invention in combination.

The ISVs, Nanobodies, amino acid sequences, polypeptides, compounds and/or constructs of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, ISVs, Nanobodies, polypeptides, compounds and/or constructs of the invention may be used in combination with other pharmaceutically active compounds or principles that are or can be used for the prevention and/or treatment of the hyperproliferative cell disorder, e.g., cancer, disease and/or disorder cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

In one aspect, the disclosure provides methods for the administration of immunoglobulin single variable domains and polypeptide constructs thereof comprising one or more immunoglobulin single variable domains, polypeptides, compounds and/or constructs. In some embodiments, the immunoglobulin single variable domain, polypeptide, compound and/or construct is administered as a pharmaceutical composition. The pharmaceutical composition, in addition to the immunoglobulin single variable domains and polypeptide constructs thereof includes a pharmaceutically-acceptable carrier.

As described in detail, the pharmaceutical compositions of the disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Formulations of the disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (e.g., immunoglobulin single variable domain or polypeptide constructs thereof) which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation comprises an excipient selected from the group consisting of cyclodextrins, liposomes, micelle forming agents, e.g., bile acids, and polymeric carriers, e.g., polyesters and polyanhydrides. In certain embodiments, an aforementioned formulation renders orally bioavailable an immunoglobulin single variable domain or polypeptide construct.

Methods of preparing these formulations or compositions include the step of bringing into association an immunoglobulin single variable domain or polypeptide construct with the carrier and, optionally, one or more accessory ingredients. In general, the formulations are prepared by uniformly and intimately bringing into association an immunoglobulin single variable domain or polypeptide construct with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an immunoglobulin single variable domain or polypeptide construct as an active ingredient. An immunoglobulin single variable domain or polypeptide construct invention may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents.

Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxy-propylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal or vaginal administration may be presented as a suppository, which may be prepared by mixing an immunoglobulin single variable domain or polypeptide construct with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations suitable for vaginal administration also include pessaries, tampons, creams, gels, pastes, foams or spray formulations containing such carriers as are known in the art to be appropriate.

Dosage forms for the topical or transdermal administration of an immunoglobulin single variable domain or polypeptide construct include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an immunoglobulin single variable domain or polypeptide construct to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this disclosure.

Pharmaceutical compositions suitable for parenteral administration comprise one or more an immunoglobulin single variable domains or polypeptide constructs in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers, which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly-(anhydrides). Depot injectable formulations are also prepared by entrapping the drug in liposomes or microemulsions, which are compatible with body tissue.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1 TCR αβ/CD3 Cell Lines

Transient and stable CHO-K1 (ATCC: CCL-61), HEK293H (Life technologies 11631-017), Llana (Fibroblast cells from llama Navel cord cells) cell lines with recombinant overexpression of all 6 chains of the full human T-cell Receptor complex were generated. For this, the coding sequences of the TCR alpha (α) and TCR beta (β) chain were cloned in a pcDNA3.1-derived vector, downstream of a CMV promotor and a 2A-like viral peptide sequence was inserted between both chains to induce ribosomal skipping during translation of the polyprotein. In the same vector, the coding sequences of the epsilon, delta, gamma and zeta chains of the CD3 complex were cloned downstream of an additional CMV promotor, also using 2A-like viral peptide sequences between the respective chains. In addition, a stable HEK293H clone with recombinant overexpression of the 4 chains of the human CD3 was generated as described above using a single gene vector.

The sequences for the human CD3 and the human TCRα/β constant domains were retrieved from UniProtKB (CD3 delta: P04234, CD3 gamma: P09693, CD3 epsilon: P07766, CD3 zeta: P20963, TCRα: P01848 and TCRβ: P01850). The sequences for the human TCRα/β variable domains were retrieved from crystal structure. (PDB codes: 2IAN, 2XN9 and 3TOE).

The cell surface expression of the human T cell receptor complex was confirmed using a functional mouse IgG2b anti-human TCR/β antibody, clone BW242/412 (Miltenyi 130-098-219) and a functional mouse IgG2a anti-CD3 PE labelled antibody, clone OKT-3 (eBioscience 12-0037). (FIG. 1)

Example 2 Immunization of Llamas with TCR/CD3, Cloning of the Heavy Chain-Only Antibody Fragment Repertoires and Preparation of Phage 2.1 Immunization After approval of the Ethical Committee (Faculty of Veterinary Medicine of the University of Ghent, Belgium—EC2004/044 en EC2005/053), Llamas (llama glama) were immunized with either human peripheral blood lymphocytes (PBMC) isolated by Ficol density centrifugation from a single buffy coat, or with mouse or human T- and NK cells enriched from PBMC by magnetic cell separation using biotin-conjugated antibodies. None of these immunization strategies resulted in specific immune response.

After approval of the Ethical Committee (CRIA, LA1400575, Belgium—EC2012 #1), 3 additional llamas were immunized with a pVAX1-human TCR(2IAN)/CD3 (described in Example 1) plasmid vector (Invitrogen, Carlsbad, CA, USA) and with a pVAX1-human TCR(2XN9)/CD3 (described in Example 1) plasmid vector (Invitrogen, Carlsbad, CA, USA) according to standard protocols. Two llamas received additionally 1 subcutaneous injection of primary human T cells. Human T Cells were collected from Buffy Coat blood, from healthy volunteers (Blood bank Gent) using RosetteSep (StemCell Technologies, #15061) followed by an enrichment on Ficoll-Paque™ PLUS (GE Healthcare #17-1440-03) according to manufactures instructions and stored in liquid nitrogen. After thawing, cells were washed, and re-suspended in D-PBS from Gibco and kept on ice prior to injection.

2.2 Cloning of the Heavy Chain-Only Antibody Fragment Repertoires and Preparation of Phages.

Per animal, blood samples were collected after the injection of one type of immunization antigen. From these blood samples, PBMC were prepared using Ficoll-Hypaque according to the manufacturer's instructions (Amersham Biosciences, Piscataway, NJ, USA). For each immunized llama, libraries were constructed by pooling the total RNA isolated from samples originating from a certain subset of the immunization schedule, i.e. after one type of immunization antigen.

In short, the PCR-amplified VHH repertoire was cloned via specific restriction sites into a vector designed to facilitate phage display of the VHH library. The vector was derived from pUC119. In frame with the VHH coding sequence, the vector encodes a C-terminal 3×FLAG and His6 tag. Phages were prepared according to standard protocols (see for example WO 04/041865, WO 04/041863, WO 04/062551, WO 05/044858 and other prior art and applications filed by Ablynx N.V. cited herein).

Example 3 Selection of TCR/CD3 Specific VHHs Via Phage Display

VHH repertoires obtained from all llamas and cloned as phage library were used in different selection strategies, applying a multiplicity of selection conditions. Variables included: i) the presentation form of the human TCR α/β/CD3 (on different cell backgrounds or on purified primary T cells (isolated as described in Example 2.1, ii) the antigen concentration, iii) the number of selection rounds. In brief cells were incubated for 2 h with the phage libraries followed by extensive washing; bound phages were eluted with trypsin (1 mg/mL) for 15 minutes. When trypsin was used for phage elution, the protease activity was immediately neutralized by applying 0.8 mM protease inhibitor ABSF. As control, selections with parental cell line or without antigen were performed in parallel.

Phage outputs were used to infect *E. coli* for analysis of individual VHH clones. Periplasmic extracts were prepared according to standard protocols (see for example WO 03/035694, WO 04/041865, WO 04/041863, WO 04/062551 and other prior art and applications filed by Ablynx N.V. cited herein).

Example 4 Screening 4.1 Screening for TCR/CD3 Binding Nanobodies in a Flow Cytometry Assay Periplasmic extracts were screened for cell expressed TCR/CD3 binding using human TCR/CD3 transfected CHO-K1 or HEK293H cells and the respective CHO-K1 or HEK293H reference cell line in a mixed cell line setup. To this end, a large batch of the reference cell lines were labelled with 8 μM PKH26 and frozen. $5 \times 10^4$ PKH labelled reference cells were mixed with $5 \times 10^4$ target cells and incubated with periplasmic extracts for 30 min at 4° C., and washed 3 times. Next, cells were incubated with 1 μg/ml monoclonal ANTI-FLAG® M2 antibody (Sigma-Aldrich, cat #F1804) for 30 min at 4° C., washed again, and incubated for 30 min at 4° C. with goat anti-mouse APC labelled antibody (Jackson Immunoresearch 115-135-164, 1:100). Samples were washed, resuspended in FACS Buffer (D-PBS from Gibco, with 10% FBS from Sigma and 0.05% sodium azide from Merck) and then analysed on a BD FACSArray. First a P1 population which represents more than 80% of the total cell population was selected based on FSC-SSC distribution. In this gate, 20,000 cells were counted during acquisition. Based on PKH26-SSC distribution, the PKH labelled parental population and the human TCR/CD3 unlabelled target population was selected. For these 2 populations the mean APC value was calculated.

4.2 Screening for TCR/CD3 Binding Nanobodies in a Human T Cell Activation Assay

After several attempts, it turned out that activation of purified human T cells by antibodies or Nanobodies according to standard protocols, i.e. coated onto a 96 well plate, was not sensitive enough (data not shown).

In order to assess activity, a different assay was developed, based on a bead coupled T cell activation. In short, goat anti-mouse IgG dynabeads (Life technologies #11033) were coated with mouse anti-flag IgG antibodies (Sigma F1804), (15 μg/1E7beads). After an incubation period of 2 h at 4° C., beads were washed and incubated with 80 μl periplasmic extract for 20 min at 4° C. while shaking. Non-coupled Nanobodies were washed away before adding the bead complex together with soluble mouse anti-CD28 antibody (Pelicluster CD28—Sanquin #M1650) to purified primary human T cells (isolated as described in Example 2.1). As control condition, non-stimulated human T cells were used. In brief, goat anti-mouse IgG dynabeads coupled to mouse anti-flag IgG were incubated in 80 μl periplasmic extract containing irrelevant Nanobodies. After removal of the non-coupled Nanobodies during a wash step the irrelevant Nanobody-bead complex was added to purified primary human T cells.

After an incubation of 24 h at 37° and 5% $CO_2$ the activation status of the human T cells was determined by measuring the CD69 expression level in flow cytometry using monoclonal mouse anti-human CD69PE (BD #557050).

Nanobodies which scored positive in the flow cytometric binding screen and the T cell activation assay were sequenced.

The sequence analysis resulted in the identification of 6 distinct clusters. Corresponding alignments are provided (Table A-1, Table A-2, Table A-3, Table A-4, Table A-5, Table A-6). Clustering was based on sequence similarities and differences in CDR2 and CDR3. Cluster A is the most prominent comprising 50 clones (SEQ ID NO:s 1-50), cluster B and cluster D are each represented by only 1 clone (SEQ ID NO: 51 and SEQ ID NO: 52, respectively), cluster C comprises 4 clones ((SEQ ID NO:s 53-56), cluster E comprises 9 clones (SEQ ID NO:s 57-65) and cluster F comprises 15 clones (SEQ ID NO:s 66-80).

Sequence variability of the CDRs was determined for the different clusters. For cluster A, the amino acid sequence of the CDRs of clone 117G03 was used as a reference, against which the CDRs of all other cluster A clones were compared. The sequence variability against 117G03 is depicted in the tables below.

| 117G03 Kabat numbering | 26 | 27 | 28 | 29 | 30 | 31 | 32 | 33 | 34 | 35 |
|---|---|---|---|---|---|---|---|---|---|---|
| absolute numbering | 1* | 2 | 3 | 4 | 5 | 6 | 7 | 8 | 9 | 10 |
| 117G03 sequence | G | R | T | Y | R | G | Y | S | M | G |
| Variations | R |  | A | F |  |  |  |  | G | A |

*in case position 1 is an R, then position 10 is also A

| 117G03 Kabat numbering | 50 | 51 | 52 | 52a | 53 | 54 | 55 | 56 | 57 | 58 |
|---|---|---|---|---|---|---|---|---|---|---|
| absolute numbering | 1 | 2 | 3* | 4 | 5 | 6 | 7 | 8 | 9 | 10 |
| 117G03 sequence | A | I | V | W | S | G | G | N | T | Y |
| variations |  |  | T |  | T | D |  |  | S |  |
| variations |  |  | A |  |  | E |  |  | A |  |
| variations |  |  |  |  |  |  |  |  | P |  |

*in case position 3 is an T, then position 6 is also E

| 117G03 Kabat numbering | 95 | 96 | 97 | 98 | 99 | 100 | 100a | 100b | 100c | 100d | 100e | 100f | 100g | 101 | 102 |
|---|---|---|---|---|---|---|---|---|---|---|---|---|---|---|---|
| absolute numbering | 1 | 2 | 3 | 4 | 5 | 6 | 7 | 8 | 9 | 10 | 11 | 12 | 13 | 14 | 15 |
| 117G03 sequence | K | I | R | P | Y | I | F | K | I | A | G | Q | Y | D | Y |
| variations |  | T |  |  |  |  |  |  |  | V | P |  |  |  |  |

For cluster B, the amino acid sequence of the CDRs of clone 60E11 is depicted in the tables below.

| 60E11 Kabat numbering | 26 | 27 | 28 | 29 | 30 | 31 | 32 | 33 | 34 | 35 |
|---|---|---|---|---|---|---|---|---|---|---|
| absolute numbering | 1 | 2 | 3 | 4 | 5 | 6 | 7 | 8 | 9 | 10 |
| 60E11 sequence | G | D | I | Y | K | S | F | D | M | G |

| 60E11 Kabat numbering | 95 | 96 | 97 | 98 | 99 | 95 | 101 | 102 |
|---|---|---|---|---|---|---|---|---|
| absolute numbering | 1 | 2 | 3 | 4 | 5 | 6 | 7 | 8 |
| 60E11 sequence | A | P | L | V | A | G | R | P |

For cluster C, the amino acid sequence of the CDRs of clone 33G03 was used as a reference, against which the CDRs of all other cluster C clones were compared. The sequence variability against 33G03 is depicted in the tables below.

| 33G03 Kabat numbering | 26 | 27 | 28 | 29 | 30 | 31 | 32 | 33 | 34 | 35 |
|---|---|---|---|---|---|---|---|---|---|---|
| absolute numbering | 1 | 2 | 3 | 4 | 5 | 6 | 7 | 8 | 9 | 10 |
| 33G03 sequence | G | R | T | F | S | T | N | P | M | G |

| 33G03 Kabat numbering | 50 | 51 | 52 | 52a | 53 | 54 | 55 | 56 | 57 | 58 |
|---|---|---|---|---|---|---|---|---|---|---|
| absolute numbering | 1 | 2 | 3 | 4 | 5 | 6 | 7 | 8 | 9 | 10 |
| 33G03 sequence | A | V | R | W | A | D | G | N | T | F |
| Variations |  |  | A |  |  |  |  |  |  |  |

| 60E11 Kabat numbering | 50 | 51 | 52 | 52a | 52b | 52c | 52d | 53 | 54 | 55 | 56 | 57 | 58 |
|---|---|---|---|---|---|---|---|---|---|---|---|---|---|
| absolute numbering | 1 | 2 | 3 | 4 | 5 | 6 | 7 | 8 | 9 | 10 | 11 | 12 | 13 |
| 60E11 sequence | V | I | G | S | R | G | N | N | R | G | R | T | N |

| 33G03 Kabat numbering | 95 | 96 | 97 | 98 | 99 | 100 | 100a | 100b | 100c | 100d | 100e | 100f | 100g | 101 | 102 |
|---|---|---|---|---|---|---|---|---|---|---|---|---|---|---|---|
| absolute numbering | 1 | 2 | 3 | 4 | 5 | 6 | 7 | 8 | 9 | 10 | 11 | 12 | 13 | 14 | 15 |
| 33G03 sequence | G | R | P | W | S | A | Y | H | S | P | A | E | Y | V | H |

For cluster D, the amino acid sequence of the CDRs of clone 11A10 is depicted in the tables below.

| 11A10 Kabat numbering | 26 | 27 | 28 | 29 | 30 | 31 | 32 | 33 | 34 | 35 |
|---|---|---|---|---|---|---|---|---|---|---|
| absolute numbering | 1 | 2 | 3 | 4 | 5 | 6 | 7 | 8 | 9 | 10 |
| 11A10 sequence | G | R | T | F | S | S | Y | A | M | A |

| 11A10 Kabat numbering | 50 | 51 | 52 | 52a | 53 | 54 | 55 | 56 | 57 | 58 |
|---|---|---|---|---|---|---|---|---|---|---|
| absolute numbering | 1 | 2 | 3 | 4 | 5 | 6 | 7 | 8 | 9 | 10 |
| 11A10 sequence | S | I | S | W | S | G | E | N | T | N |

| 11A10 Kabat numbering | 95 | 96 | 97 | 98 | 99 | 100 | 100a | 100b | 100c | 100d | 100e | 100f | 100g | 100h | 100i | 100j | 100k | 100l | 101 | 102 |
|---|---|---|---|---|---|---|---|---|---|---|---|---|---|---|---|---|---|---|---|---|
| absolute numbering | 1 | 2 | 3 | 4 | 5 | 6 | 7 | 8 | 9 | 10 | 11 | 12 | 13 | 14 | 15 | 16 | 17 | 18 | 19 | 20 |
| 11A10 sequence | K | I | A | K | T | Y | P | D | N | W | Y | W | T | K | S | N | N | Y | N | Y |

For cluster E, the amino acid sequence of the CDRs of clone 52G04 was used as a reference, against which the CDRs of all other cluster E clones were compared. The sequence variability against 52G04 is depicted in the tables below.

| 52G04 Kabat numbering | 26 | 27 | 28 | 29 | 30 | 31 | 32 | 33 | 34 | 35 |
|---|---|---|---|---|---|---|---|---|---|---|
| absolute numbering | 1 | 2 | 3 | 4 | 5 | 6 | 7 | 8 | 9 | 10 |
| 52G04 sequence | G | I | R | I | S | R | N | M | M | G |
| variations | | | | | | N | H | T | | |
| variations | | | | | | T | | | | |

| 52G04 Kabat numbering | 50 | 51 | 52 | 53 | 54 | 55 | 56 | 57 | 58 |
|---|---|---|---|---|---|---|---|---|---|
| absolute numbering | 1 | 2 | 3 | 4 | 5 | 6 | 7 | 8 | 9 |
| 52G04 sequence | R | I | T | P | G | G | D | T | Y |
| variations | Q | S | | | | | A | | |
| variations | | | | | | | K | | |

| 52G04 Kabat numbering | 95 | 96 | 97 | 98 | 101 | 102 |
|---|---|---|---|---|---|---|
| absolute numbering | 1 | 2 | 3 | 4 | 5 | 6 |
| 52G04 sequence | Y | S | T | L | G | S |
| variations | | | R | | | V |

For cluster F, the amino acid sequence of the CDRs of clone 50A11 was used as a reference, against which the CDRs of all other cluster F clones were compared. The sequence variability against 50A11 is depicted in the tables below.

| 50A11 Kabat numbering | 26 | 27 | 28 | 29 | 30 | 31 | 32 | 33 | 34 | 35 |
|---|---|---|---|---|---|---|---|---|---|---|
| absolute numbering | 1 | 2 | 3 | 4 | 5 | 6 | 7 | 8 | 9 | 10 |

-continued

| 50A11 Kabat numbering | 26 | 27 | 28 | 29 | 30 | 31 | 32 | 33 | 34 | 35 |
|---|---|---|---|---|---|---|---|---|---|---|
| 50A11 sequence | G | R | S | F | N | M | N | P | L | G |
| variations | | | T | | S | T | | | M | |
| variations | | | A | | A | | | | | |
| variations | | | G | | | | | | | |

| 50A11 Kabat numbering | 50 | 51 | 52 | 52a | 53 | 54 | 55 | 56 | 57 | 58 |
|---|---|---|---|---|---|---|---|---|---|---|
| absolute numbering | 1 | 2 | 3 | 4 | 5 | 6 | 7 | 8 | 9 | 10 |
| 50A11 sequence | A | H | R | W | S | D | G | N | T | Y |
| variations | | V | | | H | | S | | | F |
| variations | | | | | A | | | | | |

| 50A11 Kabat numbering | 95 | 96 | 97 | 98 | 99 | 100 | 100a | 100b | 100c | 100d | 100e | 100f | 100g | 101 | 102 |
|---|---|---|---|---|---|---|---|---|---|---|---|---|---|---|---|
| absolute numbering | 1 | 2 | 3 | 4 | 5 | 6 | 7 | 8 | 9 | 10 | 11 | 12 | 13 | 14 | 15 |
| 50A11 sequence | G | R | P | W | S | A | F | R | S | P | G | E | Y | V | Y |
| variations | | | | | | S | Y | | H | A | D | | | I | |
| variations | | | | | | D | A | | | | T | | | | |
| variations | | | | | | | | | | | N | | | | |
| variations | | | | | | | | | | | S | | | | |
| variations | | | | | | | | | | | K | | | | |
| variations | | | | | | | | | | | R | | | | |

The clustering based on the sequence transmuted into functional differences (see infra).

4.3 Purification of Monovalent Nanobodies

Since it is not practicable to characterize all clones identified in Example 4.2, representative Nanobodies were selected and expressed in *E. coli* TG1 as triple Flag, His6-tagged proteins. Expression was induced by addition of 1 mM IPTG and allowed to continue for 4 hours at 37° C. After spinning the cell cultures, periplasmic extracts were prepared by freeze-thawing the pellets. These extracts were used as starting material and Nanobodies were purified via IMAC and size exclusion chromatography (SEC).

The Nanobodies were purified to 95% purity as assessed via SDS-PAGE (data not shown).

Example 5 Binding of CD3 Nanobodies to Human TCR/CD3 Expressed on CHO-K1 Cells and to Purified Primary Human T Cells Binding of purified monovalent CD3 Nanobodies to human TCR(2XN9)/CD3 expressed on CHO-K1 cells and to purified primary human T cells was evaluated in flow cytometry as outlined in Example 4.1. Dilution series of CD3 Nanobodies 117G03 (cluster A), 60E11 (cluster B), 33G03 (cluster C), 11A10 (cluster D), 52G04 (cluster E) and 50A11 (cluster F) starting from 1 µM were applied to the cells.

Figure 2:
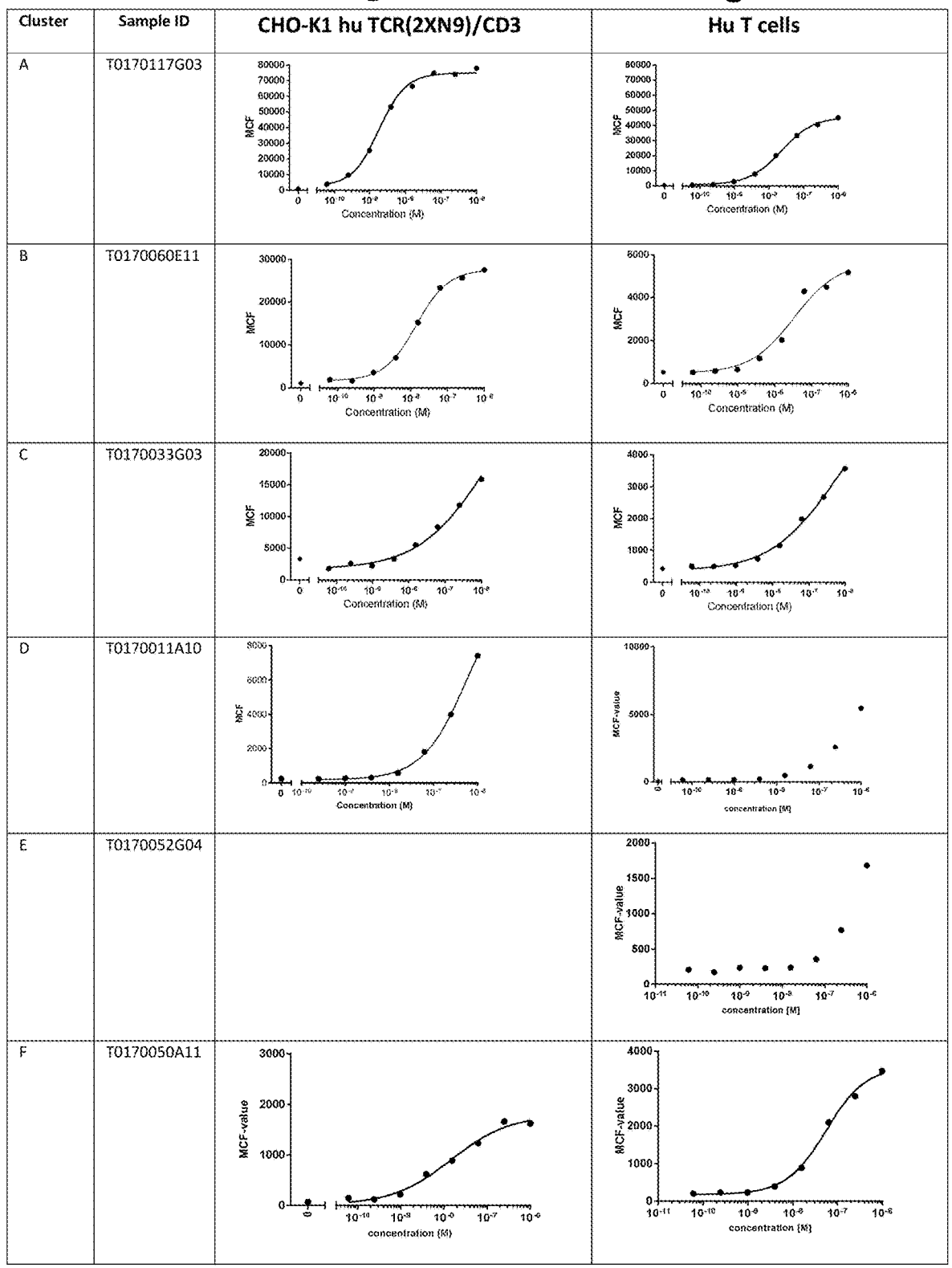

The results are shown in FIG. 2.

Nanobodies clearly bound to human TCR/CD3 expressed on CHO-K1 cells. The cluster A representative showed the best affinity, followed by the cluster B, C, F, D and E representatives.

Nanobodies bound to purified primary human T cells although with slightly lower potency compared to the CHO-K1 human TCR(2XN9)/CD3 cells. The representative of cluster A showed the best affinity on human primary T cells, in line with the data on the CHO-K1 (2XN9)/CD3. The $EC_{50}$ values obtained from the dose response curve are represented in Table 1.

TABLE 1

EC50 (M) of anti-CD3 monovalent Nanobodies to CHO-K1 human TCR(2XN9)/CD3 cells and to purified primary T cells as determined in flow cytometry.

| | | CHO-K1TCR(2XN9)/CD3 | | | Primary human T cells | | |
|---|---|---|---|---|---|---|---|
| Cluster | sample ID | EC50 (M) | 95% LCI | 95% UCI | EC50 (M) | 95% LCI | 95% UCI |
| A | T0170117G03 | 1.8E−09 | 1.4E−09 | 2.3E−09 | 2.2E−08 | 1.8E−08 | 2.8E−08 |
| B | T0170060E11 | 1.4E−08 | 1.3E−08 | 1.6E−08 | 3.4E−08 | 1.6E−08 | 7.0E−08 |
| C | T0170033G03 | >1E−07 | / | / | >1E−07 | / | / |
| D | T0170011A10 | >1E−07 | / | / | >1E−07 | / | / |
| E | T0170052G04 | No binding | | | >1E−07 | / | / |
| F | T0170050A11 | 1.5E−08 | 3.5E−09 | 6.3E−08 | 5.6E−08 | 3.4E−08 | 9.2E−08 |

Example 6 Determination of Binding Epitope

Binding to human TCR(2IAN)/CD3 expressed on HEK293H cells was evaluated and compared with the binding to HEK293H human CD3 cells in flow cytometry as outlined in Example 5. Dilution series of CD3 Nanobodies starting from 1 µM were applied to the cells. The parental HEK293H cell line was included as TCR/CD3 negative cell line.

The results are shown in FIG. 3.

Binding to HEK293H transfected with human CD3 was observed for all Nanobodies. In addition, some Nbs showed binding to HEK293H transfected with human TCR/CD3. No binding to the HEK293H parental cell lines was observed. The $EC_{50}$ values obtained from the dose response curve are depicted in Table 2.

TABLE 2

EC50 (M) of anti-CD3 monovalent Nanobodies to human TCR(2IAN)/CD3
or human CD3 expressed on HEK293H as determined in flow cytometry.

| | | HEK293H CD3 | | | | HEK293H TCR(2IAN)/CD3 | | | |
|---|---|---|---|---|---|---|---|---|---|
| Cluster | sample ID | EC50 (M) | 95% LCI | 95% UCI | MCF at 1 μM/top | EC50 (M) | 95% LCI | 95% UCI | MCF at 1 μM/top |
| A | T0170117G03 | NT | / | / | / | NT | / | / | / |
| A | T0170075G11 | 8.4E−08 | 3.8E−08 | 1.8E−07 | 47652 | 2.0E−08 | 1.7E−08 | 2.4E−08 | 89865 |
| B | T0170060E11 | 6.1E−09 | 5.2E−09 | 7.0E−09 | 115329 | no fit | / | / | 13708 |
| C | T0170033G03 | 2.9E−08 | 1.1E−08 | 7.5E−08 | 68578 | no fit | / | / | 6694 |
| D | T0170011A10 | >1E−07 | / | / | 3303 | >1E−07 | / | / | 15882 |
| E | T0170052G04 | >1E−07 | / | / | 2852 | >1E−07 | / | / | 4952 |
| F | T0170050A11 | 1.5E−09 | 9.8E−10 | 2.4E−09 | 106019 | no fit | / | / | 7457 |

Example 7 Primary Human T Cell Activation Capacity of Purified CD3 Reactive Nanobodies Functionality of purified monovalent CD3 Nanobodies was evaluated in the human T cell activation assay. Goat anti-mouse IgG dynabeads (Life technologies #11033) were coated with mouse anti-flag IgG antibodies (Sigma F1804), (15 μg/1E7beads). After an incubation period of 2 h at 4° C., beads were washed and incubated with a fixed (1 μg) concentration of purified flag tagged Nanobody for 20 min at 4° C. while shaking. Non-coupled Nanobodies were washed away before adding the bead complex together with soluble mouse anti-CD28 antibody (Pelicluster CD28—Sanquin #M1650) to purified primary human T cells (isolated as described in Example 2.1) from distinct healthy donors.

In addition, the effect of monovalent CD3 binding by the Nanobodies was evaluated by the incubation of the Nanobody with the purified primary human T cells isolated from distinct healthy donors, without prior capture onto beads, in the presence of anti-CD28 antibody.

The activation status of the purified primary human T cells was monitored by measuring the CD69 expression in flow cytometry using monoclonal mouse anti-human CD69PE (BD #557050) after an incubation of 24 h at 37° C. and 5% CO2 as described in Example 4.2.

In conclusion, CD3 Nanobodies showed clear CD69 upregulation after capturing onto anti-mouse IgG dynabeads (FIG. 4A). None of the CD3 reactive Nanobodies, when applied in solution were able to activate purified primary human T cells as measured by increased expression of CD69 (FIG. 4B).

Example 8 Binding of Bispecific CD3 Polypeptides to Human T Cell Receptor Complex Expressed on Cells To demonstrate that redirection of engaged T cells to tumour cells is possible by the Nanobodies, the CD20 antigen was chosen as exemplary tumour target.

Different CD3 building blocks (i.e. Nanobodies) were formatted into a bispecific construct with a human CD20 targeting Nanobody (see Table 3). The effector and tumour Nanobodies were genetically linked with 35GS linker and subsequently expressed in the yeast *Pichia* according to standard protocols (bispecific polypeptides).

Irrelevant constructs were generated by replacing the effector or tumour Nanobody with an irrelevant anti-egg lysozyme (cablys) Nanobody (Table 3).

TABLE 3

Sample ID and description of bispecific constructs

| | Target Nb × Effector Nb | | Effector Nb × Target Nb | |
|---|---|---|---|---|
| Cluster | Clone ID | Description | Clone ID | Description |
| C | T017000016 | 20CD019C07-35GS-T0170033G03-FLAG3-HIS6 | T017000021 | T0170033G03-35GS-20CD019C07-FLAG3-HIS6 |
| C | T017000059 | 20CD019C07-35GS-T0170033G03-FLAG3-HIS6 | T017000045 | T0170033G03-35GS-20CD019C07-FLAG3-HIS6 |
| D | T017000017 | 20CD019C07-35GS-T0170011A10-FLAG3-HIS6 | T017000022 | T0170011A10-35GS-20CD019C07-FLAG3-HIS6 |
| / | T017000006 | 20CD019C07-5GS-cAbLys3-FLAG3-HIS6 | | |
| / | T017000018 | 20CD019C07-35GS-cAbLys3-FLAG3-HIS6 | T017000023 | cAbLys3(D1E)-35GS-20CD019C07-FLAG3-HIS6 |
| C | | | T017000024 | T0170033G03-35GS-cAbLys3-FLAG3-HIS6 |
| D | | | T017000027 | T0170011A10-35GS-cAbLys3-FLAG3-HIS6 |
| D | T017000061 | 20CD019C07-35GS-T0170011A10-FLAG3-HIS6 | T017000047 | T0170011A10-35GS-20CD019C07-FLAG3-HIS6 |
| F | T017000057 | 20CD019C07-35GS-T0170050A11-FLAG3-HIS6 | T017000043 | T0170050A11-35GS-20CD019C07-FLAG3-HIS6 |
| E | T017000056 | 20CD019C07-35GS-T0170052G04-FLAG3-HIS6 | T017000048 | T0170052G04-35GS-20CD019C07-FLAG3-HIS6 |
| A | T017000066 | 20CD019C07-35GS-T0170061D09-FLAG3-HIS6 | T017000072 | T0170061D09-35GS-20CD019C07-FLAG3-HIS6 |
| A | T017000071 | 20CD019C07-35GS-T0170061F07-FLAG3-HIS6 | T017000034 | T0170061F07-35GS-20CD019C07-FLAG3-HIS6 |
| A | T017000052 | 20CD019C07-35GS-T0170061F04-FLAG3-HIS6 | T017000039 | T0170061F04-35GS-20CD019C07-FLAG3-HIS6 |
| A | T017000062 | 20CD019C07-35GS-T0170117G03-FLAG3-HIS6 | T017000036 | T0170117G03-35GS-20CD019C07-FLAG3-HIS6 |
| B | T017000053 | 20CD019C07-35GS-T0170060E11-FLAG3-HIS6 | T017000040 | T0170060E11-35GS-20CD019C07-FLAG3-HIS6 |

Binding of the bispecific constructs to human TCR/CD3 expressed on CHO-K1 cells, purified primary human T cells and human CD20 positive Ramos cells (ATCC: CRL-1596) was evaluated in flow cytometry as outlined in Example 5 and is presented in FIG. 5.

The $EC_{50}$ values obtained from the dose response curve are depicted in Table 4.

TABLE 4

EC50 (M) of anti-CD3 monovalent Nanobodies to CHO-K1 human TCR(2XN9)/CD3,
primary human T cells and Ramos cells as determined inflow cytometry.

| | | CHO-K1 huTCR(2XN9)/CD3 | | | hu T cells | | | Ramos | | |
|---|---|---|---|---|---|---|---|---|---|---|
| Cluster | sample ID | EC50 (M) | 95% LCI | 95% UCI | EC50 (M) | 95% LCI | 95% UCI | EC50 (M) | 95% LCI | 95% UCI |
| A | T017000062 | 1.5E−07 | 1.1E−07 | 2.1E−07 | 8.9E−08 | 7.2E−08 | 1.1E−07 | 1.9E−09 | 1.8E−09 | 2.1E−09 |
| A | T017000036 | 7.6E−09 | 5.9E−09 | 9.6E−09 | 3.5E−08 | 2.8E−08 | 4.4E−08 | 2.1E−08 | 1.9E−08 | 2.3E−08 |
| B | T017000053 | 1.5E−07 | 1.3E−07 | 1.7E−07 | >1E−07 | / | / | 1.8E−09 | 1.6E−09 | 2.0E−09 |
| B | T017000040 | 1.6E−07 | 1.5E−07 | 1.8E−07 | >1E−07 | / | / | 3.2E−08 | 2.9E−08 | 3.7E−08 |
| C | T017000016 | >1E−07 | / | / | >1E−07 | / | / | 1.5E−09 | 1.4E−09 | 1.6E−09 |
| C | T017000021 | >1E−07 | / | / | 5.4E−08 | 4.0E−08 | 7.3E−08 | 4.7E−09 | 4.4E−09 | 5.0E−09 |

The data indicate similar binding of the CD3×CD20 bispecific Nanobody (dotted line) compared to their monovalent counterparts, but a reduced binding of the CD20×CD3 bispecific Nanobody (full line) compared to their monovalent counterparts to CHO-K1 human TCR(2XN9)/CD3 cells and to primary human T cells. On the human CD20 Ramos cell, the bispecific CD3 Nanobodies with the CD20 at the C terminus showed reduced binding.

Example 9 Functional Characterization of Bispecific CD20×CD3 Polypeptides in Flow Cytometry Based Killing Assay In order to assess whether bispecific polypeptides were able to kill tumour cells, cytotoxicity assays were performed with isolated human T cells as effector cells.

Human T cells were isolated as described in Example 2.1. The quality and purity of the purified human T cells was checked with anti-CD3 (eBioscience #12-0037-73); anti-CD8 (BD Bioscience #345775); anti-CD4 (BD Bioscience #345771); anti-CD45RO (BD Bioscience #555493); anti-CD45RA (BD Bioscience #550855) and anti-CD19 (BD Bioscience #555413), anti-CD25 (BD Pharmigen #557138), anti-CD69 (BD Pharmigen #557050) fluorescently labelled antibodies in a flow cytometric assay. Human CD20 expressing Ramos cells and human CD20 expressing Raji cells (ECACC: 85011429), labelled with the PKH-26 membrane dye as described above were used as target cells. $2.5 \times 10^5$ effector and $2.5 \times 10^4$ target cells were co-incubated in 96-well V-bottom plates at an effector versus target ratio of 10:1. For measurement of the concentration-dependent cell lysis, serial dilutions of bispecific polypeptides (Table 3) were added to the samples and incubated for 18 h in a 5% $CO_2$ atmosphere at 37° C. After incubation, cells were pelleted by centrifugation and washed with FACS buffer. Subsequently, cells were resuspended in FACS buffer supplemented with 5 nM TOPRO3 (Molecular Probes cat #T3605) to distinguish live from dead cells. Cells were analysed using a FACS Array flow cytometer (BD Biosciences). Per sample, a total sample volume of 80 μl was acquired. Gating was set on PKH26 positive cells, and within this population the TOPRO3 positive cells were determined.

The CD3 bispecific polypeptides showed dose dependent killing of the Ramos cells (FIG. 6A). T017000045 (cluster C, T0170033G03-35GS-20CD019C07-FLAG3-HIS6) showed a dose dependent killing on both Ramos (FIG. 6A) and Raji (FIG. 6B) cells confirming that the observed cytotoxic effect was not restricted to a single tumour cell line. The expression level of the tumour antigen, CD20, was determined for both cell lines (FIG. 7).

The $IC_{50}$ values and the % lysis obtained from the dose response curve are depicted in Table 5 (% lysis=% death cells at 500 nM of Nanobody minus % dead cells of the no Nanobody control).

TABLE 5

Average IC50 (M) of the bispecific constructs in the flow cytometry based purified primary
human T cell mediated Ramos killing assay using an effector to target ration of 10 to 1.

| Cluster | ID monovalent Nb | ID construct (CD20 × CD3) | n | IC50 (M) | % lysis | % lysis (stdev) | ID construct (CD3 × CD20) | n | IC50 (M) | % lysis | % lysis (stdev) |
|---|---|---|---|---|---|---|---|---|---|---|---|
| A | T0170117G03 | T017000062 | 6 | 3.9E−09 | 22 | 7 | T017000036 | 3 | 5.5E−09 | 26 | 6 |
| B | T0170060E11 | T017000053 | 2 | 7.0E−09 | 22 | 3 | T017000040 | 3 | 6.8E−09 | 29 | 5 |
| C | T0170033G03 | T017000016 | 2 | 9.2E−09 | 4 | 2 | T017000045 | 1 | / | 0 | |
| D | T0170011A10 | T017000061 | 2 | 2.9E−08 | 13 | 0 | T017000047 | 0 | | | |
| E | T0170052G04 | T017000056 | 2 | 1.5E−08 | 4 | 6 | T017000048 | 0 | | | |
| F | T0170050A11 | T017000057 | 2 | 1.4E−09 | 3 | 4 | T017000043 | 0 | | | |

These results demonstrate that the CD3 bispecific polypeptides can induce T cell mediated killing of tumour target positive cell lines. When either the targeting Nanobody or the effector Nanobody was replaced by an irrelevant no effect on the viability of the Ramos cells could be observed. There was no clear preference of the orientation between the individual binding blocks in the bispecific polypeptide.

Example 10 Functional Characterization of Bispecific CD20×CD3 Polypeptides in an xCELLigence Based Killing Assay The CD3 multispecific polypeptides (Table 3) were also tested for their cell toxicity on human CD20 transfected adherent target cells in the presence of human effector T cells using real-time electrical impedance based technique. Here, fluctuations in impedance induced by the adherence of cells to the surface of an electrode were measured. T cells are non-adherent and therefore do not impact the impedance measurements.

In brief, the xCELLigence station was placed in a 37° C. incubator at 5% $CO_2$. 50 μl of assay medium was added to each well of E-pate 96 (ACEA Biosciences; cat #05 232 368 001) and a blank reading on the xCELLigence system was performed to measure background impedance in absence of cells. Subsequently, human CD20 transfected CHO-K1 or CHO-K1 parental cells ($1 \times 10^4$) were seeded onto the E-plates 96, and 50 μl of a serial dilution of Nanobody was added. After 30 min at RT 50 μl of human T cells were added per well ($3 \times 10^5$) to have an effector to target ratio of 30:1. The plate was placed in the xCELLigence station and impedance was measured every 15 min during 3 days. The data were analysed 44 h after start of the assay.

The $IC_{50}$ values are depicted in Table 6.

The multispecific polypeptides showed tumour antigen dependent killing, they induced a dose dependent human T cell mediated killing of the human CD20 transfected CHO-K1 cells (FIG. 8) but the constructs were not able to induce T cell mediated killing of CHO-K1 parental cells (FIG. 9).

TABLE 6

Average IC50 (M) of the multispecific constructs in the xCELLigence based human T cell mediated CHO-K1 CD20 killing assay using an effector to target ration of 30 to 1, analysed at 44 h after seeding.

| Cluster | ID monovalent Nb | sample ID (CD20 × CD3) | n | IC50 (M) | sample ID (CD3 × CD20) | n | IC50 (M) |
|---|---|---|---|---|---|---|---|
| A | T0170117G03 | T017000062 | 5 | 7.88E−10 | T017000036 | 2 | 1.04E−09 |
| B | T0170060E11 | T017000053 | 2 | 2.81E−10 | T017000040 | 2 | 4.89E−10 |
| C | T0170033G03 | T017000016 | 3 | 6.81E−12 | T017000021 | 2 | 1.52E−10 |

These results confirm the outcome obtained in the flow cytometry based killing assay of Example 9. In addition, only when the tumour target antigen is present T cell mediated killing was observed, indicating that the bispecific polypeptides are critically dependent on their target for induction of cytotoxicity.

Example 11 Linker Length Evaluation of the Bispecific Polypeptides

To evaluate the impact of the linker length used in the CD20/CD3 bispecific polypeptides on the cytotoxic capacity, the effector and tumour Nanobodies were genetically linked with a 5GS, 9GS or 35GS linker and subsequently expressed in *Pichia* according to standard protocols (see Table 7).

TABLE 7

Sample ID and description of bispecific constructs to evaluate impact of linker length

| | Target Nb × Effector Nb | | Effector Nb × Target Nb | |
|---|---|---|---|---|
| Cluster | Clone ID | Description | Clone ID | Description |
| C | T017000004 | 20CD019C07-5GS-T0170033G03-FLAG3-HIS6 | | |
| D | T017000005 | 20CD019C07-5GS-T0170011A10-FLAG3-HIS6 | | |
| C | T017000010 | 20CD019C07-9GS-T0170033G03-FLAG3-HIS6 | T017000020 | T0170033G03-9GS-20CD019C07-FLAG3-HIS6 |
| D | T017000011 | 20CD019C07-9GS-T0170011A10-FLAG3-HIS6 | T017000026 | T0170011A10-9GS-20CD019C07-FLAG3-HIS6 |
| C | T017000016 | 20CD019C07-35GS-T0170033G03-FLAG3-HIS6 | T017000021 | T0170033G03-35GS-20CD019C07-FLAG3-HIS6 |
| D | T017000017 | 20CD019C07-35GS-T0170011A10-FLAG3-HIS6 | T017000022 | T0170011A10-35GS-20CD019C07-FLAG3-HIS6 |
| / | T017000006 | 20CD019C07-5GS-cAbLys3-FLAG3-HIS6 | | |
| / | T017000012 | 20CD019C07-9GS-cAbLys3-FLAG3-HIS6 | | |
| / | T017000018 | 20CD019C07-35GS-cAbLys3-FLAG3-HIS6 | T017000023 | cAbLys3(D1E)-35GS-20CD019C07-FLAG3-HIS6 |
| C | | | T017000024 | T0170033G03-35GS-cAbLys3-FLAG3-HIS6 |
| D | | | T017000027 | T0170011A10-35GS-cAbLys3-FLAG3-HIS6 |

The impact of the linker length used in the CD20/CD3 bispecific polypeptides on the human primary effector T cell induced cellular toxicity on the adherent CHO-K1 human CD20 target was evaluated using real-time electrical impedance based technique as described in Example 9.

The results are summarized in FIG. 10.

All bispecific polypeptides, i.e. all linker lengths demonstrated specific cell killing. Little difference in potency was observed between the different linkers 9GS and 35GS linker for these bispecific polypeptides.

Example 12 Effector to Target Ratio Evaluation of the CD3 Bispecific Polypeptides To evaluate the effect of different effector to target (E:T) ratios on the killing properties of the Nanobodies, CD20×CD3 bispecific polypeptides were incubated with $2.5 \times 10^4$ PKH labelled Ramos cells in the presence of respectively $2.5 \times 10^5$ (E:T=10:1), $1.25 \times 10^5$ (E:T=5:1), $5 \times 10^4$ (E:T=2:1), $2.5 \times 10^4$ (E:T=1:1), human T cells as described Example 2.

Exemplary results are shown in FIG. 11. The $IC_{50}$ values are depicted in Table 8.

TABLE 8

IC50 (M) of the bispecific constructs in the flow cytometry based T cell mediated Ramos killing assay using different effector to target ratio's.

| Cluster | ID monovalent Nb | sample ID (CD20 × CD3) | E:T | n | IC50 (M) | 95% LCI | 95% UCI | % lysis |
|---|---|---|---|---|---|---|---|---|
| A | T0170117G03 | T017000062 | 10 | 1 | 7.3E−09 | 5.2E−09 | 1.0E−08 | 15 |
| A | T0170117G03 | T017000062 | 5 | 1 | 8.7E−09 | 5.3E−09 | 1.4E−08 | 10 |
| A | T0170117G03 | T017000062 | 2 | 1 | 7.1E−09 | 3.1E−09 | 1.6E−08 | 6 |
| A | T0170117G03 | T017000062 | 1 | 1 | 2.5E−08 | 1.9E−09 | 3.3E−07 | 2 |

The bispecific construct induced killing of the human CD20 target cells at different E:T ratios, even at a ratio of 1:1, after an incubation time of 18 h with little difference in potency. Although there is an impact on the E:T ratio on the % lysis, this can also be linked to the incubation time (see below).

Example 13 Time Dependent Cytolytic Activity of CD20/CD3 Bispecific Constructs in the Purified Primary Human T Cell Mediated Assay in xCELLigence To evaluate the impact of incubation time on the killing properties of the CD20×CD3 bispecific constructs, specific lysis of target cells was calculated for different time-points in xCELLigence. In brief, the xCELLigence station was placed in a 37° C. incubator at 5% $CO_2$. 50 μl of assay medium was added to each well of E-pate 96 (ACEA Biosciences; cat #05 232 368 001) and a blank reading on the xCELLigence system was performed to measure background impedance in absence of cells. Subsequently, human CD20 transfected CHO-K1 or CHO-K1 parental cells ($1 \times 10^4$) were seeded onto the E-plates 96. After 20 h, purified primary human T cells (described supra) and either 100 nM or 1.5 nM bispecific constructs were added, respectively. The cell index (CI) was measured every 15 min during 5 days. Using the normalized CI (The normalized Cell Index—NCI, is calculated by dividing the Cell Index value at a particular time point by the Cell Index value of the time-point when purified primary human T cells were added) specific lysis at different time points of the condition with constructs was calculated in relation to the condition lacking construct. (% specific lysis=$((NCI_{no\ construct} - NCI_{with\ construct})/NCI_{no\ construct}) \times 100$.

The results are depicted in FIG. 12.

Already one hour after the addition of human primary T cells and the multispecific construct, an increase of the cell index can be observed which clearly increased further upon longer incubation times. The maximal effect was clearly dependent on the incubation time but the obtained IC50 value did not change with increased incubation times. The irrelevant construct did not show any killing of the human CD20 CHO-K1 cells.

Example 14 Exploration of Half-Life Extension

It was hypothesized that HLE via albumin binding might be suitable to comply with various requirements, including (i) half-life extension (HLE) of the moiety; and (ii) efficacy of the multispecific. Preferably, the HLE function would not impair the penetration of tumours and tissues.

Alb11, a Nanobody binding to human serum albumin (HSA) was linked to the multispecific CD20×CD3 polypeptides to increase the in vivo half-life of the formatted molecules (WO 06/122787). A number of formats were generated based on the CD20 tumour targeting building block at the N-terminus, the CD3 recruiting building blocks in the middle and the albumin targeting Nanobody at the C-terminus using a 35GS linker and expressed as indicated above. An overview of the explored formats is shown in Table 9.

TABLE 9

Sample ID and description of HLE constructs

| Cluster | Sample ID | Description |
|---|---|---|
| A | T017000094 | 20CD019C07-35GS-T0170117G03-35GS-ALB11-FLAG3-HIS6 |
| B | T017000096 | 20CD019C07-35GS-T0170060E11-35GS-ALB11-FLAG3-HIS6 |

As the binding of HSA to the Alb11 Nanobody might have an impact on the affinity or potency of the HLE constructs, the half-life extended Nanobodies were characterized for binding to CD3 overexpressing CHO-K1 and primary human T cells. In addition, the potency in the functional T cell dependent Ramos B cell killing assay was evaluated in the presence and absence of HSA (described in 14.1 and 14.2 below).

14.1 Impact of Human Serum Albumin on the Binding Properties

Analogous to the experiments described in Example 5, binding of half-life extended anti-CD3 multispecific constructs to CHO-K1 human TCR(2XN9)/CD3 cells, primary human T cells and Ramos cells was evaluated in a flow cytometric assay.

The results are provided in FIG. 13. The $EC_{50}$ values obtained in this assay are listed in Table 10.

TABLE 10

Table with EC50 values of cell based binding to CHO-K1 human TCR(2XN9)/CD3, primary human T cells and Ramos cells as determined in flow cytometry

| | | CHO-K1-K1 huTCR (2XN9)/CD3 | | | hu T cells | | | Ramos | | |
|---|---|---|---|---|---|---|---|---|---|---|
| Cluster | sample ID | EC50 (M) | 95% LCI | 95% UCI | EC50 (M) | 95% LCI | 95% UCI | EC50 (M) | 95% LCI | 95% UCI |
| A | T017000094 | >1E−07 | / | / | >1E−07 | / | / | 1.9E−09 | 1.7E−09 | 2.1E−09 |
| B | T017000096 | 1.6E−07 | 1.4E−07 | 1.8E−07 | 3.2E−08 | 2.0E−08 | 5.3E−08 | 1.7E−09 | 1.5E−09 | 1.9E−09 |

Comparison of the CD20-35GS-CD3 HLE construct with the non-HLE constructs showed similar binding on all three cell lines tested. The data presented showed that coupling of the Alb11 building block did not influence the binding properties.

14.2 Impact of Human Serum Albumin on Potency in Human T Cell Mediated B Cell Killing Assay The functionality of half-life extended anti-CD3 Nanobodies (Table 9) was evaluated in the human T cell mediated Ramos killing assay as described in Example 10 in the presence and absence of 301M HSA and compared with the functionality of the non-HLE bispecific constructs.

The results are depicted in FIG. 14. The $IC_{50}$ values obtained in this assay are listed in Table 11.

TABLE 11

Table with IC50 and % lysis of the CD20 x CD3 Nanobodies in the T cell dependent B-cell (Ramos) killing assay to evaluate the effect of HLE

| Cluster | sample ID | EC50 (M) | 95% LCI | 95% UCI | % lysis |
|---|---|---|---|---|---|
| A | T017000062 | 6.4E−10 | 3.5E−10 | 1.2E−09 | 15 |
| A | T017000094 | 3.2E−09 | 1.7E−09 | 6.1E−09 | 14 |
| A | T017000094 | 2.0E−09 | 1.2E−09 | 3.3E−09 | 14 |
| A | T017000094 + HSA | 2.0E−08 | 7.0E−09 | 5.5E−08 | 7 |
| B | T017000053 | 1.8E−09 | 8.9E−10 | 3.8E−09 | 12 |
| B | T017000096 | 3.8E−09 | 2.1E−09 | 7.0E−09 | 15 |
| B | T017000096 | 2.6E−09 | 1.5E−09 | 4.7E−09 | 16 |
| B | T017000096 + HSA | 4.8E−09 | 1.1E−09 | 2.0E−08 | 6 |

The results indicate that the inclusion of the albumin targeting Nb in the construct as such did not have an essential impact on the obtained potency or efficacy. Although a minor loss of efficacy/potency was observed in the presence of HSA, the half-life extended CD3 bispecific polypeptides were still potent in tumour cell killing.

Example 15 Functional Characterization of Multispecific Polypeptides in an xCELLigence Based Human T Cell Mediated HER2-Positive Tumour Killing Assay In order to assess the general applicability of the CD3 building blocks in directing T cells to tumour cells, CD3 building blocks were combined with a different TAA, in this case a Nanobody binding to HER2.

The anti-CD3 building block was combined with a Nanobody against the HER2 solid tumour antigen in two orientations (Table 12) and characterized in the xCELLigence based human T cell mediated HER2-Positive Tumour Killing assay as described in Example 10 using two HER2 expressing cell lines: SK-BR-3 (ATCC: HTB-30), MCF-7 (ATCC: HTB-22) and a HER2 negative reference cell line, MDA-MB-468 (ATCC HTB-132) as target cell population. Human HER2 expression levels were confirmed using the monovalent anti-HER2 Nanobody HER2005F07 in flow cytometry as described in Example 9 using 100 nM of anti-HER2 Nanobody and shown in FIG. 15.

tumour cells via the CD3 Nanobody. Hence, the CD3 building blocks are broadly applicable for directing CTLs to tumours. Despite the large difference in tumour antigen density on SKBR3 and MCF-7 cells, both are efficiently killed by the addition of multispecific Nanobody constructs.

Example 16 Effect of CD20/CD3 Polypeptides on IFN-γ Release by Human T Cells in the xCELLigence Killing Assay The CD20×CD3 polypeptides were evaluated for their capacity to induce cytokine secretion in the human T cell mediated CHO_K1 human CD20 killing assay based on xCELLigence as described in Example 10. The release of the cytokine IFN-γ was measured by ELISA. Briefly, CHO-K1 human CD20 cells were seeded in 96 E plate and after 20 h, purified human primary T cells with or without bispecific CD20×CD3/irrelevant constructs were added to the E plates as described in Example 13. 72 h after the addition of the human primary T cells/constructs to the E-plates, IFN-γ production by the human primary T cells was measured. Maxisorp 96-well ELISA plates (Nunc) were coated with anti-human IFN-γ antibody (BD Bioscence

TABLE 12

Sample ID and description of HER2/CD3 constructs

| Cluster | Sample ID | Description |
|---------|-----------|-------------|
| A | T017000101 | HER2005F07(Q108L)-35GS-T0170117G03-FLAG3-HIS6 |
| A | T017000100 | T0170117G03-35GS-HER2005F07(Q108L)-FLAG3-HIS6 |

In brief, SKBR3 ($4 \times 10^4$ cells/well), MDA-MB-468 ($4 \times 10^4$ cells/well) or MCF-7 ($2 \times 10^4$ cells/well) were seeded in 96well E-plates and incubated with $6 \times 10^5$ cells and $3 \times 10^5$ cells human primary T cells (effector target ratio of 15 to 1) in the presence or absence of multispecific constructs and followed over time. Data were analysed after 18 h after start of the experiment and shown in FIG. 16.

The $IC_{50}$ values obtained in this assay are listed in Table 13.

551221). After overnight incubation, plates were washed and blocked with PBS+2% BSA for 1 h at room temperature. Next, plates were incubated with 100l of the supernatants (2 fold diluted) and 1 μg/ml biotinylated anti-human IFN-γ antibody (BD Bioscence, #554550) 2 h 30 min while shaking, washed again and incubated with streptavidin-HRP (Dakocytomation #P0397). After 30 min, TMB One Solution (Promega #G7431) was added. The reaction was stopped with 2M H2SO4 and the Nanobody dose dependent

TABLE 13

Overview IC50 of the HER2/CD3 constructs in the T cell mediated HER2-Positive Tumour Killing assay

| Cluster | ID monovalent Nb | ID construct (HER2 × CD3) | n | IC50 (M) | 95% LCI | 95% UCI | ID construct (CD3 × HER20) | n | IC50 (M) | 95% LCI | 95% UCI |
|---------|------------------|---------------------------|---|----------|---------|---------|----------------------------|---|----------|---------|---------|
| xCELLigence based cytotoxicity (readout 18 h) - SKBR3 (E/T = 15:1) |
| A | T0170117G03 | T017000101 | 1 | 2.6E−11 | 2.2E−11 | 3.1E−11 | T017000100 | 1 | 9.5E−12 | 8.1E−12 | 1.1E−11 |
| xCELLigence based cytotoxicity (readout 18 h) - MCF-7 (E/T = 15:1) |
| A | T0170117G03 | T017000101 | 1 | 1.1E−10 | 7.3E−11 | 1.8E−10 | T017000100 | 1 | 6.9E−11 | 4.5E−11 | 1.0E−10 |
| xCELLigence based cytotoxicity (readout 18 h) - MDA-MB-468(E/T = 15:1) |
| A | T0170117G03 | T017000101 | 1 | / | / | / | T017000100 | 1 | / | / | / |

The data indicate specific killing of HER2 positive tumour cell lines by directing human primary T cells to the production of IFN-γ was determined by measurement the OD at 405 nm using the Tecan sunrise 4.

The results are shown in FIG. 17. The $EC_{50}$ values obtained in this assay are listed in Table 14.

TABLE 14

EC50 (M) of the CD20/CD3 dependent IFN-γ secretion by human T cells in the human T cell mediated xCELLigence based killing assay.

| ID monovalent Nb | ID construct (CD20 × CD3) | n | EC50 (M) | 95% LCI | 95% UCI |
|---|---|---|---|---|---|
| T0170117G03 | T017000062 | 1 | 6.2E−10 | 5.3E−10 | 7.5E−10 |
| T0170060E11 | T017000053 | 1 | 9.1E−10 | 7.2E−10 | 1.1E−09 |

The bispecific CD20/CD3 polypeptide showed a dose dependent production of IFN-γ. Incubation with the irrelevant construct or the condition without bispecific construct did not induce any IFN-γ production.

Example 17 In Vivo Proof-of-Concept in a PBMC B Cell Depletion Model

In this B-cell depletion model, human PBMC were injected intraperitoneally to NOG mice. PBMC-derived B cell killing by polypeptide-mediated recruitment of T cells present in the PBMC population was evaluated reflecting the potential of multispecific polypeptides to activate T cells by direct linkage of T cells via CD3 to target B cells via CD20, resulting in target cell killing.

The in vivo efficacy of a CD3/CD20 multispecific polypeptides (T017000084, CD20×CD3 binding, cluster A) on B cell depletion in a PBMC NOG mouse model was evaluated and compared with the irrelevant polypeptide T017000088. The study demonstrated a clear effect on PBMC-derived B cell depletion in spleen.

In detail, the B cell depletion was evaluated in mice, intraperitoneally injected with $3 \times 10^7$ PBMCs in 500 µL of PBS at day 3 (D3) after a whole body irradiation of mice with a γ-source (1.44 Gy, 60Co) on day 0 (D0) and randomization of the mice into groups each of 12 animals. The treatment started on D3 one hour after PBMC injection and was repeated for 5 consecutive days, in total until day 7 (D7) (FIG. 18). One dose level of the CD3/CD20 binding NB was tested (24 mg/kg).

On day 18 (D18), mice were sacrificed and the spleen was collected for FACS analysis (mCD45, hCD45, hCD19, hCD20) to analyze and quantify the presence of PBMC-derived human B cells (hCD19+ hCD20+ hCD45+ mCD45−).

Results for PBMC-derived B cell depletion are represented in FIG. 19. In the spleen, B cell counts in the group treated with T017000084 were clearly different from the irrelevant polypeptide-treated group at the dose level tested. The dose is estimated to be on the maximum effect.

In conclusion, these results demonstrate that CD3/CD20 binding multispecific polypeptides are clearly able to decrease PBMC-derived B cells in spleen in this model. This confirmed the polypeptide-induced T cell activation by cross-linking T cells to target B cells and killing of the latter.

Example 18: In Vivo Proof-of-Concept in a Ramos B-Cell Depletion Model

In this B-cell depletion model, Ramos cells (a Burkitt's lymphoma cell line) and human PBMC were injected respectively intravenously and intraperitoneally to NOG mice. Ramos B cell and PBMC-derived B cell killing by polypeptide-mediated recruitment of T cells present in the PBMC population was evaluated reflecting the potential of multispecific polypeptides to activate T cells by direct linkage of T cells via CD3 to target B cells via CD20, resulting in target cell killing.

The in vivo efficacy of the multispecific polypeptide T017000084 (CD20×CD3 binding) on B cell depletion in a Ramos NOG mouse model was evaluated and compared with the irrelevant bispecific polypeptide T017000088 (irrelevant Nanobody+CD3 binding Nanobody). The study demonstrated a statistically significant effect in bone marrow and spleen on Ramos B-cell depletion and on PBMC derived B cell depletion in spleen.

In detail, the B cell depletion was evaluated in mice, intravenously injected with $10^6$ Ramos cells in 200 µL of Roswell Park Memorial Institute (RPMI) medium 1640 at day one (D1). This injection took place 24 hours after a whole body irradiation of mice with a γ-source (1.44 Gy, 60Co) (D0). $10^7$ PBMCs (500 µL in PBS) were injected on D3 (i.e. two days after tumor cell injection) after randomization of the mice into groups each of 12 animals. The treatment started on D3 one hour after PBMC injection and was repeated for 5 consecutive days in total until D7 (FIG. 20). One dose level of the CD3/CD20 binding polypeptide was tested (24 mg/kg).

On D20 or on D21, mice were sacrificed and spleen and bone marrow (femur) were collected for FACS analysis (mCD45, hCD45, hCD19, hCD20, hCD10) to analyze and quantify the presence of Ramos B cells (hCD19+ hCD20+ hCD45+ mCD45−hCD10+) and PBMC-derived B cells (hCD19+ hCD20+ hCD45+ mCD45− hCD10−).

Results for Ramos B cell depletion are represented in FIG. 21. Mice treated with an irrelevant bispecific polypeptide were considered as control group for analyses. Statistical analysis has been performed with F-tests from the mixed-effects ANOVA analysis. For the bone marrow and spleen, B cell counts in the group treated with T017000084 were statistically significantly different from the irrelevant polypeptide-treated group at the tested dose level. In the spleen, the dose is close to or estimated to be on the maximum effect.

Results for PBMC-derived B cell depletion are represented in FIG. 22. Both in bone marrow and in spleen, a statistically significant difference in human B cell numbers was seen for T017000084 versus the irrelevant polypeptide at the tested dose level. The dose is estimated to be on the maximum effect.

In conclusion, these results demonstrate that CD3/CD20 bispecific polypeptides are able to significantly decrease Ramos B cells and PBMC-derived B cells in spleen and bone marrow in this model. This confirms the Nanobody-induced T cell activation by cross-linking T cells to target B cells and killing of the latter.

Example 19 Targeting of Tumour Cells with Multispecific T Cell Engaging Polypeptides The therapeutic activity of T cell engaging strategy can be improved by the simultaneous targeting of multiple tumour associated antigens. Often tumour cells create an escape mechanism by the down-regulation of targeted antigens within a therapy. The simultaneous targeting of multiple antigens is likely to reduce the probability of generating tumour escape variants. The individual affinity of the respective tumour targeting Nanobodies may be varied such that preferable binding to either a single marker or simultaneous binding to both tumour markers is achieved. Antigens present on different cell populations can be combined or even soluble proteins can be targeted in combination with a tumour associated antigen.

As the Nanobody platform is ideally suited to combine different specificities into a multispecific format, the CD3 Nanobodies of the invention are combined into formats illustrating these concepts, i.e. with different tumour antigen binding Nanobodies in a multispecific polypeptide.

For the double tumour antigen targeting concept, a Nanobody reactive towards a first tumour antigen (TA1, e.g. CEA) is linked to a second Nanobody with different specificity (TA2, e.g. EGFR), different from TA1, in combination with a CD3 reactive Nanobody. The specific order of the building blocks is varied within the format as well as the applied linker lengths in between the different building blocks. Combinations of TA1 and TA2 which are tested are depicted in Table 15.

TABLE 15

Combination of CD3, TA1, TA2 and Alb binding building blocks in multispecific polypeptides.

| T-cell ISV | TA1 ISV | TA2 ISV | ALB-ISV |
|---|---|---|---|
| CD3 | CEA | Irr | + |
| CD3 | CEA | Irr | − |
| CD3 | CEA | EGFR | + |
| CD3 | CEA | EGFR | − |
| CD3 | Irr | EGFR | + |
| CD3 | Irr | EGFR | − |

In order to test half-life extension, an albumin binding Nanobody is included as well in the polypeptides as set out in Table 15.

To demonstrate the specific killing, a mixed cell culture assay system is used where TA1 single positive (e.g. MC38-huCEA or MKN45) and TA2 single positive tumour cells (e.g. Hela or Her14) are co-incubated. The expression level of the respective tumour antigens was determined in different cell lines and is represented in FIG. 23. Upon addition of the polypeptides of the invention, primary human T cells and albumin if required, the T cell mediated cytotoxicity is monitored based on a cytometric read out. A comparison is made with respect to double negative cells or formats containing one or more irrelevant Nanobodies.

In order to verify the specific killing, the induced killing of double positive tumour (for TA1 and TA2, e.g. LS174T or LoVo) cells is compared with the induced killing of single positive tumour cells. For this, a T cell mediated cytotoxicity assay is used as described above with a single type of tumour cells positive for both markers (cf. Example 17).

Example 20 Targeting of Tumour Cells with Multispecific T Cell Engaging Polypeptides As mentioned above, the therapeutic activity of T cell engaging strategy can be improved by the simultaneous targeting of multiple tumour associated antigens. Not only tumour cells create an escape mechanism by the down-regulation of targeted antigens within a therapy, but also by introducing (point-)mutations. Also in this case, simultaneous targeting of multiple epitopes on an antigen is likely to reduce the probability of generating tumour escape variants. Moreover, targeting multiple epitopes on a single antigen can increase the affinity of binding (avidity effect).

As the Nanobody platform is ideally suited to combine different specificities into a multivalent format, the anti-CD3 Nanobodies of the invention are combined into formats illustrating these concepts, i.e. with different tumour antigen binding Nanobodies in a multispecific polypeptide.

For the multivalent tumour antigen targeting concept, two Nanobodies reactive towards an antigen are linked (TA1 and TA2, respectively), followed by a CD3 reactive Nanobody. The specific order of the building blocks is varied within the format as well as the applied linker lengths in between the different building blocks. Combinations of TA1 and TA2 which are tested are depicted in Table 16.

TABLE 16

Combination of CD3, TA1, TA2 and Alb binding building blocks in multispecific polypeptides.

| T-cell ISV | TA1 ISV | TA2 ISV | ALB-ISV |
|---|---|---|---|
| CD3 | EGFR-1 (7D12) | EGFR-2 (9G08) | + |
| CD3 | EGFR-1 (7D12) | EGFR-2 (9G08) | − |
| CD3 | Her2-1 (5F07) | Her2-2 (47D05) | + |
| CD3 | Her2-1 (5F07) | Her2-2 (47D05) | − |

In order to test half-life extension, an Alb Nanobody is included as well in the polypeptides as set out in Table 16.

The potency and efficacy of these multivalent formats is evaluated and compared with the respective bispecific formats in an in vitro tumour cell killing assay comparable to the assay described in Example 10 but with the relevant cell lines (e.g. Hela, Her14, Ls174T, SKBR3, MCF7). Additionally, the effector-target ratio is varied such that an estimate is made whether a multivalent/multispecific polypeptide has a higher efficacy with lower effector target ratios.

TABLE A-1

Sequence alignment of CD3 cluster A binders

| Sequence ID | Sequence (differences from reference; dots = identical) |
|---|---|
| T0170PMP117G03: | EVQLVESGGGPVQAGGSLRLSCAASGRTYRGYSMGWFRQAPGKEREFVAAIWSGGNTYYEDSVKGRFTISRDNAKNTMYLQMTSLKPEDSATYYCAAKIRPYIFKIAGQYDYWGQGTQVTVSS |
| T0170PMP061F04: | ..........................................A....S................D......F..........S......L.......N....T.L................................. |
| T0170PMP08ED02: | ..........................................A....S................D......F.........SV......L.......N....T.L................................. |
| T0170PMP120D07: | ..........................................A.....................D......F..........S......L.......N.E..T.L................................. |
| T0170PMP118D11: | ..........................................A.....................D......F..........S......L.......N.E..T.L................................. |
| T0170PMP062A11: | ..........................................A.....................D......F..........S......L.......N.E.G.T.L................................. |
| T0170PMP118A08: | ...P........................................A.....................D......F..........S.....LS.H..N....T.V................................. |
| T0170PMP122C07: | ..........................................A.....................D......F..........S.....LS.H..N....T.V................................. |
| T0170PMP062D09: | ............S...............N..............A.....................D..S...F..........S....I.......L.......T.V.......................L......... |
| T0170PMP062G08: | ............................N..............A...S...............G........F.................L.......N....T.L.......................L......... |
| T0170PMP126E04: | ............................N..............A...S........................F.................L.......N....T.L.......................L......... |
| T0170PMP116E01: | ............................N..............A...S.........................T.E..A....F.................L.......N....T.L.......................L......... |
| T0170PMP117E03: | ............................N.R............A...S.........................T.E..A....F.R...............L.......N....T.L.......................L......... |
| T0170PMP062B10: | ............................S...............A...S.........................T.E..A....F.................L.......N....T.L.......................L......... |
| T0170PMP118E11: | ............................N...............A...S.........................T.E..A....F.................L.......N....T.L.....T.................L......... |
| T0170PMP075A10: | ............................D...............A...S.........................T.E..A....F.................L.......N....T.L.......................L......... |
| T0170PMP062C06: | ............................N...............A...S.........................T.E..A....F.................L.......N....T.L.......................L......... |
| T0170PMP112G06: | ............................N...............A...S.........................T.E..A....F.................L.......N.R..T.L.......................L......... |
| T0170PMP061A09: | L...........................N...T............A.....P.......................T.E..P....F.................L.R..R.E..T.L.......................L......... |
| T0170PMP061B06: | ............................N...T............A.....P.......................T.E..P....F.................L.R..R.E..T.L.......................L......... |
| T0170PMP111C01: | ............................N...T............A.....P.......................T.E..P...FA.................L.R..R.E..T.L.......................L......... |
| T0170PMP061D06: | ............................N..A..A.T..........A.....P.......................T.E..P....F.................L.R..R.E..T.L.......................L......... |
| T0170PMP061E09: | ............................N...T............A.....P.......................T.E..P....F.................L.R..R.E..T.L..................V......L......... |
| T0170PMP078A07: | ............................N.R..A..T..........A.....P.......................T.E......F.................L.R..R.E..T.L.......................L......... |
| T0170PMP061A04: | ..................V........T.................A.....P.......................T.E......F.................L......G.....T.L.................P......L......... |

TABLE A-1-continued

Sequence alignment of CD3 cluster A binders

| | | | | | | | | | | | |
|---|---|---|---|---|---|---|---|---|---|---|---|
| T0170PMP115A03: | . | . | . | T | . | . | . | . | . A . . P | . . T . E . . . F | . . . . . . . L | . . . . T . L | . . . . . . P | . . . L |
| T0170PMP061F09: | P | . | . | T | . | . | . | . | . A . . P | . . T . E . . . F | . . . . . . . L | . . . . T . L | . . . . . . P | . . . L |
| T0170PMP112D04: | . | . | . | T | . | . | . | . | . A . . P | . . T . E . . . F | . . . . . . . L | . . . . T . L | . . . . . . P | . . . L |
| T0170PMP114E06: | . | . | . | T | . | . | V . P | . | . A . . P . . G | . . T . E . . . F | . . . . . . . L | . . . . T . L | . . . . . . P | . . . L |
| T0170PMP113G04: | . | . | . | T | . | . | . | . | . A . . P | . . T . E . . . F | . . . . . . . L | . . . . T . L | . . . . . . P | . . . L |
| T0170PMP061D09: | . | . | . | L . T | . | . | . | . | . A . . P | . . T . E . . . F | . . . . . . L . A | . . . . T . L | . . . . . . P | . . . L |
| T0170PMP062G05: | . | . | . | T | . | . | . | . | . A . . P | . . T . E . . . F | . . . . . . S . L | . . . . T . L | . . . . . . P | . . . L |
| T0170PMP114C05: | . | . | . | T | . | . | . | . | . A . . P | . . T . E . . . L | . . . . . . . L | . . . . T . L | . . . . . . P | . . . L |
| T0170PMP117G05: | . | . | . | T | . | . | V | . | . A . . P | . . T . E . . . F | . . . . . . . L | . . . . T . L | . . . . . V P | . . . L |
| T0170PMP061F07: | . | . | . | . | . | F | . | . | . A . . P | . . T . E . . . F | . . . . . . . L | . . . . T . L | . . . . . . . | . . . L |
| T0170PMP061C09: | . | . | . | . | . | . | . | . | . . . . . R | . . . . D . . . . | . . . . . . . . | . . . . . . . | . . . . . . . | . . . . |
| T0170PMP124E06: | . | A | . | . | . | . | . | . | . . . . . R | . . . . D . . . . | . . . . . . . . | . . . . . . . | . . . . . . . | . . . L |
| T0170PMP111B02: | . | . | . | . | . | . | . | . | . R . R | . . . . D . . . P | . . . . . . . . | . . . . . . . | . . . . . . . | . . . L |
| T0170PMP062E08: | . | . | . | . D | . | . | . A | . | . . V | . . . . T D . . . | . . . . . . I T | . . . . . . . | . . . . . . . | . . . L |
| T0170PMP062G03: | . | F | . | . D | . | . | . A | . | . . V | . . . . T D . . . | . . . . . . I T | . . . . . . . | . . . . . . . | . . . L |
| T0170PMP062G10: | . | . | . | . D | . | . | . A | . | . . V | . . A . T D . . . | . . . . . . I T | . . . . . . . | . . . . . . . | . . . L |
| T0170PMP078E10: | . | . | . | . D | . | . | . A | . | . . V | . . . . T D . . . | . . . . . . V T | . . . . . . . | . . . . . . . | . . . L |
| T0170PMP115E06: | . | R | . | . D | . | . | . A | . | . . V | . . . . T D . . . | . . . . . . I T | . . . . . . . | . . . . . . . | . . . L |
| T0170PMP122B02: | . | . | . | . D | . | . | . A | . | . . V | . . . . T D . A . | . . . . . . I T | . . . . . . . | . . . . . . . | . . . L |
| T0170PMP061D07: | . | . | . | . D | . | . | . A | . | . R V | . . . . T D . . . | . . . . . . I T | . . . . . . . | . . . . . . . | . . . L |
| T0170PMP126D09: | . | - | . | . D | . | . | . A | . | . . V | . . . . T D . . . | . . . . . . . T | . . . . . . . | . . . . . . . | . . . . |
| T0170PMP126B03: | . | . | . | . D | . | . | . A | . | . . V | . . . . T D . . . | . . . . . . I T | . . . . . . . | . . . . . . . | . . . L |
| T0170PMP126B02: | K | . | . | . D | . | . | . | . | . . V | . . . . T D . . . | . . . . . . . T | . . . . . . . | . . . . . . . | . . . . |
| T0170PMP075G11: | . | . | . | . | . | . | . | . | . . V | . . . . T D . . . | . . . . . . I T . H | . . . . . . . | . . . . . . . | . . . L |
| T0170PMP080E07: | . | L | . | . | . | . | . A | . | . . V | . . . . T D . . . | . . . . . . I T | . . . . . . . | . . . . . . . | . . . . |

TABLE A-2

Sequence alignment of CD3 cluster B binders

```
T0170PMP060E11:EVQLVESGGGLVQPGGSLRLSCAASGDIYKSFDMGWYRQAPGKQRDLVAVIGSRGNNRGT
               NYADSVKGRFTISEDGTGNTVYLLMNKLRPEDTAIYYCNTAPLVAGRPWGRGTLVTVSS
```

TABLE A-3

Sequence alignment of CD3 cluster C binders

```
T0170PMP033G03:EVQLVESGGGSVQAGGSLRLSCAASGRTFSTNPMGWFRQVPGKERELIAAVRWADGNTFYAD
T0170PMP044A09:..........L.................S.....S................
T0170PMP043E10:..........L.................S.....S....A...........
T0170PMP044B10:..........L.................S.....S................

T0170PMP033G03:SVKGRFTISRDNAKKTVYLQMNSLKSEDTATYYCAAGRPWSAYHSPAEYVHWGQGTQVTVSS
T0170PMP044A09:..............................................................
T0170PMP043E10:..............................................................
T0170PMP044B10:.................R.................................L.....
```

TABLE A-4

Sequence alignment of CD3 cluster D binders

```
T0170PMP011A10:EVQLVESGGGLVQGGGSLSLSCAASGRTFSSYAMAWFRQPPGKEREFVASISWSGENTNYRNSVK
               GRFTISRDNAKNTVYLQMNSLKPEDTAVYYCAAKIAKTYPDNWYWTKSNNYNYWGQGTQVTVSS
```

TABLE A-5

Sequence alignment of CD cluster E binders

```
T0170PMP052G04:EVQLVESGGGAVQPGGSLRLSCAASGIRISRNMMGWFRQAPGKQRDLVARITPGGDTYY
T0170PMP062B02:.....................V...........RT..RE.NM....S...A...
T0170PMP114D01:.....................V...........RT..RE.NM....S...A...
T0170PMP080F02:.....................V...........RT..RG.NM....S...A...
T0170PMP122A11:..................................S..M....S.....
T0170PMP113E06:.....................V......NH..........E...M...S......V
T0170PMP061E10:..........V.................THT........E...EM..Q.S...K...
T0170PMP061D03:..........V.................THT........E...EM..Q.S...K...
T0170PMP113E03:..........V.................THT........E...EM..Q.S...K...

T0170PMP052G04:VDSVKGRFSISKDNAKNTVYLQMNSLKPEDTAVYYCNSYSTLGSWGQGTQVTVSS
T0170PMP062B02:.............DS........D..............................
T0170PMP114D01:.............DS........D................L.....
T0170PMP080F02:.............DS........D..............................
T0170PMP122A11:......................R.....I..........L.....
T0170PMP113E06:....................N..L.........R...............
T0170PMP061E10:I.......T..........F.R..D...D........V....L.....
```

TABLE A-5-continued

Sequence alignment of CD cluster E binders

```
T0170PMP061D03:I.......T..........F.R..D...D.............V...........
T0170PMP113E03:I.......T..........F.R..D...DG............V...........
```

TABLE A-6

Sequence alignment of CD3 cluster F binders

| ID | Sequence |
|---|---|
| T0170PMP050A11: | EVQLVESGGGLVQAGGSLRLSCAASGRSFNMNPLGWFRQSPGKEREFVAAHRWSDGNTYYVDSVKGRFTISRDNAKNTVYLQMNSLKSEDTAVYYCAAGRPWSAFRSPGEYVYWGQGTQVTVSS |
| T0170PMP044A06: | ..........................................T.ST.M.....N.................................A.........A........K..........................SY..D........... |
| T0170PMP044D11: | ..........................................A.T.M....FA.................................................A..........................SY..D........... |
| T0170PMP043E08: | ..........................................A.S..M....R........................................S..........................................SY..T.....L..... |
| T0170PMP043E06: | .....A....................................ST.M....F.R..................................H.................................................AH..N........... |
| T0170PMP043E07: | ..........................................SA.M....F...S................................H.................................................AH..N........... |
| T0170PMP039D06: | ..........................................G.ST.M....................................A....................................................DY.A.S..I....... |
| T0170PMP044F10: | .....R....................................G.ST.M....................................A....................................................D..A.S..I.S..P... |
| T0170PMP044B11: | ..........................................A..T.M....L.V.H.S..T.....C..........................................................YH..N.....L... |
| T0170PMP044C08: | ..........................................A..T.M....L.V.H.S..T..........................................................YH..N........... |
| T0170PMP043B03: | .....F....................................A.ST.M....G.V..S.SA....VF..........................................................YH..K.....L... |
| T0170PMP039E06: | .....D....................................A.ST.M....S.FVA...............................S..........A......................YH..R..I....R.. |
| T0170PMP049A04: | .....D....................................A.ST.M....S.FVA...............................S..........A......................YH..R..I..R..L.. |
| T0170PMP043F09: | .....A....................................A.ST.M...Q.L.V.A.....T.............K..L.N......A......................YHA.K..I....L.. |
| T0170PMP044C11: | .....A....................................A.ST.M...Q.L.V.A.....T.............K..L.N......A......................YHA.K..I....... |

TABLE A-7

Amino acid sequences of monovalent anti-CD3 Nanobodies ("ID" refers to the SEQ ID NO as used herein)

| Name | ID | Amino acid sequence |
|---|---|---|
| T0170PMP117G03 | 1 | EVQLVESGGGPVQAGGSLRLSCAASGRTYRGYSMGWFRQAPGKEREFVAAIVWSGGNTYYEDSVKGRFTISRDNAKNTMYLQMTSLKPEDSATYYCAAKIRPYIFKIAGQYDYWGQGTQVTVSS |
| T0170PMP061F04 | 2 | EVQLVESGGGPVQAGGSLRLSCAASGRTYRGYSMAWFRQSPGKEREFVAAIVWSDGNTYYEDFVKGRFTISRDSAKNTLYLQMTNLKPEDTALYYCAAKIRPYIFKIAGQYDYWGQGTQVTVSS |
| T0170PMP081D02 | 3 | EVQLVESGGGPVQAGGSLRLSCAASGRTYRGYSMAWFRQSPGKEREFVAAIVWSDGNTYYEDFVKGRFTISRDSVKNTLYLQMTNLKPEDTALYYCAAKIRPYIFKIAGQYDYWGQGTQVTVSS |
| T0170PMP120D07 | 4 | EVQLVESGGGPVQAGGSLRLSCAASGRTYRGYSMAWFRQAPGKEREFVAAIVWSDGNTYYEDFVKGRFTISRDSAKNTLYLQMTNLEPEDTALYYCAAKIRPYIFKIAGQYDYWGQGTQVTVSS |
| T0170PMP118D11 | 5 | EVQLVESGGGPVQAGGSLRLSCAASGRTYRGYSMAWFRQAPGKEREFVAAIVWSDGNTYYEDFVKGRFTISRDSAKNTLYLQMTNLEPGDTALYYCAAKIRPYIFKIAGQYDYWGQGTLVTVSS |
| T0170PMP062A11 | 6 | EVQLVESGGGPVQAGGSLRLSCAASGRTYRGYSMAWFRQAPGKEREFVAAIVWSDGNTYYEDFVKGRFTISRDSAKNTLSLHMTNLKPEDTAVYYCAAKIRPYIFKIAGQYDYWGQGTQVTVSS |
| T0170PMP118A08 | 7 | EVQPVESGGGPVQAGGSLRLSCAASGRTYRGYSMAWFRQAPGKEREFVAAIVWSDGNTYYEDFVKGRFTISRDSAKNTLSLHMTNLKPEDTAVYYCAAKIRPYIFKIAGQYDYWGQGTQVTVSS |
| T0170PMP122C07 | 8 | EVQLVESGGGPVQAGGSLRLSCAASGRTYRGYSMAWFRQAPGKEREFVAAIVWSDGNTYYEDFVKGRFTISRDSAKNTLSLHMANLKPEDTAVYYCAAKIRPYIFKIAGQYDYWGQGTLVTVSS |
| T0170PMP062D09 | 9 | EVQLVESGGGPVQSGGSLRLSCANSGRTYRGYSMGWFRQAPGKEREFVAAIVWSDGNSYYEDFVKGRFTISRDSAKNIMYLQMTNLKPEDTAVYYCAAKIRPYIFKIAGQYDYWGQGTLVTVSS |
| T0170PMP062G08 | 10 | EVQLVESGGGPVQAGGSLRLSCANSGRTYRGYSMAWFRQSPGKERGFVAAITWSEGNAYYEDFVKGRFTISRDNAKNTLYLQMTNLKPEDTALYYCAAKIRPYIFKIAGQYDYWGQGTLVTVSS |
| T0170PMP126E04 | 11 | EVQLVESGGGPVQAGGSLRLSCANSGRTYRGYSMAWFRQSPGKEREFVAAITWSEGNAYYEDFVKGRFTISRDNAKNTLYLQMTNLKPEDTALYYCAAKIRPYIFKIAGQYDYWGQGTLVTVSS |
| T0170PMP116E01 | 12 | EVQLVESGGGPVQAGGSLRLSCANSGRTYRGYSMAWFRQSPGKEREFVAAITWSEGNAYYEDFVRGRFTISRDNAKNTLYLQMTNLKPEDTALYYCAAKIRPYIFKIAGQYDYWGQGTLVTVSS |
| T0170PMP117E03 | 13 | EVQLVESGGGPVQAGGSLRLSCANSRRTYRGYSMAWFRQSPGKEREFVAAITWSEGNAYYEDFVKGRFTISRDNAKNTLYLQMTNLKPEDTALYYCAAKIRPYIFKIAGQYDYWGQGTLVTVSS |
| T0170PMP062B10 | 14 | EVQLVESGGGPVQAGGSLRLSCASSGRTYRGYSMAWFRQSPGKEREFVAAITWSEGNAYYEDFVKGRFTISRDNAKNTLYLQMTNLKPEDTALYYCAAKIRPYIFKIAGQYDYWGQGTLVTVSS |
| T0170PMP118E11 | 15 | EVQLVESGGGPVQAGGSLRLSCANSGRTYRGYSMAWFRQSPGKEREFVAAITWSEGNAYYEDFVKGRFTISRDNAKNTLYLQMTNLKPEDTALYYCAAKTRPYIFKIAGQYDYWGQGTLVTVSS |
| T0170PMP075A10 | 16 | EVQLVESGGGPVQAGGSLRLSCADSGRTYRGYSMAWFRQSPGKEREFVAAITWSEGNAYYEDFVKGRFTISRDNAKNTLYLQMTNLKPEDTALYYCAAKIRPYIFKIAGQYDYWGQGTLVTVSS |
| T0170PMP062C06 | 17 | EVQLVESGGGPVQAGGSLRLSCANSGRTYRGYGMAWFRQSPGKEREFVAAITWSEGNAYYEDFVKGRFTISRDNAKNTLYLQMTNLKPEDTALYYCAAKIRPYIFKIAGQYDYWGQGTQVTVSS |
| T0170PMP112G06 | 18 | EVQLVESGGGPVQAGGSLRLSCANSGRTYRGYSMAWFRQSPGKEREFVAAITWSEGNAYYEDFVKGRFTISRDNAKNTLYLQMTNLRPEDTALYYCAAKIRPYIFKIAGQYDYWGQGTQVTVSS |
| T0170PMP061A09 | 19 | EVQLVESGGGLVQAGGSLTLSCANSGRTYRGYSMAWFRQPPGKEREFVAAITWSEGNPYYEDFVKGRFTISRDNAKNTLYLRMTRLEPEDTALYYCAAKIRPYIFKIAGQYDYWGQGTLVTVSS |
| T0170PMP061B06 | 20 | EVQLVESGGGPVQAGGSLTLSCANSGRTYRGYSMAWFRQPPGKEREFVAAITWSEGNPYYEDFVKGRFTISRDNAKNTLYLRMTRLEPEDTALYYCAAKIRPYIFKIAGQYDYWGQGTLVTVSS |
| T0170PMP111C01 | 21 | EVQLVESGGGPVQAGGSLTLSCANSGRTYRGYSMAWFRQPPGKEREFVAAITWSEGNPYYEDFAKGRFTISRDNAKNTLYLRMTRLEPEDTALYYCAAKIRPYIFKIAGQYDYWGQGTLVTVSS |
| T0170PMP061D06 | 22 | EVQLVESGGGPVQAGGSLTLSCANSGRAYRGYSMAWFRQPPGKEREFVAAITWSEGNPYYEDFVKGRFTISRDNAKNTLYLRMTRLEPEDTALYYCAAKIRPYIFKIAGQYDYWGQGTQVTVSS |
| T0170PMP061E09 | 23 | EVQLVESGGGPVQAGGSLTLSCANSGRTYRGYSMAWFRQPPGKEREFVAAITWSEGNPYYEDFVKGRFTISRDNAKNTLYLRMTRLEPEDTALYYCAAKIRPYIFKVAGQYDYWGQGTQVTVSS |
| T0170PMP078A07 | 24 | EVQLVESGGGPVQAGGSLTLSCANSRRTYRGYSMAWFRQPPGKEREFVAAITWSEGNPYYEDFVKGRFTISRDNAKNTLYLRMTRLEPEDTALYYCAAKIRPYIFKIAGQYDYWGQGTQVTVSS |

TABLE A-7-continued

Amino acid sequences of monovalent anti-CD3 Nanobodies ("ID" refers to the SEQ ID NO as used herein)

| Name | ID | Amino acid sequence |
|---|---|---|
| T0170PMP061A04 | 25 | EVQLVESGGGPVQTGGSLRLSCVASGRTYRGYSMAWFRQPPGKEREFVAAITWSEGNTYYEDFVKGRFTISRDNAKNTLY<br>LQMTGLKPEDTALYYCAAKIRPYIFKIPGQYDYWGQGTLVTVSS |
| T0170PMP115A03 | 26 | EVQLVESGGGPVQTGGSLRLSCVASGRTYRGYSMAWFRQPPGKEREFVAAITWSEGNTYYEDFVKGRFTISRDNAKNTLY<br>LQMTSLKPEDTALYYCAAKIRPYIFKIPGQYDYWGQGTLVTVSS |
| T0170PMP061F09 | 27 | EVQPVESGGGPVQTGGSLRLSCVASGRTYRGYSMAWFRQPPGKEREFVAAITWSEGNTYYEDFVKGRFTISRDNAKNTLY<br>LQMTSLKPEDTALYYCAAKIRPYIFKIPGQYDYWGQGTLVTVSS |
| T0170PMP112D04 | 28 | EVQLVESGGGPVQTGGSLRLSCVASGRTYRGYSMAWFRQPPGKERGFVAAITWSEGNTYYEDFVKGRFTISRDNAKNTLY<br>LQMTSLKPEDTALYYCAAKIRPYIFKIPGQYDYWGQGTLVTVSS |
| T0170PMP114E06 | 29 | EVQLVESGGGPVQTGGSLRLSCVAPGRTYRGYSMAWFRQPPGKEREFVAAITWSEGNTYYEDFVKGRFTISRDNAKNTLY<br>LQMTSLKPEDTALYYCAAKIRPYIFKIPGQYDYWGQGTLVTVSS |
| T0170PMP113G04 | 30 | EVQLVESGGGPVQTGGSLRLSCVASGRTYRGYSMAWFRQPPGKEREFVAAITWSEGNTYYEDFVKGRFTISRDNAKNTLY<br>LQMASLKPEDTALYYCAAKIRPYIFKIPGQYDYWGQGTLVTVSS |
| T0170PMP061D09 | 31 | EVQLVESGGGLVQTGGSLRLSCVASGRTYRGYSMAWFRQPPGKEREFVAAITWSEGNTYYEDFVKGRFTISRDNAKNTLY<br>LQMTSLKPEDTALYYCAAKIRPYIFKIPGQYDYWGQGTQVTVSS |
| T0170PMP062G05 | 32 | EVQLVESGGGPVQTGGSLRLSCVASGRTYRGYSMAWFRQPPGKEREFVAAITWSEGNTYYEDFVKGRFTISRDNAKSTLY<br>LQMTSLKPEDTALYYCAAKIRPYIFKIPGQYDYWGQGTQVTVSS |
| T0170PMP114C05 | 33 | EVQLVESGGGPVQTGGSLRLSCVASGRTYRGYSMAWFRQPPGKEREFVAAITWSEGNTYYEDLVKGRFTISRDNAKNTLY<br>LQMTSLKPEDTALYYCAAKIRPYIFKIPGQYDYWGQGTQVTVSS |
| T0170PMP117G05 | 34 | EVQLVESGGGPVQTGGSLRLSCVASGRTYRGYSMAWFRQPPGKEREFVAAITWSEGNTYYEDFVKGRFTISRDNAKNTLY<br>LQMTSLKPEDTALYYCAAKIRPYIFKVPGQYDYWGQGTQVTVSS |
| T0170PMP061F07 | 35 | EVQLVESGGGPVQAGGSLRLSCAASGRTFRGYSMAWFRQPPGKEREFVAAITWSEGNTYYEDFVKGRFTISRDNAKNTLY<br>LQMTSLKPEDTALYYCAAKIRPYIFKIAGQYDYWGQGTLVTVSS |
| T0170PMP061C09 | 36 | EVQLVESGGGPVQAGGSLRLSCAASGRTYRGYSMGWFRQAPGREREFVAAIVWSDGNTYYEDSVKGRFTISRDNAKNT<br>MYLQMTSLKPEDSATYYCAAKIRPYIFKIAGQYDYWGQGTQVTVSS |
| T0170PMP124E06 | 37 | EVQLVESGGGPAQAGGSLRLSCAASGRTYRGYSMGWFRQAPGREREFVAAIVWSDGNTYYEDSVKGRFTISRDNAKNT<br>MYLQMTSLKPEDSATYYCAAKIRPYIFKIAGQYDYWGQGTLVTVSS |
| T0170PMP111B02 | 38 | EVQLVESGGGPVQAGGSLRLSCAASGRTYRGYSMGWFRRAPGREREFVAAIVWSDGNTYYEDPVKGRFTISRDNAKNT<br>MYLQMTSLKPEDSATYYCAAKIRPYIFKIAGQYDYWGQGTQVTVSS |
| T0170PMP062E08 | 39 | EVQLVESGGGPVQAGDSLRLSCAASGRAYRGYSMGWFRQVPGKEREFVAAIVWTDGNTYYEDSVKGRFTISRDITKNTM<br>YLQMTSLKPEDSATYYCAAKIRPYIFKIAGQYDYWGQGTLVTVSS |
| T0170PMP062G03 | 40 | EVQLVEFGGGPVQAGDSLRLSCAASGRAYRGYSMGWFRQVPGKEREFVAAIVWTDGNTYYEDSVKGRFTISRDITKNTM<br>YLQMTSLKPEDSATYYCAAKIRPYIFKIAGQYDYWGQGTLVTVSS |
| T0170PMP062G10 | 41 | EVQLVESGGGPVQAGDSLRLSCAASGRAYRGYSMGWFRQVPGKEREFVAAIAWTDGNTYYEDSVKGRFTISRDITKNTM<br>YLQMTSLKPEDSATYYCAAKIRPYIFKIAGQYDYWGQGTLVTVSS |
| T0170PMP078E10 | 42 | EVQLVESGGGPVQAGDSLRLSCAASGRAYRGYSMGWFRQVPGKEREFVAAIVWTDGNTYYEDSVKGRFTISRDVTKNT<br>MYLQMTSLKPEDSATYYCAAKIRPYIFKIAGQYDYWGQGTLVTVSS |
| T0170PMP115E06 | 43 | EVQLVESRGGPVQAGDSLRLSCAASGRAYRGYSMGWFRQVPGKEREFVAAIVWTDGNTYYEDSVKGRFTISRDITKNTM<br>YLQMTSLKPEDSATYYCAAKIRPYIFKIAGQYDYWGQGTLVTVSS |
| T0170PMP122602 | 44 | EVQLVESGGGPVQAGDSLRLSCAASGRAYRGYSMGWFRQVPGKEREFVAAIVWTDGNAYYEDSVKGRFTISRDITKNTM<br>YLQMTSLKPEDSATYYCAAKIRPYIFKIAGQYDYWGQGTLVTVSS |
| T0170PMP061D07 | 45 | EVQLVESGGGPVQAGDSLRLSCAASGRAYRGYSMGWFRRVPGKEREFVAAIVWTDGNTYYEDSVKGRFTISRDITKNTM<br>YLQMTSLKPEDSATYYCAAKIRPYIFKIAGQYDYWGQGTQVTVSS |
| T0170PMP126D09 | 46 | EVQLVSGGGPVQAGDSLRLSCAASGRAYRGYSMGWFRQVPGKEREFVAAIVWTDGNTYYEDSVKGRFTISRDITKNTMY<br>LQMTSLKPEDSATYYCAAKIRPYIFKIAGQYDYWGQGTQVTVSS |
| T0170PMP126B03 | 47 | EVQLVESGGGPVQAGDSLRLSCAASGRTYRGYSMGWFRQVPGKEREFVAAIVWTDGNTYYEDSVKGRFTISRDNTKNT<br>MYLQMTSLKPEDSATYYCAAKIRPYIFKIAGQYDYWGQGTLVTVSS |
| T0170PMP126B02 | 48 | KVQLVESGGGPVQAGDSLRLSCAASGRTYRGYSMGWFRQVPGKEREFVAAIVWTDGNTYYEDSVKGRFTISRDNTKNT<br>MYLQMTSLKPEDSATYYCAAKIRPYIFKIAGQYDYWGQGTLVTVSS |

TABLE A-7-continued

Amino acid sequences of monovalent anti-CD3 Nanobodies ("ID" refers to the SEQ ID NO as used herein)

| Name | ID | Amino acid sequence |
|---|---|---|
| T0170PMP075G11 | 49 | EVQLVESGGGPVQAGDSLRLSCAASGRTYRGYSMGWFRQVPGKEREFVAAIVWTDGNTYYEDSVKGRFTISRDITKNTM YLHMTSLKPEDSATYYCAAKIRPYIFKIAGQYDYWGQGTQVTVSS |
| T0170PMP080E07 | 50 | EVQLVESGGGLVQAGGSLRLSCAASGRAYRGYSMGWFRQVPGKEREFVAAIVWTDGNTYYEDSVKGRFTISRDITKNTM YLQMTSLKPEDSATYYCAAKIRPYIFKIAGQYDYWGQGTQVTVSS |
| T0170PMP060E11 | 51 | EVQLVESGGGLVQPGGSLRLSCAASGDIYKSFDMGWYRQAPGKQRDLVAVIGSRGNNRGRTNYADSVKGRFTISRDGTG NTVYLLMNKLRPEDTAIYYCNTAPLVAGRPWGRGTLVTVSS |
| T0170PMP011A10 | 52 | EVQLVESGGGLVQGGGSLSLSCAASGRTFSSYAMAWFRQPPGKEREFVASISWSGENTNYRNSVKGRFTISRDNAKNTVY LQMNSLKPEDTAVYYCAAKIAKTYPDNWYWTKSNNYNYWGQGTQVTVSS |
| T0170PMP033G03 | 53 | EVQLVESGGGSVQAGGSLRLSCAASGRTFSTNPMGWFRQVPGKERELIAAVRWADGNTFYADSVKGRFTISRDNAKKTV YLQMNSLKSEDTATYYCAAGRPWSAYHSPAEYVHWGQGTQVTVSS |
| T0170PMP044A09 | 54 | EVQLVESGGGLVQAGGSLRLSCAASGRTFSTNPMGWFRQSPGKERSLIAAVRWADGNTFYADSVKGRFTISRDNAKKTV YLQMNSLKSEDTATYYCAAGRPWSAYHSPAEYVHWGQGTQVTVSS |
| T0170PMP043E10 | 55 | EVQLVESGGGLVQAGGSLRLSCAASGRTFSTNPMGWFRQSPGKERSLIAAARWADGNTFYADSVKGRFTISRDNAKKTV YLQMNSLKSEDTATYYCAAGRPWSAYHSPAEYVHWGQGTQVTVSS |
| T0170PMP044B10 | 56 | EVQLVESGGGLVQAGGSLRLSCAASGRTFSTNPMGWFRQSPGKERSLIAAVRWADGNTFYADSVKGRFTISRDNAKKTV YLQMNSLRSEDTATYYCAAGRPWSAYHSPAEYVHWGQGTLVTVSS |
| T0170PMP052G04 | 57 | EVQLVESGGGAVQPGGSLRLSCAASGIRISRNMMGWFRQAPGKQRDLVARITPGGDTYYVDSVKGRFSISKDNAKNTVY LQMNSLKPEDTAVYYCNSYSTLGSWGQGTQVTVSS |
| T0170PMP062B02 | 58 | EVQLVESGGGAVQPGGSLRLSCVASGIRISRNMMGWFRRTPGRERNMVARISPGGATYYVDSVKGRFSISKDDSKNTVYL QMDSLKPEDTAVYYCNSYSTLGSWGQGTQVTVSS |
| T0170PMP114D01 | 59 | EVQLVESGGGAVQPGGSLRLSCVASGIRISRNMMGWFRRTPGRERNMVARISPGGATYYVDSVKGRFSISKDDSKNTVYL QMDSLKPEDTAVYYCNSYSTLGSWGQGTLVTVSS |
| T0170PMP080F02 | 60 | EVQLVESGGGAVQPGGSLRLSCVASGIRISRNMMGWFRRTPGRGRNMVARISPGGATYYVDSVKGRFSISKDDSKNTVY LQMDSLKPEDTAVYYCNSYSTLGSWGQGTQVTVSS |
| T0170PMP122A11 | 61 | EVQLVESGGGAVQPGGSLRLSCAASGIRISRNMMGWFRQAPGKSRDMVARISPGGDTYYVDSVKGRFSISKDNAKNTVY LQMNSLRPEDTAIYYCNSYSTLGSWGQGTLVTVSS |
| T0170PMP113E06 | 62 | EVQLVESGGGAVQPGGSLRLSCVASGIRISNHMMGWFRQAPGEQRDMVARISPGGDTYYVDSVKGRFSISKDNAKNTV YLQMNNLKLEDTAVYYCNSYRTLGSWGQGTQVTVSS |
| T0170PMP061E10 | 63 | EVQLVESGGGVVQPGGSLRLSCAASGIRISTHTMGWFRQAPEKQREMVAQISPGGKTYYIDSVKGRFTISKDNAKNTVFL RMNDLKPDDTAVYYCNSYSTLGVWGQGTLVTVSS |
| T0170PMP061D03 | 64 | EVQLVESGGGVVQPGGSLRLSCAASGIRISTHTMGWFRQAPEKQREMVAQISPGGKTYYIDSVKGRFTISKDNAKNTVFL RMNDLKPDDTAVYYCNSYSTLGVWGQGTQVTVSS |
| T0170PMP113E03 | 65 | EVQLVESGGGVVQPGGSLRLSCAASGIRISTHTMGWFRQAPEKQREMVAQISPGGKTYYIDSVKGRFTISKDNAKNTVFL RMNDLKPDGTAVYYCNSYSTLGVWGQGTQVTVSS |
| T0170PMP050A11 | 66 | EVQLVESGGGLVQAGGSLRLSCAASGRSFNMNPLGWFRQSPGKEREFVAAHRWSDGNTYYVDSVKGRFTISRDNAKNT VYLQMNSLKSEDTAVYYCAAGRPWSAFRSPGEYVYWGQGTQVTVSS |
| T0170PMP044A06 | 67 | EVQLVESGGGLVQAGGSLRLSCAASGRTFSTNPMGWFRQSPGNEREFVAAHRWSDGNTYYADSVKGRFAISRDNAKKT VYLQMNSLKSEDTAVYYCAAGRPWSSYRSPDEYVYWGQGTQVTVSS |
| T0170PMP044D11 | 68 | EVQLVESGGGLVQAGGSLRLSCAASGRAFNTNPMGWFRQFAGKEREFVAAHRWSDGNTYYVDSVKGRFTISRDNAKNT VYLQMNSLKSEDTAVYYCAAGRPWSSYRSPDEYVYWGQGTQVTVSS |
| T0170PMP043E08 | 69 | EVQLVESGGGLVQAGGSLRLSCAASGRAFSMNPMGWFRQSPGREREFVAAHRWSDGNTYYVDSVKGRFTISRDNAKNT VYLQMSSLKSEDTAVYYCAAGRPWSSYRSPTEYVYWGQGTLVTVSS |
| T0170PMP043E06 | 70 | EVQLVESGGGAVQAGGSLRLSCAASGRSFSTNPMGWFRQFPRKEREFVAAHRWSDGNTYYADSVKGRFTISRDNAKHT VYLQMNSLKSEDTAVYYCAAGRPWSAAHSPNEYVYWGQGTQVTVSS |
| T0170PMP043E07 | 71 | EVQLVESGGGLVQAGGSLRLSCAASGRSFSANPMGWFRQFPGKERESVAAHRWSDGNTYYADSVKGRFTISRDNAKHT VYLQMNSLKSEDTAVYYCAAGRPWSAAHSPNEYVYWGQGTQVTVSS |
| T0170PMP039D06 | 72 | EVQLVESGGGLVQAGGSLRLSCAASGRGFSTNPMGWFRQSPGKEREFVAAHRWSDGNTYYVDSVKGRFAISRDNAKNT VHLQMNSLKSEDTAVYYCAAGRPWSDYRAPSEYIYWGQGTQVTVSS |
| T0170PMP044F10 | 73 | EVQLVESGGGLVRAGGSLRLSCAASGRGFSTNPMGWFRQSPGKEREFVAAHRWSDGNTYYVDSVKGRFAISRDNAKNT VHLQMNSLKSEDTAVYYCAAGRPWSDFRAPSEYIYSGPGTQVTVSS |

TABLE A-7-continued

Amino acid sequences of monovalent anti-CD3 Nanobodies ("ID" refers to the SEQ ID NO as used herein)

| Name | ID | Amino acid sequence |
| --- | --- | --- |
| T0170PMP044B11 | 74 | EVQLVESGGGLVQAGGSLRLSCAASGRAFNTNPMGWFRQSPGKEREFLAAVRWHDGSTYYTDSVKGRFTISRDNAKNTVYLQMNSLKSEDTAVYYCAAGRPWSAYHSPNEYVYWGQGTLVTVSS |
| T0170PMP044C08 | 75 | EVQLVESGGGLVQAGGSLRLSCAASGRAFNTNPMGWFRQSPGKEREFLAAVRWHDGSTYYTDSVKGRFTISRDNAKNTVCLQMNSLKSEDTAVYYCAAGRPWSAYHSPNEYVYWGQGTQVTVSS |
| T0170PMP043B03 | 76 | EVQLVEFGGGLVQAGGSLRLSCAASGRAFSTNPMGWFRQSPGKEREFVGAVRWSDGSTYSADSVKGRFTVFRDNAKNTVYLQMNSLKSEDTAVYYCAAGRPWSAYHSPKEYVYWGQGTLVTVSS |
| T0170PMP039E06 | 77 | EVQLVESGGGLVQAGDSLRLSCAASGRAFSTNPMGWFRQSPGKEREFVAAHRWSDGSTFVADSVKGRFTISRDNAKNTVSLQMNSLKSADTAVYYCAAGRPWSAYHSPREYIYWGRGTQVTVSS |
| T0170PMP049A04 | 78 | EVQLVESGGGLVQAGDSLRLSCAASGRAFSTNPMGWFRQSPGKEREFVAAHRWSDGSTFVADSVKGRFTISRDNAKNTVSLQMNSLKSADTAVYYCAAGRPWSAYHSPREYIYWGRGTLVTVSS |
| T0170PMP043F09 | 79 | EVQLVESGGGLVQAGASLRLSCAASGRAFSTNPMGWFRQSPGQEREFLAAVRWADGNTYYTDSVKGRATISRDNAKKTVYLQLNNLKSEDAAVYYCAAGRPWSAYHAPKEYIYWGQGTLVTVSS |
| T0170PMP044C11 | 80 | EVQLVESGGGLVQAGASLRLSCAASGRAFSTNPMGWFRQSPGQEREFLAAVRWADGNTYYTDSVKGRATISRDNAKKTVYLQLNNLKSEDAAVYYCAAGRPWSAYHAPKEYIYWGQGTQVTVSS |

TABLE A-8

Sequences for CDRs and frameworks, plus preferred combinations as provided in formula I, namely FR1-CDR1-FR2-CDR2-FR3-CDR3-FR4. "ID" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| ID | Name | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 1 | T0170PMP 117G03 | 144 | EVQLVESGGGPVQ AGGSLRLSCAAS | 81 | GRTYRGY SMG | 174 | WFRQAPGK EREFVA | 101 | AIVWSG GNTY | 200 | YEDSVKGRFTISRDNAKNTM YLQMTSLKPEDSATYYCAA | 123 | KIRPYIFKIAGQY DY | 243 | WGQGT QVTVSS |
| 2 | T0170PMP 061F04 | 144 | EVQLVESGGGPVQ AGGSLRLSCAAS | 82 | GRTYRGY SMA | 175 | WFRQSPGKE REFVA | 102 | AIVWSD GNTY | 201 | YEDFVKGRFTISRDSAKNTLY LQMTNLKPEDTALYYCAA | 123 | KIRPYIFKIAGQY DY | 243 | WGQGT QVTVSS |
| 3 | T0170PMP 081D02 | 144 | EVQLVESGGGPVQ AGGSLRLSCAAS | 82 | GRTYRGY SMA | 175 | WFRQSPGKE REFVA | 102 | AIVWSD GNTY | 202 | YEDFVKGRFTISRDSVKNTLY LQMTNLKPEDTALYYCAA | 123 | KIRPYIFKIAGQY DY | 243 | WGQGT QVTVSS |
| 4 | T0170PMP 120D07 | 144 | EVQLVESGGGPVQ AGGSLRLSCAAS | 82 | GRTYRGY SMA | 174 | WFRQAPGK EREFVA | 102 | AIVWSD GNTY | 203 | YEDFVKGRFTISRDSAKNTLY LQMTNLEPEDTALYYCAA | 123 | KIRPYIFKIAGQY DY | 243 | WGQGT QVTVSS |
| 5 | T0170PMP 118D11 | 144 | EVQLVESGGGPVQ AGGSLRLSCAAS | 82 | GRTYRGY SMA | 174 | WFRQAPGK EREFVA | 102 | AIVWSD GNTY | 204 | YEDFVKGRFTISRDSAKNTLY LQMTNLEPGDTALYYCAA | 123 | KIRPYIFKIAGQY DY | 244 | WGQGTL VTVSS |
| 6 | T0170PMP 062A11 | 144 | EVQLVESGGGPVQ AGGSLRLSCAAS | 82 | GRTYRGY SMA | 174 | WFRQAPGK EREFVA | 102 | AIVWSD GNTY | 205 | YEDFVKGRFTISRDSAKNTLS LHMTNLKPEDTAVYYCAA | 123 | KIRPYIFKIAGQY DY | 243 | WGQGT QVTVSS |
| 7 | T0170PMP 118A08 | 145 | EVQPVESGGGPVQ AGGSLRLSCAAS | 82 | GRTYRGY SMA | 174 | WFRQAPGK EREFVA | 102 | AIVWSD GNTY | 205 | YEDFVKGRFTISRDSAKNTLS LHMTNLKPEDTAVYYCAA | 123 | KIRPYIFKIAGQY DY | 243 | WGQGT QVTVSS |
| 8 | T0170PMP 122C07 | 144 | EVQLVESGGGPVQ AGGSLRLSCAAS | 82 | GRTYRGY SMA | 174 | WFRQAPGK EREFVA | 102 | AIVWSD GNTY | 206 | YEDFVKGRFTISRDSAKNTLS LHMANLKPEDTAVYYCAA | 123 | KIRPYIFKIAGQY DY | 244 | WGQGTL VTVSS |
| 9 | T0170PMP 062D09 | 146 | EVQLVESGGGPVQ SGGSLRLSCAAS | 81 | GRTYRGY SMG | 174 | WFRQAPGK EREFVA | 103 | AIVWSD GNSY | 207 | YEDFVKGRFTISRDSAKNIM YLQMTNLKPEDTAVYYCAA | 123 | KIRPYIFKIAGQY DY | 244 | WGQGTL VTVSS |
| 10 | T0170PMP 062G08 | 147 | EVQLVESGGGPVQ AGGSLRLSCANS | 82 | GRTYRGY SMA | 176 | WFRQSPGKE RGFVA | 104 | AITWSEG NAY | 208 | YEDFVKGRFTISRDNAKNTL YLQMTNLKPEDTALYYCAA | 123 | KIRPYIFKIAGQY DY | 244 | WGQGTL VTVSS |
| 11 | T0170PMP 126E04 | 147 | EVQLVESGGGPVQ AGGSLRLSCANS | 82 | GRTYRGY SMA | 175 | WFRQSPGKE REFVA | 104 | AITWSEG NAY | 208 | YEDFVKGRFTISRDNAKNTL YLQMTNLKPEDTALYYCAA | 123 | KIRPYIFKIAGQY DY | 244 | WGQGTL VTVSS |
| 12 | T0170PMP 116E01 | 147 | EVQLVESGGGPVQ AGGSLRLSCANS | 82 | GRTYRGY SMA | 175 | WFRQSPGKE REFVA | 104 | AITWSEG NAY | 209 | YEDFVRGRFTISRDSAKNTL YLQMTNLKPEDTALYYCAA | 123 | KIRPYIFKIAGQY DY | 244 | WGQGTL VTVSS |
| 13 | T0170PMP 117E03 | 147 | EVQLVESGGGPVQ AGGSLRLSCANS | 83 | RRTYRGY SMA | 175 | WFRQSPGKE REFVA | 104 | AITWSEG NAY | 208 | YEDFVKGRFTISRDNAKNTL YLQMTNLKPEDTALYYCAA | 123 | KIRPYIFKIAGQY DY | 244 | WGQGTL VTVSS |
| 14 | T0170PMP 062B10 | 148 | EVQLVESGGGPVQ AGGSLRLSCASS | 82 | GRTYRGY SMA | 175 | WFRQSPGKE REFVA | 104 | AITWSEG NAY | 208 | YEDFVKGRFTISRDNAKNTL YLQMTNLKPEDTALYYCAA | 123 | KIRPYIFKIAGQY DY | 244 | WGQGTL VTVSS |
| 15 | T0170PMP 118E11 | 147 | EVQLVESGGGPVQ AGGSLRLSCANS | 82 | GRTYRGY SMA | 175 | WFRQSPGKE REFVA | 104 | AITWSEG NAY | 208 | YEDFVKGRFTISRDNAKNTL YLQMTNLKPEDTALYYCAA | 124 | KTRPYIFKIAGQY DY | 243 | WGQGT QVTVSS |

TABLE A-8-continued

Sequences for CDRs and frameworks, plus preferred combinations as provided in formula I, namely FR1-CDR1-FR2-CDR2-FR3-CDR3-FR4. "ID" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| ID | Name | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 16 | T0170PMP 075A10 | 149 | EVQLVESGGGPVQ AGGSLRLSCADS | 82 | GRTYRGY SMA | 175 | WFRQSPGKE REFVA | 104 | AITWSEG NAY | 208 | YEDFVKGRFTISRDNAKNTL YLQMTNLKPEDTALYYCAA | 123 | KIRPYIFKIAGQY DY | 243 | WGQGT QVTVSS |
| 17 | T0170PMP 062C06 | 147 | EVQLVESGGGPVQ AGGSLRLSCANS | 84 | GRTYRGY GMA | 175 | WFRQSPGKE REFVA | 104 | AITWSEG NAY | 208 | YEDFVKGRFTISRDNAKNTL YLQMTNLKPEDTALYYCAA | 123 | KIRPYIFKIAGQY DY | 243 | WGQGT QVTVSS |
| 18 | T0170PMP 112G06 | 147 | EVQLVESGGGPVQ AGGSLRLSCANS | 82 | GRTYRGY SMA | 175 | WFRQSPGKE REFVA | 104 | AITWSEG NAY | 210 | YEDFVKGRFTISRDNAKNTL YLQMTNLRPEDTALYYCAA | 123 | KIRPYIFKIAGQY DY | 243 | WGQGT QVTVSS |
| 19 | T0170PMP 061A09 | 150 | EVQLVESGGGLVQ AGGSLTLSCANS | 82 | GRTYRGY SMA | 177 | WFRQPPGKE REFVA | 105 | AITWSEG NPY | 211 | YEDFVKGRFTISRDNAKNTL YLRMTRLEPEDTALYYCAA | 123 | KIRPYIFKIAGQY DY | 244 | WGQGTL VTVSS |
| 20 | T0170PMP 061B06 | 151 | EVQLVESGGGPVQ AGGSLTLSCANS | 82 | GRTYRGY SMA | 177 | WFRQPPGKE REFVA | 105 | AITWSEG NPY | 211 | YEDFVKGRFTISRDNAKNTL YLRMTRLEPEDTALYYCAA | 123 | KIRPYIFKIAGQY DY | 244 | WGQGTL VTVSS |
| 21 | T0170PMP 111C01 | 151 | EVQLVESGGGPVQ AGGSLTLSCANS | 82 | GRTYRGY SMA | 177 | WFRQPPGKE REFVA | 105 | AITWSEG NPY | 212 | YEDFAKGRFTISRDNAKNTL YLRMTRLEPEDTALYYCAA | 123 | KIRPYIFKIAGQY DY | 244 | WGQGTL VTVSS |
| 22 | T0170PMP 061D06 | 151 | EVQLVESGGGPVQ AGGSLTLSCANS | 85 | GRAYRGY SMA | 177 | WFRQPPGKE REFVA | 105 | AITWSEG NPY | 211 | YEDFVKGRFTISRDNAKNTL YLRMTRLEPEDTALYYCAA | 123 | KIRPYIFKIAGQY DY | 243 | WGQGT QVTVSS |
| 23 | T0170PMP 061E09 | 151 | EVQLVESGGGPVQ AGGSLTLSCANS | 82 | GRTYRGY SMA | 177 | WFRQPPGKE REFVA | 105 | AITWSEG NPY | 211 | YEDFVKGRFTISRDNAKNTL YLRMTRLEPEDTALYYCAA | 125 | KIRPYIFKVAGQ YDY | 243 | WGQGT QVTVSS |
| 24 | T0170PMP 078A07 | 152 | EVQLVESGGGPVQ TGGSLRLSCVAS | 83 | RRTYRGY SMA | 177 | WFRQPPGKE REFVA | 105 | AITWSEG NPY | 211 | YEDFVKGRFTISRDNAKNTL YLRMTRLEPEDTALYYCAA | 123 | KIRPYIFKIAGQY DY | 243 | WGQGT QVTVSS |
| 25 | T0170PMP 061A04 | 152 | EVQLVESGGGPVQ TGGSLRLSCVAS | 82 | GRTYRGY SMA | 177 | WFRQPPGKE REFVA | 106 | AITWSEG NTY | 213 | YEDFVKGRFTISRDNAKNTL YLQMTGLKPEDTALYYCAA | 126 | KIRPYIFKIPGQY DY | 244 | WGQGTL VTVSS |
| 26 | T0170PMP 115A03 | 153 | EVQPVESGGGPVQ TGGSLRLSCVAS | 82 | GRTYRGY SMA | 177 | WFRQPPGKE REFVA | 106 | AITWSEG NTY | 214 | YEDFVKGRFTISRDNAKNTL YLQMTSLKPEDTALYYCAA | 126 | KIRPYIFKIPGQY DY | 244 | WGQGTL VTVSS |
| 27 | T0170PMP 061F09 | 152 | EVQLVESGGGPVQ TGGSLRLSCVAS | 82 | GRTYRGY SMA | 178 | WFRQPPGKE RGFVA | 106 | AITWSEG NTY | 214 | YEDFVKGRFTISRDNAKNTL YLQMTSLKPEDTALYYCAA | 126 | KIRPYIFKIPGQY DY | 244 | WGQGTL VTVSS |
| 28 | T0170PMP 112D04 | 152 | EVQLVESGGGPVQ TGGSLRLSCVAS | 82 | GRTYRGY SMA | 177 | WFRQPPGKE REFVA | 106 | AITWSEG NTY | 214 | YEDFVKGRFTISRDNAKNTL YLQMTSLKPEDTALYYCAA | 126 | KIRPYIFKIPGQY DY | 244 | WGQGTL VTVSS |
| 29 | T0170PMP 114E06 | 154 | EVQLVESGGGPVQ TGGSLRLSCVAP | 82 | GRTYRGY SMA | 177 | WFRQPPGKE REFVA | 106 | AITWSEG NTY | 214 | YEDFVKGRFTISRDNAKNTL YLQMTSLKPEDTALYYCAA | 126 | KIRPYIFKIPGQY DY | 244 | WGQGTL VTVSS |
| 30 | T0170PMP 113G04 | 152 | EVQLVESGGGPVQ TGGSLRLSCVAS | 82 | GRTYRGY SMA | 177 | WFRQPPGKE REFVA | 106 | AITWSEG NTY | 215 | YEDFVKGRFTISRDNAKNTL YLQMASLKPEDTALYYCAA | 126 | KIRPYIFKIPGQY DY | 244 | WGQGTL VTVSS |

TABLE A-8-continued

Sequences for CDRs and frameworks, plus preferred combinations as provided in formula I, namely FR1-CDR1-FR2-CDR2-FR3-CDR3-FR4. "ID" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| ID | Name | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 31 | T0170PMP 061D09 | 155 | EVQLVESGGGLVQ TGGSLRLSCVAS | 82 | GRTYRGY SMA | 177 | WFRQPPGKE REFVA | 106 | AITWSEG NTY | 214 | YEDFVKGRFTISRDNAKNTL YLQMTSLKPEDTALYYCAA | 126 | KIRPYIFKIPGQY DY | 243 | WGQGT QVTVSS |
| 32 | T0170PMP 062G05 | 152 | EVQLVESGGGPVQ TGGSLRLSCVAS | 82 | GRTYRGY SMA | 177 | WFRQPPGKE REFVA | 106 | AITWSEG NTY | 216 | YEDFVKGRFTISRDNAKSTLY LQMTSLKPEDTALYYCAA | 126 | KIRPYIFKIPGQY DY | 243 | WGQGT QVTVSS |
| 33 | T0170PMP 114C05 | 152 | EVQLVESGGGPVQ TGGSLRLSCVAS | 82 | GRTYRGY SMA | 177 | WFRQPPGKE REFVA | 106 | AITWSEG NTY | 217 | YEDLVKGRFTISRDNAKNTLY LQMTSLKPEDTALYYCAA | 126 | KIRPYIFKIPGQY DY | 243 | WGQGT QVTVSS |
| 34 | T0170PMP 117G05 | 152 | EVQLVESGGGPVQ TGGSLRLSCVAS | 82 | GRTYRGY SMA | 177 | WFRQPPGKE REFVA | 106 | AITWSEG NTY | 214 | YEDFVKGRFTISRDNAKNTL YLQMTSLKPEDTALYYCAA | 127 | KIRPYIFKVPGQ YDY | 243 | WGQGT QVTVSS |
| 35 | T0170PMP 061F07 | 144 | EVQLVESGGGPVQ AGGSLRLSCAAS | 86 | GRTFRGY SMA | 177 | WFRQPPGKE REFVA | 106 | AITWSEG NTY | 214 | YEDFVKGRFTISRDNAKNTL YLQMTSLKPEDTALYYCAA | 123 | KIRPYIFKIAGQY DY | 244 | WGQGTL VTVSS |
| 36 | T0170PMP 061C09 | 144 | EVQLVESGGGPVQ AGGSLRLSCAAS | 81 | GRTYRGY SMG | 179 | WFRQAPGR EREFVA | 102 | AIVWSD GNTY | 200 | YEDSVKGRFTISRDNAKNTM YLQMTSLKPEDSATYYCAA | 123 | KIRPYIFKIAGQY DY | 243 | WGQGT QVTVSS |
| 37 | T0170PMP 124E06 | 156 | EVQLVESGGGPAQ AGGSLRLSCAAS | 81 | GRTYRGY SMG | 179 | WFRQAPGR EREFVA | 102 | AIVWSD GNTY | 200 | YEDSVKGRFTISRDNAKNTM YLQMTSLKPEDSATYYCAA | 123 | KIRPYIFKIAGQY DY | 244 | WGQGTL VTVSS |
| 38 | T0170PMP 111B02 | 144 | EVQLVESGGGPVQ AGGSLRLSCAAS | 81 | GRTYRGY SMG | 180 | WFRRAPGRE REFVA | 102 | AIVWSD GNTY | 218 | YEDPVKGRFTISRDNAKNT MYLQMTSLKPEDSATYYCA A | 123 | KIRPYIFKIAGQY DY | 243 | WGQGT QVTVSS |
| 39 | T0170PMP 062E08 | 157 | EVQLVESGGGPVQ AGDSLRLSCAAS | 87 | GRAYRGY SMG | 181 | WFRQVPGK EREFVA | 107 | AIVWTD GNTY | 219 | YEDSVKGRFTISRDITKNTMY LQMTSLKPEDSATYYCAA | 123 | KIRPYIFKIAGQY DY | 244 | WGQGTL VTVSS |
| 40 | T0170PMP 062G03 | 158 | EVQLVEFGGGPVQ AGDSLRLSCAAS | 87 | GRAYRGY SMG | 181 | WFRQVPGK EREFVA | 107 | AIVWTD GNTY | 219 | YEDSVKGRFTISRDITKNTMY LQMTSLKPEDSATYYCAA | 123 | KIRPYIFKIAGQY DY | 244 | WGQGTL VTVSS |
| 41 | T0170PMP 078E10 | 157 | EVQLVESGGGPVQ AGDSLRLSCAAS | 87 | GRAYRGY SMG | 181 | WFRQVPGK EREFVA | 108 | AIAWTD GNTY | 219 | YEDSVKGRFTISRDITKNTM YLQMTSLKPEDSATYYCAA | 123 | KIRPYIFKIAGQY DY | 244 | WGQGTL VTVSS |
| 42 | T0170PMP 062G10 | 157 | EVQLVESGGGPVQ AGDSLRLSCAAS | 87 | GRAYRGY SMG | 181 | WFRQVPGK EREFVA | 107 | AIVWTD GNTY | 220 | YEDSVKGRFTISRDVTKNTM YLQMTSLKPEDSATYYCAA | 123 | KIRPYIFKIAGQY DY | 244 | WGQGTL VTVSS |
| 43 | T0170PMP 115E06 | 159 | EVQLVESRGGPVQ AGDSLRLSCAAS | 87 | GRAYRGY SMG | 181 | WFRQVPGK EREFVA | 107 | AIVWTD GNTY | 219 | YEDSVKGRFTISRDITKNTMY LQMTSLKPEDSATYYCAA | 123 | KIRPYIFKIAGQY DY | 244 | WGQGTL VTVSS |
| 44 | T0170PMP 122B02 | 157 | EVQLVESGGGPVQ AGDSLRLSCAAS | 87 | GRAYRGY SMG | 181 | WFRQVPGK EREFVA | 109 | AIVWTD GNAY | 219 | YEDSVKGRFTISRDITKNTMY LQMTSLKPEDSATYYCAA | 123 | KIRPYIFKIAGQY DY | 244 | WGQGTL VTVSS |
| 45 | T0170PMP 061D07 | 157 | EVQLVESGGGPVQ AGDSLRLSCAAS | 87 | GRAYRGY SMG | 182 | WFRRVPGKE REFVA | 107 | AIVWTD GNTY | 219 | YEDSVKGRFTISRDITKNTMY LQMTSLKPEDSATYYCAA | 123 | KIRPYIFKIAGQY DY | 243 | WGQGT QVTVSS |

TABLE A-8-continued

Sequences for CDRs and frameworks, plus preferred combinations as provided in formula I, namely FR1-CDR1-FR2-CDR2-FR3-CDR3-FR4. "ID" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| ID | Name | FR1 | ID | CDR1 | ID | FR2 | ID | CDR2 | ID | FR3 | ID | CDR3 | ID | FR4 |
|---|---|---|---|---|---|---|---|---|---|---|---|---|---|---|
| 46 | T0170PMP126D09 | EVQLVSGGGPVQA GDSLRLSCAAS | 160 | GRAYRGY SMG | 87 | WFRQVPGK EREFVA | 181 | AIVWTD GNTY | 107 | YEDSVKGRFTISRDITKNTMY LQMTSLKPEDSATYYCAA | 219 | KIRPYIFKIAGQY DY | 123 | WGQGT QVTVSS |
| 47 | T0170PMP126B03 | EVQLVESGGGPVQ AGDSLRLSCAAS | 157 | GRTYRGY SMG | 81 | WFRQVPGK EREFVA | 181 | AIVWTD GNTY | 107 | YEDSVKGRFTISRDNTKNTM YLQMTSLKPEDSATYYCAA | 221 | KIRPYIFKIAGQY DY | 123 | WGQGTL VTVSS |
| 48 | T0170PMP126B02 | KVQLVESGGGPVQ AGDSLRLSCAAS | 161 | GRTYRGY SMG | 81 | WFRQVPGK EREFVA | 181 | AIVWTD GNTY | 107 | YEDSVKGRFTISRDNTKNTM YLQMTSLKPEDSATYYCAA | 221 | KIRPYIFKIAGQY DY | 123 | WGQGTL VTVSS |
| 49 | T0170PMP075G11 | EVQLVESGGGPVQ AGDSLRLSCAAS | 157 | GRTYRGY SMG | 81 | WFRQVPGK EREFVA | 181 | AIVWTD GNTY | 107 | YEDSVKGRFTISRDITKNTMY LHMTSLKPEDSATYYCAA | 222 | KIRPYIFKIAGQY DY | 123 | WGQGT QVTVSS |
| 50 | T0170PMP080E07 | EVQLVESGGGLVQ AGGSLRLSCAAS | 162 | GRAYRGY SMG | 87 | WFRQVPGK EREFVA | 181 | AIVWTD GNTY | 107 | YEDSVKGRFTISRDITKNTMY LQMTSLKPEDSATYYCAA | 219 | KIRPYIFKIAGQY DY | 123 | WGQGT QVTVSS |
| 51 | T0170PMP060E11 | EVQLVESGGGLVQ PGGSLRLSCAAS | 163 | GDIKSF DMG | 88 | WYRQAPGK QRDLVA | 183 | VIGSRGN NRGRTN | 110 | YADSVKGRFTISRDGTGNTV YLLMNKLRPEDTAIYYCNT | 223 | APLVAGRP | 128 | WGRGTL VTVSS |
| 52 | T0170PMP011A10 | EVQLVESGGGLVQ GGGSLSLSCAAS | 164 | GRTFSSY AMA | 89 | WFRQPPGKE REFVA | 177 | SISWSGE NTN | 111 | YRNSVKGRFTISRDNAKNTV YLQMNSLKPEDTAVYYCAA | 224 | KIAKTYPDNWY WTKSNNYNY | 129 | WGQGT QVTVSS |
| 53 | T0170PMP033G03 | EVQLVESGGGSVQ AGGSLRLSCAAS | 165 | GRTFSTN PMG | 90 | WFRQVPGK ERELIA | 184 | AVRWAD GNTF | 112 | YADSVKGRFTISRDNAKKTV YLQMNSLKSEDTATYYCAA | 225 | GRPWSAYHSPA EYVH | 130 | WGQGT QVTVSS |
| 54 | T0170PMP044A09 | EVQLVESGGGLVQ AGGSLRLSCAAS | 162 | GRTFSTN PMG | 90 | WFRQSPGKE RSLIA | 185 | AVRWAD GNTF | 112 | YADSVKGRFTISRDNAKKTV YLQMNSLKSEDTATYYCAA | 225 | GRPWSAYHSPA EYVH | 130 | WGQGT QVTVSS |
| 55 | T0170PMP043E10 | EVQLVESGGGLVQ AGGSLRLSCAAS | 162 | GRTFSTN PMG | 90 | WFRQSPGKE RSLIA | 185 | AARWAD GNTF | 113 | YADSVKGRFTISRDNAKKTV YLQMNSLKSEDTATYYCAA | 225 | GRPWSAYHSPA EYVH | 130 | WGQGT QVTVSS |
| 56 | T0170PMP044B10 | EVQLVESGGGLVQ AGGSLRLSCAAS | 162 | GRTFSTN PMG | 90 | WFRQSPGKE RSLIA | 185 | AVRWAD GNTF | 112 | YADSVKGRFTISRDNAKKTV YLQMNSLRSEDTATYYCAA | 226 | GRPWSAYHSPA EYVH | 130 | WGQGTL VTVSS |
| 57 | T0170PMP052G04 | EVQLVESGGGAVQ AGGSLRLSCAAS | 166 | GIRISRN MMG | 91 | WFRQAPGK QRDLVA | 186 | RITPGGD TY | 114 | YVDSVKGRFTISKDNAKNTV YLQMNSLKPEDTAVYYCNS | 227 | YSTLGS | 131 | WGQGT QVTVSS |
| 58 | T0170PMP062B02 | EVQLVESGGGAVQ PGGSLRLSCVAS | 167 | GIRISRN MMG | 91 | WFRRTPGRE RNMVA | 187 | RISPGGA TY | 115 | YVDSVKGRFSISKDDSKNTV YLQMDSLKPEDTAVYYCNS | 228 | YSTLGS | 131 | WGQGT QVTVSS |
| 59 | T0170PMP114D01 | EVQLVESGGGAVQ PGGSLRLSCVAS | 167 | GIRISRN MMG | 91 | WFRRTPGRE RNMVA | 187 | RISPGGA TY | 115 | YVDSVKGRFSISKDDSKNTV YLQMDSLKPEDTAVYYCNS | 228 | YSTLGS | 131 | WGQGTL VTVSS |
| 60 | T0170PMP080F02 | EVQLVESGGGAVQ PGGSLRLSCVAS | 167 | GIRISRN MMG | 91 | WFRRTPGRG RNMVA | 188 | RISPGGA TY | 115 | YVDSVKGRFSISKDDSKNTV YLQMDSLKPEDTAVYYCNS | 228 | YSTLGS | 131 | WGQGT QVTVSS |

TABLE A-8-continued

Sequences for CDRs and frameworks, plus preferred combinations as provided in formula I, namely FR1-CDR1-FR2-CDR2-FR3-CDR3-FR4. "ID" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| ID | Name | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 61 | T0170PMP 122A11 | 166 | EVQLVESGGGAVQ PGGSLRLSCAAS | 91 | GIRISRN MMG | 189 | WFRQAPGK SRDMVA | 116 | RISPGGD TY | 229 | VVDSVKGRFSISKDNAKNTV YLQMNSLRPEDTAIYYCNS | 131 | YSTLGS | 244 | WGQGTL VTVSS |
| 62 | T0170PMP 113E06 | 167 | EVQLVESGGGAVQ PGGSLRLSCVAS | 92 | GIRISNH MMG | 190 | WFRQAPGE QRDMVA | 116 | RISPGGD TY | 230 | VVDSVKGRFSISKDNAKNTV YLQMNNLKLEDTAVYYCNS | 132 | YRTLGS | 243 | WGQGT QVTVSS |
| 63 | T0170PMP 061E10 | 168 | EVQLVESGGGVVQ PGGSLRLSCAAS | 93 | GIRISTHT MG | 191 | WFRQAPEK QREMVA | 117 | QISPGGK TY | 231 | YIDSVKGRFTISKDNAKNTVF LRMNDLKPDDTAVYYCNS | 133 | YSTLGV | 244 | WGQGTL VTVSS |
| 64 | T0170PMP 061D03 | 168 | EVQLVESGGGVVQ PGGSLRLSCAAS | 93 | GIRISTHT MG | 191 | WFRQAPEK QREMVA | 117 | QISPGGK TY | 231 | YIDSVKGRFTISKDNAKNTVF LRMNDLKPDDTAVYYCNS | 133 | YSTLGV | 243 | WGQGT QVTVSS |
| 65 | T0170PMP 113E03 | 168 | EVQLVESGGGVVQ PGGSLRLSCAAS | 93 | GIRISTHT MG | 191 | WFRQAPEK QREMVA | 117 | QISPGGK TY | 232 | YIDSVKGRFTISKDNAKNTVF LRMNDLKPDGTAVYYCNS | 133 | YSTLGV | 243 | WGQGT QVTVSS |
| 66 | T0170PMP 050A11 | 162 | EVQLVESGGGLVQ AGGSLRLSCAAS | 94 | GRSFNM NPLG | 175 | WFRQSPGKE REFLA | 118 | AHRWSD GNTY | 233 | VVDSVKGRFTISRDNAKHTV YLQMNSLKSEDTAVYYCAA | 134 | GRPWSAFRSPG EYVY | 243 | WGQGT QVTVSS |
| 67 | T0170PMP 044A06 | 162 | EVQLVESGGGLVQ AGGSLRLSCAAS | 90 | GRTFSTN PMG | 192 | WFRQSPGN EREFVA | 118 | AHRWSD GNTY | 234 | YADSVKGRFAISRDNAKKTV YLQMNSLKSEDTAVYYCAA | 135 | GRPWSYRSPD EYVY | 243 | WGQGT QVTVSS |
| 68 | T0170PMP 044D11 | 162 | EVQLVESGGGLVQ AGGSLRLSCAAS | 95 | GRAFNT NPMG | 193 | WFRQPAGKE REFLA | 118 | AHRWSD GNTY | 233 | VVDSVKGRFTISRDNAKHTV YLQMNSLKSEDTAVYYCAA | 135 | GRPWSYRSPD EYVY | 243 | WGQGT QVTVSS |
| 69 | T0170PMP 043E08 | 162 | EVQLVESGGGLVQ AGGSLRLSCAAS | 96 | GRAFSM NPMG | 194 | WFRQSPGRE REFLA | 118 | AHRWSD GNTY | 235 | VVDSVKGRFTISRDNAKHTV YLQMSSLKSEDTAVYYCAA | 136 | GRPWSYRSPT EYVY | 244 | WGQGTL VTVSS |
| 70 | T0170PMP 043E06 | 169 | EVQLVESGGGAVQ AGGSLRLSCAAS | 97 | GRSFSTN PMG | 195 | WFRQPPRKE REFVA | 118 | AHRWSD GNTY | 236 | YADSVKGRFTISRDNAKHTV YLQMNSLKSEDTAVYYCAA | 137 | GRPWSAAHSP NEYVY | 243 | WGQGT QVTVSS |
| 71 | T0170PMP 043E07 | 162 | EVQLVESGGGLVQ AGGSLRLSCAAS | 98 | GRSFSAN PMG | 196 | WFRQPPGKE RESVA | 118 | AHRWSD GNTY | 236 | YADSVKGRFTISRDNAKHTV YLQMNSLKSEDTAVYYCAA | 137 | GRPWSAAHSP NEYVY | 243 | WGQGT QVTVSS |
| 72 | T0170PMP 039D06 | 162 | EVQLVESGGGLVQ AGGSLRLSCAAS | 99 | GRGFSTN PMG | 175 | WFRQSPGKE REFLA | 118 | AHRWSD GNTY | 237 | VVDSVKGRFAISRDNAKHTV HLQMNSLKSEDTAVYYCAA | 138 | GRPWSDYRAPS EYIY | 243 | WGQGT QVTVSS |
| 73 | T0170PMP 044F10 | 162 | EVQLVESGGGLVQ AGGSLRLSCAAS | 99 | GRGFSTN PMG | 175 | WFRQSPGKE REFLA | 118 | AHRWSD GNTY | 237 | VVDSVKGRFAISRDNAKHTV HLQMNSLKSEDTAVYYCAA | 139 | GRPWSDFRAPS EYIY | 246 | SGPGTQ VTVSS |
| 74 | T0170PMP 044B11 | 162 | EVQLVESGGGLVQ AGGSLRLSCAAS | 95 | GRAFNT NPMG | 197 | WFRQSPGKE REFLA | 119 | AVRWH DGSTY | 238 | YTDSVKGRFTISRDNAKNTV YLQMNSLKSEDTAVYYCAA | 140 | GRPWSAYHSPN EYVY | 244 | WGQGTL VTVSS |
| 75 | T0170PMP 044C08 | 162 | EVQLVESGGGLVQ AGGSLRLSCAAS | 95 | GRAFNT NPMG | 197 | WFRQSPGKE REFLA | 119 | AVRWH DGSTY | 239 | YTDSVKGRFTISRDNAKNTV CLQMNSLKSEDTAVYYCAA | 140 | GRPWSAYHSPN EYVY | 243 | WGQGT QVTVSS |

TABLE A-8-continued

Sequences for CDRs and frameworks, plus preferred combinations as provided in formula I, namely FR1-CDR1-FR2-CDR2-FR3-CDR3-FR4. "ID" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| ID | Name | FR1 | ID | CDR1 | ID | FR2 | ID | CDR2 | ID | FR3 | ID | CDR3 | ID | FR4 |
|---|---|---|---|---|---|---|---|---|---|---|---|---|---|---|
| 76 | T0170PMP 043B03 | EVQLVEFGGGLVQ AGGSLRLSCAAS | 171 | GRAFSTN PMG | 100 | WFRQSPGKE REFVG | 198 | AVRWSD GSTY | 120 | SADSVKGRFTVFRDNAKNT VYLQMNSLKSEDTAVYYCA A | 240 | GRPWSAYHSPK EYVY | 141 | WGQGTL VTVSS | 244 |
| 77 | T0170PMP 039E06 | EVQLVESGGGLVQ AGDSLRLSCAAS | 172 | GRAFSTN PMG | 100 | WFRQSPGKE REFVA | 175 | AHRWSD GSTF | 121 | VADSVKGRFTISRDNAKNTV SLQMNSLKSADTAVYYCAA | 241 | GRPWSAYHSPR EYIY | 142 | WGRGT QVTVSS | 247 |
| 78 | T0170PMP 049A04 | EVQLVESGGGLVQ AGDSLRLSCAAS | 172 | GRAFSTN PMG | 100 | WFRQSPGKE REFVA | 175 | AHRWSD GSTF | 121 | VADSVKGRFTISRDNAKNTV SLQMNSLKSADTAVYYCAA | 241 | GRPWSAYHSPR EYIY | 142 | WGRGTL VTVSS | 245 |
| 79 | T0170PMP 043F09 | EVQLVESGGGLVQ AGASLRLSCAAS | 173 | GRAFSTN PMG | 100 | WFRQSPGQ EREFLA | 199 | AVRWAD GNTY | 122 | YTDSVKGRATISRDNAKKTV YLQLNNLKSEDAAVYYCAA | 242 | GRPWSAYHAPK EYIY | 143 | WGQGTL VTVSS | 244 |
| 80 | T0170PMP 044C11 | EVQLVESGGGLVQ AGASLRLSCAAS | 173 | GRAFSTN PMG | 100 | WFRQSPGQ EREFLA | 199 | AVRWAD GNTY | 122 | YTDSVKGRATISRDNAKKTV YLQLNNLKSEDAAVYYCAA | 242 | GRPWSAYHAPK EYIY | 143 | WGQGT QVTVSS | 243 |

TABLE A-9

Sequences of multispecific polypeptides (with and without tags). "ID" refers to the SEQ ID NO as used herein.

| ID | Name | Description | Amino acid sequence |
|---|---|---|---|
| 248 | T017000001 | T017011A10-35GS-T017011A10FLAG3-HIS6 | EVQLVESGGGLVQGGGSLSLSCAASGRTFSSYAMAWFRQPPGKEREFVASISWSGENTNYRNSVKGRFTISRDNAKNTVYL QMNSLKPEDTAVYYCAAKIAKTYPDNWYTKSNNYNYWGQGTLVTVSSGGGGSGGGGSGGGGSGGGGSGGGGSGGGGS GSGGGGSEVQLVESGGGLVQGGGSLSLSCAASGRTFSSYAMAWFRQPPGKEREFVASISWSGENTNYRNSVKGRFTISRDN AKNTVYLQMNSLKPEDTAVYYCAAKIAKTYPDNWYTKSNNYNYWGQGTLVTVSSGAADYKDHDGDYKDHDIDYKDDDD KGAAHHHHHH |
| 249 | T017000004 | 20CD019C07-5GS-T017033G03-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSEVQLVESGGGSVQAGGSLRLSCAASGRTFSTNPM GWFRQVPGKERELIAAVRWADGNTPYADSVKGRFTISRDNAKKTVYLQMNSLKSEDTATYYCAAGRPWSAYHSPAEYVHW GGQTLVTVSSGAADYKDHDGDYKDHDIDYKDDDDKGAAHHHHHH |
| 250 | T017000005 | 20CD019C07-5GS-T017011A10-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSEVQLVESGGGLVQGGGSLSLSCAASGRTFSSYAMA WFRQPPGKEREFVASISWSGENTNYRNSVKGRFTISRDNAKNTVYLQMNSLKPEDTAVYYCAAKIAKTYPDNWYTKSNN YNYWGQGTLVTVSSGAADYKDHDGDYKDHDIDYKDDDDKGAAHHHHHH |
| 251 | T017000006 | 20CD019C07-5GS-cAbLys3-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSDVQLQASGGGSVQAGGSLRLSCAASGYTIGPYCM GWFRQAPGKEREGVAAINMGGITYYADSVKGRFTISQDNAKNTVYLLMNSLEPEDTAIYYCAADSTIYASYECGHGLSTG GYGYDSWGQGTQVTVSSGAADYKDHDGDYKDHDIDYKDDDDKGAAHHHHHH |
| 252 | T017000010 | 20CD019C07-9GS-T017033G03-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSEVQLVESGGGSVQAGGSLRLSCAASGRTFST NPMGWFRQVPGKERELIAAVRWADGNTPYADSVKGRFTISRDNAKKTVYLQMNSLKSEDTATYYCAAGRPWSAYHSPAEY VHWGQGTLVTVSSGAADYKDHDGDYKDHDIDYKDDDDKGAAHHHHHH |
| 253 | T017000011 | 20CD019C07-9GS-T017011A10-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSEVQLVESGGGLVQGGGSLSLSCAASGRTFSS YAMAWFRQPPGKEREFVASISWSGENTNYRNSVKGRFTISRDNAKNTVYLQMNSLKPEDTAVYYCAAKIAKTYPDNWYT KSNNYNYWGQGTLVTVSSGAADYKDHDGDYKDHDIDYKDDDDKGAAHHHHHH |
| 254 | T017000012 | 20CD019C07-9GS-cAbLys3-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSDVQLQASGGGSVQAGGSLRLSCAASGYTIG PYCMGWFRQAPGKEREGVAAINMGGITYYADSVKGRFTISQDNAKNTVYLLMNSLEPEDTAIYYCAADSTIYASYECGHG LSTGGYGYDSWGQGTQVTVSSGAADYKDHDGDYKDHDIDYKDDDDKGAAHHHHHH |
| 255 | T017000016 | 20CD019C07-35GS-T017033G03-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSGGGGSGGGGSGGGGSGGGGSGGGGSEV QLVESGGGSVQAGGSLRLSCAASGRTFSTNPMGWFRQVPGKERELIAAVRWADGNTPYADSVKGRFTISRDNAKKTVYLQ MNSLKSEDTATYYCAAGRPWSAYHSPAEYVHWGQGTLVTVSSGAADYKDHDGDYKDHDIDYKDDDDKGAAHHHHHH |
| 256 | T017000017 | 20CD019C07-35GS-T017011A10-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSGGGGSGGGGSGGGGSGGGGSGGGGSEV QLVESGGGLVQGGGSLSLSCAASGRTFSSYAMAWFRQPPGKEREFVASISWSGENTNYRNSVKGRFTISRDNAKNTVYLQM NSLKPEDTAVYYCAAKIAKTYPDNWYTKSNNYNYWGQGTLVTVSSGAADYKDHDGDYKDHDIDYKDDDDKGAAHHHHH H |

TABLE A-9-continued

Sequences of multispecific polypeptides (with and without tags). "ID" refers to the SEQ ID NO as used herein.

| ID | Name | Description | Amino acid sequence |
|---|---|---|---|
| 257 | T017000018 | 20CD019C07-35GS-cAbLys3-FLAG3-HIS6 | EVQLVESGGGLVQPGGSLRLSCTFSGGTFSSYTMGWFRQAPGKEREFVAEVRWGGVTTYSNLKDRFSISEDSVKNAVYLQ MNSLKPEDTAVYYCAAVRQMYMTVVPDYWGQGTLVTVSSGGGGSGGGGSGGGGSGGGGSGGGGSDV QLQASGGSVQAGGSLRLSCAASGRPWSAYHSPAEYVHWGQGTLVTVSSGGGGSGGGGSEVQLVESGGGLVQPGGSLRLSCTFSGGT MNSLKPEDTAIYYCAADSTIYASYECHGLSTGGYGYDSWGQGTQVTVSSGAADYKDHDGDYKDHDIDYKDDDDKGAAH HHHHH |
| 258 | T017000020 | T0170033G03-9GS-20CD019C07-FLAG3-HIS6 | EVQLVESGGGSVQAGGSLRLSCAAGRPWSAYHSPAEYVHWGQGTLVTVSSGGGGSGGGGSEVQLVESGGGLVQPGGSLRLSCTFSGGT QMNSLKSEDTATYYCAAGRPWSAYHSPAEYVHWGQGTLVTVSSGGGGSGGGGSEVQLVESGGGLVQPGGSLRLSCTFSGGT FSSYTMGWFRQAPGKEREFVAEVRWGGVTTYSNLKDRFSISEDSVRNAVYLQMNSLKPEDTAVYYCAAVRQMYMTVPD YWGQGTLVTVSSGAADYKDHDGDYKDHDIDYKDDDDKGAAHHHHHH |
| 259 | T017000021 | T0170033G03-35GS-20CD019C07-FLAG3-HIS6 | EVQLVESGGGSVQAGGSLRLSCAASGRTFSTNPMGWFRQVPGKERELIAAVRWADGNTFYADSVKGRFTISRDNAKKTVYL QMNSLKSEDTATYYCAAGRPWSAYHSPAEYVHWGQGTLVTVSSGGGGSGGGGSGGGGSGGGGSGGGGS GSEVQLVESGGGLVQPGGSLRLSCTFSGGTFSSYTMGWFRQAPGKEREFVAEVRWGGVTTYSNLKDRFSISEDSVKNAVYL QMNSLKPEDTAVYYCAAVRQMYMTVVPDYWGQGTLVTVSSGAADYKDHDGDYKDHDIDYKDDDDKGAAHHHHHH |
| 260 | T017000022 | T0170011A10-9GS-20CD019C07-FLAG3-HIS6 | EVQLVESGGGLVQPGGSLSLSCAASGRTFSSYAMAWFRQPPGKEREFVASISWSGENTNYRNSVKGRFTISRDNAKNTVYL QMNSLKPEDTAVYYCAAKIAKTYPDNWYWTKSNNYNYWGQGTLVTVSSGGGGSGGGGSGGGGSGGGGS GSGGGGSEVQLVESGGGLVQPGGSLRLSCTFSGGTFSSYTMGWFRQAPGKEREFVAEVRWGGVTTYSNLKDRFSISEDSV KNAVYLQMNSLKPEDTAVYYCAAVRQMYMTVVPDYWGQGTLVTVSSGAADYKDHDGDYKDHDIDYKDDDDKGAAHHH HHH |
| 261 | T017000023 | cAbLys3(D1E)-35GS-20CD019C07-FLAG3-HIS6 | EVQLQASGGSVQAGGSLRLSCAASGRTFSSYAMAWFRQPPGKEREGVAAINMGGITYYADSVKGRFTISQDNAKNTVY LLMNSLEPEDTAIYYCAADSTIYASYECHGLSTGGYGYDSWGQGTQVTVSSGGGGSGGGGSGGGGSGGGGSGGGGSG GGSGGGGSEVQLVESGGGLVQPGGSLRLSCTFSGGTFSSYTMGWFRQAPGKEREFVAEVRWGGVTTYSNLKDRFSISED SVKNAVYLQMNSLKPEDTAVYYCAAVRQMYMTVVPDYWGQGTLVTVSSGAADYKDHDGDYKDHDIDYKDDDDKGAAH HHHHH |
| 262 | T017000024 | T0170033G03-35GS-cAbLys3-FLAG3-HIS6 | EVQLVESGGGSVQAGGSLRLSCAASGRTFSTNPMGWFRQVPGKERELIAAVRWADGNTFYADSVKGRFTISRDNAKKTVYL QMNSLKSEDTATYYCAAGRPWSAYHSPAEYVHWGQGTLVTVSSGGGGSGGGGSGGGGSGGGGSGGGGSGGGG GSDVQLQASGGSVQAGGSLRLSCAASGYTIGPYCMGWFRQAPGKEREGVAAINMGGITYYADSVKGRFTISQDNAKNT VYLLMNSLEPEDTAIYYCAADSTIYASYECHGLSTGGYGYDSWGQGTQVTVSSGAADYKDHDGDYKDHDIDYKDDDDKG AAHHHHHH |
| 263 | T017000026 | T0170011A10-9GS-20CD019C07-FLAG3-HIS6 | EVQLVESGGGLVQPGGSLRLSCAASGRTFSSYAMAWFRQPPGKEREFVASISWSGENTNYRNSVKGRFTISRDNAKNTVYL QMNSLKPEDTAVYYCAAKIAKTYPDNWYWTKSNNYNYWGQGTLVTVSSGGGGSGGGGSEVQLVESGGGLVQPGGSLRLSC TFSGGTFSSYTMGWFRQAPGKEREFVAEVRWGGVTTYSNLKDRFSISEDSVKNAVYLQMNSLKPEDTAVYYCAAVRQMY MTVVPDYWGQGTLVTVSSGAADYKDHDGDYKDHDIDYKDDDDKGAAHHHHHH |
| 264 | T017000027 | T0170011A10-35GS-cAbLys3-FLAG3-HIS6 | EVQLVESGGGLVQPGGSLSLSCAASGRTFSSYAMAWFRQPPGKEREFVASISWSGENTNYRNSVKGRFTISRDNAKNTVYL QMNSLKPEDTAVYYCAAKIAKTYPDNWYWTKSNNYNYWGQGTLVTVSSGGGGSGGGGSGGGGSGGGG GSGGGGSDVQLQASGGSVQAGGSLRLSCAASGYTIGPYCMGWFRQAPGKEREGVAAINMGGITYYADSVKGRFTISQD NAKNTVYLLMNSLEPEDTAIYYCAADSTIYASYECHGLSTGGYGYDSWGQGTQVTVSSGAADYKDHDGDYKDHDIDYKD DDKGAAHHHHHH |
| 265 | T017000034 | T0170061F07-35GS-20CD019C07-FLAG3-HIS6 | EVQLVESGGGPVQAGGSLRLSCAASGRTFRGYSMAWFRQPPGKEREFVAAITWSEGNTYYEDFVKGRFTISRDNAKNTLYL QMTSLKPEDTALYYCAAKIRPYIFKIAGQYDYWGQGTLVTVSSGGGGSGGGGSGGGGSGGGGSGGGGSE VQLVESGGGLVQPGGSLRLSCTFSGGTFSSYTMGWFRQAPGKEREFVAEVRWGGVTTYSNLKDRFSISEDSVKNAVYLQM NSLKPEDTAVYYCAAVRQMYMTVVPDYWGQGTLVTVSSGAADYKDHDGDYKDHDIDYKDDDDKGAAHHHHHH |

TABLE A-9-continued

Sequences of multispecific polypeptides (with and without tags). "ID" refers to the SEQ ID NO as used herein.

| ID | Name | Description | Amino acid sequence |
|---|---|---|---|
| 266 | T017000036 | T017017G03-35GS-20CD019C07-FLAG3-HIS6 | EVQLVESGGGPVQAGGSLRLSCAASGRTYRGYSMGWFRQAPGKEREFVAAIWSGGNTYYEDSVKGRFTISRDNAKNTMY LQMTSLKPEDSATYYCAAKIRPYIFKIAGQYDYWGQGTLVTVSSGGGSGGGSGGGSGGGSGGGSGGGSGGGGS EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGAADYKDHDIDYKDDDDKGAAHHHHHH |
| 267 | T017000039 | T017061F04-35GS-20CD019C07-FLAG3-HIS6 | EVQLVESGGPVQAGGSLRLSCAASGRTYRGYSMAWFRQSPGKEREFVAAIWSDGNTYYEDFVKGRFTISRDSAKNTLYL QMTNLKPEDTALYYCAAKIRPYIFKIAGQYDYWGQGTLVTVSSGGGSGGGSGGGSGGGSGGGSGGGSGGGGSE VQLVESGGGLVQPGGSLRLSCTFSGGTFSSYTMGWFRQAPGKEREFVAEVRWGGVTTYSNSLKDRFSISEDSVKNAVYLQM NSLKPEDTAVYYCAAVRQMYMTVVPDYWGQGTLVTVSSGAADYKDHDGDYKDHDIDYKDDDDKGAAHHHHHH |
| 268 | T017000040 | T017060E11-35GS-20CD019C07-FLAG3-HIS6 | EVQLVESGGGLVQPGGSLRLSCAASGDIYKSFDMGWYRQAPGKQRDLVAVIGSRGNNRGRTNYADSVKGRFTISRDGTGN TVYLLMNKLRPEDTAIYYCNTAPLVAGRPWGRGTLVTVSSGGGSGGGSGGGSGGGSGGGSGGGSGGGGSEVQ LVESGGGLVQPGGSLRLSCTFSGGTFSSYTMGWFRQAPGKEREFVAEVRWGGVTTYSNSLKDRFSISEDSVKNAVYLQMNS LKPEDTAVYYCAAVRQMYMTVVPDYWGQGTLVTVSSGAADYKDHDGDYKDHDIDYKDDDDKGAAHHHHHH |
| 269 | T017000043 | T017050A11-35GS-20CD019C07-FLAG3-HIS6 | EVQLVESGGGLVQAGGSLRLSCAAGRSFNMMPLGWFRQSPGKEREFVAAHRWSDGNTYYVDSVKGRFTISRDNAKNTVY LQMNSLKSEDTAVYYCAAGRPWSAFRSPGEYYVWGQGTLVTVSSGGGSGGGSGGGSGGGSGGGSGGGSGGGG GSEVQLVESGGGLVQPGGSLRLSCTFSGGTFSSYTMGWFRQAPGKEREFVAEVRWGGVTTYSNSLKDRFSISEDSVKNAVYL QMNSLKPEDTAVYYCAAVRQMYMTVVPDYWGQGTLVTVSSGAADYKDHDGDYKDHDIDYKDDDDKGAAHHHHHH |
| 270 | T017000045 | T017033G03-35GS-20CD019C07-FLAG3-HIS6 | EVQLVESGGGSVQPGGGLVQPGGSLRLSCAASGRTFSTNPMGWFRQVPGKERELIAAVRWADGNTFYADSVKGRFTISRDNAKKTVYL QMNSLKSEDTATYYCAAGRPWSAYHSPAEYVHWGQGTLVTVSSGGGSGGGSGGGSGGGSGGGSGGGG GSEVQLVESGGGLVQPGGSLRLSCTFSGGTFSSYTMGWFRQAPGKEREFVAEVRWGGVTTYSNSLKDRFSISEDSVKNAVYL QMNSLKPEDTAVYYCAAVRQMYMTVVPDYWGQGTLVTVSSGAADYKDHDGDYKDHDIDYKDDDDKGAAHHHHHH |
| 271 | T017000047 | T017011A10-35GS-20CD019C07-FLAG3-HIS6 | EVQLVESGGGLVQGGGSLSLSCAASGRTFSSYAMAWFRQPPGKEREFVASISWSGENTNYRNSVKGRFTISRDNAKNTVYL QMNSLKPEDTAVYYCAAKIAKTYPDNWYWTKSNNYNYWGQGTLVTVSSGGGSGGGSGGGSGGGSGGGSGGG GSGGGGSEVQLVESGGGLVQPGGSLRLSCTFSGGTFSSYTMGWFRQAPGKEREFVAEVRWGGVTTYSNSLKDRFSISEDSV KNAVYLQMNSLKPEDTAVYYCAAVRQMYMTVVPDYWGQGTLVTVSSGAADYKDHDGDYKDHDIDYKDDDDKGAAHHH HHH |
| 272 | T017000048 | T017052G04-35GS-20CD019C07-FLAG3-HIS6 | EVQLVESGGGLVQPGGAVQPGGSLRLSCAASGIRISRNMMGWFRQAPGKQRDLVARITPGGDTYYVDSVKGRFSISDNAKNTVYLQ MNSLKPEDTAVYYCNSYSTLGSWGQGTFSSYTMGWFRQAPGKEREFVAEVRWGGVTTYSNSLKDRFSISEDSVKNAVYLQMNSLKPEDTAV LVQPGGSLRLSCTFSGGTFSSYTMGWFRQAPGKEREFVAEVRWGGVTTYSNSLKDRFSISEDSVKNAVYLQMNSLKPEDTAV YYCAAVRQMYMTVVPDYWGQGTLVTVSSGAADYKDHDIDYKDDDDKGAAHHHHHH |
| 273 | T017000052 | 20CD019C07-T017061F04-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGSGGGSGGGSGGGSGGGSGGGSGGGGSEV QLVESGGGLVQPGGSLRLSCAASGRTYRGYSMAWFRQSPGKEREFVAAIWSDGNTYYEDFVKGRFTISRDSAKNTLYLQM TNLKPEDTALYYCAAKIRPYIFKIAGQYDYWGQGTLVTVSSGAADYKDHDGDYKDHDIDYKDDDDKGAAHHHHHH |
| 274 | T017000053 | 20CD019C07-T017060E11-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGSGGGSGGGSGGGSGGGSGGGSGGGGSEV QLVESGGGLVQPGGSLRLSCAASGDIYKSFDMGWYRQAPGKQRDLVAVIGSRGNNRGRTNYADSVKGRFTISRDGTNTV YLLMNKLRPEDTAIYYCNTAPLVAGRPWGRGTLVTVSSGAADYKDHDGDYKDHDIDYKDDDDKGAAHHHHHH |
| 275 | T017000056 | 20CD019C07-T017052G04- | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGSGGGSGGGSGGGSEV |

TABLE A-9-continued

Sequences of multispecific polypeptides (with and without tags). "ID" refers to the SEQ ID NO as used herein.

| ID | Name | Description | Amino acid sequence |
|---|---|---|---|
| 276 | T017000057 | FLAG3-HIS6 | QLVESGGAVQPGGSLRLSCAASGIRISRNMMGWFRQAPGKQRDLVARITPGGDTYVVDSVKGRFSISKDNAKHHHHHH NSLKPEDTAVYYCNSYSTLGSWGQGTLVTVSSGAADYKDHDIDYKDDDDKGAAHHHHHH |
| 277 | T017000059 | 20CD019C07-35GS-T017050A11-FLAG3-HIS6 | EVQLVESGGGLVQPGGSLRLSCTFSGGTFSSYTMGWFRQAPGKEREFVAEVRWGGVTTYSNLKDRFSISEDSVKNAVYLQ MNSLKPEDTAVYYCAAVRQMYMTVVPDYWGQGTLVTVSSGGGGSGGGGSGGGGSGGGGSGGGGSEV QLVESGGGLVQAGGSLRLSCAASGRSFNMNPLGWFRQSPGKEREFVAAHRWSDGNTYYVDSVKGRFTISRDNAKNTVYLQ MNSLKSEDTAVYYCAAGRPWSAFRPSPGEYVYWGQGTLVTVSSGAADYKDHDGDYKDHDIDYKDDDDKGAAHHHHHH |
| 278 | T017000061 | 20CD019C07-35GS-T017033G03-FLAG3-HIS6 | EVQLVESGGGLVQPGGSLRLSCTFSGGTFSSYTMGWFRQAPGKEREFVAEVRWGGVTTYSNLKDRFSISEDSVKNAVYLQ MNSLKPEDTAVYYCAAVRQMYMTVVPDYWGQGTLVTVSSGGGGSGGGGSGGGGSGGGGSGGGGSEV QLVESGGGLVQAGGSLRLSCAASGRTFSTNPMGWFRQVPGKERELIAAVRWADGNTFYADSVKGRFTISRDNAKKTVYLQ MNSLKSEDTATYYCAAGRPWSAVHSPAEYVHWGQGTLVTVSSGAADYKDHDGDYKDHDIDYKDDDDKGAAHHHHHH |
| 279 | T017000062 | 20CD019C07-35GS-T017011A10-FLAG3-HIS6 | EVQLVESGGGLVQPGGSLRLSCTFSGGTFSSYTMGWFRQAPGKEREFVAEVRWGGVTTYSNLKDRFSISEDSVKNAVYLQ MNSLKPEDTAVYYCAAVRQMYMTVVPDYWGQGTLVTVSSGGGGSGGGGSGGGGSGGGGSGGGGSEV QLVESGGGLVQQGGSLSLSCAASGRTFSSYAMAWFRQPPGKEREFVASISWSGENTNYRNSVKGRFTISRDNAKNTVYLQM NSLKPEDTAVYYCAAKIAKTYPDNWTWTKSNNYNYWGQGTLVTVSSGAADYKDHDGDYKDHDIDYKDDDDKGAAHHHH HH |
| 280 | T017000066 | 20CD019C07-35GS-T017117G03-FLAG3-HIS6 | EVQLVESGGGLVQPGGSLRLSCTFSGGTFSSYTMGWFRQAPGKEREFVAEVRWGGVTTYSNLKDRFSISEDSVKNAVYLQ MNSLKPEDTAVYYCAAVRQMYMTVVPDYWGQGTLVTVSSGGGGSGGGGSGGGGSGGGGSGGGGSEV QLVESGGGPVQAGGSLRLSCAASGRTRGYSMGWFRQAPGKEREFVAAIVWSGGNTYYEDFVKGRFTISRDNAKNTMYLQ MTSLKPEDTAVYYCAAKIRPYIFKIAGQYDYWGQGTLVTVSSGAADYKDHDGDYKDHDIDYKDDDDKGAAHHHHHH |
| 281 | T017000071 | 20CD019C07-35GS-T017061D09-FLAG3-HIS6 | EVQLVESGGGLVQPGGSLRLSCTFSGGTFSSYTMGWFRQAPGKEREFVAEVRWGGVTTYSNLKDRFSISEDSVKNAVYLQ MNSLKPEDTAVYYCAAVRQMYMTVVPDYWGQGTLVTVSSGGGGSGGGGSGGGGSGGGGSGGGGSEV QLVESGGGLVQTGGSLRLSCVASGRTYRGYSMAWFRQPPGKEREFVAAITWSEGNTYYEDFVKGRFTISRDNAKNTLYLQM TSLKPEDTALYYCAAKIRPYIFKIPGQYDYWGQGTLVTVSSGAADYKDHDGDYKDHDIDYKDDDDKGAAHHHHHH |
| 282 | T017000072 | 20CD019C07-35GS-T017061F07-FLAG3-HIS6 | EVQLVESGGGLVQPGGSLRLSCTFSGGTFSSYTMGWFRQAPGKEREFVAEVRWGGVTTYSNLKDRFSISEDSVKNAVYLQ MNSLKPEDTAVYYCAAVRQMYMTVVPDYWGQGTLVTVSSGGGGSGGGGSGGGGSGGGGSGGGGSEV QLVESGGGPVQAGGSLRLSCAASGRTRGYSMAWFRQPPGKEREFVAAITWSEGNTYYEDFVKGRFTISRDNAKNTLYLQM TSLKPEDTALYYCAAKIRPYIFKIAGQYDYWGQGTLVTVSSGAADYKDHDGDYKDHDIDYKDDDDKGAAHHHHHH |
| 283 | T017000084 | 20CD019C07-35GS-T017061D09-35GS-20CD019C07-FLAG3-HIS6 | EVQLVESGGGLVQTGGSLRLSCVASGRTYRGYSMAWFRQPPGKEREFVAAITWSEGNTYYEDFVKGRFTISRDNAKNTLYLQ MTSLKPEDTALYYCAAKIRPYIFKIPGQYDYWGQGTLVTVSSGGGGSGGGGSGGGGSGGGGSGGGGSEV QLVESGGGLVQPGGSLRLSCTFSGGTFSSYTMGWFRQAPGKEREFVAEVRWGGVTTYSNLKDRFSISEDSVKNAVYLQMN SLKPEDTAVYYCAAVRQMYMTVVPDYWGQGTLVTVSSGAADYKDHDGDYKDHDIDYKDDDDKGAAHHHHHH |
| 284 | T017000090 | 20CD019C07(E1D)-35GS-T017117G03-A | DVQLVESGGGLVQPGGSLRLSCTFSGGTFSSYTMGWFRQAPGKEREFVAEVRWGGVTTYSNLKDRFSISEDSVKNAVYLQ MNSLKPEDTAVYYCAAVRQMYMTVVPDYWGQGTLVTVSSGGGGSGGGGSGGGGSGGGGSGGGGSEV QLVESGGGPVQAGGSLRLSCAASGRTRGYSMGWFRQAPGKEREFVAAIVWSGGNTYYEDFVKGRFTISRDNAKNTMYLQ MTSLKPEDTAVYYCAAKIRPYIFKIAGQYDYWGQGTLVTVSSA |
| 285 | T017000090 | RSV007B02-35GS-T017061F04-FLAG3-HIS6 | EVQLVESGGGLVQAGDSLRLSCAASGTFSSYAMGWFRQAPGKEREFVAAISWSDGSTYYADSVKGRFTISRDNAKNTVYL QMNSLKPEDTAVYYCAADLTSTNPGSYIYIWAYDYWGQGTQVTVSSGGGGSGGGGSGGGGSGGGGSGGGGSGG GGSEVQLVESGGGPVQAGGSLRLSCAASGGTRYGYSMAWFRQSPGKEREFVAAIVWSDGNTYYEDFVKGRFTISRDSAKNT LYLQMTNLKPEDTALYYCAAKIRPYIFKIAGQYDYWGQGTLVTVSSGAADYKDHDGDYKDHDIDYKDDDDKGAAHHHHHH |

TABLE A-9-continued

Sequences of multispecific polypeptides (with and without tags). "ID" refers to the SEQ ID NO as used herein.

| ID | Name | Description | Amino acid sequence |
|---|---|---|---|
| 285 | T017000091 | RSV007B02-35GS-T0170117G03-FLAG3-HIS6 | EVQLVESGGGLVQAGDSLRLSCAASGRTFSSYAMGWFRQAPGKEREFVAAISWSDGSTYYADSVKGRFTISRDNAKNTVYLQMNSLKPEDTAVYYCAADLTSNPGSYIYIWAYDYWGQGTQVTVSSGGGGSGGGGSGGGGSGGGGSGGGGSGGSEVQLVESGGGPVQAGGSLRLSCAASGRTYRGYSMGWFRQAPGKEREFVAAIVWSGNTYYEDSVKGRFTISRDNAKNTMYLQMTSLKPEDSATYYCAAKIRPYIFKIAGQYDYWGQGTLVTVSSGAADYKDHDGYKDHDIDYKDDDDKGAAHHHHHH |
| 286 | T017000094 | 20CD019C07-35GS-T0170117G03-35GS-ALB11-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSGGSEVQLVESGGGPVQAGGSLRLSCAASGRTFSSFGMSWVRQAPGKGLEWVSSISGSGSDTLYADSVKGRFTISRDNAKTTLYLQMNSLRPEDTAVYYCTIGGSLSRSSQGTLVTVSSGAADYKDHDGYKDHDIDYKDDDDKGAAHHHHHH |
| 287 | T017000096 | 20CD019C07-35GS-T017060E11-35GS-ALB11-FLAG3-HIS6 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSEVQLVESGGGLVQPGGSLRLSCAASGDIYKSFDMGWYRQAPGKQRDLVAVIGSRGNNRGRTNYADSVKGRFTISRDGTGNTVYLLMNKLRPEDTAIYYCNTAPLVAGRPWGRGTLVTVSSGGGGSGGGGSGGGGSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAADYKDHDGYKDHDIDYKDDDDKGAAHHHHHH |
| 288 | T017000100 | T0170117G03-35GS-HER2005F07(Q108L)-FLAG3-HIS6 | EVQLVESGGGPVQAGGSLRLSCAASGRTYRGYSMGWFRQAPGKEREFVAAIVWSGGNTYYEDSVKGRFTISRDNAKNTMYLQMTSLKPEDSATYYCAAKIRPYIFKIAGQYDYWGQGTLVTVSSGGGGSGGGGSGGGGSGGGGSGGGGSEVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSGGGGSGGGGSGGGGSGGGGSGGGGSEVQLVESGGGPVQAGGSLRLSCAASGRTYRGYSMGWFRQAPGKEREFVAAIVWSGNTYYEDSVKGRFTISRDNAKNTMYLQMTSLKPEDSATYYCAAKIRPYIFKIAGQYDYWGQGTLVTVSSGAADYKDHDGYKDHDIDYKDDDDKGAAHHHHHH |
| 289 | T017000101 | HER2005F07(Q108L)-35GS-T0170117G03-FLAG3-HIS6 | EVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSGGGGSGGGGSGGGGSGGGGSGGGGSEVQLVESGGGPVQAGGSLRLSCAASGRTYRGYSMGWFRQAPGKEREFVAAIVWSGNTYYEDSVKGRFTISRDNAKNTMYLQMTSLKPEDSATYYCAAKIRPYIFKIAGQYDYWGQGTLVTVSSGAADYKDHDGYKDHDIDYKDDDDKGAAHHHHHH |
| 290 | T017000088 | RSV007B02(E1D)-35GS-T017055A02A | DVQLVESGGGLVQAGDSLRLSCAASGRTFSSYAMGWFRQAPGKEREFVAAISWSDGSTYYADSVKGRFTISRDNAKNTVYLQMNSLKPEDTAVYYCAADLTSNPGSYIYIWAYDYWGQGTQVTVSSGGGGSGGGGSGGGGSGGGGSGGGGSGGSEVQLVESGGGLVQPGGSLRLSCAASGDVHKINILGWYRQAPAKEREMVAHITIGDATDYADSAKGRFTISRDEAKNMVYLQMNSLKPEDTAVYFCRAYSRIYPYNYWGQGTLVTVSSA |
| 305 | T017000001 | T017011A10 | EVQLVESGGGLVQGGGSLSLSCAASGRTFSSYAMAWFRQPPGKEREFVASISWSGENTNYRNSVKGRFTISRDNAKNTVYLQMNSLKPEDTAVYYCAAKIAKTYPDNWYWTKSNNYNYWGQGTLVTVSSGGGGSGGGGSGGGGSGGGGSGGGGSEVQLVESGGGLVQGGGSLSLSCAASGRTFSSYAMAWFRQPPGKEREFVASISWSGENTNYRNSVKGRFTISRDNAKNTVYLQMNSLKPEDTAVYYCAAKIAKTYPDNWYWTKSNNYNYWGQGTLVTVSS |
| 306 | T017000004 | 20CD019C07-5GS-T0170033G03 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSEVQLVESGGSVQAGGSLRLSCAASGRTFSTNPMGWFRQVPGKERELIAAVRMADGNTFYADSVKGRFTISRDNAKKTVYLQMNSLKSEDTATYYCAAGRPWSAYHSPAEYVHMGQGTLVTVSS |
| 307 | T017000005 | 20CD019C07-5GS-T017011A10 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSEVQLVESGGGLVQGGGSLSLSCAASGRTFSSYAMAWFRQPPGKEREFVASISWSGENTNYRNSVKGRFTISRDNAKNTVYLQMNSLKPEDTAVYYCAAKIAKTYPDNWYWTKSNNYNYWGQGTLVTVSS |

TABLE A-9-continued

Sequences of multispecific polypeptides (with and without tags). "ID" refers to the SEQ ID NO as used herein.

| ID | Name | Description | Amino acid sequence |
|---|---|---|---|
| 308 | T017000006 | 20CD019C07-5GS-cAbLys3 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSDVQLQASGGGSVQAGGSLRLSCAASGYTIGPYCM GWFRQAPGKEREGVAAINMGGITYYADSVKGRFTISQDNAKNTVYLLMNSLEPDTAIYYCAADSTIYASYYECGHGLSTG GYGYDSWGQGTQVTVSS |
| 309 | T017000010 | 20CD019C07-9GS-T017033G03 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGGSEVQLVESGGGSVQAGGSLRLSCAASGRTFST NPMGWFRQVPGKERELIAAVRWADGNTFYADSVKGRFTISRDNAKKTVYLQMNSLKSEDTATYYCAAGRPWSAYHSPAEY VHWGQGTLVTVSS |
| 310 | T017000011 | 20CD019C07-9GS-T017011A10 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGGSEVQLVESGGGSLSLSCAASGRTFSS YAMAWFRQPPGKEREFVASISWSGENTNYRNSVKGRFTISRDNAKNTVYLQMNSLKPEDTAVYYCAAKIAKTYPDNWYWT KSNNYNYWGQGTLVTVSS |
| 311 | T017000012 | 20CD019C07-9GS-cAbLys3 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGGSDVQLQASGGGSVQAGGSLRLSCAASGYTIG PYCMGWFRQAPGKEREGVAAINMGGITYYADSVKGRFTISQDNAKNTVYLLMNSLEPDTAIYYCAADSTIYASYYECGHG LSTGGYGYDSWGQGTQVTVSS |
| 312 | T017000016 | 20CD019C07-35GS-T017033G03 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGGSGGGGSGGGGSGGGGSEV QLQASGGGSVQAGGSLRLSCAASGRTFSTNPMGWFRQVPGKERELIAAVRWADGNTFYADSVKGRFTISRDNAKKTVYLQ MNSLKSEDTATYYCAAGRPWSAYHSPAEYVHWGQGTLVTVSS |
| 313 | T017000017 | 20CD019C07-35GS-T017011A10 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGGSGGGGSGGGGSGGGGSEV QLVESGGGLVQGGGSLSLSCAASGRTFSSYAMAWFRQPPGKEREFVASISWSGENTNYRNSVKGRFTISRDNAKNTVYLQM NSLKPEDTAVYYCAAKIAKTYPDNWYMTKSNNYNYWGQGTLVTVSS |
| 314 | T017000018 | 20CD019C07-35GS-cAbLys3 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGSGGGGSGGGGSGGGGSGGGGSDV QLQASGGGSVQAGGSLRLSCAASGYTIGPYCMGWFRQAPGKEREGVAAINMGGITYYADSVKGRFTISQDNAKNTVYLL MNSLEPDTAIYYCAADSTIYASYYECGHGLSTGGYGYDSWGQGTQVTVSS |
| 315 | T017000020 | T017033G03-9GS-20CD019C07 | EVQLVESGGGSVQAGGSLRLSCAASGRTFSTNPMGWFRQVPGKERELIAAVRWADGNTFYADSVKGRFTISRDNAKKTVYL QMNSLKSEDTATYYCAAGRPWSAYHSPAEYVHWGQGTLVTVSSGGGSGGGGSEVQLVESGGGLVQPGGSLRLSCTFSGGT FSSYTMGWFRQAPGKEREFVAEVRWGGVTTYSNSLKDRFSISEDSVKNAVYLQMNSLKPEDTAVYYCAAVRQMYMTVVPD YWGQGTLVTVSS |
| 316 | T017000021 | T017033G03-35GS-20CD019C07 | EVQLVESGGGSVQAGGSLRLSCAASGRTFSTNPMGWFRQVPGKERELIAAVRWADGNTFYADSVKGRFTISRDNAKKTVYL QMNSLKSEDTATYYCAAGRPWSAYHSPAEYVHWGQGTLVTVSSGGGSGGGGSGGGGSGGGGSGGGG SGEVQLVESGGGLVQPGGSLRLSCTFSGGTFSSYTMGWFRQAPGKEREFVAEVRWGGVTTYSNSLKDRFSISEDSVKNAVYL QMNSLKPEDTAVYYCAAVRQMYMTVVPDYWGQGTLVTVSS |

TABLE A-9-continued

Sequences of multispecific polypeptides (with and without tags). "ID" refers to the SEQ ID NO as used herein.

| ID | Name | Description | Amino acid sequence |
|---|---|---|---|
| 317 | T017000022 | T0170011A10-35GS-20CD019C07 | EVQLVESGGGLVQGGGSLSLSCAASGRTFSSYAMAWFRQPPGKEREFVASISWSGENTNYRNSVKGRFTISRDNAKNTVYL QMNSLKPEDTAVYYCAAKIAKTYPDNWYWTKSNNYNYWGQGTLVTVSSGGGGSGGGGSGGGGSGGGGSGGGGSGGGGSGGG GSGGGGSEVQLVESGGGLVQPGGSLRLSCTFSGGTFSSYTMGWFRQAPGKEREFVAEVRWGGVTTYSNSLKDRFSISEDSV KNAVYLQMNSLKPEDTAVYYCAAVRQMYMTVVPDYWGQGTLVTVSS |
| 318 | T017000023 | cAbLys3(D1E)-35GS-20CD019C07 | EVQLQASGGGSVQAGGSLRLSCAASGYTIGPYCMGWFRQAPGKEREGVAAINMGGGITYYADSVKGRFTISQDNAKNTVY LLMNSLEPEDTAIYYCAADSTIYASYYECGHGLSTGGYGYDSWGQGTQVTVSSGGGGSGGGGSGGGGSGGGGSGGGGSGG GGSGGGGSEVQLVESGGGLVQPGGSLRLSCTFSGGTFSSYTMGWFRQAPGKEREFVAEVRWGGVTTYSNSLKDRFSISED SVKNAVYLQMNSLKPEDTAVYYCAAVRQMYMTVVPDYWGQGTLVTVSS |
| 319 | T017000024 | T0170033G03-35GS-cAbLys3 | EVQLVESGGGSVQAGGSLRLSCAASGRTFSTNPMGWFRQVPGKERELIAAVRWADGNTFYADSVKGRFTISRDNAKKTVYL QMNSLKSEDTATYYCAAGRPWSAVHSPAEYVHWGQGTLVTVSSGGGGSGGGGSGGGGSGGGGSGGGGSGGGGSGGGGSGGG GSDVQLQASGGGSVQAGGSLRLSCAASGYTIGPYCMGWFRQAPGKEREGVAAINMGGGITYYADSVKGRFTISQDNAKNT VYLLMNSLEPEDTAIYYCAADSTIYASYYECGHGLSTGGYGYDSWGQGTQVTVSS |
| 320 | T017000026 | T0170011A10-9GS-20CD019C07 | EVQLVESGGGLVQGGGSLSLSCAASGRTFSSYAMAWFRQPPGKEREFVASISWSGENTNYRNSVKGRFTISRDNAKNTVYL QMNSLKPEDTAVYYCAAKIAKTYPDNWYWTKSNNYNYWGQGTLVTVSSGGGSGGGSEVQLVESGGGLVQPGGSLRLSC TFSGGTFSSYTMGWFRQAPGKEREFVAEVRWGGVTTYSNSLKDRFSISEDSVKNAVYLQMNSLKPEDTAVYYCAAVRQMY MTVVPDYWGQGTLVTVSS |
| 321 | T017000027 | T0170011A10-35GS-cAbLys3 | EVQLVESGGGLVQGGGSLSLSCAASGRTFSSYAMAWFRQPPGKEREFVASISWSGENTNYRNSVKGRFTISRDNAKNTVYL QMNSLKPEDTAVYYCAAKIAKTYPDNWYWTKSNNYNYWGQGTLVTVSSGGGGSGGGGSGGGGSGGGGSGGGGSGGGG GSGGGGSDVQLQASGGGSVQAGGSLRLSCAASGYTIGPYCMGWFRQAPGKEREGVAAINMGGGITYYADSVKGRFTISQD NAKNTVYLLMNSLEPEDTAIYYCAADSTIYASYYECGHGLSTGGYGYDSWGQGTQVTVSS |
| 322 | T017000034 | T0170061F07-35GS-cAbLys3 | EVQLVESGGGPVQAGGSLRLSCAASGRTYRGYSMAWFRQPPGKEREFVAAITWSEGNTYYEDFVKGRFTISRDNAKNTLYL QMTSLKPEDTALYYCAAKIRPYIFKIAGQYDYWGQGTLVTVSSGGGGSGGGGSGGGGSGGGGSGGGGSGGGGSGGGGSE VQLVESGGGLVQPGGSLRLSCTFSGGTFSSYTMGWFRQAPGKEREFVAEVRWGGVTTYSNSLKDRFSISEDSVKNAVYLQM NSLKPEDTAVYYCAAVRQMYMTVVPDYWGQGTLVTVSS |
| 323 | T017000036 | T0170117G03-35GS-20CD019C07 | EVQLVESGGGPVQAGGSLRLSCAASGRTYRGYSMGWFRQAPGKEREFVAAPGKEREFVAAIVWSGNTYYEDSVKGRFTISRDNAKNTMY LQMTSLKPEDSATYYCAAKIRPYIFKIAGQYDYWGQGTLVTVSSGGGGSGGGGSGGGGSGGGGSGGGGSGGGGSGGGGS EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSS |
| 324 | T017000039 | T0170061F04-35GS-20CD019C07 | EVQLVESGGGPVQAGGSLRLSCAASGRTYRGYSMAWFRQSPGKEREFVAAIVWSDGNTYYEDFVKGRFTISRDSAKNTLYL QMTNLKPEDTALYYCAAKIRPYIFKIAGQYDYWGQGTLVTVSSGGGGSGGGGSGGGGSGGGGSGGGGSGGGGSGGGGSE VQLVESGGGLVQPGGSLRLSCTFSGGTFSSYTMGWFRQAPGKEREFVAEVRWGGVTTYSNSLKDRFSISEDSVKNAVYLQM NSLKPEDTAVYYCAAVRQMYMTVVPDYWGQGTLVTVSS |
| 325 | T017000040 | T0170060E11-35GS-20CD019C07 | EVQLVESGGGLVQPGGSLRLSCAASGDIYKSFDMGWYRQAPGKQRDLVAVIGSRGNNRGRTNVADSVKGRFTISRDGTGN TVYLLMNKLRPEDTAIYYCNTAPLVAGRPWGRGTLVTVSSGGGGSGGGGSGGGGSGGGGSGGGGSGGGGSGGGGSEVQ LVESGGGLVQPGGSLRLSCTFSGGTFSSYTMGWFRQAPGKEREFVAEVRWGGVTTYSNSLKDRFSISEDSVKNAVYLQMNS LKPEDTAVYYCAAVRQMYMTVVPDYWGQGTLVTVSS |
| 326 | T017000043 | T0170050A11-35GS-20CD019C07 | EVQLVESGGGLVQAGGSLRLSCAASGRSFNMNPLGWFRQSPGKEREFVAAHRWSDGNTYYVDSVKGRFTISRDNAKNTVY LQMNSLKSEDTAVYYCAAGRPWSAFRSPGEYYVWGQGTLVTVSSGGGGSGGGGSGGGGSGGGGSGGGGSGGGGSGGG GSEVQLVESGGGLVQPGGSLRLSCTFSGGTFSSYTMGWFRQAPGKEREFVAEVRWGGVTTYSNSLKDRFSISEDSVKNAVYL QMNSLKPEDTAVYYCAAVRQMYMTVVPDYWGQGTLVTVSS |

TABLE A-9-continued

Sequences of multispecific polypeptides (with and without tags). "ID" refers to the SEQ ID NO as used herein.

| ID | Name | Description | Amino acid sequence |
|---|---|---|---|
| 327 | T017000045 | T0170033G03-35GS-20CD019C07 | EVQLVESGGGSVQAGGSLRLSCAASGRTFSTNPMGWFRQVPGKERELIAAVRWADGNTFYADSVKGRFTISRDNAKKTVYL QMNSLKSEDTATYYCAAGRPWSAYHSPAEYVHWGQGTLVTVSSGGGGSGGGGSGGGGSGGGGSGGGGSGGGGSGGGGGGG GSEVQLVESGGGLVQPGGSLRLSCTFSGGTFSSYTMGWFRQAPGKEREFVAEVRWGGVTTYSNSLKDRFSISEDSVKNAVYL QMNSLKPEDTAVYYCAAVRQMYMTVVPDYWGQGTLVTVSS |
| 328 | T017000047 | T0170011A10-35GS-20CD019C07 | EVQLVESGGGLVQGGGSLSLSCAASGRTFSSYAMAWFRQPPGKEREFVASISWSGENTNYRNSVKGRFTISRDNAKNTVYL QMNSLKPEDTAVYYCAAKIAKTYPDNWYWTKSNNYNYWGQGTLVTVSSGGGGSGGGGSGGGGSGGGGSGGGGSGGGGGGGG GSGGGGSEVQLVESGGGLVQPGGSLRLSCTFSGGTFSSYTMGWFRQAPGKEREFVAEVRWGGVTTYSNSLKDRFSISEDSV KNAVYLQMNSLKPEDTAVYYCAAVRQMYMTVVPDYWGQGTLVTVSS |
| 329 | T017000048 | T0170052G04-35GS-20CD019C07 | EVQLVESGGGAVQPGGSLRLSCAASGIRISRNMMGWFRQAPGKQRDLVARITPGGDTYYVDSVKGRFSISKDNAKNTVYLQ MNSLKPEDTAVYYCNSYSTLGSWGQGTLVTVSSGGGGSGGGGSGGGGSGGGGSGGGGSGGGGSEVQLVESGGG LVQPGGSLRLSCTFSGGTFSSYTMGWFRQAPGKEREFVAEVRWGGVTTYSNSLKDRFSISEDSVKNAVYLQMNSLKPEDTAV YYCAAVRQMYMTVVPDYWGQGTLVTVSS |
| 330 | T017000052 | 20CD019C07-35GS-T0170061F04 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSGGGGSGGGGSGGGGSGGGGSEV QLVESGGGPVQAGGSLRLSCAASGRTYRGYSMAWFRQSPGKEREFVAAIVWSDGNTYYEDFVKGRFTISRDSAKNTLYLQM TNLKPEDTALYYCAAKIRPYIFKIAGQYDYWGQGTLVTVSS |
| 331 | T017000053 | 20CD019C07-35GS-T0170060E11 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSGGGGSGGGGSGGGGSGGGGSEV QLVESGGGLVQPGGSLRLSCAASGDIYKSFDMGWYRQAPGKQRDLVAVIGSRGNNRGRTNYADSVKGRFTISRDGTGNTV YLLMNKLRPEDTAIYYCNTAPLVAGRPWGRGTLVTVSS |
| 332 | T017000056 | 20CD019C07-35GS-T0170052G04 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSGGGGSGGGGSGGGGSGGGGSEV QLVESGGGAVQPGGSLRLSCAASGIRISRNMMGWFRQAPGKQRDLVARITPGGDTYYVDSVKGRFSISKDNAKNTVVLQM NSLKPEDTAVYYCNSYSTLGSWGQGTLVTVSS |
| 333 | T017000057 | 20CD019C07-35GS-T0170050A11 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSGGGGSGGGGSGGGGSGGGGSEV QLVESGGGLVQAGGSLRLSCAASGRSFNMNPLGWFRQSPGKEREFVAAHRWSDGNTYVDSVKGRFTISRDNAKNTVYLQ MNSLKSEDTAVYYCAAGRPWSAPRSPGEYVYWGQGTLVTVSS |
| 334 | T017000059 | 20CD019C07-35GS-T0170033G03 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSGGGGSGGGGSGGGGSGGGGSEV QLVESGGGSVQAGGSLRLSCAASGRTFSTNPMGWFRQVPGKERELIAAVRWADGNTFYADSVKGRFTISRDNAKKTVYLQ MNSLKSEDTATYYCAAGRPWSAYHSPAEYVHWGQGTLVTVSS |
| 335 | T017000061 | 20CD019C07-35GS-T0170011A10 | EVQLVESGGGLVQPGGSLRLSCTFSGGTFSSYTMGWFRQAPGKEREFVAEVRWGGVTTYSNSLKDRFSISEDSVKNAVYLQ MNSLKPEDTAVYYCAAVRQMYMTVVPDYWGQGTLVTVSSGGGGSGGGGSGGGGSGGGGSGGGGSGGGGSEV QLVESGGGLVQGGGSLSLSCAASGRTFSSYAMAWFRQPPGKEREFVASISWSGENTNYRNSVKGRFTISRDNAKNTVYLQM NSLKPEDTAVYYCAAKIAKTYPDNWYWTKSNNYNYWGQGTLVTVSS |

TABLE A-9-continued

Sequences of multispecific polypeptides (with and without tags). "ID" refers to the SEQ ID NO as used herein.

| ID | Name | Description | Amino acid sequence |
|---|---|---|---|
| 336 | T017000062 | 20CD019C07-35GS-T017117G03 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSEVQLVESGGGPVQAGGSLRLSCAASGRTYRGYSMGWFRQAPGKEREFVAAIVWSGNTYYEDSVKGRFTISRDNAKNTMYLQMTSLKPEDSATYYCAAKIRPYIFKIAGQYDYWGQGTLVTVSS |
| 337 | T017000066 | 20CD019C07-35GS-T017061D09 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSEVQLVESGGGLVQTGGSLRLSCVASGRTYRGYSMAWFRQPPGKEREFVAAITWSEGNTYYEDFVKGRFTISRDNAKNTLYLQMTSLKPEDTALYYCAAKIRPYIFKIPGQYDYWGQGTLVTVSS |
| 338 | T017000071 | 20CD019C07-35GS-T017061F07 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSEVQLVESGGGPVQAGGSLRLSCAASGRTYRGYSMAWFRQPPGKEREFVAAITWSEGNTYYEDFVKGRFTISRDNAKNTLYLQMTSLKPEDTALYYCAAKIRPYIFKIAGQYDYWGQGTLVTVSS |
| 339 | T017000072 | T017061D09-35GS-20CD019C07 | EVQLVESGGGLVQTGGSLRLSCVASGRTYRGYSMAWFRQPPGKEREFVAAITWSEGNTYYEDFVKGRFTISRDNAKNTLYLQMTSLKPEDTALYYCAAKIRPYIFKIPGQYDYWGQGTLVTVSSGGGGSGGGGSGGGGSGGGGSGGGGSEVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSS |
| 340 | T017000084 | 20CD019C07(E1D)-35GS-T017117G03 | DVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSEVQLVESGGGPVQAGGSLRLSCAASGRTYRGYSMGWFRQAPGKEREFVAAIVWSGNTYYEDSVKGRFTISRDNAKNTMYLQMTSLKPEDSATYYCAAKIRPYIFKIAGQYDYWGQGTLVTVSS |
| 341 | T017000090 | RSV007B02-35GS-T017061F04 | EVQLVESGGGLVQAGDSLRLSCAASGRTFSSYAMGWFRQAPGKEREFVAAISWSDGSTYYADSVKGRFTISRDNAKNTVYLQMNSLKPEDTAVYYCAADLTSTNPGSYIYIWAYDYWGQGTQVTVSSGGGGSGGGGSGGGGSGGGGSGGGGSGGSEVQLVESGGGPVQAGGSLRLSCAASGRTYRGYSMAWFRQSPGKEREFVAAIVWSDGNTYYEDFVKGRFTISRDSAKNTLYLQMTNLKPEDTALYYCAAKIRPYIFKIAGQYDYWGQGTLVTVSS |
| 342 | T017000091 | RSV007B02-35GS-T017117G03 | EVQLVESGGGLVQAGDSLRLSCAASGRTFSSYAMGWFRQAPGKEREFVAAISWSDGSTYYADSVKGRFTISRDNAKNTVYLQMNSLKPEDTAVYYCAADLTSTNPGSYIYIWAYDYWGQGTQVTVSSGGGGSGGGGSGGGGSGGGGSGGGGSGGSEVQLVESGGGPVQAGGSLRLSCAASGRTYRGYSMGWFRQAPGKEREFVAAIVWSGNTYYEDSVKGRFTISRDNAKNTMYLQMTSLKPEDSATYYCAAKIRPYIFKIAGQYDYWGQGTLVTVSS |
| 343 | T017000094 | 20CD019C07-35GS-T017117G03-35GS-ALB11 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSEVQLVESGGGPVQAGGSLRLSCAASGRTYRGYSMGWFRQAPGKEREFVAAIVWSGNTYYEDSVKGRFTISRDNAKNTMYLQMTSLKPEDSATYYCAAKIRPYIFKIAGQYDYWGQGTLVTVSSGGGGSGGGGSGGGGSGGGGSGGGGSEVQLVQPGNSLRLSCAASGFTFSSFGMSWVRQAPGKGLEWVSSISGSSDTLYADSVKGRFTISRDNAKTTLYLQMNSLRPEDTAVYYCTIGGSLSRSSQGTLVTVSS |
| 344 | T017000096 | 20CD019C07-35GS-T017060E11-35GS-ALB11 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSSGGGGSGGGGSGGGGSGGGGSGGGGSEVQLVESGGGLVQPGGSLRLSCAASGDIYKSFDMGWYRQRDLVAVIGSRGNNRGRTNYADSVKGRFTISRDGTGNTVYLLMNKLRPEDTAIYYCNTAPLVAGRPWGRGTLVTVSSGGGGSGGGGSGGGGSGGGGSGGGGSEVQLVESGGGLVQPGNSLRLSCAASGFTFSSFGMSWVRQAPGKGLEWVSSISGSSDTLYADSVKGRFTISRDNAKTTLYLQMNSLRPEDTAVYYCTIGGSLSRSSQGTLVTVSS |

TABLE A-9-continued

Sequences of multispecific polypeptides (with and without tags). "ID" refers to the SEQ ID NO as used herein.

| ID | Name | Description | Amino acid sequence |
|---|---|---|---|
| 345 | T017000100 | T0170117G03-35GS-HER2005F07(Q108L) | EVQLVESGGGPVQAGGSLRLSCAASGRTYRGYSMGWFRQAPGKEREFVAAIVWSGGNTYYEDSVKGRFTISRDNAKNTMY LQMTSLKPEDSATYYCAAKIRPYIFKIAGQYDYWGQGTLVTVSSGGGGSGGGGSGGGGSGGGGSGGGGSGGGGSGGGGS EVQLVESGGGLVQAGGSLRLSCAASGITFSINTMGWYRQAPGKQRELVALISSIGDTYYADSVKGRFTISRDNAKNTVYLQM NSLKPEDTAVYYCKRFRTAAQGTDYWGQGTLVTVSS |
| 346 | T017000101 | HER2005F07(Q108L)-35GS-T0170117G03 | EVQLVESGGGLVQAGGSLRLSCAASGITFSINTMGWYRQAPGKQRELVALISSIGDTYYADSVKGRFTISRDNAKNTVYLQM NSLKPEDTAVYYCKRFRTAAQGTDYWGQGTLVTVSSGGGGSGGGGSGGGGSGGGGSGGGGSGGGGSEVQLVES GGGPVQAGGSLRLSCAASGRTYRGYSMGWFRQAPGKEREFVAAIVWSGGNTYYEDSVKGRFTISRDNAKNTMYLQMTSLK PEDSATYYCAAKIRPYIFKIAGQYDYWGQGTLVTVSS |
| 347 | T017000088 | RSV007B02(E1D)-35GS-T0170055A02 | DVQLVESGGGLVQAGDSLRLSCAASGRTFSSYAMGWFRQAPGKEREFVAAISWSDGSTYYADSVKGRFTISRDNAKNTVYL QMNSLKPEDTAVYYCAADLTSNPGSYIYIWAYDYWGQGTQVTVSSGGGGSGGGGSGGGGSGGGGSGGGGSGGGGSGG GGSEVQLVESGGGLVQPGGSLRLSCAASGDVHKINILGWYRQAPAKEREMVAHITIGDATDYADSAKGRFTISRDEAKNMV YLQMNSLKPEDTAVYFCRAYSRIYPYNYWGQGTLVTVSS |

TABLE A-10

Sequences of components of TCR complex. "ID" refers to the SEQ ID NO as used herein

| ID | Name | Amino acid sequence |
|---|---|---|
| 291 | HUMAN CD3 DELTA (P04234) | MEHSTFLSGLVLATLLSQVSPFKIPIEELEDRVFVNCNTSITWVEGTVGTLLSDITRLDLGKRILDPRGIYRCNGTDIYKDKESTVQVHYRMCQSCVELDPATVAGIIVTDVIATLLLALGVFCFAGHETGRLSGAADTQALLRNDQVYQPLRDRDDAQYSHLGGNWARNK |
| 292 | HUMAN CD3 GAMMA (P09693) | MEQGKGLAVLILAIILLQGTLAQSIKGNHLVKVYDYQEDGSVLLTCDAEAKNITWFKDGKMIGFLTEDKKKWNLGSNAKDPRGMYQCKGSQNKSKPLQVYYRMCQNCIELAEIVSIFVLAVGVYFIAGQDGVRQSRASDKQTLLPNDQLYQPLKDREDDQYSHLQGNQLRNAATISGFLFRN |
| 293 | HUMAN CD3 EPSILON (P07766) | MQSGTHWRVLGLCLLSVGVWGQDGNEEMGGITQTPYKVSISGTTVILTCPQYPGSEILWQHNDKNIGSDEDHLSLKEFSELEQSGYTVCYPPPVPNPDYEPIRKGQRDLYSGLNQRRIRGSKPEDANFNCMEMDVMSVATIVIVDICITGGLLLLVYYWSKNRKAKAKPVTRGAGAGRQRGQNKERPYLYLRARVCE |
| 294 | HUMAN CD3 ZETA (P20963) | MKWKALFTAAILQAQLPITEAQSFGLLDPKLCYLLDGILFIYGVILTALFLRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |
| 295 | HUMAN TCR ALPHA CONSTANT DOMAIN (P01848) | PNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 296 | HUMAN TCR BETA CONSTANT DOMAIN (P01850) | EDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 379 | HUMAN CD3 GAMMA (P09693) | MEQGKGLAVLILAIILLQGTLAQSIKGNHLVKVYDYQEDGSVLLTCDAEAKNITWFKDGKMIGFLTEDKKKWNLGSNAKDPRGMYQCKGSQNKSKPLQVYYRMCQNCIELNAATISGFLFAEIVSIFVLAVGVYFIAGQDGVRQSRASDKQTLLPNDQLYQPLKDREDDQYSHLQGNQLRRN |
| 380 | HUMAN CD3 EPSILON (P07766) | MQSGTHWRVLGLCLLSVGVWGQDGNEEMGGITQTPYKVSISGTTVILTCPQYPGSEILWQHNDKNIGSDEDHLSLKEFSELEQSGYTVCYPPGSKPEDANFVYLRARVCENCMEMDVMSVATIVIVDICITGGLLLLVYYWSKNRKAKAKPVTRGAGAGRQRGQNKERPPPVPNPDYEPIRKGQRDLYSGLNQRRI |
| 381 | HUMAN TCR ALPHA VARIABLE DOMAIN DERIVED FROM 2IAN | IQVEQSPPDLILQEGANSTLRCNFSDSVNNLQWFHQNPWGQLINLFYIPSGTKQNGRLSATTVATERYSLLYISSSQTTDSGVYFCAALIQGAQKLVFGQGTRLTIN |
| 382 | HUMAN TCR BETA VARIABLE DOMAIN DERIVED FROM 2IAN | NAGVTQTPKFRILKIGQSMTLQCTQDMNHNYMWYRQDPGMGLKLIYYSVGAGITDKGEVPNGYNVSRSTTEDFPLRLELAAPSQTSVYFCASTYHGTGYFGEGSWLTVV |
| 383 | HUMAN TCR ALPHA VARIABLE DOMAIN DERIVED FROM 2XN9 | QLLEQSPQFLSIQEGENLTVYCNSSSVFSSLQWYRQEPGEGPVLLVTVTGEVKKLKRLTFQFGDARKDSSLHITAAQPGDTGLYLCAGAGSQNLIFGKGTKLSVK |
| 384 | HUMAN TCR BETA VARIABLE DOMAIN DERIVED FROM 2XN9 | DGGITQSPKYLFRKEGQNVTLSCEQNLNHDAMYWYRQDPGQGLRLIYYSQIVNDFQKGDIABGYSVSREKKESFPLITVTSAQKNPTAFYLCASSSRSYEQYFGPGTRLTVT |

TABLE A-10-continued

Sequences of components of TCR complex. "ID" refers to the SEQ ID NO as used herein

| ID | Name | Amino acid sequence |
|---|---|---|
| 385 | HUMAN TCR ALPHA VARIABLE DOMAIN DERIVED FROM 3TOE | GDAKTTQPNSMESNEEEPVHLPCNHSTISGTDYIHWYRQLPSQGPEYVIHGLTSNVNNRMASLAIAEDRKSSTLILHRATLRDAAVYYCTVYGGATNKLIFGTGTLLAVQ |
| 386 | HUMAN TCR BETA VARIABLE DOMAIN DERIVED FROM 3TOE | VVSQHPSWVIAKSGTSVKIECRSLDFQATTMFWYRQFPKQSLMLMATSNEGSKATYEQGVEKDKFLINHASLTLSTLTVTSAHPEDSSFYICSARGGSYNSPLHFGNGTRLTVT |

TABLE A-11

Sequences of TAA building blocks. "ID" refers to the SEQ ID NO as used herein

| ID | Name | Amino acid sequence |
|---|---|---|
| 297 | HER2005F07 (Q108L) | EVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSS |
| 298 | HER2047D05 (L108Q) | EVQLVESGGGLVQPGGSLRLSCAASGSIFGFNDMAWYRQAPGKQRELVALISRVGVTSSADSVKGRFTISRVNAKDTVYLQMNSLKPEDTAVYYCMDQRLDGSTLAYWGQGTQVTVSS |
| 299 | EGFR009G08 | EVQLVESGGGLVQAGGSLRLSCAASGRTFSSYAMGWFRQAPGKEREFVVAINWSSGSTYYADSVKGRFTISRDNAKNETMYLQMNSLKPDTAVYYCAAGYQINSGNYNFKDYEYDYWGQGTQVTVSS |
| 300 | NbCEA5 (CEA#1) | EVQLVESGGGSVQAGGSLRLSCAASGDTYGSYWMGWFRQAPGKEREGVAAINRGGGYTVYADSVKGRFTISRDTAKNTVYLQMNSLRPDDTADYYCAASGVLGGLHEDWFNYWGQGTLVTVSS |
| 301 | T023200005 (CEA#5) | EVQLVESGGGSVQAGGSLRLSCAASGDTYGSYWMGWFRQAPGQEREAVAAINRGGGYTVYADSVKGRFTISRDNAKNTLYLQMNSLRPDDTADYYCAASGVLGGLHEDWFNYWGQGTLVTVSS |
| 302 | 7D12 (EGFR#1) | EVQLVESGGGSVQTGGSLRLTCAASGRTSRSYGMGWFRQAPGKEREFVSGISWRGDSTGYADSVKGRFTISRDNAKNTVDLQMNSLKPEDTAIYYCAAAAGSAWYGTLYEYDYWGQGTLVTVSS |
| 303 | T023200033 (EGFR#33) | EVQLVESGGGSVQAGGSLRLTCAASGSTSRSYGMGWFRQAPGKEREFVSGISWRGDSTGYADSVKGRFTISRDNAKNTVDLQMNSLKPEDTAIYYCAAAAGSTWYGTLYEYDYWGQGTLVTVSS |
| 304 | 20CD019C07 | EVQLVESGGGLVQPGGSLRLSCTFSGGTFSSYTMGWFRQAPGKEREFVAEVRWGGVTTYSNSLKDRFSISEDSVKNAVYLQMNSLKPEDTAVYYCAAVRQMYMTVVPDYWGQGTLVTVSS |
| 387 | cAblys3 | DVQLQASGGGSVQAGGSLRLSCAASGYTIGPYCMGWFRQAPGKEREGVAAINMGGGITYYADSVKGRFTISQDNAKNTVYLLMNSLEPEDTAIYYCAADSTIYASYYECGHGLSTGGYGYDSWGQGTQVTVSS |
| 388 | RSV007B02 | EVQLVESGGGLVQAGDSLRLSCAASGRTFSSYAMGWFRQAPGKEREFVAAISWSDGSTYYADSVKGRFTISRDNAKNTVYLQMNSLKPEDTAVYYCAADLTSTNPGSYIYIWAYDYWGQGTQVTVSS |

The invention claimed is:

1. A polypeptide comprising a first and a second immunoglobulin single variable domain (ISV), wherein each of the first ISV and the second ISV is a Nanobody, a $V_{HH}$, or a camelized $V_H$, and wherein:
   said first ISV binds to cluster of differentiation 3 (CD3) present on a T cell;
   said second ISV binds to a first antigen on a target cell;
   wherein said first antigen is different from said CD3;
   wherein said target cell is different from said T cell; and
   wherein said first ISV consists of 4 framework regions (FR1 to FR4, respectively) and 3 complementarity determining regions (CDR1 to CDR3, respectively), in which:
   CDR1 comprises the amino acid sequence of SEQ ID NO: 94, CDR2 comprises the amino acid sequence of SEQ ID NO: 118, and CDR3 comprises the amino acid sequence of SEQ ID NO: 134;
   CDR1 comprises the amino acid sequence of SEQ ID NO: 90, CDR2 comprises the amino acid sequence of SEQ ID NO: 118, and CDR3 comprises the amino acid sequence of SEQ ID NO: 135;
   CDR1 comprises the amino acid sequence of SEQ ID NO: 95, CDR2 comprises the amino acid sequence of SEQ ID NO: 118, and CDR3 comprises the amino acid sequence of SEQ ID NO: 135;
   CDR1 comprises the amino acid sequence of SEQ ID NO: 96, CDR2 comprises the amino acid sequence of SEQ ID NO: 118, and CDR3 comprises the amino acid sequence of SEQ ID NO: 136;
   CDR1 comprises the amino acid sequence of SEQ ID NO: 97, CDR2 comprises the amino acid sequence of SEQ ID NO: 118, and CDR3 comprises the amino acid sequence of SEQ ID NO: 137;
   CDR1 comprises the amino acid sequence of SEQ ID NO: 98, CDR2 comprises the amino acid sequence of SEQ ID NO: 118, and CDR3 comprises the amino acid sequence of SEQ ID NO: 137;
   CDR1 comprises the amino acid sequence of SEQ ID NO: 99, CDR2 comprises the amino acid sequence of SEQ ID NO: 118, and CDR3 comprises the amino acid sequence of SEQ ID NO: 138;
   CDR1 comprises the amino acid sequence of SEQ ID NO: 99, CDR2 comprises the amino acid sequence of SEQ ID NO: 118, and CDR3 comprises the amino acid sequence of SEQ ID NO: 139;
   CDR1 comprises the amino acid sequence of SEQ ID NO: 95, CDR2 comprises the amino acid sequence of SEQ ID NO: 119, and CDR3 comprises the amino acid sequence of SEQ ID NO: 140;
   CDR1 comprises the amino acid sequence of SEQ ID NO: 100, CDR2 comprises the amino acid sequence of SEQ ID NO: 120, and CDR3 comprises the amino acid sequence of SEQ ID NO: 141;
   CDR1 comprises the amino acid sequence of SEQ ID NO: 100, CDR2 comprises the amino acid sequence of SEQ ID NO: 121, and CDR3 comprises the amino acid sequence of SEQ ID NO: 142; or
   CDR1 comprises the amino acid sequence of SEQ ID NO: 100, CDR2 comprises the amino acid sequence of SEQ ID NO: 122, and CDR3 comprises the amino acid sequence of SEQ ID NO: 143.

2. The polypeptide according to claim 1, wherein said first antigen is a tumor antigen.

3. The polypeptide according to claim 1, further comprising a third ISV, which binds to a second antigen on a target cell, wherein said second antigen is different from said first antigen, wherein the third ISV is a Nanobody, a $V_{HH}$, or a camelized $V_H$.

4. The polypeptide according to claim 3, wherein said second antigen is a tumor antigen.

5. The polypeptide according to claim 1, further comprising a serum protein binding moiety, wherein the serum binding moiety is an ISV that binds serum albumin, wherein the ISV that binds serum albumin is a Nanobody, a $V_{HH}$, or a camelized $V_H$.

6. The polypeptide according to claim 5, wherein the ISV that binds serum albumin is a humanized $V_{HH}$.

7. A polypeptide that comprises an immunoglobulin single variable (ISV) domain that specifically binds CD3, wherein the ISV is a Nanobody, a $V_{HH}$, or a camelized $V_H$ that comprises or consists of 4 framework regions (FR1 to FR4, respectively) and 3 complementarity determining regions (CDR1 to CDR3, respectively), in which:
   CDR1 comprises the amino acid sequence of SEQ ID NO: 94, CDR2 comprises the amino acid sequence of SEQ ID NO: 118, and CDR3 comprises the amino acid sequence of SEQ ID NO: 134;
   CDR1 comprises the amino acid sequence of SEQ ID NO: 90, CDR2 comprises the amino acid sequence of SEQ ID NO: 118, and CDR3 comprises the amino acid sequence of SEQ ID NO: 135;
   CDR1 comprises the amino acid sequence of SEQ ID NO: 95, CDR2 comprises the amino acid sequence of SEQ ID NO: 118, and CDR3 comprises the amino acid sequence of SEQ ID NO: 135;
   CDR1 comprises the amino acid sequence of SEQ ID NO: 96, CDR2 comprises the amino acid sequence of SEQ ID NO: 118, and CDR3 comprises the amino acid sequence of SEQ ID NO: 136;
   CDR1 comprises the amino acid sequence of SEQ ID NO: 97, CDR2 comprises the amino acid sequence of SEQ ID NO: 118, and CDR3 comprises the amino acid sequence of SEQ ID NO: 137;
   CDR1 comprises the amino acid sequence of SEQ ID NO: 98, CDR2 comprises the amino acid sequence of SEQ ID NO: 118, and CDR3 comprises the amino acid sequence of SEQ ID NO: 137;
   CDR1 comprises the amino acid sequence of SEQ ID NO: 99, CDR2 comprises the amino acid sequence of SEQ ID NO: 118, and CDR3 comprises the amino acid sequence of SEQ ID NO: 138;

CDR1 comprises the amino acid sequence of SEQ ID NO: 99, CDR2 comprises the amino acid sequence of SEQ ID NO: 118, and CDR3 comprises the amino acid sequence of SEQ ID NO: 139;

CDR1 comprises the amino acid sequence of SEQ ID NO: 95, CDR2 comprises the amino acid sequence of SEQ ID NO: 119, and CDR3 comprises the amino acid sequence of SEQ ID NO: 140;

CDR1 comprises the amino acid sequence of SEQ ID NO: 100, CDR2 comprises the amino acid sequence of SEQ ID NO: 120, and CDR3 comprises the amino acid sequence of SEQ ID NO: 141;

CDR1 comprises the amino acid sequence of SEQ ID NO: 100, CDR2 comprises the amino acid sequence of SEQ ID NO: 121, and CDR3 comprises the amino acid sequence of SEQ ID NO: 142; or CDR1 comprises the amino acid sequence of SEQ ID NO: 100, CDR2 comprises the amino acid sequence of SEQ ID NO: 122, and CDR3 comprises the amino acid sequence of SEQ ID NO: 143.

8. The polypeptide according to claim 7, further comprising a serum protein binding moiety, wherein the serum binding moiety is an ISV that binds serum albumin, wherein the ISV that binds serum albumin is a Nanobody, a $V_{HH}$, or a camelized $V_H$.

9. The polypeptide according to claim 8, wherein the ISV that binds serum albumin is a humanized $V_{HH}$.

10. A pharmaceutical composition comprising a polypeptide according to claim 1.

11. The polypeptide according to claim 1, wherein each of the first ISV and the second ISV is a humanized $V_{HH}$.

12. The polypeptide according to claim 1, wherein the first ISV consists of 4 framework regions (FR1 to FR4, respectively) and 3 complementarity determining regions (CDR1 to CDR3, respectively), in which: CDR1 comprises the amino acid sequence of SEQ ID NO: 94; CDR2 comprises the amino acid sequence of SEQ ID NO: 118; and CDR3 comprises the amino acid sequence of SEQ ID NO: 134.

13. The polypeptide according to claim 1, wherein the first ISV is selected from the group consisting of SEQ ID NOs: 66-80.

14. The polypeptide according to claim 2, wherein the first antigen is a tumor-associated antigen.

15. The polypeptide according to claim 4, wherein the second antigen is a tumor-associated antigen.

16. The polypeptide according to claim 3, wherein the third ISV is a humanized $V_{HH}$.

17. The polypeptide according to claim 7, wherein the ISV is a humanized $V_{HH}$.

18. The polypeptide according to claim 7, wherein the ISV consists of 4 framework regions (FR1 to FR4, respectively) and 3 complementarity determining regions (CDR1 to CDR3, respectively), in which: CDR1 comprises the amino acid sequence of SEQ ID NO: 94; CDR2 comprises the amino acid sequence of SEQ ID NO: 118; and CDR3 comprises the amino acid sequence of SEQ ID NO: 134.

19. The polypeptide according to 7, wherein the polypeptide is selected from the group consisting of SEQ ID NOs: 66-80.

* * * * *

UNITED STATES PATENT AND TRADEMARK OFFICE
CERTIFICATE OF CORRECTION

| | | |
|---|---|---|
| PATENT NO. | : 12,371,496 B2 | Page 1 of 1 |
| APPLICATION NO. | : 17/246771 | |
| DATED | : July 29, 2025 | |
| INVENTOR(S) | : Annelies Roobrouck et al. | |

It is certified that error appears in the above-identified patent and that said Letters Patent is hereby corrected as shown below:

In the Claims

In Claim 19, at Column 492, Line 28, the phrase:
"The polypeptide according to 7, wherein the"
Should read:
--The polypeptide according to claim 7, wherein the--.

Signed and Sealed this
Thirtieth Day of September, 2025

John A. Squires
*Director of the United States Patent and Trademark Office*